US011713464B2

(12) United States Patent
Sullenger et al.

(10) Patent No.: US 11,713,464 B2
(45) Date of Patent: Aug. 1, 2023

(54) NUCLEOLIN-TARGETING APTAMERS AND METHODS OF USING THE SAME

(71) Applicant: Duke University, Durham, NC (US)

(72) Inventors: Bruce A. Sullenger, Durham, NC (US); Michael Goldstein, Durham, NC (US); Elizabeth D. Pratico, Durham, NC (US); Michael Kastan, Durham, NC (US); Bethany Gray, Durham, NC (US)

(73) Assignee: Duke University, Durham, NC (US)

( * ) Notice: Subject to any disclaimer, the term of this patent is extended or adjusted under 35 U.S.C. 154(b) by 281 days.

(21) Appl. No.: 16/645,762

(22) PCT Filed: Sep. 10, 2018

(86) PCT No.: PCT/US2018/050240
§ 371 (c)(1),
(2) Date: Mar. 9, 2020

(87) PCT Pub. No.: WO2019/051397
PCT Pub. Date: Mar. 14, 2019

(65) Prior Publication Data
US 2020/0283773 A1 Sep. 10, 2020

Related U.S. Application Data

(60) Provisional application No. 62/555,745, filed on Sep. 8, 2017.

(51) Int. Cl.
*C12N 15/115* (2010.01)
*A61P 35/00* (2006.01)
*C12Q 1/68* (2018.01)

(52) U.S. Cl.
CPC ............ *C12N 15/115* (2013.01); *A61P 35/00* (2018.01); *C12N 2310/16* (2013.01)

(58) Field of Classification Search
None
See application file for complete search history.

(56) References Cited

U.S. PATENT DOCUMENTS

| | | | |
|---|---|---|---|
| 7,396,664 | B2 | 7/2008 | Daly |
| 2008/0207546 | A1 | 8/2008 | Sullenger |
| 2011/0178161 | A1* | 7/2011 | Trent ................. A61K 31/7088 514/44 R |
| 2011/0197292 | A1 | 8/2011 | Sullenger |
| 2013/0115254 | A1 | 5/2013 | Odom |
| 2014/0213636 | A1* | 7/2014 | Lee ......................... A61P 35/02 514/44 R |
| 2015/0203848 | A1 | 7/2015 | Yu et al. |
| 2017/0165376 | A9 | 6/2017 | Rich |
| 2019/0359983 | A1* | 11/2019 | O'Neill ..................... A61K 9/51 |

FOREIGN PATENT DOCUMENTS

| | | |
|---|---|---|
| WO | 2004081021 | 9/2001 |
| WO | 2002026932 | 4/2002 |

OTHER PUBLICATIONS

Allerson, C. R. et al. "Fully 2'-Modified Oligonucleotide Duplexes with Improved in Vitro Potency and Stability Compared to Unmodified Small Interfering RNA." J. Med. Chem 48 (2005): 901-904.
Champlin, R. E. et al. T-cell depletion of bone marrow transplants for leukemia from donors other than HLA-identical siblings: advantage of T-cell antibodies with narrow specificities. Blood. 2000;95: 3996-4003.
Ellington et al., "In vitro selection of RNA molecules that bind specific ligands." (1990) Nature 346:818-22.
James et al., "A molecular imaging primer: modalities, imaging agents, and applications," (2012) Physiol Rev 92 (2):897-965.
Nimjee et al., "Aptamers as Therapeutics," (2017) Annual review of pharmacology and toxicology 57:61-79.
Ray, P. et al. "Aptamer-mediated delivery of chemotherapy to pancreatic cancer cells." Nucleic acid therapeutics 22.5 (2012): 295-305.
Schlessinger, J. "Autoinhibition control." Science 300.5620 (2003): 750-752.
Luerk et al., "Systematic evolution of ligands by exponential enrichment: RNA ligands to bacteriophage T4 DNA polymerase," (1990) Science 249:505-10.
Berenbaum et al., "Synergy, additivism and antagonism in immunosuppression. A critical review," (1977) Clin Exp Immunol 28: 1-18.
Chen et al., "Cell surface nucleolin serves as receptor for DNA nanoparticles composed of pegylated polylysine and DNA," (2008) Mol. Ther. 16(2):333-42—Abstract.
Chu et al, "Aptamer mediated siRNA delivery," (2006) Nucleic Acids Research 34(10):e73.
Farokhzad et al., "Nanoparticle aptamer bioconjugates: A new approach for targeting prostate cancer cells," (2004) Cancer Research 64:7668-7672.
Gen Bank CR446327, CR 446327 XGC-tailbud Xenopus tropicalis cDNA clone TTbA054d215-mRNA sequence. GenBank Accession No. CR446327. Jun. 19, 2004 Retrieved from teh internent: URL:https:// www.ncbi.nlm.nih.gov/nucest/CR446327.
Goldstein, Michael, et al. "Nucleolin mediates nucleosome disruption critical for DNA double-strand break repair." Proceedings of the National Academy of Sciences 110.42 (2013): 16874-16879.
International Search Report and Written Opinion for application PCT/US2018/050240, dated Jan. 29, 2019 (17 pages).
Keefe, A. D., et al. (2010). Aptamers as therapeutics. Nature reviews Drug discovery, 9(7), 537-550.
Khaled et al., "Controllable self-assembly of nanoparticles for specific delivery of multiple therapeutic molecules to cancer cells using RNA nanotechnology," (2005) Nano Letters 5(9):1797-1808.
Lai, Y.-T., et al. "A primer-free method that selects high-affinity single-stranded DNA aptamers using thermostable RNA ligase." Analytical biochemistry 414.2 (2011): 246-253.

(Continued)

*Primary Examiner* — Sean McGarry
(74) *Attorney, Agent, or Firm* — Quarles & Brady LLP

(57) ABSTRACT

Provided herein are compositions including aptamers capable of binding to and/or inhibiting the activity of nucleolin. Methods of treating cancer in a subject by administering such compositions are also provided.

20 Claims, 46 Drawing Sheets

Specification includes a Sequence Listing.

(56) References Cited

OTHER PUBLICATIONS

Nimjee et al., "Aptamers: an emerging class of therapeutics," (2005) Annual review of medicine 56:555-83.
Que-Gewirth, N.S. et al., "Gene therapy progress and prospects: RNA aptamers," (2007) Gene Therapy 14 (4):283-291.
Reyes-Reyes, E. Merit, et al. "Mechanistic studies of anticancer aptamer AS1411 reveal a novel role for nucleolin in regulating Rac1 activation." Molecular oncology 9.7 (2015): 1392-1405.
White, R. et al., "Generation of Species Cross-reactive Aptamers Using Toggle SELEX," (2001) Molecular Therapy 4 (6):567-573.
White, R. R. et al., "Developing aptamers into therapeutics," (2000) J. Clin. Investigation 106(8):929-934.
Bates P Jet al: "Discovery and development of the G-rich oligonucleotide AS1411 as a novel treatment for cancer", Experimental and Molecular Pathology, Academic Press, US, vol. 86, No. 3, Jun. 1, 2009 (Jun. 1, 2009), pp. 151-164.
Cheng, Y, et al. "AS-1411, a guanosine-rich oligonucleotide aptamer targeting nucleolin for the potential treatment of cancer, including acute myeloid leukemia", Current Opinion in Molecular Therapeutics, Current Drugs, London, GB, vol. 12, No. 1, Jan. 31, 2010 (Jan. 31, 2010), pp. 107-114.
Fangfei Li et al: "A water-soluble nucleolin aptamer-paclitaxel conjugate for tumor-specific targeting in ovarian cancer", Nature Communications, vol. 8, No. 1, Nov. 9, 2017.
Extended European Search Report—EP 18853636.1—dated Nov. 10, 2021.

* cited by examiner

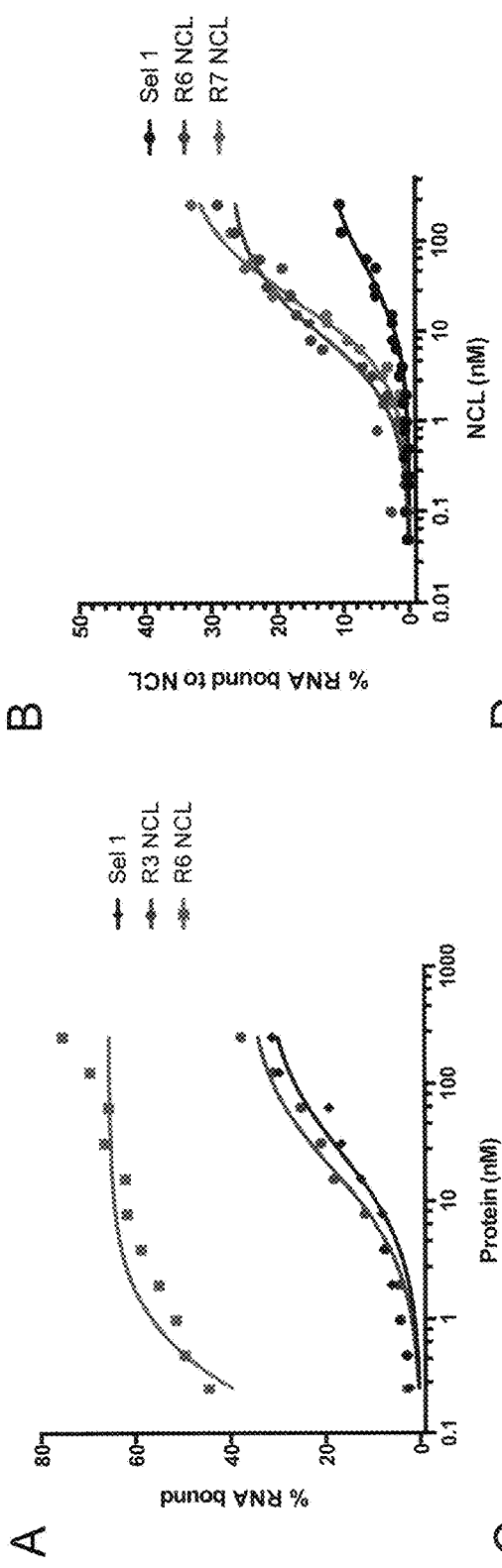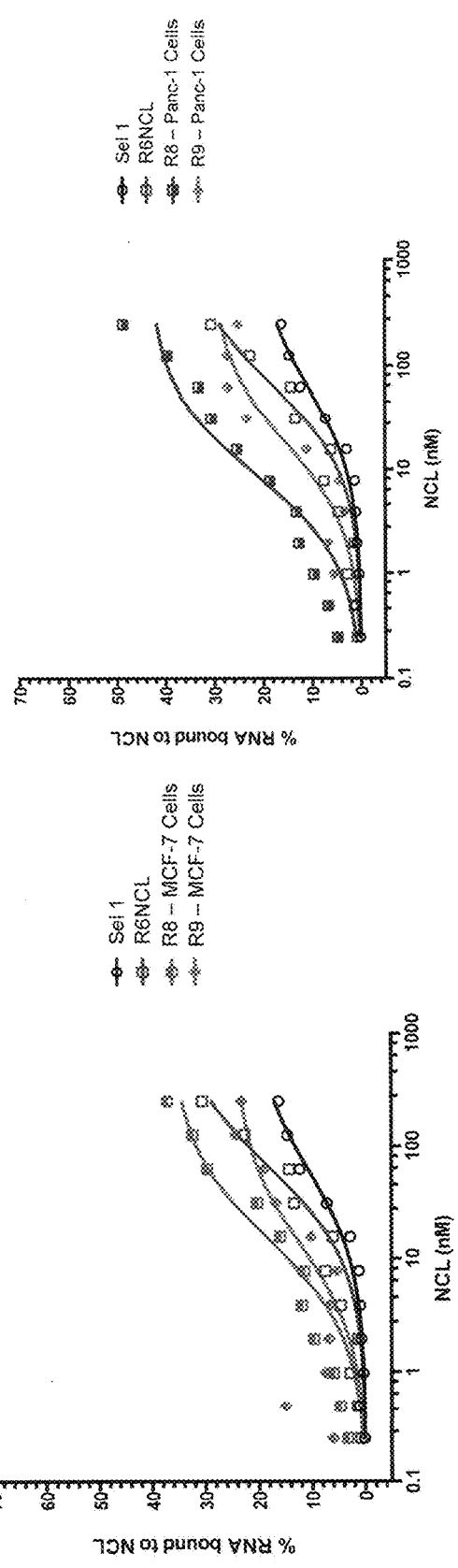

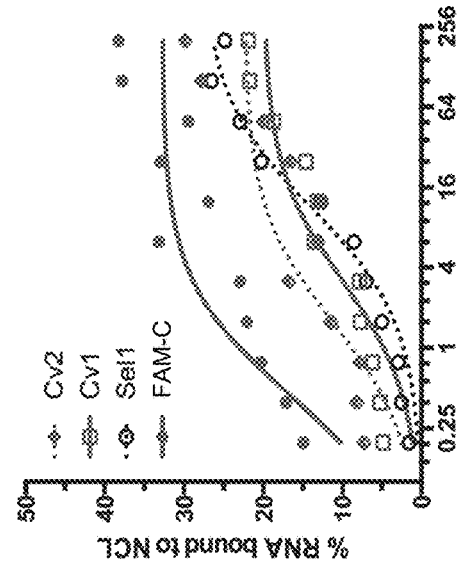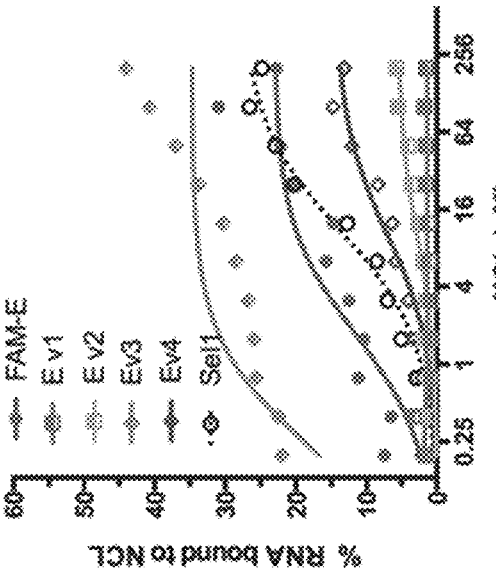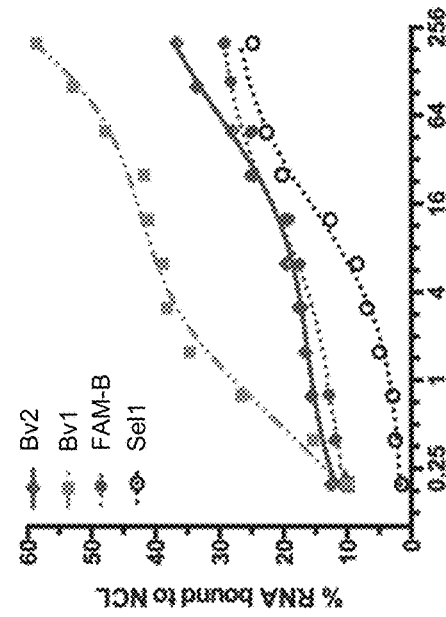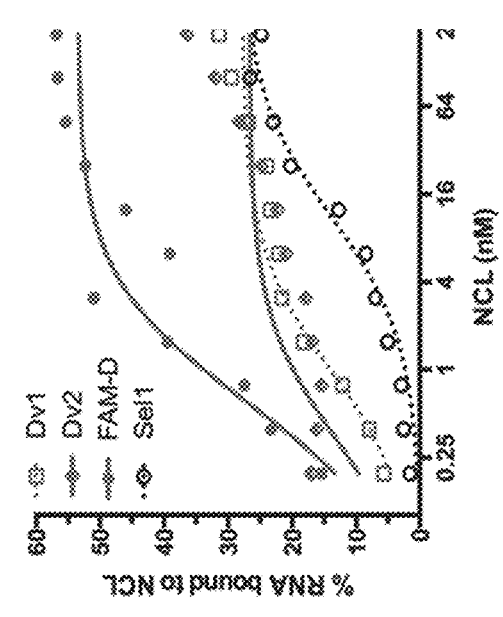
FIG. 5A NCL FAMILY B
FIG. 5B NCL FAMILY C
FIG. 5C NCL FAMILY D
FIG. 5D NCL FAMILY E

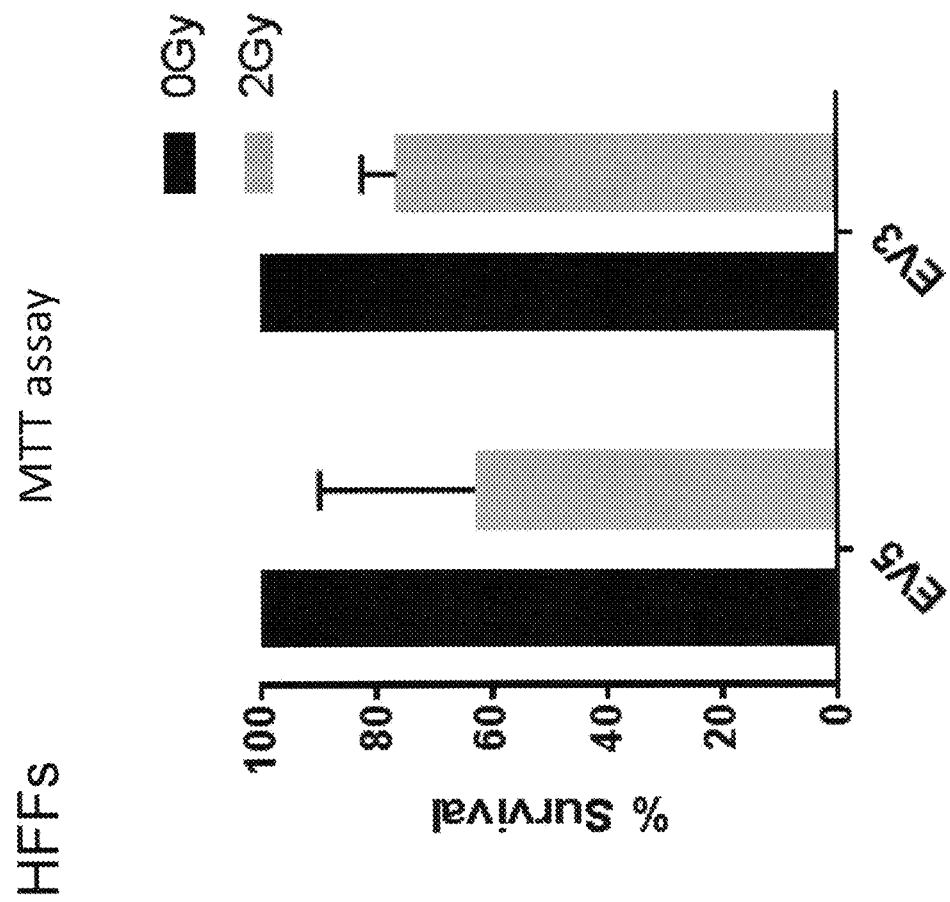

FIG. 11A
Family B (FAM-B)
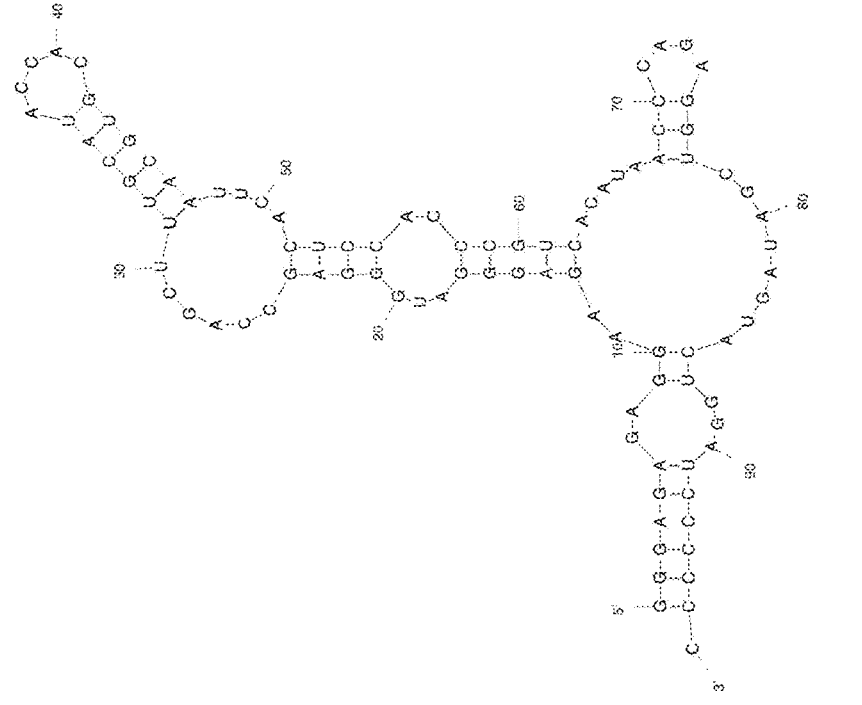
Structure 2
dG = -19.99
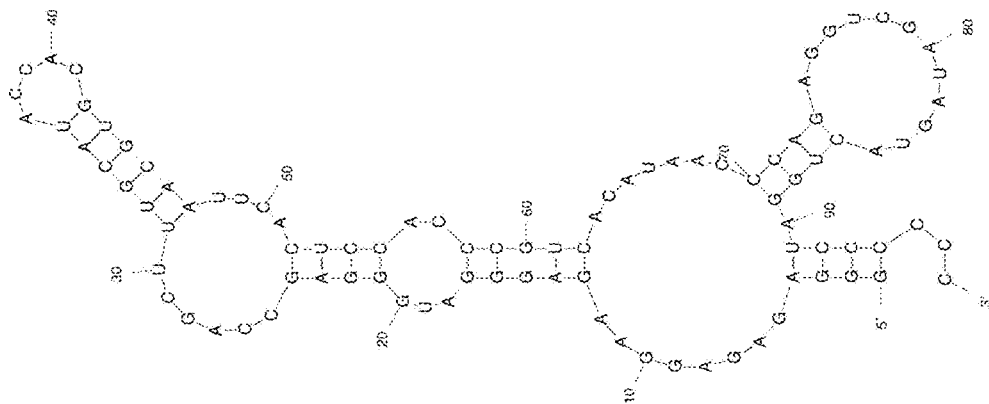
Structure 1
dG = -22.42

Family B (FAM-B)
Structure 3
dG = -22.15

FIG. 12A
Family C (FAM-C)
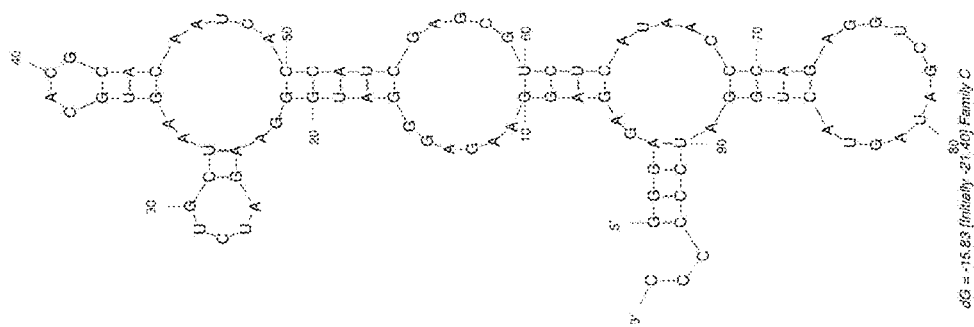
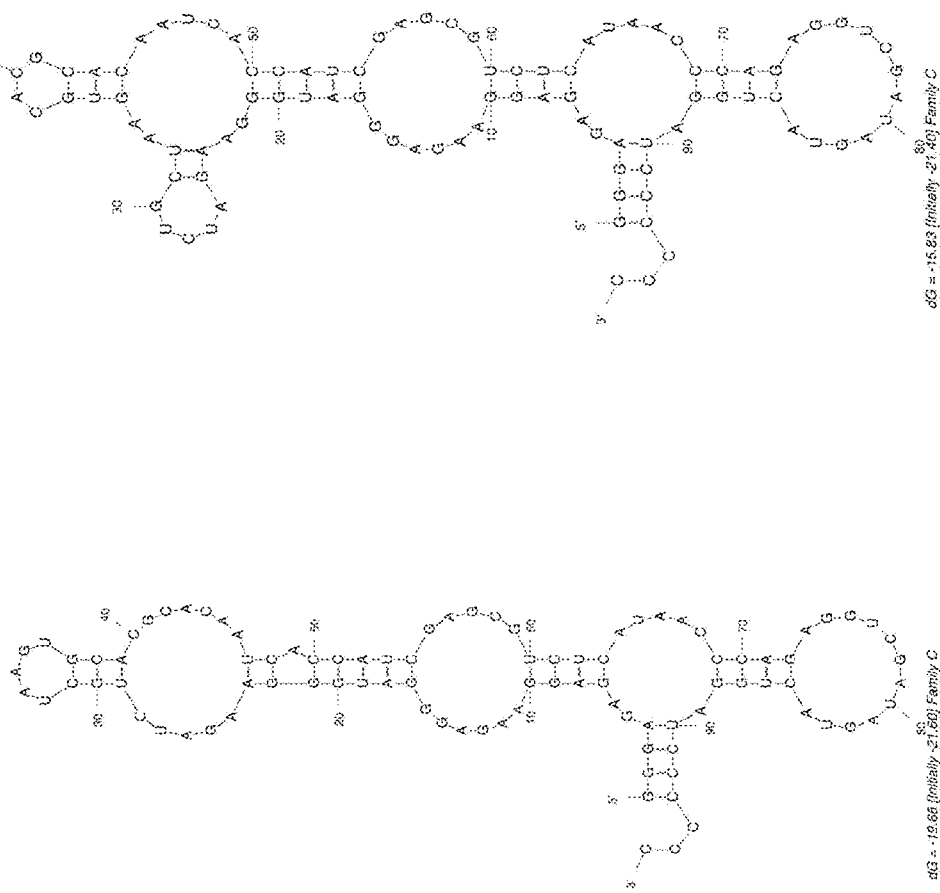

Family C (FAM-C)

FIG. 13A
Family D (FAM-D)
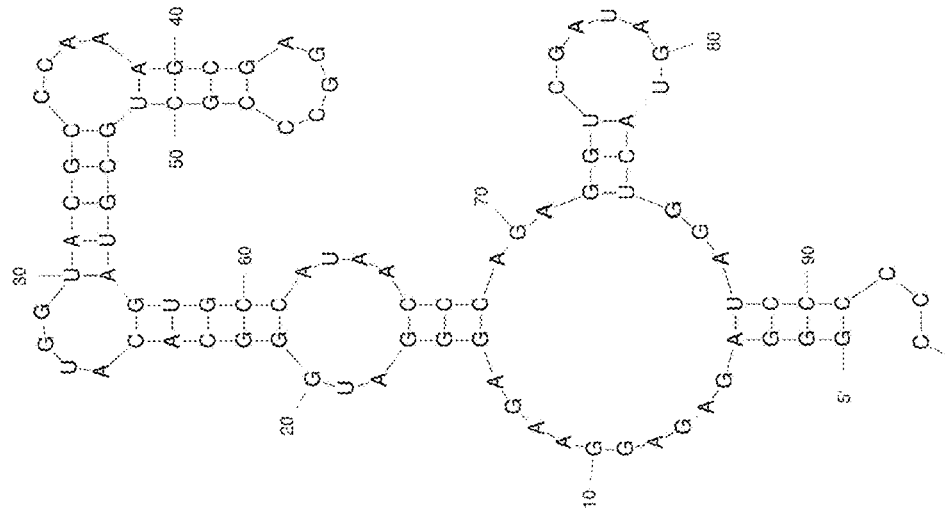
Structure 2
dG = -23.32
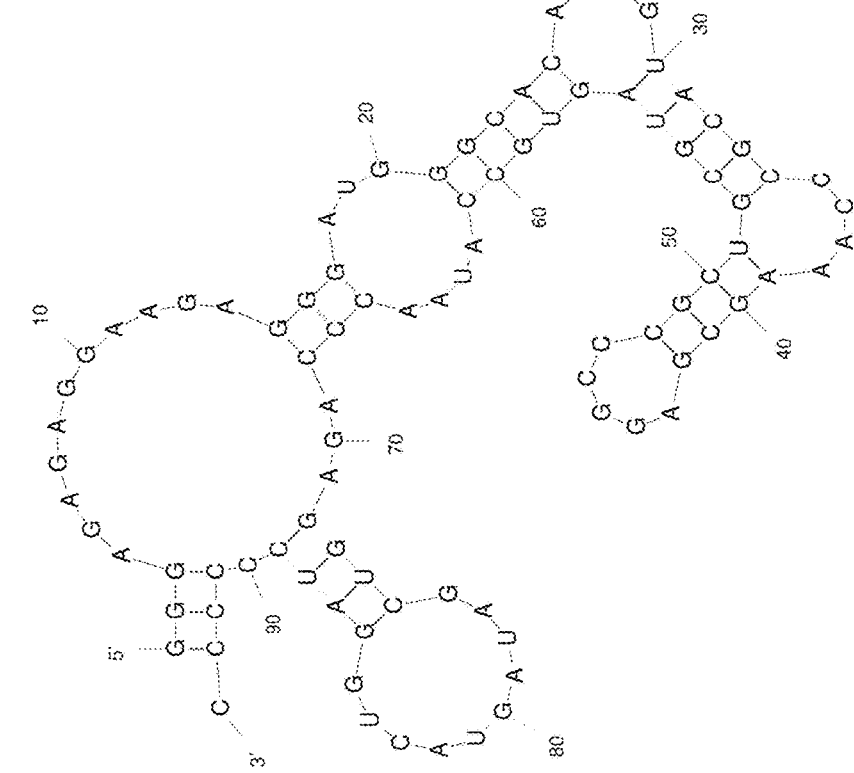
Structure 1
dG = -24.49

Family D (FAM-D)

Family D (FAM-D)

FIG. 14A
Family E (FAM-E)
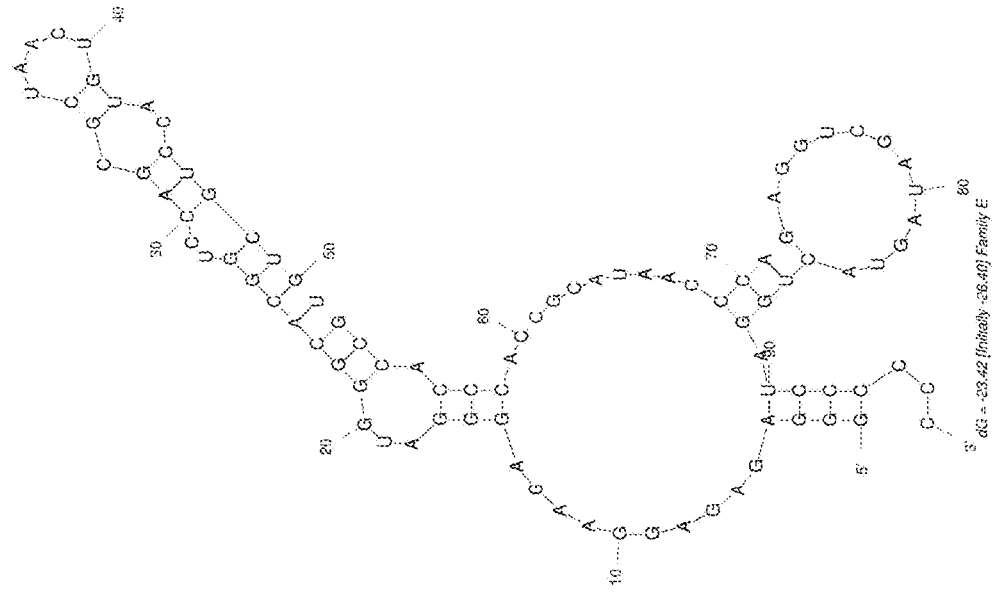
Structure 2
dG = -23.42
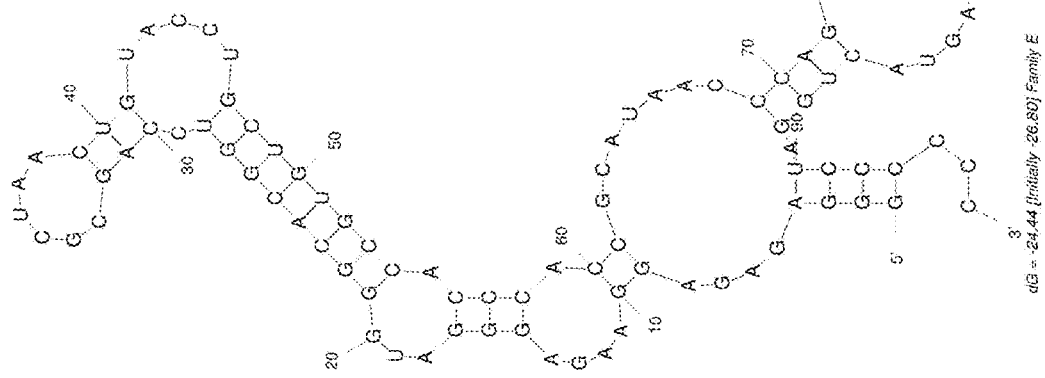
Structure 1
dG = -24.44

FIG. 14B
Family E (FAM-E)
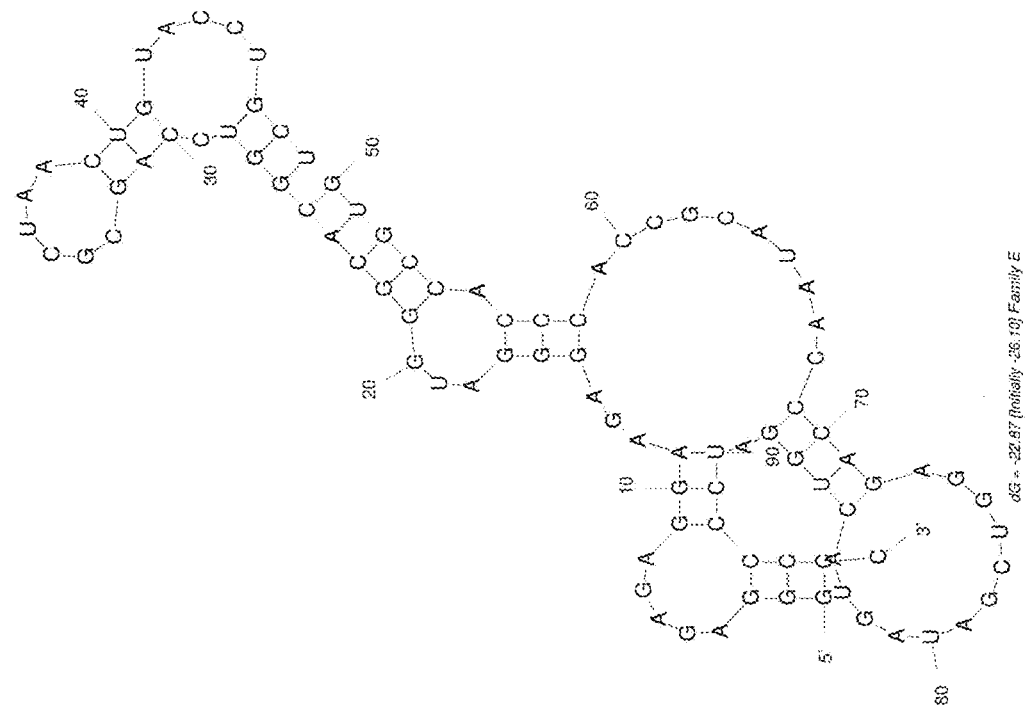
Structure 4
dG = -22.87
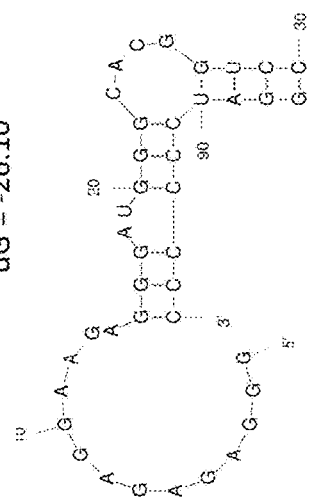
Structure 3
dG = -26.10

FIG. 14C
Family E (FAM-E)
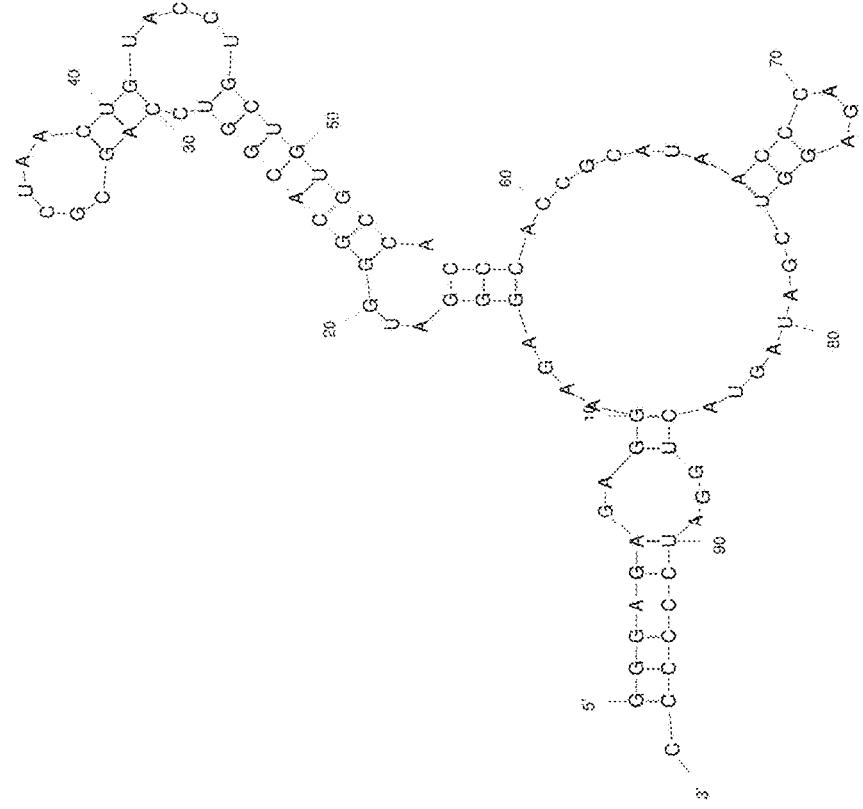
Structure 6
dG = -21.38
dG = -21.38 [Initially -25.90] Family E
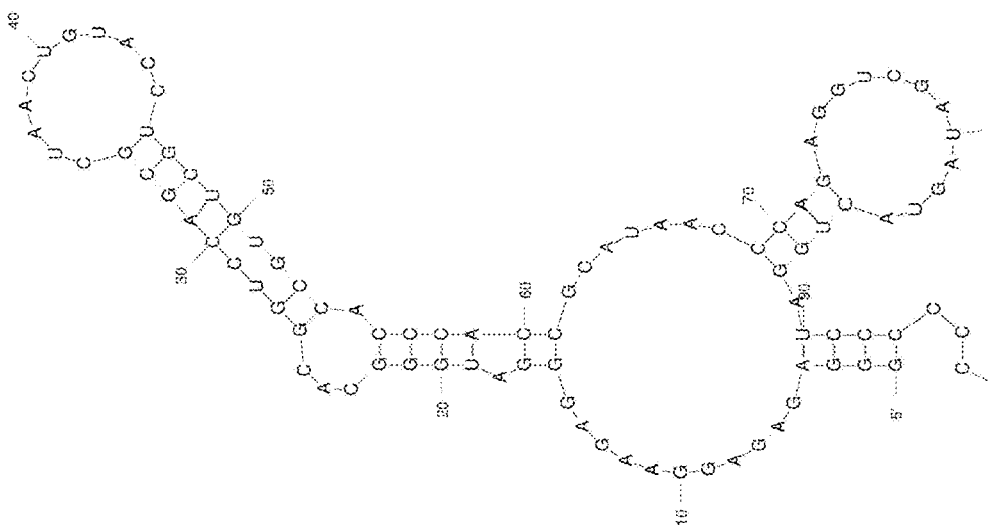
Structure 5
dG = -23.33
dG = -23.33 [Initially -26.00] Family E Family E (FAM-E)

Structure 7
dG = -22.62

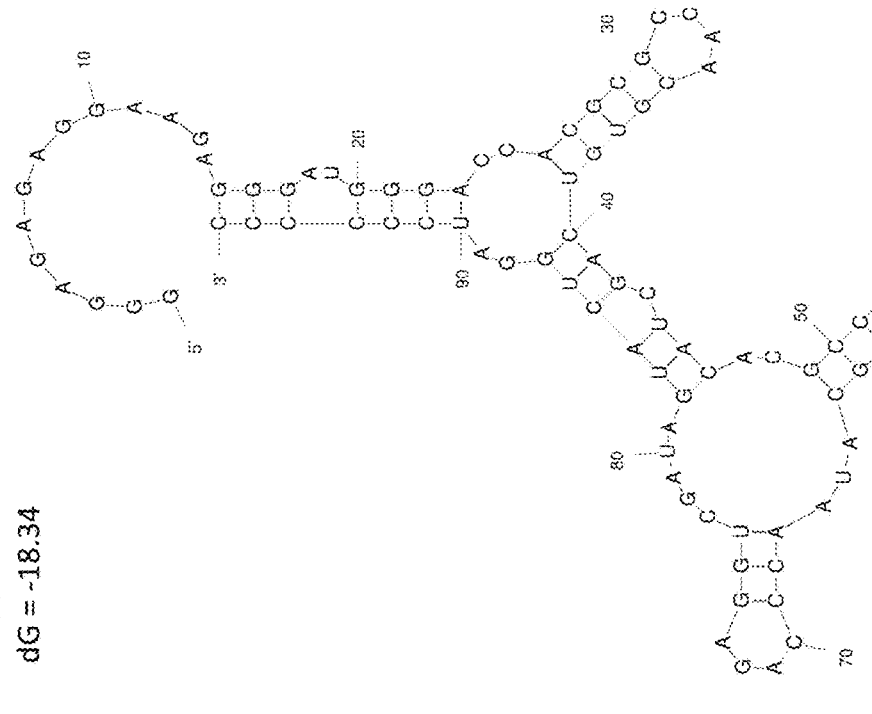
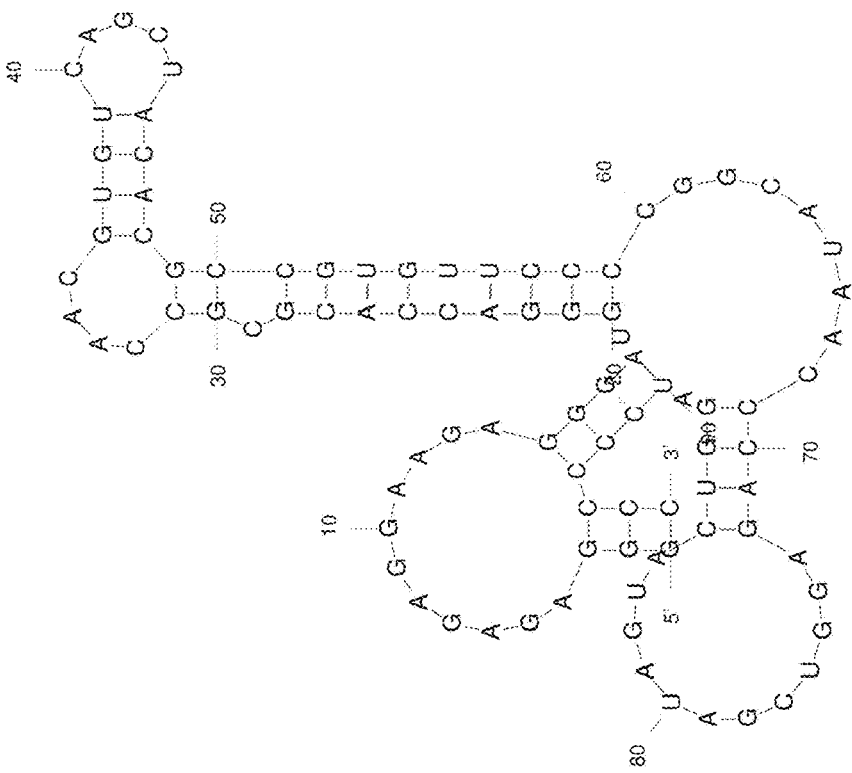
FIG. 15A
Family F (FAM-F)

Family F (FAM-F)

Structure 3
dG = -22.09

Ev3min2

Ev3min3

Ev3min4

Ev3min5

Ev3min6

Ev3min8

Ev3min10

FIG. 25
Ev3min11
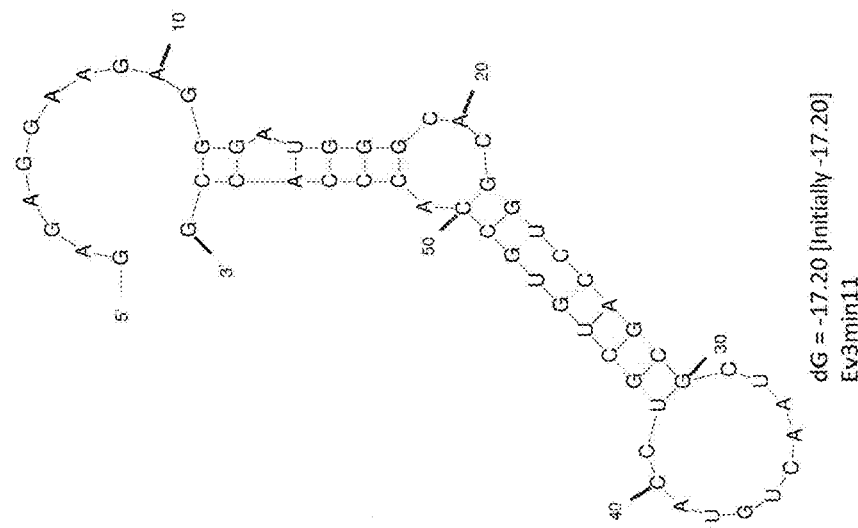
dG = -17.20 [Initially -17.20] Ev3min11
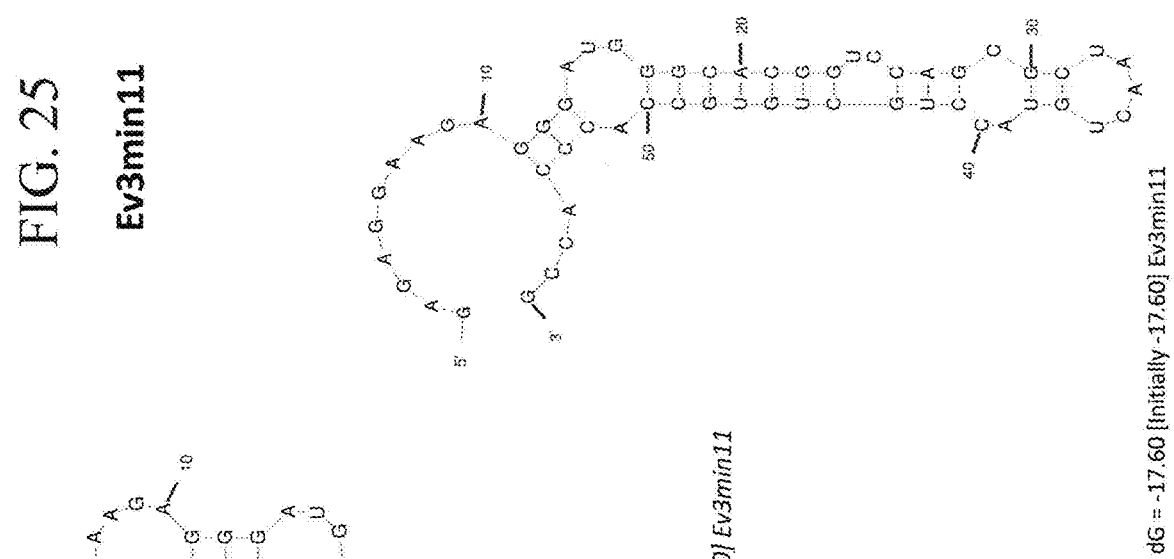
dG = -17.60 [Initially -17.60] Ev3min11
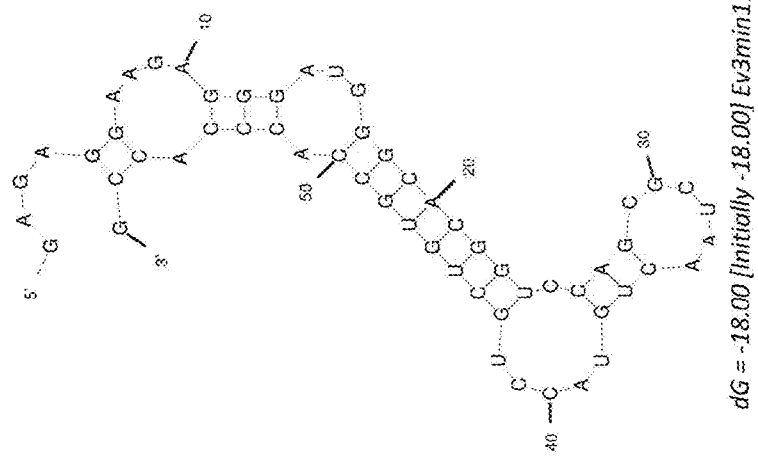
dG = -18.00 [Initially -18.00] Ev3min11

Ev3min13

Ev3min14

Ev3min15

Ev3min16

Ev3min17

Ev3min18

Ev3min20

Ev3min25

Ev3min24

SEQUENCE LISTING

```
<160> NUMBER OF SEQ ID NOS: 515

<210> SEQ ID NO 1
<211> LENGTH: 39
<212> TYPE: RNA
<213> ORGANISM: Artificial Sequence
<220> FEATURE:
<223> OTHER INFORMATION: Synthetic

<400> SEQUENCE: 1
ccaucuagau cuccguagau uccccggcu cuuucucgc                              39

<210> SEQ ID NO 2
<211> LENGTH: 41
<212> TYPE: RNA
<213> ORGANISM: Artificial Sequence
<220> FEATURE:
<223> OTHER INFORMATION: Synthetic

<400> SEQUENCE: 2
agccagcuuu gcauaccacg ugcaauucac uccacccguc a                          41

<210> SEQ ID NO 3
<211> LENGTH: 40
<212> TYPE: RNA
<213> ORGANISM: Artificial Sequence
<220> FEATURE:
<223> OTHER INFORMATION: Synthetic

<400> SEQUENCE: 3
aagaucugcu aagugcacgc acaaucacca ucgagcgucu                            40

<210> SEQ ID NO 4
<211> LENGTH: 38
<212> TYPE: RNA
<213> ORGANISM: Artificial Sequence
<220> FEATURE:
<223> OTHER INFORMATION: Synthetic

<400> SEQUENCE: 4
cacaugguac gcccaaagcg aggcccgcug cguaguge                              38
```

```
<210> SEQ ID NO 5
<211> LENGTH: 40
<212> TYPE: RNA
<213> ORGANISM: Artificial Sequence
<220> FEATURE:
<223> OTHER INFORMATION: Synthetic

<400> SEQUENCE: 5
cacgguccag cgcuaacugu accugcugug ccacccaccg                        40

<210> SEQ ID NO 6
<211> LENGTH: 40
<212> TYPE: RNA
<213> ORGANISM: Artificial Sequence
<220> FEATURE:
<223> OTHER INFORMATION: Synthetic

<400> SEQUENCE: 6
accacgcgcc aacgugucag cuacacgccg uguuccccgg                        40

<210> SEQ ID NO 7
<211> LENGTH: 95
<212> TYPE: RNA
<213> ORGANISM: Artificial Sequence
<220> FEATURE:
<223> OTHER INFORMATION: Synthetic

<400> SEQUENCE: 7
gggagagagg aagagggaug ggccaucuag aucuccguag auuccccgg cucuuucucg    60 ccauaaccca gaggucgaua guacuggauc ccccc                             95

<210> SEQ ID NO 8
<211> LENGTH: 97
<212> TYPE: RNA
<213> ORGANISM: Artificial Sequence
<220> FEATURE:
<223> OTHER INFORMATION: Synthetic

<400> SEQUENCE: 8
gggagagagg aagagggaug ggagccagcu uugcauacca cgugcaauuc acuccacccg   60
ucacauaacc cagaggucga uaguacugga ucccccc                            97

<210> SEQ ID NO 9
<211> LENGTH: 96
<212> TYPE: RNA
<213> ORGANISM: Artificial Sequence
<220> FEATURE:
<223> OTHER INFORMATION: Synthetic

<400> SEQUENCE: 9
gggagagagg aagagggaug ggaagaucug cuaagugcac gcacaaucac caucgagcgu   60
cucauaaccc agaggucgau aguacuggau cccccc                             96

<210> SEQ ID NO 10
<211> LENGTH: 94
<212> TYPE: RNA
<213> ORGANISM: Artificial Sequence
<220> FEATURE:
<223> OTHER INFORMATION: Synthetic

<400> SEQUENCE: 10
gggagagagg aagagggaug ggcacauggu acgcccaaag cgaggcccgc ugcguagugc   60
cauaacccag aggucgauag uacuggaucc cccc                              94
```

<210> SEQ ID NO 11
<211> LENGTH: 96
<212> TYPE: RNA
<213> ORGANISM: Artificial Sequence
<220> FEATURE:
<223> OTHER INFORMATION: Synthetic

<400> SEQUENCE: 11
gggagagagg aagagggaug ggcacggucc agcgcuaacu guaccgcug ugccacccac    60 cgcauaaccc agaggucgau aguacuggau cccccc                            96

<210> SEQ ID NO 12
<211> LENGTH: 96
<212> TYPE: RNA
<213> ORGANISM: Artificial Sequence
<220> FEATURE:
<223> OTHER INFORMATION: Synthetic

<400> SEQUENCE: 12
gggagagagg aagagggaug ggaccacgcg ccaacguguc agcuacacgc cguguccccc    60
ggcauaaccc agaggucgau aguacuggau cccccc                             96

<210> SEQ ID NO 13
<211> LENGTH: 39
<212> TYPE: RNA
<213> ORGANISM: Artificial Sequence
<220> FEATURE:
<223> OTHER INFORMATION: Synthetic

<400> SEQUENCE: 13
ccaucuagau cuccguagau uccccggcu cuuucucgc                            39

<210> SEQ ID NO 14
<211> LENGTH: 41
<212> TYPE: RNA
<213> ORGANISM: Artificial Sequence
<220> FEATURE:
<223> OTHER INFORMATION: Synthetic

<400> SEQUENCE: 14
agccagcuuu gcauaccacg ugcaauucac uccacccguc a                        41

<210> SEQ ID NO 15
<211> LENGTH: 40
<212> TYPE: RNA
<213> ORGANISM: Artificial Sequence
<220> FEATURE:
<223> OTHER INFORMATION: Synthetic

<400> SEQUENCE: 15
aagaucugcu aagugcacgc acaaucacca ucgagcgucu                          40

<210> SEQ ID NO 16
<211> LENGTH: 38
<212> TYPE: RNA
<213> ORGANISM: Artificial Sequence
<220> FEATURE:
<223> OTHER INFORMATION: Synthetic

<400> SEQUENCE: 16
cacaugguac gcccaaagcg aggcccgcug cguagugc                            38

<210> SEQ ID NO 17
<211> LENGTH: 40

```
<212> TYPE: RNA
<213> ORGANISM: Artificial Sequence
<220> FEATURE:
<223> OTHER INFORMATION: Synthetic

<400> SEQUENCE: 17
cacgguccag cgcuaacugu accugcugug ccacccaccg                           40

<210> SEQ ID NO 18
<211> LENGTH: 40
<212> TYPE: RNA
<213> ORGANISM: Artificial Sequence
<220> FEATURE:
<223> OTHER INFORMATION: Synthetic

<400> SEQUENCE: 18
accacgcgcc aacgugucag cuacacgccg uguuccccgg                           40

<210> SEQ ID NO 19
<211> LENGTH: 39
<212> TYPE: RNA
<213> ORGANISM: Artificial Sequence
<220> FEATURE:
<223> OTHER INFORMATION: Synthetic

<400> SEQUENCE: 19
aagauccucg cgcaucugcc gagcaaucac caucggacg                            39

<210> SEQ ID NO 20
<211> LENGTH: 40
<212> TYPE: RNA
<213> ORGANISM: Artificial Sequence
<220> FEATURE:
<223> OTHER INFORMATION: Synthetic

<400> SEQUENCE: 20
ccaaaugcca agccguagcc cggccaguag cccacacguc                           40

<210> SEQ ID NO 21
<211> LENGTH: 40
<212> TYPE: RNA
<213> ORGANISM: Artificial Sequence
<220> FEATURE:
<223> OTHER INFORMATION: Synthetic

<400> SEQUENCE: 21
ugccaagccg aggcccggcc accauccacu gauaugggc                            40

<210> SEQ ID NO 22
<211> LENGTH: 40
<212> TYPE: RNA
<213> ORGANISM: Artificial Sequence
<220> FEATURE:
<223> OTHER INFORMATION: Synthetic

<400> SEQUENCE: 22
aagauccuga cgcgacacag caaucaccau cgaaccagcu                           40

<210> SEQ ID NO 23
<211> LENGTH: 40
<212> TYPE: RNA
<213> ORGANISM: Artificial Sequence
<220> FEATURE:
<223> OTHER INFORMATION: Synthetic

<400> SEQUENCE: 23
```
aagaucugcg gcaacgcaca aucaccaucg auuccgaauu    40

<210> SEQ ID NO 24
<211> LENGTH: 39
<212> TYPE: RNA
<213> ORGANISM: Artificial Sequence
<220> FEATURE:
<223> OTHER INFORMATION: Synthetic

<400> SEQUENCE: 24
gagcucucga uuccuccgc gacacccauc caaaccuca    39

<210> SEQ ID NO 25
<211> LENGTH: 40
<212> TYPE: RNA
<213> ORGANISM: Artificial Sequence
<220> FEATURE:
<223> OTHER INFORMATION: Synthetic

<400> SEQUENCE: 25
cucuccgguc uaccauccgg accggcgaca aagucaacuu    40

<210> SEQ ID NO 26
<211> LENGTH: 41
<212> TYPE: RNA
<213> ORGANISM: Artificial Sequence
<220> FEATURE:
<223> OTHER INFORMATION: Synthetic

<400> SEQUENCE: 26
aagaucugcu augcacaauc accaucgggc gcuccgggga a    41

<210> SEQ ID NO 27
<211> LENGTH: 40
<212> TYPE: RNA
<213> ORGANISM: Artificial Sequence
<220> FEATURE:
<223> OTHER INFORMATION: Synthetic

<400> SEQUENCE: 27
uugacucugc ugcguaguuc gcaccaagau caaccacuuc    40

<210> SEQ ID NO 28
<211> LENGTH: 38
<212> TYPE: RNA
<213> ORGANISM: Artificial Sequence
<220> FEATURE:
<223> OTHER INFORMATION: Synthetic

<400> SEQUENCE: 28
uaccaagucg uggcccgacu acccagcacg augcgcaa    38

<210> SEQ ID NO 29
<211> LENGTH: 39
<212> TYPE: RNA
<213> ORGANISM: Artificial Sequence
<220> FEATURE:
<223> OTHER INFORMATION: Synthetic

<400> SEQUENCE: 29
cuauucgagu ucccacgaau cccccaucg agaaccuac    39

<210> SEQ ID NO 30
<211> LENGTH: 40
<212> TYPE: RNA
<213> ORGANISM: Artificial Sequence -continued

```
<220> FEATURE:
<223> OTHER INFORMATION: Synthetic

<400> SEQUENCE: 30
ugccaagccg aggcccggcc accguccccg cggcugauga                              40

<210> SEQ ID NO 31
<211> LENGTH: 40
<212> TYPE: RNA
<213> ORGANISM: Artificial Sequence
<220> FEATURE:
<223> OTHER INFORMATION: Synthetic

<400> SEQUENCE: 31
aaugaucucg ccaaugggcg acaaucacca ugucuucaca                              40

<210> SEQ ID NO 32
<211> LENGTH: 38
<212> TYPE: RNA
<213> ORGANISM: Artificial Sequence
<220> FEATURE:
<223> OTHER INFORMATION: Synthetic

<400> SEQUENCE: 32
ucagugcgcc aaguggaggc cccaccgcag cccaucaa                                38

<210> SEQ ID NO 33
<211> LENGTH: 40
<212> TYPE: RNA
<213> ORGANISM: Artificial Sequence
<220> FEATURE:
<223> OTHER INFORMATION: Synthetic

<400> SEQUENCE: 33
uguaugccag cuuugacgau aacugucgcg cgucaauuca                              40

<210> SEQ ID NO 34
<211> LENGTH: 40
<212> TYPE: RNA
<213> ORGANISM: Artificial Sequence
<220> FEATURE:
<223> OTHER INFORMATION: Synthetic

<400> SEQUENCE: 34
uacgccaaag uggagcccac ucguacccca ucaugagcug                              40

<210> SEQ ID NO 35
<211> LENGTH: 40
<212> TYPE: RNA
<213> ORGANISM: Artificial Sequence
<220> FEATURE:
<223> OTHER INFORMATION: Synthetic

<400> SEQUENCE: 35
ccgccagcuu ugggtacccu gaccaauuca cggccaucca                              40

<210> SEQ ID NO 36
<211> LENGTH: 40
<212> TYPE: RNA
<213> ORGANISM: Artificial Sequence
<220> FEATURE:
<223> OTHER INFORMATION: Synthetic

<400> SEQUENCE: 36
guaauugucu gagaccaccg gacaaucaac aagaaauccu                              40
```

```
<210> SEQ ID NO 37
<211> LENGTH: 40
<212> TYPE: RNA
<213> ORGANISM: Artificial Sequence
<220> FEATURE:
<223> OTHER INFORMATION: Synthetic

<400> SEQUENCE: 37
ucaggccaaa gugugauagc cacacccgca cccaucagga                         40

<210> SEQ ID NO 38
<211> LENGTH: 40
<212> TYPE: RNA
<213> ORGANISM: Artificial Sequence
<220> FEATURE:
<223> OTHER INFORMATION: Synthetic

<400> SEQUENCE: 38
ccgaccgccg accagggugc cacucguacc ccuguccgcc                         40

<210> SEQ ID NO 39
<211> LENGTH: 40
<212> TYPE: RNA
<213> ORGANISM: Artificial Sequence
<220> FEATURE:
<223> OTHER INFORMATION: Synthetic

<400> SEQUENCE: 39
ugccaagucg aagcccgacc acgccauccc uaacagugcc                         40

<210> SEQ ID NO 40
<211> LENGTH: 40
<212> TYPE: RNA
<213> ORGANISM: Artificial Sequence
<220> FEATURE:
<223> OTHER INFORMATION: Synthetic

<400> SEQUENCE: 40
acuugugcug agucgccaaa gugaggccca cucgccagca                         40

<210> SEQ ID NO 41
<211> LENGTH: 40
<212> TYPE: RNA
<213> ORGANISM: Artificial Sequence
<220> FEATURE:
<223> OTHER INFORMATION: Synthetic

<400> SEQUENCE: 41
ccgccagcuc cucugaggca caagagguuc acggugaucc                         40

<210> SEQ ID NO 42
<211> LENGTH: 40
<212> TYPE: RNA
<213> ORGANISM: Artificial Sequence
<220> FEATURE:
<223> OTHER INFORMATION: Synthetic

<400> SEQUENCE: 42
caccagguuc ugcuguccccc aagcgcugac ccauccuucc                        40

<210> SEQ ID NO 43
<211> LENGTH: 40
<212> TYPE: RNA
<213> ORGANISM: Artificial Sequence
<220> FEATURE:
<223> OTHER INFORMATION: Synthetic
```

<400> SEQUENCE: 43
aagauccggu aacuccccac cgcaaucacc gucgacuacu                                40

<210> SEQ ID NO 44
<211> LENGTH: 40
<212> TYPE: RNA
<213> ORGANISM: Artificial Sequence
<220> FEATURE:
<223> OTHER INFORMATION: Synthetic

<400> SEQUENCE: 44
ccaucuagau cuccguagau uccccccggc ucuuucucgc                                40

<210> SEQ ID NO 45
<211> LENGTH: 40
<212> TYPE: RNA
<213> ORGANISM: Artificial Sequence
<220> FEATURE:
<223> OTHER INFORMATION: Synthetic

<400> SEQUENCE: 45
ccaucugaac ccacagauuc ccccaucauc agccacagug                                40

<210> SEQ ID NO 46
<211> LENGTH: 40
<212> TYPE: RNA
<213> ORGANISM: Artificial Sequence
<220> FEATURE:
<223> OTHER INFORMATION: Synthetic

<400> SEQUENCE: 46
cacuaaguug guagccccaa cugccccgac acgaggaugu                                40

<210> SEQ ID NO 47
<211> LENGTH: 40
<212> TYPE: RNA
<213> ORGANISM: Artificial Sequence
<220> FEATURE:
<223> OTHER INFORMATION: Synthetic

<400> SEQUENCE: 47
uugugcuccg uggcuccccg gaccaaccgc uuccagcagu                                40

<210> SEQ ID NO 48
<211> LENGTH: 39
<212> TYPE: RNA
<213> ORGANISM: Artificial Sequence
<220> FEATURE:
<223> OTHER INFORMATION: Synthetic

<400> SEQUENCE: 48
caaucacgcg uaguacgucg cggaagaucc ccaugccga                                 39

<210> SEQ ID NO 49
<211> LENGTH: 39
<212> TYPE: RNA
<213> ORGANISM: Artificial Sequence
<220> FEATURE:
<223> OTHER INFORMATION: Synthetic

<400> SEQUENCE: 49
cacaugguac gcccaaaagc gaggcccgcu gcguagugc                                 39

<210> SEQ ID NO 50

```
<211> LENGTH: 40
<212> TYPE: RNA
<213> ORGANISM: Artificial Sequence
<220> FEATURE:
<223> OTHER INFORMATION: Synthetic

<400> SEQUENCE: 50 ugccaucgc gguucgaagu cgaagcccga caacccggca                    40

<210> SEQ ID NO 51
<211> LENGTH: 40
<212> TYPE: RNA
<213> ORGANISM: Artificial Sequence
<220> FEATURE:
<223> OTHER INFORMATION: Synthetic

<400> SEQUENCE: 51
guuauucaca ugccucccgu gaaucaacaa gaauuccuug                    40

<210> SEQ ID NO 52
<211> LENGTH: 40
<212> TYPE: RNA
<213> ORGANISM: Artificial Sequence
<220> FEATURE:
<223> OTHER INFORMATION: Synthetic

<400> SEQUENCE: 52
aaagaucuag acuguaaguc uccaaucgcc caguuaauuc                    40

<210> SEQ ID NO 53
<211> LENGTH: 39
<212> TYPE: RNA
<213> ORGANISM: Artificial Sequence
<220> FEATURE:
<223> OTHER INFORMATION: Synthetic

<400> SEQUENCE: 53
gcccaaucgc caguggaacg cgcugaagga ucugcaccc                     39

<210> SEQ ID NO 54
<211> LENGTH: 40
<212> TYPE: RNA
<213> ORGANISM: Artificial Sequence
<220> FEATURE:
<223> OTHER INFORMATION: Synthetic

<400> SEQUENCE: 54
ugcaacguaa aagagaguca ucucaggcua gucgucuacc                    40

<210> SEQ ID NO 55
<211> LENGTH: 40
<212> TYPE: RNA
<213> ORGANISM: Artificial Sequence
<220> FEATURE:
<223> OTHER INFORMATION: Synthetic

<400> SEQUENCE: 55
guguacgcca agucgaggcc cgaccguacc cauacgcgac                    40

<210> SEQ ID NO 56
<211> LENGTH: 40
<212> TYPE: RNA
<213> ORGANISM: Artificial Sequence
<220> FEATURE:
<223> OTHER INFORMATION: Synthetic

<400> SEQUENCE: 56
```
uuagcucuac uuccucuuc aguaagacua accgcuucuu          40

<210> SEQ ID NO 57
<211> LENGTH: 40
<212> TYPE: RNA
<213> ORGANISM: Artificial Sequence
<220> FEATURE:
<223> OTHER INFORMATION: Synthetic

<400> SEQUENCE: 57
uccaagcgga ggccccgcac ccacccucca acgggcacgg          40

<210> SEQ ID NO 58
<211> LENGTH: 40
<212> TYPE: RNA
<213> ORGANISM: Artificial Sequence
<220> FEATURE:
<223> OTHER INFORMATION: Synthetic

<400> SEQUENCE: 58
uaucgcucca caacgacucc cguggacuac ccaauuccaa          40

<210> SEQ ID NO 59
<211> LENGTH: 40
<212> TYPE: RNA
<213> ORGANISM: Artificial Sequence
<220> FEATURE:
<223> OTHER INFORMATION: Synthetic

<400> SEQUENCE: 59
gucgugccca agugaaggcc ucacgcacgc auccuaaccu          40

<210> SEQ ID NO 60
<211> LENGTH: 40
<212> TYPE: RNA
<213> ORGANISM: Artificial Sequence
<220> FEATURE:
<223> OTHER INFORMATION: Synthetic

<400> SEQUENCE: 60
aagaucugcg ccagcacaau caccaucguc cugagaaugg          40

<210> SEQ ID NO 61
<211> LENGTH: 40
<212> TYPE: RNA
<213> ORGANISM: Artificial Sequence
<220> FEATURE:
<223> OTHER INFORMATION: Synthetic

<400> SEQUENCE: 61
augccaagca guggcccugc cacccaccua ucacugucga          40

<210> SEQ ID NO 62
<211> LENGTH: 40
<212> TYPE: RNA
<213> ORGANISM: Artificial Sequence
<220> FEATURE:
<223> OTHER INFORMATION: Synthetic

<400> SEQUENCE: 62
aacagaccaa gcagcggccc ugcucugcca ucauacgccu          40

<210> SEQ ID NO 63
<211> LENGTH: 40
<212> TYPE: RNA

<213> ORGANISM: Artificial Sequence
<220> FEATURE:
<223> OTHER INFORMATION: Synthetic

<400> SEQUENCE: 63
gucauucgcu gacgaaucaa caugaauucc uaacugcuga        40

<210> SEQ ID NO 64
<211> LENGTH: 40
<212> TYPE: RNA
<213> ORGANISM: Artificial Sequence
<220> FEATURE:
<223> OTHER INFORMATION: Synthetic

<400> SEQUENCE: 64
acacgccaag cugguagccc cagccgugcc cauuacggcc        40

<210> SEQ ID NO 65
<211> LENGTH: 40
<212> TYPE: RNA
<213> ORGANISM: Artificial Sequence
<220> FEATURE:
<223> OTHER INFORMATION: Synthetic

<400> SEQUENCE: 65
uagccaagca gcagcccugc caacccaucc uacccgggcg        40

<210> SEQ ID NO 66
<211> LENGTH: 40
<212> TYPE: RNA
<213> ORGANISM: Artificial Sequence
<220> FEATURE:
<223> OTHER INFORMATION: Synthetic

<400> SEQUENCE: 66
gcccaaggcg aggcccgccg cuccauccag acgcugaggg        40

<210> SEQ ID NO 67
<211> LENGTH: 40
<212> TYPE: RNA
<213> ORGANISM: Artificial Sequence
<220> FEATURE:
<223> OTHER INFORMATION: Synthetic

<400> SEQUENCE: 67
aagaucucgu caugcuuuga cgucaaucac cauuguuccc        40

<210> SEQ ID NO 68
<211> LENGTH: 39
<212> TYPE: RNA
<213> ORGANISM: Artificial Sequence
<220> FEATURE:
<223> OTHER INFORMATION: Synthetic

<400> SEQUENCE: 68 auccccagg augagcacgu ugccauggac uggcuaucc        39

<210> SEQ ID NO 69
<211> LENGTH: 40
<212> TYPE: RNA
<213> ORGANISM: Artificial Sequence
<220> FEATURE:
<223> OTHER INFORMATION: Synthetic

<400> SEQUENCE: 69
cuguuacagu cucgcguaac cccccccaucg auguccucga        40

```
<210> SEQ ID NO 70
<211> LENGTH: 40
<212> TYPE: RNA
<213> ORGANISM: Artificial Sequence
<220> FEATURE:
<223> OTHER INFORMATION: Synthetic

<400> SEQUENCE: 70
agccagcuuu cggcaaaccg aauucacucc acccugcuca                          40

<210> SEQ ID NO 71
<211> LENGTH: 40
<212> TYPE: RNA
<213> ORGANISM: Artificial Sequence
<220> FEATURE:
<223> OTHER INFORMATION: Synthetic

<400> SEQUENCE: 71
cacgguauaa ccuccucaua uaccugcugu gccacccgcg                          40

<210> SEQ ID NO 72
<211> LENGTH: 40
<212> TYPE: RNA
<213> ORGANISM: Artificial Sequence
<220> FEATURE:
<223> OTHER INFORMATION: Synthetic

<400> SEQUENCE: 72
ccggaagauc ugcucgcacu agccggagcc caaucacggc                          40

<210> SEQ ID NO 73
<211> LENGTH: 40
<212> TYPE: RNA
<213> ORGANISM: Artificial Sequence
<220> FEATURE:
<223> OTHER INFORMATION: Synthetic

<400> SEQUENCE: 73
ccugccgaac ggcuaagucg cagcccgacc cgcggcaggg                          40

<210> SEQ ID NO 74
<211> LENGTH: 40
<212> TYPE: RNA
<213> ORGANISM: Artificial Sequence
<220> FEATURE:
<223> OTHER INFORMATION: Synthetic

<400> SEQUENCE: 74
cuccgacccg cggacgaagu caacuuccac agucccacac                          40

<210> SEQ ID NO 75
<211> LENGTH: 40
<212> TYPE: RNA
<213> ORGANISM: Artificial Sequence
<220> FEATURE:
<223> OTHER INFORMATION: Synthetic

<400> SEQUENCE: 75
acauuaggau cugcgugaug gggaucaccc gcuacauguc                          40

<210> SEQ ID NO 76
<211> LENGTH: 40
<212> TYPE: RNA
<213> ORGANISM: Artificial Sequence
<220> FEATURE:
```

<223> OTHER INFORMATION: Synthetic

<400> SEQUENCE: 76
ucuaagaugg ggaagaucuc cggagcaccg ggcaaucacc                              40

<210> SEQ ID NO 77
<211> LENGTH: 38
<212> TYPE: RNA
<213> ORGANISM: Artificial Sequence
<220> FEATURE:
<223> OTHER INFORMATION: Synthetic

<400> SEQUENCE: 77
cuauucgagu ucccacgaau cccccaucga gaaccuac                                38

<210> SEQ ID NO 78
<211> LENGTH: 40
<212> TYPE: RNA
<213> ORGANISM: Artificial Sequence
<220> FEATURE:
<223> OTHER INFORMATION: Synthetic

<400> SEQUENCE: 78
ugccaagccg aggcccggcc agcaucccuc acgagagagg                              40

<210> SEQ ID NO 79
<211> LENGTH: 40
<212> TYPE: RNA
<213> ORGANISM: Artificial Sequence
<220> FEATURE:
<223> OTHER INFORMATION: Synthetic

<400> SEQUENCE: 79
gccaagcacg uagcccgugc ccccacccgc cugugugcug                              40

<210> SEQ ID NO 80
<211> LENGTH: 40
<212> TYPE: RNA
<213> ORGANISM: Artificial Sequence
<220> FEATURE:
<223> OTHER INFORMATION: Synthetic

<400> SEQUENCE: 80
ugccaagcac gaagcccgug cccccaucca gagugugaga                              40

<210> SEQ ID NO 81
<211> LENGTH: 42
<212> TYPE: RNA
<213> ORGANISM: Artificial Sequence
<220> FEATURE:
<223> OTHER INFORMATION: Synthetic

<400> SEQUENCE: 81
agccagcuuu ugcauaccac gugcaauuca cuccacccgu ca                           42

<210> SEQ ID NO 82
<211> LENGTH: 40
<212> TYPE: RNA
<213> ORGANISM: Artificial Sequence
<220> FEATURE:
<223> OTHER INFORMATION: Synthetic

<400> SEQUENCE: 82
cuuuguaaac ccggcaaaca aaaucaacuu ccaucaucaa                              40

<210> SEQ ID NO 83
<211> LENGTH: 40
<212> TYPE: RNA
<213> ORGANISM: Artificial Sequence
<220> FEATURE:
<223> OTHER INFORMATION: Synthetic

<400> SEQUENCE: 83
ccauuguagc gaccacacaa uuccccaucg gacagcaugg          40

<210> SEQ ID NO 84
<211> LENGTH: 40
<212> TYPE: RNA
<213> ORGANISM: Artificial Sequence
<220> FEATURE:
<223> OTHER INFORMATION: Synthetic

<400> SEQUENCE: 84
cucucgccgu ucccaggcac gacaaaauca acuucccgcu          40

<210> SEQ ID NO 85
<211> LENGTH: 40
<212> TYPE: RNA
<213> ORGANISM: Artificial Sequence
<220> FEATURE:
<223> OTHER INFORMATION: Synthetic

<400> SEQUENCE: 85
aagccaagcc gcggcccggc cuucccaugu gcuacuagag          40

<210> SEQ ID NO 86
<211> LENGTH: 41
<212> TYPE: RNA
<213> ORGANISM: Artificial Sequence
<220> FEATURE:
<223> OTHER INFORMATION: Synthetic

<400> SEQUENCE: 86
ccaaaugcca aagccguagc ccggccagua gcccacacgu c          41

<210> SEQ ID NO 87
<211> LENGTH: 40
<212> TYPE: RNA
<213> ORGANISM: Artificial Sequence
<220> FEATURE:
<223> OTHER INFORMATION: Synthetic

<400> SEQUENCE: 87
ccauuacgcg acguaauucc cccaucguuu ccucguuaag          40

<210> SEQ ID NO 88
<211> LENGTH: 38
<212> TYPE: RNA
<213> ORGANISM: Artificial Sequence
<220> FEATURE:
<223> OTHER INFORMATION: Synthetic

<400> SEQUENCE: 88
ccaucuagau cuccguagau uccccggcuc uuucucgc          38

<210> SEQ ID NO 89
<211> LENGTH: 40
<212> TYPE: RNA
<213> ORGANISM: Artificial Sequence
<220> FEATURE:
<223> OTHER INFORMATION: Synthetic

<400> SEQUENCE: 89
acugucugca uacacgguau gcccaacgcc auccaaaccg                    40

<210> SEQ ID NO 90
<211> LENGTH: 40
<212> TYPE: RNA
<213> ORGANISM: Artificial Sequence
<220> FEATURE:
<223> OTHER INFORMATION: Synthetic

<400> SEQUENCE: 90
accugcggcu auugccagcg ccauaagacc cuccacagua                    40

<210> SEQ ID NO 91
<211> LENGTH: 39
<212> TYPE: RNA
<213> ORGANISM: Artificial Sequence
<220> FEATURE:
<223> OTHER INFORMATION: Synthetic

<400> SEQUENCE: 91
ccaucuagau cuccguagau uccccggcu cuuucucgc                      39

<210> SEQ ID NO 92
<211> LENGTH: 39
<212> TYPE: RNA
<213> ORGANISM: Artificial Sequence
<220> FEATURE:
<223> OTHER INFORMATION: Synthetic

<400> SEQUENCE: 92
ccaucuagau cuccguagau uccccggcu cuuccucgc                      39

<210> SEQ ID NO 93
<211> LENGTH: 39
<212> TYPE: RNA
<213> ORGANISM: Artificial Sequence
<220> FEATURE:
<223> OTHER INFORMATION: Synthetic

<400> SEQUENCE: 93
ccaucuagau cuccguagau uccccagcu cuuucucgc                      39

<210> SEQ ID NO 94
<211> LENGTH: 41
<212> TYPE: RNA
<213> ORGANISM: Artificial Sequence
<220> FEATURE:
<223> OTHER INFORMATION: Synthetic

<400> SEQUENCE: 94
agccagcuuu gcauaccacg ugcaauucac uccacccguc a                  41

<210> SEQ ID NO 95
<211> LENGTH: 41
<212> TYPE: RNA
<213> ORGANISM: Artificial Sequence
<220> FEATURE:
<223> OTHER INFORMATION: Synthetic

<400> SEQUENCE: 95
agccagcuuu gcauaccacg ugcaauucac uccacccguc g                  41

<210> SEQ ID NO 96
<211> LENGTH: 40

<212> TYPE: RNA
<213> ORGANISM: Artificial Sequence
<220> FEATURE:
<223> OTHER INFORMATION: Synthetic

<400> SEQUENCE: 96
aagaucugcu aagugcacgc acaaucacca ucgagcgucu                          40

<210> SEQ ID NO 97
<211> LENGTH: 40
<212> TYPE: RNA
<213> ORGANISM: Artificial Sequence
<220> FEATURE:
<223> OTHER INFORMATION: Synthetic

<400> SEQUENCE: 97
aagaucugcu aagugcacgc acaaucacca ucgagcgucc                          40

<210> SEQ ID NO 98
<211> LENGTH: 40
<212> TYPE: RNA
<213> ORGANISM: Artificial Sequence
<220> FEATURE:
<223> OTHER INFORMATION: Synthetic

<400> SEQUENCE: 98
aagaucugcu aagugcacgc acaaucacca ucgagcgccu                          40

<210> SEQ ID NO 99
<211> LENGTH: 39
<212> TYPE: RNA
<213> ORGANISM: Artificial Sequence
<220> FEATURE:
<223> OTHER INFORMATION: Synthetic

<400> SEQUENCE: 99
aagaucugcu aagugcacgc acaaucacca ucgagcguc                           39

<210> SEQ ID NO 100
<211> LENGTH: 40
<212> TYPE: RNA
<213> ORGANISM: Artificial Sequence
<220> FEATURE:
<223> OTHER INFORMATION: Synthetic

<400> SEQUENCE: 100
aagaucugcu aagugcacgc acaaucacca ucgagcgacu                          40

<210> SEQ ID NO 101
<211> LENGTH: 38
<212> TYPE: RNA
<213> ORGANISM: Artificial Sequence
<220> FEATURE:
<223> OTHER INFORMATION: Synthetic

<400> SEQUENCE: 101
cacaugguac gcccaaagcg aggcccgcug cguagugc                            38

<210> SEQ ID NO 102
<211> LENGTH: 38
<212> TYPE: RNA
<213> ORGANISM: Artificial Sequence
<220> FEATURE:
<223> OTHER INFORMATION: Synthetic

<400> SEQUENCE: 102

```
cacacgguac gcccaaagcg aggcccgcug cguagugc                                38
```

<210> SEQ ID NO 103
<211> LENGTH: 40
<212> TYPE: RNA
<213> ORGANISM: Artificial Sequence
<220> FEATURE:
<223> OTHER INFORMATION: Synthetic

<400> SEQUENCE: 103

```
cacgguccag cgcuaacugu accugcugug ccacccaccg                              40
```

<210> SEQ ID NO 104
<211> LENGTH: 40
<212> TYPE: RNA
<213> ORGANISM: Artificial Sequence
<220> FEATURE:
<223> OTHER INFORMATION: Synthetic

<400> SEQUENCE: 104

```
cacgguccag cgcuaacugu accugcugug ccacccacca                              40
```

<210> SEQ ID NO 105
<211> LENGTH: 40
<212> TYPE: RNA
<213> ORGANISM: Artificial Sequence
<220> FEATURE:
<223> OTHER INFORMATION: Synthetic

<400> SEQUENCE: 105

```
cacgguccag cgcuaacugu accugcugug ccacccacug                              40
```

<210> SEQ ID NO 106
<211> LENGTH: 40
<212> TYPE: RNA
<213> ORGANISM: Artificial Sequence
<220> FEATURE:
<223> OTHER INFORMATION: Synthetic

<400> SEQUENCE: 106

```
cacgguccag cgcuaacugu accugcugug ccacccaccu                              40
```

<210> SEQ ID NO 107
<211> LENGTH: 40
<212> TYPE: RNA
<213> ORGANISM: Artificial Sequence
<220> FEATURE:
<223> OTHER INFORMATION: Synthetic

<400> SEQUENCE: 107

```
cacgguccag cgcuaacugu accugcugug ccacccgccg                              40
```

<210> SEQ ID NO 108
<211> LENGTH: 40
<212> TYPE: RNA
<213> ORGANISM: Artificial Sequence
<220> FEATURE:
<223> OTHER INFORMATION: Synthetic

<400> SEQUENCE: 108

```
accacgcgcc aacgugucag cuacacgccg uguucccgg                               40
```

<210> SEQ ID NO 109
<211> LENGTH: 40
<212> TYPE: RNA
<213> ORGANISM: Artificial Sequence

```
<220> FEATURE:
<223> OTHER INFORMATION: Synthetic

<400> SEQUENCE: 109
accacgcgcc aacgugucag cuacacgccg uguucccga                                40

<210> SEQ ID NO 110
<211> LENGTH: 39
<212> TYPE: RNA
<213> ORGANISM: Artificial Sequence
<220> FEATURE:
<223> OTHER INFORMATION: Synthetic

<400> SEQUENCE: 110
accacgcgcc aacgugucag cuacacgccg uguccccg                                 39

<210> SEQ ID NO 111
<211> LENGTH: 39
<212> TYPE: RNA
<213> ORGANISM: Artificial Sequence
<220> FEATURE:
<223> OTHER INFORMATION: Synthetic

<400> SEQUENCE: 111
ccacgcgcca acgugucagc uacacgccgu guuccccgg                                39

<210> SEQ ID NO 112
<211> LENGTH: 39
<212> TYPE: RNA
<213> ORGANISM: Artificial Sequence
<220> FEATURE:
<223> OTHER INFORMATION: Synthetic

<400> SEQUENCE: 112
aagauccucg cgcaucugcc gagcaaucac caucggacg                                39

<210> SEQ ID NO 113
<211> LENGTH: 39
<212> TYPE: RNA
<213> ORGANISM: Artificial Sequence
<220> FEATURE:
<223> OTHER INFORMATION: Synthetic

<400> SEQUENCE: 113
aagauccucg cgcaucugcc gagcaaucac caucggacc                                39

<210> SEQ ID NO 114
<211> LENGTH: 39
<212> TYPE: RNA
<213> ORGANISM: Artificial Sequence
<220> FEATURE:
<223> OTHER INFORMATION: Synthetic

<400> SEQUENCE: 114
aagauccucg cgcaucugcc gagcaaucac caucggaca                                39

<210> SEQ ID NO 115
<211> LENGTH: 39
<212> TYPE: RNA
<213> ORGANISM: Artificial Sequence
<220> FEATURE:
<223> OTHER INFORMATION: Synthetic

<400> SEQUENCE: 115
aagauccucg cgcaucugcc gagcaaucac caucggacu                                39
```

<210> SEQ ID NO 116
<211> LENGTH: 40
<212> TYPE: RNA
<213> ORGANISM: Artificial Sequence
<220> FEATURE:
<223> OTHER INFORMATION: Synthetic

<400> SEQUENCE: 116
aaagauccuc gcgcaucugc cgagcaauca ccaucggacg        40

<210> SEQ ID NO 117
<211> LENGTH: 39
<212> TYPE: RNA
<213> ORGANISM: Artificial Sequence
<220> FEATURE:
<223> OTHER INFORMATION: Synthetic

<400> SEQUENCE: 117
aagauccucg cgcaccugcc gagcaaucac caucggacg         39

<210> SEQ ID NO 118
<211> LENGTH: 40
<212> TYPE: RNA
<213> ORGANISM: Artificial Sequence
<220> FEATURE:
<223> OTHER INFORMATION: Synthetic

<400> SEQUENCE: 118
ccaaaugcca agccguagcc cggccaguag cccacacguc        40

<210> SEQ ID NO 119
<211> LENGTH: 41
<212> TYPE: RNA
<213> ORGANISM: Artificial Sequence
<220> FEATURE:
<223> OTHER INFORMATION: Synthetic

<400> SEQUENCE: 119
ccaaaaugcc aagccguagc ccggccagua gcccacacgu c      41

<210> SEQ ID NO 120
<211> LENGTH: 40
<212> TYPE: RNA
<213> ORGANISM: Artificial Sequence
<220> FEATURE:
<223> OTHER INFORMATION: Synthetic

<400> SEQUENCE: 120
ccaaaugcca agccguagcc cggccaguag cccacacgac        40

<210> SEQ ID NO 121
<211> LENGTH: 40
<212> TYPE: RNA
<213> ORGANISM: Artificial Sequence
<220> FEATURE:
<223> OTHER INFORMATION: Synthetic

<400> SEQUENCE: 121
ccaaaugcca agccguagcc cggccaguag cccacacgua        40

<210> SEQ ID NO 122
<211> LENGTH: 40
<212> TYPE: RNA
<213> ORGANISM: Artificial Sequence
<220> FEATURE:
<223> OTHER INFORMATION: Synthetic

```
<400> SEQUENCE: 122
ugccaagccg aggcccggcc accauccacu gauagugggc                              40

<210> SEQ ID NO 123
<211> LENGTH: 40
<212> TYPE: RNA
<213> ORGANISM: Artificial Sequence
<220> FEATURE:
<223> OTHER INFORMATION: Synthetic

<400> SEQUENCE: 123
ugccaagccg aggcccggcc accauccacu gauaguggga                              40

<210> SEQ ID NO 124
<211> LENGTH: 39
<212> TYPE: RNA
<213> ORGANISM: Artificial Sequence
<220> FEATURE:
<223> OTHER INFORMATION: Synthetic

<400> SEQUENCE: 124
ugccaagccg aggcccggcc accauccacu gauaguggg                               39

<210> SEQ ID NO 125
<211> LENGTH: 40
<212> TYPE: RNA
<213> ORGANISM: Artificial Sequence
<220> FEATURE:
<223> OTHER INFORMATION: Synthetic

<400> SEQUENCE: 125
ugccaagccg aggcccggcc accauccacu gauagugggu                              40

<210> SEQ ID NO 126
<211> LENGTH: 40
<212> TYPE: RNA
<213> ORGANISM: Artificial Sequence
<220> FEATURE:
<223> OTHER INFORMATION: Synthetic

<400> SEQUENCE: 126
aagauccuga cgcgacacag caaucaccau cgaaccagcu                              40

<210> SEQ ID NO 127
<211> LENGTH: 40
<212> TYPE: RNA
<213> ORGANISM: Artificial Sequence
<220> FEATURE:
<223> OTHER INFORMATION: Synthetic

<400> SEQUENCE: 127
aagauccuga cgcgacacag caaucaccau cgaaccagcc                              40

<210> SEQ ID NO 128
<211> LENGTH: 40
<212> TYPE: RNA
<213> ORGANISM: Artificial Sequence
<220> FEATURE:
<223> OTHER INFORMATION: Synthetic

<400> SEQUENCE: 128
aagaucugcg gcaacgcaca aucaccaucg auuccgaauu                              40

<210> SEQ ID NO 129
```

```
<211> LENGTH: 40
<212> TYPE: RNA
<213> ORGANISM: Artificial Sequence
<220> FEATURE:
<223> OTHER INFORMATION: Synthetic

<400> SEQUENCE: 129
aagaucugcg gcaacgcaca aucaccaucg auuccgaaug                              40

<210> SEQ ID NO 130
<211> LENGTH: 40
<212> TYPE: RNA
<213> ORGANISM: Artificial Sequence
<220> FEATURE:
<223> OTHER INFORMATION: Synthetic

<400> SEQUENCE: 130
aagaucugcg gcaacgcaca aucaccaucg auuccgaauc                              40

<210> SEQ ID NO 131
<211> LENGTH: 40
<212> TYPE: RNA
<213> ORGANISM: Artificial Sequence
<220> FEATURE:
<223> OTHER INFORMATION: Synthetic

<400> SEQUENCE: 131
aagaucugcg gcaacgcaca aucaccaucg auuccgaacu                              40

<210> SEQ ID NO 132
<211> LENGTH: 40
<212> TYPE: RNA
<213> ORGANISM: Artificial Sequence
<220> FEATURE:
<223> OTHER INFORMATION: Synthetic

<400> SEQUENCE: 132
aagaucugcg gcaacguaca aucaccaucg auuccgaauu                              40

<210> SEQ ID NO 133
<211> LENGTH: 39
<212> TYPE: RNA
<213> ORGANISM: Artificial Sequence
<220> FEATURE:
<223> OTHER INFORMATION: Synthetic

<400> SEQUENCE: 133
gagcucucga uuccuccgc gacacccauc caaaccuca                                39

<210> SEQ ID NO 134
<211> LENGTH: 38
<212> TYPE: RNA
<213> ORGANISM: Artificial Sequence
<220> FEATURE:
<223> OTHER INFORMATION: Synthetic

<400> SEQUENCE: 134
agcucucgau uccuccgcg acacccaucc aaaccuca                                 38

<210> SEQ ID NO 135
<211> LENGTH: 39
<212> TYPE: RNA
<213> ORGANISM: Artificial Sequence
<220> FEATURE:
<223> OTHER INFORMATION: Synthetic

<400> SEQUENCE: 135
```
gagcucucga uuuccuccgc gacacccauc caaaccucg        39

<210> SEQ ID NO 136
<211> LENGTH: 40
<212> TYPE: RNA
<213> ORGANISM: Artificial Sequence
<220> FEATURE:
<223> OTHER INFORMATION: Synthetic

<400> SEQUENCE: 136
cucuccgguc uaccauccgg accggcgaca aagucaacuu        40

<210> SEQ ID NO 137
<211> LENGTH: 40
<212> TYPE: RNA
<213> ORGANISM: Artificial Sequence
<220> FEATURE:
<223> OTHER INFORMATION: Synthetic

<400> SEQUENCE: 137
cucuccgguc uaccacccgg accggcgaca aagucaacuu        40

<210> SEQ ID NO 138
<211> LENGTH: 41
<212> TYPE: RNA
<213> ORGANISM: Artificial Sequence
<220> FEATURE:
<223> OTHER INFORMATION: Synthetic

<400> SEQUENCE: 138
aagaucugcu augcacaauc accaucgggc gcuccgggga a        41

<210> SEQ ID NO 139
<211> LENGTH: 40
<212> TYPE: RNA
<213> ORGANISM: Artificial Sequence
<220> FEATURE:
<223> OTHER INFORMATION: Synthetic

<400> SEQUENCE: 139
aagaucugcu augcacaauc accaucgggc gcuccgggaa        40

<210> SEQ ID NO 140
<211> LENGTH: 41
<212> TYPE: RNA
<213> ORGANISM: Artificial Sequence
<220> FEATURE:
<223> OTHER INFORMATION: Synthetic

<400> SEQUENCE: 140
aagaucugcu acgcacaauc accaucgggc gcuccgggga a        41

<210> SEQ ID NO 141
<211> LENGTH: 40
<212> TYPE: RNA
<213> ORGANISM: Artificial Sequence
<220> FEATURE:
<223> OTHER INFORMATION: Synthetic

<400> SEQUENCE: 141
uugacucugc ugcguaguuc gcaccaagau caaccacuuc        40

<210> SEQ ID NO 142
<211> LENGTH: 41
<212> TYPE: RNA

<213> ORGANISM: Artificial Sequence
<220> FEATURE:
<223> OTHER INFORMATION: Synthetic

<400> SEQUENCE: 142
uugacucugc ugcguaguuc gcaccaagau caaccacuuc c                41

<210> SEQ ID NO 143
<211> LENGTH: 40
<212> TYPE: RNA
<213> ORGANISM: Artificial Sequence
<220> FEATURE:
<223> OTHER INFORMATION: Synthetic

<400> SEQUENCE: 143
uugacucugc ugcguagcuc gcaccaagau caaccacuuc                 40

<210> SEQ ID NO 144
<211> LENGTH: 40
<212> TYPE: RNA
<213> ORGANISM: Artificial Sequence
<220> FEATURE:
<223> OTHER INFORMATION: Synthetic

<400> SEQUENCE: 144
uugacucugc ugcgcaguuc gcaccaagau caaccacuuc                 40

<210> SEQ ID NO 145
<211> LENGTH: 40
<212> TYPE: RNA
<213> ORGANISM: Artificial Sequence
<220> FEATURE:
<223> OTHER INFORMATION: Synthetic

<400> SEQUENCE: 145
uugacucugc ugcguagucc gcaccaagau caaccacuuc                 40

<210> SEQ ID NO 146
<211> LENGTH: 38
<212> TYPE: RNA
<213> ORGANISM: Artificial Sequence
<220> FEATURE:
<223> OTHER INFORMATION: Synthetic

<400> SEQUENCE: 146
uaccaagucg uggcccgacu acccagcacg augcgcaa                   38

<210> SEQ ID NO 147
<211> LENGTH: 39
<212> TYPE: RNA
<213> ORGANISM: Artificial Sequence
<220> FEATURE:
<223> OTHER INFORMATION: Synthetic

<400> SEQUENCE: 147
uaccaaaguc guggcccgac uacccagcac gaugcgcaa                  39

<210> SEQ ID NO 148
<211> LENGTH: 38
<212> TYPE: RNA
<213> ORGANISM: Artificial Sequence
<220> FEATURE:
<223> OTHER INFORMATION: Synthetic

<400> SEQUENCE: 148
uaccaagucg uggcccgacu acccagcacg gugcgcaa                   38

<210> SEQ ID NO 149
<211> LENGTH: 38
<212> TYPE: RNA
<213> ORGANISM: Artificial Sequence
<220> FEATURE:
<223> OTHER INFORMATION: Synthetic

<400> SEQUENCE: 149
uaccaagucg uggcccgacu acccagcacg augcgcag            38

<210> SEQ ID NO 150
<211> LENGTH: 38
<212> TYPE: RNA
<213> ORGANISM: Artificial Sequence
<220> FEATURE:
<223> OTHER INFORMATION: Synthetic

<400> SEQUENCE: 150
uaccaagucg uggcccgacu acccagcaca augcgcaa            38

<210> SEQ ID NO 151
<211> LENGTH: 38
<212> TYPE: RNA
<213> ORGANISM: Artificial Sequence
<220> FEATURE:
<223> OTHER INFORMATION: Synthetic

<400> SEQUENCE: 151
uaccaagucg cggcccgacu acccagcacg augcgcaa            38

<210> SEQ ID NO 152
<211> LENGTH: 39
<212> TYPE: RNA
<213> ORGANISM: Artificial Sequence
<220> FEATURE:
<223> OTHER INFORMATION: Synthetic

<400> SEQUENCE: 152
cuauucgagu ucccacgaau cccccaucg agaaccuac            39

<210> SEQ ID NO 153
<211> LENGTH: 38
<212> TYPE: RNA
<213> ORGANISM: Artificial Sequence
<220> FEATURE:
<223> OTHER INFORMATION: Synthetic

<400> SEQUENCE: 153
cuauucgagu ucccacgaau cccccaucg agaaccua            38

<210> SEQ ID NO 154
<211> LENGTH: 39
<212> TYPE: RNA
<213> ORGANISM: Artificial Sequence
<220> FEATURE:
<223> OTHER INFORMATION: Synthetic

<400> SEQUENCE: 154
cuauucgagu ucccacgaau cccccaucg agaaccuau            39

<210> SEQ ID NO 155
<211> LENGTH: 39
<212> TYPE: RNA
<213> ORGANISM: Artificial Sequence
<220> FEATURE:

<223> OTHER INFORMATION: Synthetic

<400> SEQUENCE: 155
cuauucgagu ucccacgaau cccccaucg agaaccuaa         39

<210> SEQ ID NO 156
<211> LENGTH: 40
<212> TYPE: RNA
<213> ORGANISM: Artificial Sequence
<220> FEATURE:
<223> OTHER INFORMATION: Synthetic

<400> SEQUENCE: 156
ugccaagccg aggcccggcc accguccccg cggcugauga         40

<210> SEQ ID NO 157
<211> LENGTH: 41
<212> TYPE: RNA
<213> ORGANISM: Artificial Sequence
<220> FEATURE:
<223> OTHER INFORMATION: Synthetic

<400> SEQUENCE: 157
ugccaaagcc gaggcccggc caccgucccc gcggcugaug a         41

<210> SEQ ID NO 158
<211> LENGTH: 41
<212> TYPE: RNA
<213> ORGANISM: Artificial Sequence
<220> FEATURE:
<223> OTHER INFORMATION: Synthetic

<400> SEQUENCE: 158
ugccaagccg aggcccggcc accguccccg cggcugaucg a         41

<210> SEQ ID NO 159
<211> LENGTH: 40
<212> TYPE: RNA
<213> ORGANISM: Artificial Sequence
<220> FEATURE:
<223> OTHER INFORMATION: Synthetic

<400> SEQUENCE: 159
ugccaagccg aggcccggcc accguccccg cggcugaugg         40

<210> SEQ ID NO 160
<211> LENGTH: 40
<212> TYPE: RNA
<213> ORGANISM: Artificial Sequence
<220> FEATURE:
<223> OTHER INFORMATION: Synthetic

<400> SEQUENCE: 160
ugccaagccg aggcccggcc accguccccg cggcugacga         40

<210> SEQ ID NO 161
<211> LENGTH: 40
<212> TYPE: RNA
<213> ORGANISM: Artificial Sequence
<220> FEATURE:
<223> OTHER INFORMATION: Synthetic

<400> SEQUENCE: 161
aaugaucucg ccaaugggcg acaaucacca ugucuucaca         40

```
<210> SEQ ID NO 162
<211> LENGTH: 40
<212> TYPE: RNA
<213> ORGANISM: Artificial Sequence
<220> FEATURE:
<223> OTHER INFORMATION: Synthetic

<400> SEQUENCE: 162
aacgaucucg ccaaugggcg acaaucacca ugucuucaca                    40

<210> SEQ ID NO 163
<211> LENGTH: 40
<212> TYPE: RNA
<213> ORGANISM: Artificial Sequence
<220> FEATURE:
<223> OTHER INFORMATION: Synthetic

<400> SEQUENCE: 163
aaugaucucg ccaaugggcg acaaucacca ugucuucacg                    40

<210> SEQ ID NO 164
<211> LENGTH: 40
<212> TYPE: RNA
<213> ORGANISM: Artificial Sequence
<220> FEATURE:
<223> OTHER INFORMATION: Synthetic

<400> SEQUENCE: 164
aaugaucucg ccaaugugcg acaaucacca ugucuucaca                    40

<210> SEQ ID NO 165
<211> LENGTH: 38
<212> TYPE: RNA
<213> ORGANISM: Artificial Sequence
<220> FEATURE:
<223> OTHER INFORMATION: Synthetic

<400> SEQUENCE: 165
ucagugcgcc aaguggaggc cccaccgcag cccaucaa                      38

<210> SEQ ID NO 166
<211> LENGTH: 38
<212> TYPE: RNA
<213> ORGANISM: Artificial Sequence
<220> FEATURE:
<223> OTHER INFORMATION: Synthetic

<400> SEQUENCE: 166
ucagugcgcc aaguggaggc cccaccgcag cccaucga                      38

<210> SEQ ID NO 167
<211> LENGTH: 38
<212> TYPE: RNA
<213> ORGANISM: Artificial Sequence
<220> FEATURE:
<223> OTHER INFORMATION: Synthetic

<400> SEQUENCE: 167
ucagugcgcc aaguggaggc cccaccgcag cccaucag                      38

<210> SEQ ID NO 168
<211> LENGTH: 40
<212> TYPE: RNA
<213> ORGANISM: Artificial Sequence
<220> FEATURE:
<223> OTHER INFORMATION: Synthetic
```

<400> SEQUENCE: 168
uguaugccag cuuugacgau aacgucgcg cgucaauuca         40

<210> SEQ ID NO 169
<211> LENGTH: 40
<212> TYPE: RNA
<213> ORGANISM: Artificial Sequence
<220> FEATURE:
<223> OTHER INFORMATION: Synthetic

<400> SEQUENCE: 169
uacgccaaag uggagcccac ucguacccca ucaugagcug         40

<210> SEQ ID NO 170
<211> LENGTH: 41
<212> TYPE: RNA
<213> ORGANISM: Artificial Sequence
<220> FEATURE:
<223> OTHER INFORMATION: Synthetic

<400> SEQUENCE: 170
uacgccaaag uggagcccac ucguacccca ucaugagccu g         41

<210> SEQ ID NO 171
<211> LENGTH: 40
<212> TYPE: RNA
<213> ORGANISM: Artificial Sequence
<220> FEATURE:
<223> OTHER INFORMATION: Synthetic

<400> SEQUENCE: 171
uacgccaaag uggagcccac ucguacccca ucaugagcuc         40

<210> SEQ ID NO 172
<211> LENGTH: 40
<212> TYPE: RNA
<213> ORGANISM: Artificial Sequence
<220> FEATURE:
<223> OTHER INFORMATION: Synthetic

<400> SEQUENCE: 172
uacgccaaag uggagcccac ucguacccca ucaugggcug         40

<210> SEQ ID NO 173
<211> LENGTH: 40
<212> TYPE: RNA
<213> ORGANISM: Artificial Sequence
<220> FEATURE:
<223> OTHER INFORMATION: Synthetic

<400> SEQUENCE: 173
uacgccaaag uggagcccac ucguauccca ucaugagcug         40

<210> SEQ ID NO 174
<211> LENGTH: 40
<212> TYPE: RNA
<213> ORGANISM: Artificial Sequence
<220> FEATURE:
<223> OTHER INFORMATION: Synthetic

<400> SEQUENCE: 174
uacgccaaag uggagcccac ucguacccca ucgugagcug         40

<210> SEQ ID NO 175
<211> LENGTH: 40

```
<212> TYPE: RNA
<213> ORGANISM: Artificial Sequence
<220> FEATURE:
<223> OTHER INFORMATION: Synthetic

<400> SEQUENCE: 175
uacgccaaag uggagcccac ucguacucca ucaugagcug                    40

<210> SEQ ID NO 176
<211> LENGTH: 40
<212> TYPE: RNA
<213> ORGANISM: Artificial Sequence
<220> FEATURE:
<223> OTHER INFORMATION: Synthetic

<400> SEQUENCE: 176
cacgccaaag uggagcccac ucguacccca ucaugagcug                    40

<210> SEQ ID NO 177
<211> LENGTH: 40
<212> TYPE: RNA
<213> ORGANISM: Artificial Sequence
<220> FEATURE:
<223> OTHER INFORMATION: Synthetic

<400> SEQUENCE: 177
uacgccaaag uggagcccac ucgcacccca ucaugagcug                    40

<210> SEQ ID NO 178
<211> LENGTH: 40
<212> TYPE: RNA
<213> ORGANISM: Artificial Sequence
<220> FEATURE:
<223> OTHER INFORMATION: Synthetic

<400> SEQUENCE: 178
uacgccaaag uggagcccac ucguacccca ucaugagcua                    40

<210> SEQ ID NO 179
<211> LENGTH: 40
<212> TYPE: RNA
<213> ORGANISM: Artificial Sequence
<220> FEATURE:
<223> OTHER INFORMATION: Synthetic

<400> SEQUENCE: 179
ccgccagcuu uggguacccu gaccaauuca cggccaucca                    40

<210> SEQ ID NO 180
<211> LENGTH: 40
<212> TYPE: RNA
<213> ORGANISM: Artificial Sequence
<220> FEATURE:
<223> OTHER INFORMATION: Synthetic

<400> SEQUENCE: 180
ccgccagcuu uggguacccu gaccaauuca cggccauccg                    40

<210> SEQ ID NO 181
<211> LENGTH: 41
<212> TYPE: RNA
<213> ORGANISM: Artificial Sequence
<220> FEATURE:
<223> OTHER INFORMATION: Synthetic

<400> SEQUENCE: 181
```
ccgcccagcu uuggguaccc ugaccaauuc acggccaucc a            41

<210> SEQ ID NO 182
<211> LENGTH: 40
<212> TYPE: RNA
<213> ORGANISM: Artificial Sequence
<220> FEATURE:
<223> OTHER INFORMATION: Synthetic

<400> SEQUENCE: 182
guaauugucu gagaccaccg gacaaucaac aagaaauccu              40

<210> SEQ ID NO 183
<211> LENGTH: 41
<212> TYPE: RNA
<213> ORGANISM: Artificial Sequence
<220> FEATURE:
<223> OTHER INFORMATION: Synthetic

<400> SEQUENCE: 183
guaauugucu gagaccaccg gacaaucaac aagaaaaucc u            41

<210> SEQ ID NO 184
<211> LENGTH: 39
<212> TYPE: RNA
<213> ORGANISM: Artificial Sequence
<220> FEATURE:
<223> OTHER INFORMATION: Synthetic

<400> SEQUENCE: 184
uaauugucug agaccaccgg acaaucaaca agaaauccu               39

<210> SEQ ID NO 185
<211> LENGTH: 40
<212> TYPE: RNA
<213> ORGANISM: Artificial Sequence
<220> FEATURE:
<223> OTHER INFORMATION: Synthetic

<400> SEQUENCE: 185
ucaggccaaa gugugauagc cacacccgca cccaucagga              40

<210> SEQ ID NO 186
<211> LENGTH: 39
<212> TYPE: RNA
<213> ORGANISM: Artificial Sequence
<220> FEATURE:
<223> OTHER INFORMATION: Synthetic

<400> SEQUENCE: 186
ucaggccaaa gugugauagc cacacccgca cccaucaga               39

<210> SEQ ID NO 187
<211> LENGTH: 39
<212> TYPE: RNA
<213> ORGANISM: Artificial Sequence
<220> FEATURE:
<223> OTHER INFORMATION: Synthetic

<400> SEQUENCE: 187
ucaggccaaa gugugauagc cacacccgca cccaucagg               39

<210> SEQ ID NO 188
<211> LENGTH: 40
<212> TYPE: RNA
<213> ORGANISM: Artificial Sequence
<220> FEATURE:
<223> OTHER INFORMATION: Synthetic

<400> SEQUENCE: 188
ccgaccgccg accagggugc cacucguacc ccuguccgcc                        40

<210> SEQ ID NO 189
<211> LENGTH: 41
<212> TYPE: RNA
<213> ORGANISM: Artificial Sequence
<220> FEATURE:
<223> OTHER INFORMATION: Synthetic

<400> SEQUENCE: 189
ccgaccgccg accagggugc cacucguacc ccuguccgcc c                      41

<210> SEQ ID NO 190
<211> LENGTH: 41
<212> TYPE: RNA
<213> ORGANISM: Artificial Sequence
<220> FEATURE:
<223> OTHER INFORMATION: Synthetic

<400> SEQUENCE: 190
ccgaccgccg accagggugc cacucguacc ccugucccgc c                      41

<210> SEQ ID NO 191
<211> LENGTH: 39
<212> TYPE: RNA
<213> ORGANISM: Artificial Sequence
<220> FEATURE:
<223> OTHER INFORMATION: Synthetic

<400> SEQUENCE: 191
ccgaccgccg accagggugc cacucguacc ccuguccgc                         39

<210> SEQ ID NO 192
<211> LENGTH: 40
<212> TYPE: RNA
<213> ORGANISM: Artificial Sequence
<220> FEATURE:
<223> OTHER INFORMATION: Synthetic

<400> SEQUENCE: 192
ugccaagucg aagcccgacc acgccauccc uaacagugcc                        40

<210> SEQ ID NO 193
<211> LENGTH: 41
<212> TYPE: RNA
<213> ORGANISM: Artificial Sequence
<220> FEATURE:
<223> OTHER INFORMATION: Synthetic

<400> SEQUENCE: 193
ugccaaaguc gaagcccgac cacgccaucc cuaacaguge c                      41

<210> SEQ ID NO 194
<211> LENGTH: 39
<212> TYPE: RNA
<213> ORGANISM: Artificial Sequence
<220> FEATURE:
<223> OTHER INFORMATION: Synthetic

<400> SEQUENCE: 194
ugccaagucg aagcccgacc acgccauccc uaacagugc                         39

```
<210> SEQ ID NO 195
<211> LENGTH: 40
<212> TYPE: RNA
<213> ORGANISM: Artificial Sequence
<220> FEATURE:
<223> OTHER INFORMATION: Synthetic

<400> SEQUENCE: 195
ugccaagucg aagcccgacc acgccauccc uaacggugcc                              40

<210> SEQ ID NO 196
<211> LENGTH: 40
<212> TYPE: RNA
<213> ORGANISM: Artificial Sequence
<220> FEATURE:
<223> OTHER INFORMATION: Synthetic

<400> SEQUENCE: 196
ugccaagucg aagcccgacc acgccauccc uaacagugca                              40

<210> SEQ ID NO 197
<211> LENGTH: 40
<212> TYPE: RNA
<213> ORGANISM: Artificial Sequence
<220> FEATURE:
<223> OTHER INFORMATION: Synthetic

<400> SEQUENCE: 197
ugccaagucg aggcccgacc acgccauccc uaacagugcc                              40

<210> SEQ ID NO 198
<211> LENGTH: 40
<212> TYPE: RNA
<213> ORGANISM: Artificial Sequence
<220> FEATURE:
<223> OTHER INFORMATION: Synthetic

<400> SEQUENCE: 198
ugccaagccg aagcccgacc acgccauccc uaacagugcc                              40

<210> SEQ ID NO 199
<211> LENGTH: 40
<212> TYPE: RNA
<213> ORGANISM: Artificial Sequence
<220> FEATURE:
<223> OTHER INFORMATION: Synthetic

<400> SEQUENCE: 199
acuugugcug agucgccaaa gugaggccca cucgccagca                              40

<210> SEQ ID NO 200
<211> LENGTH: 40
<212> TYPE: RNA
<213> ORGANISM: Artificial Sequence
<220> FEATURE:
<223> OTHER INFORMATION: Synthetic

<400> SEQUENCE: 200
gcuugugcug agucgccaaa gugaggccca cucgccagca                              40

<210> SEQ ID NO 201
<211> LENGTH: 40
<212> TYPE: RNA
<213> ORGANISM: Artificial Sequence
<220> FEATURE:
<223> OTHER INFORMATION: Synthetic
```

```
<400> SEQUENCE: 201
accugugcug agucgccaaa gugaggccca cucgccagca                          40

<210> SEQ ID NO 202
<211> LENGTH: 40
<212> TYPE: RNA
<213> ORGANISM: Artificial Sequence
<220> FEATURE:
<223> OTHER INFORMATION: Synthetic

<400> SEQUENCE: 202
ccgccagcuc cucugaggca caagagguuc acggugaucc                          40

<210> SEQ ID NO 203
<211> LENGTH: 41
<212> TYPE: RNA
<213> ORGANISM: Artificial Sequence
<220> FEATURE:
<223> OTHER INFORMATION: Synthetic

<400> SEQUENCE: 203
ccgccagcuc cucugaggca caagagguuc acggugaucc c                        41

<210> SEQ ID NO 204
<211> LENGTH: 40
<212> TYPE: RNA
<213> ORGANISM: Artificial Sequence
<220> FEATURE:
<223> OTHER INFORMATION: Synthetic

<400> SEQUENCE: 204
caccagguuc ugcugucccc aagcgcugac ccauccuucc                          40

<210> SEQ ID NO 205
<211> LENGTH: 40
<212> TYPE: RNA
<213> ORGANISM: Artificial Sequence
<220> FEATURE:
<223> OTHER INFORMATION: Synthetic

<400> SEQUENCE: 205
caccagguuc ugcuaucccc aagcgcugac ccauccuucc                          40

<210> SEQ ID NO 206
<211> LENGTH: 40
<212> TYPE: RNA
<213> ORGANISM: Artificial Sequence
<220> FEATURE:
<223> OTHER INFORMATION: Synthetic

<400> SEQUENCE: 206
caccagguuc ugcugucucc aagcgcugac ccauccuucc                          40

<210> SEQ ID NO 207
<211> LENGTH: 40
<212> TYPE: RNA
<213> ORGANISM: Artificial Sequence
<220> FEATURE:
<223> OTHER INFORMATION: Synthetic

<400> SEQUENCE: 207
caccagguuc ugcuguuccc aagcgcugac ccauccuucc                          40

<210> SEQ ID NO 208
```

```
<211> LENGTH: 40
<212> TYPE: RNA
<213> ORGANISM: Artificial Sequence
<220> FEATURE:
<223> OTHER INFORMATION: Synthetic

<400> SEQUENCE: 208
caccaggucc ugcuguccccc aagcgcugac ccauccuucc                            40

<210> SEQ ID NO 209
<211> LENGTH: 40
<212> TYPE: RNA
<213> ORGANISM: Artificial Sequence
<220> FEATURE:
<223> OTHER INFORMATION: Synthetic

<400> SEQUENCE: 209
caccaggcuc ugcuguccccc aagcgcugac ccauccuucc                            40

<210> SEQ ID NO 210
<211> LENGTH: 40
<212> TYPE: RNA
<213> ORGANISM: Artificial Sequence
<220> FEATURE:
<223> OTHER INFORMATION: Synthetic

<400> SEQUENCE: 210
caccagguuc ugcugucccuc aagcgcugac ccauccuucc                            40

<210> SEQ ID NO 211
<211> LENGTH: 40
<212> TYPE: RNA
<213> ORGANISM: Artificial Sequence
<220> FEATURE:
<223> OTHER INFORMATION: Synthetic

<400> SEQUENCE: 211
aagauccggu aacuccccac cgcaaucacc gucgacuacu                             40

<210> SEQ ID NO 212
<211> LENGTH: 40
<212> TYPE: RNA
<213> ORGANISM: Artificial Sequence
<220> FEATURE:
<223> OTHER INFORMATION: Synthetic

<400> SEQUENCE: 212
aagauccggu gacuccccac cgcaaucacc gucgacuacu                             40

<210> SEQ ID NO 213
<211> LENGTH: 40
<212> TYPE: RNA
<213> ORGANISM: Artificial Sequence
<220> FEATURE:
<223> OTHER INFORMATION: Synthetic

<400> SEQUENCE: 213
aagauccggu aacucccuac cgcaaucacc gucgacuacu                             40

<210> SEQ ID NO 214
<211> LENGTH: 41
<212> TYPE: RNA
<213> ORGANISM: Artificial Sequence
<220> FEATURE:
<223> OTHER INFORMATION: Synthetic

<400> SEQUENCE: 214
```
aaagauccgg uaacuccccca ccgcaaucac cgucgacuac u                           41

<210> SEQ ID NO 215
<211> LENGTH: 40
<212> TYPE: RNA
<213> ORGANISM: Artificial Sequence
<220> FEATURE:
<223> OTHER INFORMATION: Synthetic

<400> SEQUENCE: 215
ccaucuagau cuccguagau uccccccggc ucuuucucgc                              40

<210> SEQ ID NO 216
<211> LENGTH: 40
<212> TYPE: RNA
<213> ORGANISM: Artificial Sequence
<220> FEATURE:
<223> OTHER INFORMATION: Synthetic

<400> SEQUENCE: 216
ccaucuagau cuccguagau uccccgggc ucuuucucgu                               40

<210> SEQ ID NO 217
<211> LENGTH: 40
<212> TYPE: RNA
<213> ORGANISM: Artificial Sequence
<220> FEATURE:
<223> OTHER INFORMATION: Synthetic

<400> SEQUENCE: 217
ccaucuagau cuccguagau uccccgggc ucuuucucga                               40

<210> SEQ ID NO 218
<211> LENGTH: 39
<212> TYPE: RNA
<213> ORGANISM: Artificial Sequence
<220> FEATURE:
<223> OTHER INFORMATION: Synthetic

<400> SEQUENCE: 218
ccaucuagau cuccguagau uccccgggc ucuuucucg                                39

<210> SEQ ID NO 219
<211> LENGTH: 40
<212> TYPE: RNA
<213> ORGANISM: Artificial Sequence
<220> FEATURE:
<223> OTHER INFORMATION: Synthetic

<400> SEQUENCE: 219
ccaucuagau cuccguagau uccccgggc ucuuucucgc                               40

<210> SEQ ID NO 220
<211> LENGTH: 40
<212> TYPE: RNA
<213> ORGANISM: Artificial Sequence
<220> FEATURE:
<223> OTHER INFORMATION: Synthetic

<400> SEQUENCE: 220
ccaucuagau cuccguagau uccccgggc ucuuucucac                               40

<210> SEQ ID NO 221
<211> LENGTH: 40
<212> TYPE: RNA

<213> ORGANISM: Artificial Sequence
<220> FEATURE:
<223> OTHER INFORMATION: Synthetic

<400> SEQUENCE: 221
ccaucuagau cuccguagau uuccccggc ucuuucucgc                                40

<210> SEQ ID NO 222
<211> LENGTH: 40
<212> TYPE: RNA
<213> ORGANISM: Artificial Sequence
<220> FEATURE:
<223> OTHER INFORMATION: Synthetic

<400> SEQUENCE: 222
ccaucuagau cuccguagau uccccgggc ucuuccucgc                                40

<210> SEQ ID NO 223
<211> LENGTH: 40
<212> TYPE: RNA
<213> ORGANISM: Artificial Sequence
<220> FEATURE:
<223> OTHER INFORMATION: Synthetic

<400> SEQUENCE: 223
ccaucuagau cuccguagau uccccgggc ucucucucgc                                40

<210> SEQ ID NO 224
<211> LENGTH: 40
<212> TYPE: RNA
<213> ORGANISM: Artificial Sequence
<220> FEATURE:
<223> OTHER INFORMATION: Synthetic

<400> SEQUENCE: 224
ccaucuagau cuccguagau uccccgggc ucuuucuugc                                40

<210> SEQ ID NO 225
<211> LENGTH: 40
<212> TYPE: RNA
<213> ORGANISM: Artificial Sequence
<220> FEATURE:
<223> OTHER INFORMATION: Synthetic

<400> SEQUENCE: 225
ccaucuagau cuccguagau uccccgggc ccuuucucgc                                40

<210> SEQ ID NO 226
<211> LENGTH: 40
<212> TYPE: RNA
<213> ORGANISM: Artificial Sequence
<220> FEATURE:
<223> OTHER INFORMATION: Synthetic

<400> SEQUENCE: 226
ccaucuagau cuccguagau uccccgggc ucuuucucuc                                40

<210> SEQ ID NO 227
<211> LENGTH: 40
<212> TYPE: RNA
<213> ORGANISM: Artificial Sequence
<220> FEATURE:
<223> OTHER INFORMATION: Synthetic

<400> SEQUENCE: 227
ccaucuagau cuccguagau uccccggcc ucuuucucgc                                40

<210> SEQ ID NO 228
<211> LENGTH: 40
<212> TYPE: RNA
<213> ORGANISM: Artificial Sequence
<220> FEATURE:
<223> OTHER INFORMATION: Synthetic

<400> SEQUENCE: 228
ccaucuagau cuccguagau ucccccgggc ucuuucuccc                              40

<210> SEQ ID NO 229
<211> LENGTH: 41
<212> TYPE: RNA
<213> ORGANISM: Artificial Sequence
<220> FEATURE:
<223> OTHER INFORMATION: Synthetic

<400> SEQUENCE: 229
ccaucuagau cuccguagau ucccccgggc ucuuucucgu c                            41

<210> SEQ ID NO 230
<211> LENGTH: 40
<212> TYPE: RNA
<213> ORGANISM: Artificial Sequence
<220> FEATURE:
<223> OTHER INFORMATION: Synthetic

<400> SEQUENCE: 230
ccaucugaac ccacagauuc ccccaucauc agccacagug                              40

<210> SEQ ID NO 231
<211> LENGTH: 40
<212> TYPE: RNA
<213> ORGANISM: Artificial Sequence
<220> FEATURE:
<223> OTHER INFORMATION: Synthetic

<400> SEQUENCE: 231
ccaucugaac ccacagauuc ccccaucauc agccacagua                              40

<210> SEQ ID NO 232
<211> LENGTH: 40
<212> TYPE: RNA
<213> ORGANISM: Artificial Sequence
<220> FEATURE:
<223> OTHER INFORMATION: Synthetic

<400> SEQUENCE: 232
ccaucugaac ccacagauuc ccccaucauc agccacagcg                              40

<210> SEQ ID NO 233
<211> LENGTH: 40
<212> TYPE: RNA
<213> ORGANISM: Artificial Sequence
<220> FEATURE:
<223> OTHER INFORMATION: Synthetic

<400> SEQUENCE: 233
ccaucugaac ccacagauuc ccccaucauc agccacaguc                              40

<210> SEQ ID NO 234
<211> LENGTH: 40
<212> TYPE: RNA
<213> ORGANISM: Artificial Sequence
<220> FEATURE:

<223> OTHER INFORMATION: Synthetic

<400> SEQUENCE: 234
ccaucugaac ccacagauuc ccccaucauc agccacggug                40

<210> SEQ ID NO 235
<211> LENGTH: 40
<212> TYPE: RNA
<213> ORGANISM: Artificial Sequence
<220> FEATURE:
<223> OTHER INFORMATION: Synthetic

<400> SEQUENCE: 235
cacuaaguug guagccccaa cugccccgac acgaggaugu                40

<210> SEQ ID NO 236
<211> LENGTH: 41
<212> TYPE: RNA
<213> ORGANISM: Artificial Sequence
<220> FEATURE:
<223> OTHER INFORMATION: Synthetic

<400> SEQUENCE: 236
cacuaaguug guagccccaa cugccccgac acgaggaugu c              41

<210> SEQ ID NO 237
<211> LENGTH: 40
<212> TYPE: RNA
<213> ORGANISM: Artificial Sequence
<220> FEATURE:
<223> OTHER INFORMATION: Synthetic

<400> SEQUENCE: 237
cacuaaguug guagccccaa cugccccgac acgaggaugc                40

<210> SEQ ID NO 238
<211> LENGTH: 40
<212> TYPE: RNA
<213> ORGANISM: Artificial Sequence
<220> FEATURE:
<223> OTHER INFORMATION: Synthetic

<400> SEQUENCE: 238
uugugcuccg uggcuccccg gaccaaccgc uuccagcagu                40

<210> SEQ ID NO 239
<211> LENGTH: 40
<212> TYPE: RNA
<213> ORGANISM: Artificial Sequence
<220> FEATURE:
<223> OTHER INFORMATION: Synthetic

<400> SEQUENCE: 239
uuguguuccg uggcuccccg gaccaaccgc uuccagcagu                40

<210> SEQ ID NO 240
<211> LENGTH: 40
<212> TYPE: RNA
<213> ORGANISM: Artificial Sequence
<220> FEATURE:
<223> OTHER INFORMATION: Synthetic

<400> SEQUENCE: 240
uugugcuccg uggcuccccg gaccaaccgc uuccagcagc                40

```
<210> SEQ ID NO 241
<211> LENGTH: 40
<212> TYPE: RNA
<213> ORGANISM: Artificial Sequence
<220> FEATURE:
<223> OTHER INFORMATION: Synthetic

<400> SEQUENCE: 241
uugcgcuccg uggcuccccg gaccaaccgc uuccagcagu                    40

<210> SEQ ID NO 242
<211> LENGTH: 39
<212> TYPE: RNA
<213> ORGANISM: Artificial Sequence
<220> FEATURE:
<223> OTHER INFORMATION: Synthetic

<400> SEQUENCE: 242
caaucacgcg uaguacgucg cggaagaucc ccaugccga                     39

<210> SEQ ID NO 243
<211> LENGTH: 39
<212> TYPE: RNA
<213> ORGANISM: Artificial Sequence
<220> FEATURE:
<223> OTHER INFORMATION: Synthetic

<400> SEQUENCE: 243
caaucacgcg uaguacgucg cggaagaucc ccaugccgg                     39

<210> SEQ ID NO 244
<211> LENGTH: 39
<212> TYPE: RNA
<213> ORGANISM: Artificial Sequence
<220> FEATURE:
<223> OTHER INFORMATION: Synthetic

<400> SEQUENCE: 244
caaucacgcg uaguacgucg cggaagaucc ccaugccaa                     39

<210> SEQ ID NO 245
<211> LENGTH: 39
<212> TYPE: RNA
<213> ORGANISM: Artificial Sequence
<220> FEATURE:
<223> OTHER INFORMATION: Synthetic

<400> SEQUENCE: 245
caaucacgcg uaguacgucg cggaagaucc ccaugccgu                     39

<210> SEQ ID NO 246
<211> LENGTH: 39
<212> TYPE: RNA
<213> ORGANISM: Artificial Sequence
<220> FEATURE:
<223> OTHER INFORMATION: Synthetic

<400> SEQUENCE: 246
caaucacgcg uagcacgucg cggaagaucc ccaugccga                     39

<210> SEQ ID NO 247
<211> LENGTH: 39
<212> TYPE: RNA
<213> ORGANISM: Artificial Sequence
<220> FEATURE:
<223> OTHER INFORMATION: Synthetic
```

<400> SEQUENCE: 247
caaucacgcg uaguacgucg cggaggaucc ccaugccga                39

<210> SEQ ID NO 248
<211> LENGTH: 39
<212> TYPE: RNA
<213> ORGANISM: Artificial Sequence
<220> FEATURE:
<223> OTHER INFORMATION: Synthetic

<400> SEQUENCE: 248
cacaugguac gcccaaaagc gaggcccgcu gcguagugc                39

<210> SEQ ID NO 249
<211> LENGTH: 39
<212> TYPE: RNA
<213> ORGANISM: Artificial Sequence
<220> FEATURE:
<223> OTHER INFORMATION: Synthetic

<400> SEQUENCE: 249
cacaugguac gccccaaagc gaggcccgcu gcguagugc                39

<210> SEQ ID NO 250
<211> LENGTH: 39
<212> TYPE: RNA
<213> ORGANISM: Artificial Sequence
<220> FEATURE:
<223> OTHER INFORMATION: Synthetic

<400> SEQUENCE: 250
cacaugguac gcccaaagcc gaggcccgcu gcguagugc                39

<210> SEQ ID NO 251
<211> LENGTH: 38
<212> TYPE: RNA
<213> ORGANISM: Artificial Sequence
<220> FEATURE:
<223> OTHER INFORMATION: Synthetic

<400> SEQUENCE: 251
cacaugguac gcccaaaagc gaggcccgcu gcguagug                 38

<210> SEQ ID NO 252
<211> LENGTH: 40
<212> TYPE: RNA
<213> ORGANISM: Artificial Sequence
<220> FEATURE:
<223> OTHER INFORMATION: Synthetic

<400> SEQUENCE: 252
ugccauacgc gguucgaagu cgaagcccga caacccggca               40

<210> SEQ ID NO 253
<211> LENGTH: 41
<212> TYPE: RNA
<213> ORGANISM: Artificial Sequence
<220> FEATURE:
<223> OTHER INFORMATION: Synthetic

<400> SEQUENCE: 253
ugccauacgc gguucgaagu cgaagcccga caacccggc a              41

<210> SEQ ID NO 254
<211> LENGTH: 40

```
<212> TYPE: RNA
<213> ORGANISM: Artificial Sequence
<220> FEATURE:
<223> OTHER INFORMATION: Synthetic

<400> SEQUENCE: 254
ugccauacgc gguucgaagu cgaggcccga caacccggca                              40

<210> SEQ ID NO 255
<211> LENGTH: 40
<212> TYPE: RNA
<213> ORGANISM: Artificial Sequence
<220> FEATURE:
<223> OTHER INFORMATION: Synthetic

<400> SEQUENCE: 255
guuauucaca ugccucccgu gaaucaacaa gaauuccuug                              40

<210> SEQ ID NO 256
<211> LENGTH: 39
<212> TYPE: RNA
<213> ORGANISM: Artificial Sequence
<220> FEATURE:
<223> OTHER INFORMATION: Synthetic

<400> SEQUENCE: 256
uuauucacau gccucccgug aaucaacaag aauuccuug                               39

<210> SEQ ID NO 257
<211> LENGTH: 40
<212> TYPE: RNA
<213> ORGANISM: Artificial Sequence
<220> FEATURE:
<223> OTHER INFORMATION: Synthetic

<400> SEQUENCE: 257
guuauucaca ugccucccgu gaaucaacaa gaauuccucg                              40

<210> SEQ ID NO 258
<211> LENGTH: 40
<212> TYPE: RNA
<213> ORGANISM: Artificial Sequence
<220> FEATURE:
<223> OTHER INFORMATION: Synthetic

<400> SEQUENCE: 258
guuauucaca ugccucucgu gaaucaacaa gaauuccuug                              40

<210> SEQ ID NO 259

<400> SEQUENCE: 259

000

<210> SEQ ID NO 260
<211> LENGTH: 40
<212> TYPE: RNA
<213> ORGANISM: Artificial Sequence
<220> FEATURE:
<223> OTHER INFORMATION: Synthetic

<400> SEQUENCE: 260
aaagaucuag acuguaaguc uccaaucgcc caguuaauuc                              40

<210> SEQ ID NO 261
<211> LENGTH: 41
```

```
<212> TYPE: RNA
<213> ORGANISM: Artificial Sequence
<220> FEATURE:
<223> OTHER INFORMATION: Synthetic

<400> SEQUENCE: 261
aaaagaucua gacuguaagu cuccaaucgc ccaguuaauu c                  41

<210> SEQ ID NO 262
<211> LENGTH: 39
<212> TYPE: RNA
<213> ORGANISM: Artificial Sequence
<220> FEATURE:
<223> OTHER INFORMATION: Synthetic

<400> SEQUENCE: 262
aaagaucuag acuguaaguc uccaaucgcc caguaauuc                     39

<210> SEQ ID NO 263
<211> LENGTH: 39
<212> TYPE: RNA
<213> ORGANISM: Artificial Sequence
<220> FEATURE:
<223> OTHER INFORMATION: Synthetic

<400> SEQUENCE: 263
gcccaaucgc caguggaacg cgcugaagga ucugcaccc                     39

<210> SEQ ID NO 264
<211> LENGTH: 38
<212> TYPE: RNA
<213> ORGANISM: Artificial Sequence
<220> FEATURE:
<223> OTHER INFORMATION: Synthetic

<400> SEQUENCE: 264
gcccaaucgc caguggaacg cgcugaagga ucugcacc                      38

<210> SEQ ID NO 265
<211> LENGTH: 39
<212> TYPE: RNA
<213> ORGANISM: Artificial Sequence
<220> FEATURE:
<223> OTHER INFORMATION: Synthetic

<400> SEQUENCE: 265
gcccaaucgc caguggaacg cacugaagga ucugcaccc                     39

<210> SEQ ID NO 266
<211> LENGTH: 40
<212> TYPE: RNA
<213> ORGANISM: Artificial Sequence
<220> FEATURE:
<223> OTHER INFORMATION: Synthetic

<400> SEQUENCE: 266
gcccaaucgc caguggaacg cgcugaagga ucugcacccc                    40

<210> SEQ ID NO 267
<211> LENGTH: 38
<212> TYPE: RNA
<213> ORGANISM: Artificial Sequence
<220> FEATURE:
<223> OTHER INFORMATION: Synthetic

<400> SEQUENCE: 267
```

```
cccaaucgcc aguggaacgc gcugaaggau cugcaccc                                  38

<210> SEQ ID NO 268
<211> LENGTH: 39
<212> TYPE: RNA
<213> ORGANISM: Artificial Sequence
<220> FEATURE:
<223> OTHER INFORMATION: Synthetic

<400> SEQUENCE: 268
gcccaaucgc cagcggaacg cgcugaagga ucugcaccc                                 39

<210> SEQ ID NO 269
<211> LENGTH: 40
<212> TYPE: RNA
<213> ORGANISM: Artificial Sequence
<220> FEATURE:
<223> OTHER INFORMATION: Synthetic

<400> SEQUENCE: 269
ugcaacguaa aagagaguca ucucaggcua gucgcuacc                                 40

<210> SEQ ID NO 270
<211> LENGTH: 39
<212> TYPE: RNA
<213> ORGANISM: Artificial Sequence
<220> FEATURE:
<223> OTHER INFORMATION: Synthetic

<400> SEQUENCE: 270
ugcaacguaa aagagaguca ucucaggcua gucgucuac                                 39

<210> SEQ ID NO 271
<211> LENGTH: 40
<212> TYPE: RNA
<213> ORGANISM: Artificial Sequence
<220> FEATURE:
<223> OTHER INFORMATION: Synthetic

<400> SEQUENCE: 271
guguacgcca agucgaggcc cgaccguacc cauacgcgac                                40

<210> SEQ ID NO 272
<211> LENGTH: 39
<212> TYPE: RNA
<213> ORGANISM: Artificial Sequence
<220> FEATURE:
<223> OTHER INFORMATION: Synthetic

<400> SEQUENCE: 272
uguacgccaa gucgaggccc gaccguaccc auacgcgac                                 39

<210> SEQ ID NO 273
<211> LENGTH: 40
<212> TYPE: RNA
<213> ORGANISM: Artificial Sequence
<220> FEATURE:
<223> OTHER INFORMATION: Synthetic

<400> SEQUENCE: 273
guguacgcca agucgaggcc cgaccguacc cauacgcggc                                40

<210> SEQ ID NO 274
<211> LENGTH: 40
<212> TYPE: RNA
<213> ORGANISM: Artificial Sequence
```

```
<220> FEATURE:
<223> OTHER INFORMATION: Synthetic

<400> SEQUENCE: 274
guguacgcca agucgaggcc cgaccguacc cauacgcgau                          40

<210> SEQ ID NO 275
<211> LENGTH: 40
<212> TYPE: RNA
<213> ORGANISM: Artificial Sequence
<220> FEATURE:
<223> OTHER INFORMATION: Synthetic

<400> SEQUENCE: 275
uuagcucuac uuccucuuc aguaagacua accgcuucuu                           40

<210> SEQ ID NO 276
<211> LENGTH: 40
<212> TYPE: RNA
<213> ORGANISM: Artificial Sequence
<220> FEATURE:
<223> OTHER INFORMATION: Synthetic

<400> SEQUENCE: 276
uuagcucuac uuccucuuc aguaagacua accgcuuccu                           40

<210> SEQ ID NO 277
<211> LENGTH: 40
<212> TYPE: RNA
<213> ORGANISM: Artificial Sequence
<220> FEATURE:
<223> OTHER INFORMATION: Synthetic

<400> SEQUENCE: 277
uuagcucuac uuccucuuc aguaagacua accgcuucuc                           40

<210> SEQ ID NO 278
<211> LENGTH: 40
<212> TYPE: RNA
<213> ORGANISM: Artificial Sequence
<220> FEATURE:
<223> OTHER INFORMATION: Synthetic

<400> SEQUENCE: 278
uuagcucuac uuccucuuc aguaagacua accgcuccuu                           40

<210> SEQ ID NO 279
<211> LENGTH: 40
<212> TYPE: RNA
<213> ORGANISM: Artificial Sequence
<220> FEATURE:
<223> OTHER INFORMATION: Synthetic

<400> SEQUENCE: 279
uccaagcgga ggccccgcac ccacccucca acgggcacgg                          40

<210> SEQ ID NO 280
<211> LENGTH: 40
<212> TYPE: RNA
<213> ORGANISM: Artificial Sequence
<220> FEATURE:
<223> OTHER INFORMATION: Synthetic

<400> SEQUENCE: 280
uccaagcgga ggccccgcac ccacccucca acgggcacgc                          40
```

<210> SEQ ID NO 281
<211> LENGTH: 40
<212> TYPE: RNA
<213> ORGANISM: Artificial Sequence
<220> FEATURE:
<223> OTHER INFORMATION: Synthetic

<400> SEQUENCE: 281
uccaagcgga ggccccguac ccacccucca acgggcacgg                              40

<210> SEQ ID NO 282
<211> LENGTH: 40
<212> TYPE: RNA
<213> ORGANISM: Artificial Sequence
<220> FEATURE:
<223> OTHER INFORMATION: Synthetic

<400> SEQUENCE: 282
uccaagcgga ggccccgcac ccaccccca acgggcacgg                               40

<210> SEQ ID NO 283
<211> LENGTH: 40
<212> TYPE: RNA
<213> ORGANISM: Artificial Sequence
<220> FEATURE:
<223> OTHER INFORMATION: Synthetic

<400> SEQUENCE: 283
uccaagcgga ggccccgcac ccacccucca acgggcacga                              40

<210> SEQ ID NO 284
<211> LENGTH: 41
<212> TYPE: RNA
<213> ORGANISM: Artificial Sequence
<220> FEATURE:
<223> OTHER INFORMATION: Synthetic

<400> SEQUENCE: 284
uccaaagcgg aggccccgca cccacccucc aacgggcacg g                            41

<210> SEQ ID NO 285
<211> LENGTH: 40
<212> TYPE: RNA
<213> ORGANISM: Artificial Sequence
<220> FEATURE:
<223> OTHER INFORMATION: Synthetic

<400> SEQUENCE: 285
uccaagcgga ggccccgcac ccacccucca acgggcacag                              40

<210> SEQ ID NO 286
<211> LENGTH: 40
<212> TYPE: RNA
<213> ORGANISM: Artificial Sequence
<220> FEATURE:
<223> OTHER INFORMATION: Synthetic

<400> SEQUENCE: 286
uaucgcucca caacgacucc cguggacuac ccaauuccaa                              40

<210> SEQ ID NO 287
<211> LENGTH: 40
<212> TYPE: RNA
<213> ORGANISM: Artificial Sequence
<220> FEATURE:
<223> OTHER INFORMATION: Synthetic

```
<400> SEQUENCE: 287
uaucgcucca caacgacucc cguggacuac ccaauuccag                              40

<210> SEQ ID NO 288
<211> LENGTH: 41
<212> TYPE: RNA
<213> ORGANISM: Artificial Sequence
<220> FEATURE:
<223> OTHER INFORMATION: Synthetic

<400> SEQUENCE: 288
uaucgcucca caacgacucc cguggacuac ccaauuccaa a                            41

<210> SEQ ID NO 289
<211> LENGTH: 40
<212> TYPE: RNA
<213> ORGANISM: Artificial Sequence
<220> FEATURE:
<223> OTHER INFORMATION: Synthetic

<400> SEQUENCE: 289
uaucgcucca caacgacucc cguggacuac ccaauuccau                              40

<210> SEQ ID NO 290
<211> LENGTH: 40
<212> TYPE: RNA
<213> ORGANISM: Artificial Sequence
<220> FEATURE:
<223> OTHER INFORMATION: Synthetic

<400> SEQUENCE: 290
gucgugccca agugaaggcc ucacgcacgc auccuaaccu                              40

<210> SEQ ID NO 291
<211> LENGTH: 39
<212> TYPE: RNA
<213> ORGANISM: Artificial Sequence
<220> FEATURE:
<223> OTHER INFORMATION: Synthetic

<400> SEQUENCE: 291
ucgugcccaa gugaaggccu cacgcacgca uccuaaccu                               39

<210> SEQ ID NO 292
<211> LENGTH: 40
<212> TYPE: RNA
<213> ORGANISM: Artificial Sequence
<220> FEATURE:
<223> OTHER INFORMATION: Synthetic

<400> SEQUENCE: 292
gucgugccca agugaaggcc ucacgcacgc auccuaaccc                              40

<210> SEQ ID NO 293
<211> LENGTH: 40
<212> TYPE: RNA
<213> ORGANISM: Artificial Sequence
<220> FEATURE:
<223> OTHER INFORMATION: Synthetic

<400> SEQUENCE: 293
aagaucugcg ccagcacaau caccaucguc cugagaaugg                              40

<210> SEQ ID NO 294
```

```
<211> LENGTH: 40
<212> TYPE: RNA
<213> ORGANISM: Artificial Sequence
<220> FEATURE:
<223> OTHER INFORMATION: Synthetic

<400> SEQUENCE: 294
aagaucugcg ccagcacaau caccaucguc cugagaaugc                              40

<210> SEQ ID NO 295
<211> LENGTH: 40
<212> TYPE: RNA
<213> ORGANISM: Artificial Sequence
<220> FEATURE:
<223> OTHER INFORMATION: Synthetic

<400> SEQUENCE: 295
aagaucugcg ccagcacaau caccaucguc cugagaauga                              40

<210> SEQ ID NO 296
<211> LENGTH: 40
<212> TYPE: RNA
<213> ORGANISM: Artificial Sequence
<220> FEATURE:
<223> OTHER INFORMATION: Synthetic

<400> SEQUENCE: 296
aagaucugcg ccagcacaau caccaucguc cugagagugg                              40

<210> SEQ ID NO 297
<211> LENGTH: 40
<212> TYPE: RNA
<213> ORGANISM: Artificial Sequence
<220> FEATURE:
<223> OTHER INFORMATION: Synthetic

<400> SEQUENCE: 297
aagaucugcg ccagcacaau caccaucguc cugggaaugg                              40

<210> SEQ ID NO 298
<211> LENGTH: 40
<212> TYPE: RNA
<213> ORGANISM: Artificial Sequence
<220> FEATURE:
<223> OTHER INFORMATION: Synthetic

<400> SEQUENCE: 298
augccaagca guggcccugc cacccaccua ucacugucga                              40

<210> SEQ ID NO 299
<211> LENGTH: 40
<212> TYPE: RNA
<213> ORGANISM: Artificial Sequence
<220> FEATURE:
<223> OTHER INFORMATION: Synthetic

<400> SEQUENCE: 299
augccaagca gucggccugc cacccaccua ucacugucga                              40

<210> SEQ ID NO 300
<211> LENGTH: 40
<212> TYPE: RNA
<213> ORGANISM: Artificial Sequence
<220> FEATURE:
<223> OTHER INFORMATION: Synthetic

<400> SEQUENCE: 300
```

```
augccaagca guggcccugc cacccaccua ucacuaucga          40

<210> SEQ ID NO 301
<211> LENGTH: 40
<212> TYPE: RNA
<213> ORGANISM: Artificial Sequence
<220> FEATURE:
<223> OTHER INFORMATION: Synthetic

<400> SEQUENCE: 301
augccaagca guggcccugc cacccaccua ccacugucga          40

<210> SEQ ID NO 302
<211> LENGTH: 40
<212> TYPE: RNA
<213> ORGANISM: Artificial Sequence
<220> FEATURE:
<223> OTHER INFORMATION: Synthetic

<400> SEQUENCE: 302
augccaagca gcggcccugc cacccaccua ucacugucga          40

<210> SEQ ID NO 303
<211> LENGTH: 40
<212> TYPE: RNA
<213> ORGANISM: Artificial Sequence
<220> FEATURE:
<223> OTHER INFORMATION: Synthetic

<400> SEQUENCE: 303
aacagaccaa gcagcggccc ugcucugcca ucauacgccu          40

<210> SEQ ID NO 304
<211> LENGTH: 40
<212> TYPE: RNA
<213> ORGANISM: Artificial Sequence
<220> FEATURE:
<223> OTHER INFORMATION: Synthetic

<400> SEQUENCE: 304
gacagaccaa gcagcggccc ugcucugcca ucauacgccu          40

<210> SEQ ID NO 305
<211> LENGTH: 40
<212> TYPE: RNA
<213> ORGANISM: Artificial Sequence
<220> FEATURE:
<223> OTHER INFORMATION: Synthetic

<400> SEQUENCE: 305
aacagaccaa gcaguggccc ugcucugcca ucauacgccu          40

<210> SEQ ID NO 306
<211> LENGTH: 40
<212> TYPE: RNA
<213> ORGANISM: Artificial Sequence
<220> FEATURE:
<223> OTHER INFORMATION: Synthetic

<400> SEQUENCE: 306
aacagaccaa gcagcggccc ugcucugcca ucauacgccc          40

<210> SEQ ID NO 307
<211> LENGTH: 40
<212> TYPE: RNA
```

```
<213> ORGANISM: Artificial Sequence
<220> FEATURE:
<223> OTHER INFORMATION: Synthetic

<400> SEQUENCE: 307
aacagaccaa gcagcggccc ugcucugcca ucauacaccu                   40

<210> SEQ ID NO 308
<211> LENGTH: 39
<212> TYPE: RNA
<213> ORGANISM: Artificial Sequence
<220> FEATURE:
<223> OTHER INFORMATION: Synthetic

<400> SEQUENCE: 308
acagaccaag cagcggcccu gcucugccau cauacgccu                    39

<210> SEQ ID NO 309
<211> LENGTH: 41
<212> TYPE: RNA
<213> ORGANISM: Artificial Sequence
<220> FEATURE:
<223> OTHER INFORMATION: Synthetic

<400> SEQUENCE: 309
aacagaccaa gcagcggccc ugcucugcca ucaucgccc u                  41

<210> SEQ ID NO 310
<211> LENGTH: 40
<212> TYPE: RNA
<213> ORGANISM: Artificial Sequence
<220> FEATURE:
<223> OTHER INFORMATION: Synthetic

<400> SEQUENCE: 310
gucauucgcu gacgaaucaa caugaauucc uaacugcuga                   40

<210> SEQ ID NO 311
<211> LENGTH: 39
<212> TYPE: RNA
<213> ORGANISM: Artificial Sequence
<220> FEATURE:
<223> OTHER INFORMATION: Synthetic

<400> SEQUENCE: 311
ucauucgcug acgaaucaac augaauuccu aacugcuga                    39

<210> SEQ ID NO 312
<211> LENGTH: 40
<212> TYPE: RNA
<213> ORGANISM: Artificial Sequence
<220> FEATURE:
<223> OTHER INFORMATION: Synthetic

<400> SEQUENCE: 312
gucauucgcu gacgaaucaa caugaauucc uaacugccga                   40

<210> SEQ ID NO 313
<211> LENGTH: 40
<212> TYPE: RNA
<213> ORGANISM: Artificial Sequence
<220> FEATURE:
<223> OTHER INFORMATION: Synthetic

<400> SEQUENCE: 313
gucauucgcu gacgaaucaa caugaauucc uaacugcugg                   40
```

<210> SEQ ID NO 314
<211> LENGTH: 40
<212> TYPE: RNA
<213> ORGANISM: Artificial Sequence
<220> FEATURE:
<223> OTHER INFORMATION: Synthetic

<400> SEQUENCE: 314
acacgccaag cugguagccc cagccgugcc cauuacggcc                           40

<210> SEQ ID NO 315
<211> LENGTH: 39
<212> TYPE: RNA
<213> ORGANISM: Artificial Sequence
<220> FEATURE:
<223> OTHER INFORMATION: Synthetic

<400> SEQUENCE: 315
acacgccaag cugguagccc cagccgugcc cauuacggc                            39

<210> SEQ ID NO 316
<211> LENGTH: 40
<212> TYPE: RNA
<213> ORGANISM: Artificial Sequence
<220> FEATURE:
<223> OTHER INFORMATION: Synthetic

<400> SEQUENCE: 316
acacgccaag cugguagccc cagccgugcc cauuacgguc                           40

<210> SEQ ID NO 317
<211> LENGTH: 40
<212> TYPE: RNA
<213> ORGANISM: Artificial Sequence
<220> FEATURE:
<223> OTHER INFORMATION: Synthetic

<400> SEQUENCE: 317
acacgccaag cugguagccc cagccguacc cauuacggcc                           40

<210> SEQ ID NO 318
<211> LENGTH: 40
<212> TYPE: RNA
<213> ORGANISM: Artificial Sequence
<220> FEATURE:
<223> OTHER INFORMATION: Synthetic

<400> SEQUENCE: 318
uagccaagca gcagcccugc caacccaucc uacccgggcg                           40

<210> SEQ ID NO 319
<211> LENGTH: 39
<212> TYPE: RNA
<213> ORGANISM: Artificial Sequence
<220> FEATURE:
<223> OTHER INFORMATION: Synthetic

<400> SEQUENCE: 319
uagccaagca gcagcccugc caacccaucc uacccggcg                            39

<210> SEQ ID NO 320
<211> LENGTH: 40
<212> TYPE: RNA
<213> ORGANISM: Artificial Sequence
<220> FEATURE:

<223> OTHER INFORMATION: Synthetic

<400> SEQUENCE: 320
uagccaagca gcagcccugc caacccaucc uacccgggca                         40

<210> SEQ ID NO 321
<211> LENGTH: 40
<212> TYPE: RNA
<213> ORGANISM: Artificial Sequence
<220> FEATURE:
<223> OTHER INFORMATION: Synthetic

<400> SEQUENCE: 321
uagccaagca gcagcccugc caacccaucc uacccgggug                         40

<210> SEQ ID NO 322
<211> LENGTH: 40
<212> TYPE: RNA
<213> ORGANISM: Artificial Sequence
<220> FEATURE:
<223> OTHER INFORMATION: Synthetic

<400> SEQUENCE: 322
uagccaagca gcggcccugc caacccaucc uacccgggcg                         40

<210> SEQ ID NO 323
<211> LENGTH: 40
<212> TYPE: RNA
<213> ORGANISM: Artificial Sequence
<220> FEATURE:
<223> OTHER INFORMATION: Synthetic

<400> SEQUENCE: 323
gcccaaggcg aggcccgccg cuccauccag acgcugaggg                         40

<210> SEQ ID NO 324
<211> LENGTH: 39
<212> TYPE: RNA
<213> ORGANISM: Artificial Sequence
<220> FEATURE:
<223> OTHER INFORMATION: Synthetic

<400> SEQUENCE: 324
gcccaaggcg aggcccgccg cuccauccag acgcugagg                          39

<210> SEQ ID NO 325
<211> LENGTH: 39
<212> TYPE: RNA
<213> ORGANISM: Artificial Sequence
<220> FEATURE:
<223> OTHER INFORMATION: Synthetic

<400> SEQUENCE: 325
cccaaggcga ggcccgccgc uccauccaga cgcugaggg                          39

<210> SEQ ID NO 326
<211> LENGTH: 38
<212> TYPE: RNA
<213> ORGANISM: Artificial Sequence
<220> FEATURE:
<223> OTHER INFORMATION: Synthetic

<400> SEQUENCE: 326
cccaaggcga ggcccgccgc uccauccaga cgcugagg                           38

```
<210> SEQ ID NO 327
<211> LENGTH: 40
<212> TYPE: RNA
<213> ORGANISM: Artificial Sequence
<220> FEATURE:
<223> OTHER INFORMATION: Synthetic

<400> SEQUENCE: 327
gcccaaggcg aggcccgccg cuccauccag acgcugaggc                    40

<210> SEQ ID NO 328
<211> LENGTH: 41
<212> TYPE: RNA
<213> ORGANISM: Artificial Sequence
<220> FEATURE:
<223> OTHER INFORMATION: Synthetic

<400> SEQUENCE: 328
gcccaaaggc gaggcccgcc gcuccaucca gacgcugagg g                  41

<210> SEQ ID NO 329
<211> LENGTH: 40
<212> TYPE: RNA
<213> ORGANISM: Artificial Sequence
<220> FEATURE:
<223> OTHER INFORMATION: Synthetic

<400> SEQUENCE: 329
gcccaaggcg aggcccgccg cuccauccag acgcugagga                    40

<210> SEQ ID NO 330
<211> LENGTH: 41
<212> TYPE: RNA
<213> ORGANISM: Artificial Sequence
<220> FEATURE:
<223> OTHER INFORMATION: Synthetic

<400> SEQUENCE: 330
gccccaaggc gaggcccgcc gcuccaucca gacgcugagg g                  41

<210> SEQ ID NO 331
<211> LENGTH: 40
<212> TYPE: RNA
<213> ORGANISM: Artificial Sequence
<220> FEATURE:
<223> OTHER INFORMATION: Synthetic

<400> SEQUENCE: 331
aagaucucgu caugcuuuga cgucaaucac cauuguuccc                    40

<210> SEQ ID NO 332
<211> LENGTH: 39
<212> TYPE: RNA
<213> ORGANISM: Artificial Sequence
<220> FEATURE:
<223> OTHER INFORMATION: Synthetic

<400> SEQUENCE: 332
aagaucucgu caugcuuuga cgucaaucac cauuguucc                     39

<210> SEQ ID NO 333
<211> LENGTH: 40
<212> TYPE: RNA
<213> ORGANISM: Artificial Sequence
<220> FEATURE:
<223> OTHER INFORMATION: Synthetic
```

<400> SEQUENCE: 333
aagaucucgu caugcuuuga cgccaaucac cauuguuccc          40

<210> SEQ ID NO 334
<211> LENGTH: 40
<212> TYPE: RNA
<213> ORGANISM: Artificial Sequence
<220> FEATURE:
<223> OTHER INFORMATION: Synthetic

<400> SEQUENCE: 334
aagaucucgu caugcuuuga cgucaaucac cauuguucca          40

<210> SEQ ID NO 335
<211> LENGTH: 40
<212> TYPE: RNA
<213> ORGANISM: Artificial Sequence
<220> FEATURE:
<223> OTHER INFORMATION: Synthetic

<400> SEQUENCE: 335
aagaucucgu caugcuuuga cgucaaucac cauuguuccu          40

<210> SEQ ID NO 336
<211> LENGTH: 41
<212> TYPE: RNA
<213> ORGANISM: Artificial Sequence
<220> FEATURE:
<223> OTHER INFORMATION: Synthetic

<400> SEQUENCE: 336
aagaucucgu caugcuuuga cgucaaucac cauuguuccc c          41

<210> SEQ ID NO 337
<211> LENGTH: 41
<212> TYPE: RNA
<213> ORGANISM: Artificial Sequence
<220> FEATURE:
<223> OTHER INFORMATION: Synthetic

<400> SEQUENCE: 337
aaagaucucg ucaugcuuug acgucaauca ccauuguucc c          41

<210> SEQ ID NO 338
<211> LENGTH: 40
<212> TYPE: RNA
<213> ORGANISM: Artificial Sequence
<220> FEATURE:
<223> OTHER INFORMATION: Synthetic

<400> SEQUENCE: 338
aagaucucgu caugccuuga cgucaaucac cauuguuccc          40

<210> SEQ ID NO 339
<211> LENGTH: 39
<212> TYPE: RNA
<213> ORGANISM: Artificial Sequence
<220> FEATURE:
<223> OTHER INFORMATION: Synthetic

<400> SEQUENCE: 339 auccccagg augagcacgu ugccauggac uggcuaucc          39

<210> SEQ ID NO 340
<211> LENGTH: 38

```
<212> TYPE: RNA
<213> ORGANISM: Artificial Sequence
<220> FEATURE:
<223> OTHER INFORMATION: Synthetic

<400> SEQUENCE: 340
auccccagga ugagcacguu gccauggacu ggcuaucc                        38

<210> SEQ ID NO 341
<211> LENGTH: 40
<212> TYPE: RNA
<213> ORGANISM: Artificial Sequence
<220> FEATURE:
<223> OTHER INFORMATION: Synthetic

<400> SEQUENCE: 341
cuguuacagu cucgcguaac cccccaucg auguccucga                        40

<210> SEQ ID NO 342
<211> LENGTH: 40
<212> TYPE: RNA
<213> ORGANISM: Artificial Sequence
<220> FEATURE:
<223> OTHER INFORMATION: Synthetic

<400> SEQUENCE: 342
cuguuacagu cucgcguaac cccccaucg auguccucgg                        40

<210> SEQ ID NO 343
<211> LENGTH: 40
<212> TYPE: RNA
<213> ORGANISM: Artificial Sequence
<220> FEATURE:
<223> OTHER INFORMATION: Synthetic

<400> SEQUENCE: 343
cuguuacagu cucgaguaac cccccaucg auguccucga                        40

<210> SEQ ID NO 344
<211> LENGTH: 40
<212> TYPE: RNA
<213> ORGANISM: Artificial Sequence
<220> FEATURE:
<223> OTHER INFORMATION: Synthetic

<400> SEQUENCE: 344
cuguuacagu cucgcguaac cccuccaucg auguccucga                        40

<210> SEQ ID NO 345
<211> LENGTH: 40
<212> TYPE: RNA
<213> ORGANISM: Artificial Sequence
<220> FEATURE:
<223> OTHER INFORMATION: Synthetic

<400> SEQUENCE: 345
cuguuacagc cucgcguaac cccccaucg auguccucga                        40

<210> SEQ ID NO 346
<211> LENGTH: 40
<212> TYPE: RNA
<213> ORGANISM: Artificial Sequence
<220> FEATURE:
<223> OTHER INFORMATION: Synthetic

<400> SEQUENCE: 346
```
cguuuacagu cucccguaac cccccaucg auguccucga          40

<210> SEQ ID NO 347
<211> LENGTH: 40
<212> TYPE: RNA
<213> ORGANISM: Artificial Sequence
<220> FEATURE:
<223> OTHER INFORMATION: Synthetic

<400> SEQUENCE: 347
agccagcuuu cggcaaaccg aauucacucc acccugcuca          40

<210> SEQ ID NO 348
<211> LENGTH: 40
<212> TYPE: RNA
<213> ORGANISM: Artificial Sequence
<220> FEATURE:
<223> OTHER INFORMATION: Synthetic

<400> SEQUENCE: 348
agccagcuuu cggcaaaccg aauucacucc acccuccuca          40

<210> SEQ ID NO 349
<211> LENGTH: 40
<212> TYPE: RNA
<213> ORGANISM: Artificial Sequence
<220> FEATURE:
<223> OTHER INFORMATION: Synthetic

<400> SEQUENCE: 349
agccagcuuu cggcaaaccg aauucacucc gcccugcuca          40

<210> SEQ ID NO 350
<211> LENGTH: 38
<212> TYPE: RNA
<213> ORGANISM: Artificial Sequence
<220> FEATURE:
<223> OTHER INFORMATION: Synthetic

<400> SEQUENCE: 350
agccagcuuu cggcaaaccg aauucacucc acccugcu          38

<210> SEQ ID NO 351
<211> LENGTH: 40
<212> TYPE: RNA
<213> ORGANISM: Artificial Sequence
<220> FEATURE:
<223> OTHER INFORMATION: Synthetic

<400> SEQUENCE: 351
agccagcuuu cggcgaaccg aauucacucc acccugcuca          40

<210> SEQ ID NO 352
<211> LENGTH: 40
<212> TYPE: RNA
<213> ORGANISM: Artificial Sequence
<220> FEATURE:
<223> OTHER INFORMATION: Synthetic

<400> SEQUENCE: 352
agccagcuuu cggcaaaccg aauucacucc acccugcucg          40

<210> SEQ ID NO 353
<211> LENGTH: 39
<212> TYPE: RNA
<213> ORGANISM: Artificial Sequence

```
<220> FEATURE:
<223> OTHER INFORMATION: Synthetic

<400> SEQUENCE: 353
agccagcuuu cggcaaaccg aauucacucc acccugcuc                               39

<210> SEQ ID NO 354
<211> LENGTH: 40
<212> TYPE: RNA
<213> ORGANISM: Artificial Sequence
<220> FEATURE:
<223> OTHER INFORMATION: Synthetic

<400> SEQUENCE: 354
agccagcuuu cggcaaaccg aauucacucc acccugcaca                              40

<210> SEQ ID NO 355
<211> LENGTH: 40
<212> TYPE: RNA
<213> ORGANISM: Artificial Sequence
<220> FEATURE:
<223> OTHER INFORMATION: Synthetic

<400> SEQUENCE: 355
cacgguauaa ccuccucaua uaccugcugu gccacccgcg                              40

<210> SEQ ID NO 356
<211> LENGTH: 40
<212> TYPE: RNA
<213> ORGANISM: Artificial Sequence
<220> FEATURE:
<223> OTHER INFORMATION: Synthetic

<400> SEQUENCE: 356
cacgguauaa ccuccucaua uaccugcugu gccacccgca                              40

<210> SEQ ID NO 357
<211> LENGTH: 41
<212> TYPE: RNA
<213> ORGANISM: Artificial Sequence
<220> FEATURE:
<223> OTHER INFORMATION: Synthetic

<400> SEQUENCE: 357
cacgguauaa ccuccucaua uaccugcugu gccacccacc g                            41

<210> SEQ ID NO 358
<211> LENGTH: 40
<212> TYPE: RNA
<213> ORGANISM: Artificial Sequence
<220> FEATURE:
<223> OTHER INFORMATION: Synthetic

<400> SEQUENCE: 358
cacgguauaa ccuccucaua uaccugcugu gccacccgcu                              40

<210> SEQ ID NO 359
<211> LENGTH: 40
<212> TYPE: RNA
<213> ORGANISM: Artificial Sequence
<220> FEATURE:
<223> OTHER INFORMATION: Synthetic

<400> SEQUENCE: 359
cacgguauaa ccuccucaua uaccugcugu gccacccacg                              40
```

<210> SEQ ID NO 360
<211> LENGTH: 40
<212> TYPE: RNA
<213> ORGANISM: Artificial Sequence
<220> FEATURE:
<223> OTHER INFORMATION: Synthetic

<400> SEQUENCE: 360
cacgguauaa ccuccucaua uaccugcugu gccacccgug          40

<210> SEQ ID NO 361
<211> LENGTH: 40
<212> TYPE: RNA
<213> ORGANISM: Artificial Sequence
<220> FEATURE:
<223> OTHER INFORMATION: Synthetic

<400> SEQUENCE: 361
cacgguauaa ccuccucaua uaccugcugu gccgcccgcg          40

<210> SEQ ID NO 362
<211> LENGTH: 40
<212> TYPE: RNA
<213> ORGANISM: Artificial Sequence
<220> FEATURE:
<223> OTHER INFORMATION: Synthetic

<400> SEQUENCE: 362
ccggaagauc ugcucgcacu agccggagcc caaucacggc          40

<210> SEQ ID NO 363
<211> LENGTH: 40
<212> TYPE: RNA
<213> ORGANISM: Artificial Sequence
<220> FEATURE:
<223> OTHER INFORMATION: Synthetic

<400> SEQUENCE: 363
ccggaagauc ugcucgcacu agucggagcc caaucacggc          40

<210> SEQ ID NO 364
<211> LENGTH: 40
<212> TYPE: RNA
<213> ORGANISM: Artificial Sequence
<220> FEATURE:
<223> OTHER INFORMATION: Synthetic

<400> SEQUENCE: 364
ccggaggauc ugcucgcacu agccggagcc caaucacggc          40

<210> SEQ ID NO 365
<211> LENGTH: 40
<212> TYPE: RNA
<213> ORGANISM: Artificial Sequence
<220> FEATURE:
<223> OTHER INFORMATION: Synthetic

<400> SEQUENCE: 365
ccggaagauc ugcucgcauu agccggagcc caaucacggc          40

<210> SEQ ID NO 366
<211> LENGTH: 40
<212> TYPE: RNA
<213> ORGANISM: Artificial Sequence
<220> FEATURE:
<223> OTHER INFORMATION: Synthetic

<400> SEQUENCE: 366
ccugccgaac ggcuaagucg cagcccgacc cgcggcaggg          40

<210> SEQ ID NO 367
<211> LENGTH: 39
<212> TYPE: RNA
<213> ORGANISM: Artificial Sequence
<220> FEATURE:
<223> OTHER INFORMATION: Synthetic

<400> SEQUENCE: 367
ccugccgaac ggcuaagucg cagcccgacc cgcggcagg           39

<210> SEQ ID NO 368
<211> LENGTH: 40
<212> TYPE: RNA
<213> ORGANISM: Artificial Sequence
<220> FEATURE:
<223> OTHER INFORMATION: Synthetic

<400> SEQUENCE: 368
ccugccgaac ggcuaagucg cagcccgacc cgcggcagga          40

<210> SEQ ID NO 369
<211> LENGTH: 40
<212> TYPE: RNA
<213> ORGANISM: Artificial Sequence
<220> FEATURE:
<223> OTHER INFORMATION: Synthetic

<400> SEQUENCE: 369
ccugccgaac ggccaagucg cagcccgacc cgcggcaggg          40

<210> SEQ ID NO 370
<211> LENGTH: 40
<212> TYPE: RNA
<213> ORGANISM: Artificial Sequence
<220> FEATURE:
<223> OTHER INFORMATION: Synthetic

<400> SEQUENCE: 370
ccugccgaac ggcuaagucg cggcccgacc cgcggcaggg          40

<210> SEQ ID NO 371
<211> LENGTH: 40
<212> TYPE: RNA
<213> ORGANISM: Artificial Sequence
<220> FEATURE:
<223> OTHER INFORMATION: Synthetic

<400> SEQUENCE: 371
cuccgacccg cggacgaagu caacuuccac agucccacac          40

<210> SEQ ID NO 372
<211> LENGTH: 40
<212> TYPE: RNA
<213> ORGANISM: Artificial Sequence
<220> FEATURE:
<223> OTHER INFORMATION: Synthetic

<400> SEQUENCE: 372
cuccgacccg cggacgaagu caacuuccac agucccacaa          40

<210> SEQ ID NO 373

```
<211> LENGTH: 42
<212> TYPE: RNA
<213> ORGANISM: Artificial Sequence
<220> FEATURE:
<223> OTHER INFORMATION: Synthetic

<400> SEQUENCE: 373
cuccgacccg cggacgaagu caacuuccac agucccacac ac                    42

<210> SEQ ID NO 374
<211> LENGTH: 40
<212> TYPE: RNA
<213> ORGANISM: Artificial Sequence
<220> FEATURE:
<223> OTHER INFORMATION: Synthetic

<400> SEQUENCE: 374
cuccgacccg cggacgaagu caacuuccac agucucacac                       40

<210> SEQ ID NO 375
<211> LENGTH: 40
<212> TYPE: RNA
<213> ORGANISM: Artificial Sequence
<220> FEATURE:
<223> OTHER INFORMATION: Synthetic

<400> SEQUENCE: 375
cuccgacccg cggacgaagu caacuuccac agucccacau                       40

<210> SEQ ID NO 376
<211> LENGTH: 40
<212> TYPE: RNA
<213> ORGANISM: Artificial Sequence
<220> FEATURE:
<223> OTHER INFORMATION: Synthetic

<400> SEQUENCE: 376
cuccgacccg cggacgaagu caacuuccac agucccgcac                       40

<210> SEQ ID NO 377
<211> LENGTH: 40
<212> TYPE: RNA
<213> ORGANISM: Artificial Sequence
<220> FEATURE:
<223> OTHER INFORMATION: Synthetic

<400> SEQUENCE: 377
cuccgacccg cggacgaagu caacuuccac ggucccacac                       40

<210> SEQ ID NO 378
<211> LENGTH: 40
<212> TYPE: RNA
<213> ORGANISM: Artificial Sequence
<220> FEATURE:
<223> OTHER INFORMATION: Synthetic

<400> SEQUENCE: 378
cuccgacccg cggacgaagu caacuuccac agucccauac                       40

<210> SEQ ID NO 379
<211> LENGTH: 40
<212> TYPE: RNA
<213> ORGANISM: Artificial Sequence
<220> FEATURE:
<223> OTHER INFORMATION: Synthetic

<400> SEQUENCE: 379
```

```
acauuaggau cugcgugaug gggaucaccc gcuacauguc                    40

<210> SEQ ID NO 380
<211> LENGTH: 41
<212> TYPE: RNA
<213> ORGANISM: Artificial Sequence
<220> FEATURE:
<223> OTHER INFORMATION: Synthetic

<400> SEQUENCE: 380
acauuuagga ucugcgugau ggggaucacc cgcuacaugu c                 41

<210> SEQ ID NO 381
<211> LENGTH: 40
<212> TYPE: RNA
<213> ORGANISM: Artificial Sequence
<220> FEATURE:
<223> OTHER INFORMATION: Synthetic

<400> SEQUENCE: 381
gcauuaggau cugcgugaug gggaucaccc gcuacauguc                    40

<210> SEQ ID NO 382
<211> LENGTH: 40
<212> TYPE: RNA
<213> ORGANISM: Artificial Sequence
<220> FEATURE:
<223> OTHER INFORMATION: Synthetic

<400> SEQUENCE: 382
acauuaggau cugcgcgaug gggaucaccc gcuacauguc                    40

<210> SEQ ID NO 383
<211> LENGTH: 40
<212> TYPE: RNA
<213> ORGANISM: Artificial Sequence
<220> FEATURE:
<223> OTHER INFORMATION: Synthetic

<400> SEQUENCE: 383
ucuaagaugg ggaagaucuc cggagcaccg ggcaaucacc                    40

<210> SEQ ID NO 384
<211> LENGTH: 41
<212> TYPE: RNA
<213> ORGANISM: Artificial Sequence
<220> FEATURE:
<223> OTHER INFORMATION: Synthetic

<400> SEQUENCE: 384
ucuaagaugg ggaagaucuc cggagcaccg ggcaaucacc c                  41

<210> SEQ ID NO 385
<211> LENGTH: 40
<212> TYPE: RNA
<213> ORGANISM: Artificial Sequence
<220> FEATURE:
<223> OTHER INFORMATION: Synthetic

<400> SEQUENCE: 385
ccuaagaugg ggaagaucuc cggagcaccg ggcaaucacc                    40

<210> SEQ ID NO 386
<211> LENGTH: 40
<212> TYPE: RNA
```

```
<213> ORGANISM: Artificial Sequence
<220> FEATURE:
<223> OTHER INFORMATION: Synthetic

<400> SEQUENCE: 386
ucuaaggugg ggaagaucuc cggagcaccg ggcaaucacc                                40

<210> SEQ ID NO 387
<211> LENGTH: 40
<212> TYPE: RNA
<213> ORGANISM: Artificial Sequence
<220> FEATURE:
<223> OTHER INFORMATION: Synthetic

<400> SEQUENCE: 387
ucuaagaugg ggaagaucuc cggagcgccg ggcaaucacc                                40

<210> SEQ ID NO 388
<211> LENGTH: 38
<212> TYPE: RNA
<213> ORGANISM: Artificial Sequence
<220> FEATURE:
<223> OTHER INFORMATION: Synthetic

<400> SEQUENCE: 388
cuauucgagu ucccacgaau cccccaucga gaaccuac                                  38

<210> SEQ ID NO 389
<211> LENGTH: 38
<212> TYPE: RNA
<213> ORGANISM: Artificial Sequence
<220> FEATURE:
<223> OTHER INFORMATION: Synthetic

<400> SEQUENCE: 389
cuauucgagu ucccacgaau ccccccauca gaaccuac                                  38

<210> SEQ ID NO 390
<211> LENGTH: 38
<212> TYPE: RNA
<213> ORGANISM: Artificial Sequence
<220> FEATURE:
<223> OTHER INFORMATION: Synthetic

<400> SEQUENCE: 390
cuacucgagu ucccacgaau cccccaucga gaaccuac                                  38

<210> SEQ ID NO 391
<211> LENGTH: 38
<212> TYPE: RNA
<213> ORGANISM: Artificial Sequence
<220> FEATURE:
<223> OTHER INFORMATION: Synthetic

<400> SEQUENCE: 391
cuauucgagu ucccacgaau cccccaucaa gaaccuac                                  38

<210> SEQ ID NO 392
<211> LENGTH: 40
<212> TYPE: RNA
<213> ORGANISM: Artificial Sequence
<220> FEATURE:
<223> OTHER INFORMATION: Synthetic

<400> SEQUENCE: 392
ugccaagccg aggcccggcc agcaucccuc acgagagagg                                40
```

<210> SEQ ID NO 393
<211> LENGTH: 41
<212> TYPE: RNA
<213> ORGANISM: Artificial Sequence
<220> FEATURE:
<223> OTHER INFORMATION: Synthetic

<400> SEQUENCE: 393
ugccaaagcc gaggcccggc cagcaucccu cacgagagag g                 41

<210> SEQ ID NO 394
<211> LENGTH: 40
<212> TYPE: RNA
<213> ORGANISM: Artificial Sequence
<220> FEATURE:
<223> OTHER INFORMATION: Synthetic

<400> SEQUENCE: 394
ugccaagccg aggcccggcc agcaucccuc acgagagagc                   40

<210> SEQ ID NO 395
<211> LENGTH: 39
<212> TYPE: RNA
<213> ORGANISM: Artificial Sequence
<220> FEATURE:
<223> OTHER INFORMATION: Synthetic

<400> SEQUENCE: 395
ugccaagccg aggcccggcc agcaucccuc acgagagag                    39

<210> SEQ ID NO 396
<211> LENGTH: 40
<212> TYPE: RNA
<213> ORGANISM: Artificial Sequence
<220> FEATURE:
<223> OTHER INFORMATION: Synthetic

<400> SEQUENCE: 396
ugccaagccg aggcccggcc agcauccccc acgagagagg                   40

<210> SEQ ID NO 397
<211> LENGTH: 40
<212> TYPE: RNA
<213> ORGANISM: Artificial Sequence
<220> FEATURE:
<223> OTHER INFORMATION: Synthetic

<400> SEQUENCE: 397
ugccaagccg aggcccggcc agcaucccuc acgagagaga                   40

<210> SEQ ID NO 398
<211> LENGTH: 40
<212> TYPE: RNA
<213> ORGANISM: Artificial Sequence
<220> FEATURE:
<223> OTHER INFORMATION: Synthetic

<400> SEQUENCE: 398
ugccaagccg gggcccggcc agcaucccuc acgagagagg                   40

<210> SEQ ID NO 399
<211> LENGTH: 39
<212> TYPE: RNA
<213> ORGANISM: Artificial Sequence
<220> FEATURE:

<223> OTHER INFORMATION: Synthetic

<400> SEQUENCE: 399
ugccaagccg aggcccggcc agcaucccuc acgagaggg                    39

<210> SEQ ID NO 400
<211> LENGTH: 40
<212> TYPE: RNA
<213> ORGANISM: Artificial Sequence
<220> FEATURE:
<223> OTHER INFORMATION: Synthetic

<400> SEQUENCE: 400
gccaagcacg uagcccgugc ccccacccgc cugugugcug                   40

<210> SEQ ID NO 401
<211> LENGTH: 39
<212> TYPE: RNA
<213> ORGANISM: Artificial Sequence
<220> FEATURE:
<223> OTHER INFORMATION: Synthetic

<400> SEQUENCE: 401
ccaagcacgu agcccgugcc cccacccgcc ugugugcug                    39

<210> SEQ ID NO 402
<211> LENGTH: 40
<212> TYPE: RNA
<213> ORGANISM: Artificial Sequence
<220> FEATURE:
<223> OTHER INFORMATION: Synthetic

<400> SEQUENCE: 402
gccaagcacg uagcccgugc ccccacccgc cugugugcgg                   40

<210> SEQ ID NO 403
<211> LENGTH: 40
<212> TYPE: RNA
<213> ORGANISM: Artificial Sequence
<220> FEATURE:
<223> OTHER INFORMATION: Synthetic

<400> SEQUENCE: 403
gccaagcacg uagcccgugc ccccacccac cugugugcug                   40

<210> SEQ ID NO 404
<211> LENGTH: 40
<212> TYPE: RNA
<213> ORGANISM: Artificial Sequence
<220> FEATURE:
<223> OTHER INFORMATION: Synthetic

<400> SEQUENCE: 404
gccaagcacg uagcccgugc ccccacccgc cugugugcuc                   40

<210> SEQ ID NO 405
<211> LENGTH: 40
<212> TYPE: RNA
<213> ORGANISM: Artificial Sequence
<220> FEATURE:
<223> OTHER INFORMATION: Synthetic

<400> SEQUENCE: 405
gccaagcacg uagcccgugc ccccacccgc cugugugccg                   40

<210> SEQ ID NO 406
<211> LENGTH: 41
<212> TYPE: RNA
<213> ORGANISM: Artificial Sequence
<220> FEATURE:
<223> OTHER INFORMATION: Synthetic

<400> SEQUENCE: 406
gccaaagcac guagcccgug cccccacccg ccugugugcu g          41

<210> SEQ ID NO 407
<211> LENGTH: 40
<212> TYPE: RNA
<213> ORGANISM: Artificial Sequence
<220> FEATURE:
<223> OTHER INFORMATION: Synthetic

<400> SEQUENCE: 407
gccaagcacg uagcccgugc ccccacccgc cugugugcua            40

<210> SEQ ID NO 408
<211> LENGTH: 40
<212> TYPE: RNA
<213> ORGANISM: Artificial Sequence
<220> FEATURE:
<223> OTHER INFORMATION: Synthetic

<400> SEQUENCE: 408
ugccaagcac gaagcccgug cccccaucca gagugugaga            40

<210> SEQ ID NO 409
<211> LENGTH: 41
<212> TYPE: RNA
<213> ORGANISM: Artificial Sequence
<220> FEATURE:
<223> OTHER INFORMATION: Synthetic

<400> SEQUENCE: 409
ugccaaagca cgaagcccgu gcccccaucc agagugugag a          41

<210> SEQ ID NO 410
<211> LENGTH: 40
<212> TYPE: RNA
<213> ORGANISM: Artificial Sequence
<220> FEATURE:
<223> OTHER INFORMATION: Synthetic

<400> SEQUENCE: 410
ugccaagcac gaagcccgug cccccaucca gaguguggga            40

<210> SEQ ID NO 411
<211> LENGTH: 40
<212> TYPE: RNA
<213> ORGANISM: Artificial Sequence
<220> FEATURE:
<223> OTHER INFORMATION: Synthetic

<400> SEQUENCE: 411
ugccaagcac gaggcccgug cccccaucca gagugugaga            40

<210> SEQ ID NO 412
<211> LENGTH: 40
<212> TYPE: RNA
<213> ORGANISM: Artificial Sequence
<220> FEATURE:
<223> OTHER INFORMATION: Synthetic

```
<400> SEQUENCE: 412
ugccaagcac gaagcccgug cccccauuca gagugugaga                              40

<210> SEQ ID NO 413
<211> LENGTH: 40
<212> TYPE: RNA
<213> ORGANISM: Artificial Sequence
<220> FEATURE:
<223> OTHER INFORMATION: Synthetic

<400> SEQUENCE: 413
ugccaagcac gaagcccgug cccccaucca gagugcgaga                              40

<210> SEQ ID NO 414
<211> LENGTH: 40
<212> TYPE: RNA
<213> ORGANISM: Artificial Sequence
<220> FEATURE:
<223> OTHER INFORMATION: Synthetic

<400> SEQUENCE: 414
ugccaagcac gaagcccgug cccccaucca gagcgugaga                              40

<210> SEQ ID NO 415
<211> LENGTH: 40
<212> TYPE: RNA
<213> ORGANISM: Artificial Sequence
<220> FEATURE:
<223> OTHER INFORMATION: Synthetic

<400> SEQUENCE: 415
ugccaagcac gaagcccgug cccccaucca gagugugagg                              40

<210> SEQ ID NO 416
<211> LENGTH: 40
<212> TYPE: RNA
<213> ORGANISM: Artificial Sequence
<220> FEATURE:
<223> OTHER INFORMATION: Synthetic

<400> SEQUENCE: 416
ugccaagcac gaagcccgug cccccaucca gggugugaga                              40

<210> SEQ ID NO 417
<211> LENGTH: 42
<212> TYPE: RNA
<213> ORGANISM: Artificial Sequence
<220> FEATURE:
<223> OTHER INFORMATION: Synthetic

<400> SEQUENCE: 417
agccagcuuu ugcauaccac gugcaauuca cuccacccgu ca                          42

<210> SEQ ID NO 418
<211> LENGTH: 42
<212> TYPE: RNA
<213> ORGANISM: Artificial Sequence
<220> FEATURE:
<223> OTHER INFORMATION: Synthetic

<400> SEQUENCE: 418
agccagcuuu gccauaccac gugcaauuca cuccacccgu ca                          42

<210> SEQ ID NO 419
<211> LENGTH: 42
```

```
<212> TYPE: RNA
<213> ORGANISM: Artificial Sequence
<220> FEATURE:
<223> OTHER INFORMATION: Synthetic

<400> SEQUENCE: 419
agccagccuu ugcauaccac gugcaauuca cuccacccgu ca          42

<210> SEQ ID NO 420
<211> LENGTH: 42
<212> TYPE: RNA
<213> ORGANISM: Artificial Sequence
<220> FEATURE:
<223> OTHER INFORMATION: Synthetic

<400> SEQUENCE: 420
agccagcuuu ugcauaccac gugcaauuca cuccacccgu cg          42

<210> SEQ ID NO 421
<211> LENGTH: 42
<212> TYPE: RNA
<213> ORGANISM: Artificial Sequence
<220> FEATURE:
<223> OTHER INFORMATION: Synthetic

<400> SEQUENCE: 421
agccagcuuu ugcacaccac gugcaauuca cuccacccgu ca          42

<210> SEQ ID NO 422
<211> LENGTH: 42
<212> TYPE: RNA
<213> ORGANISM: Artificial Sequence
<220> FEATURE:
<223> OTHER INFORMATION: Synthetic

<400> SEQUENCE: 422
agccaagcuu ugcauaccac gugcaauuca cuccacccgu ca          42

<210> SEQ ID NO 423
<211> LENGTH: 40
<212> TYPE: RNA
<213> ORGANISM: Artificial Sequence
<220> FEATURE:
<223> OTHER INFORMATION: Synthetic

<400> SEQUENCE: 423
cuuuguaaac ccggcaaaca aaaucaacuu ccaucaucaa             40

<210> SEQ ID NO 424
<211> LENGTH: 40
<212> TYPE: RNA
<213> ORGANISM: Artificial Sequence
<220> FEATURE:
<223> OTHER INFORMATION: Synthetic

<400> SEQUENCE: 424
cuuuguaaac ccggcaaaca aaaucaacuu ccaucaccaa             40

<210> SEQ ID NO 425
<211> LENGTH: 40
<212> TYPE: RNA
<213> ORGANISM: Artificial Sequence
<220> FEATURE:
<223> OTHER INFORMATION: Synthetic

<400> SEQUENCE: 425
```
ccauuguagc gaccacacaa uuccccaucg gacagcaugg         40

<210> SEQ ID NO 426
<211> LENGTH: 39
<212> TYPE: RNA
<213> ORGANISM: Artificial Sequence
<220> FEATURE:
<223> OTHER INFORMATION: Synthetic

<400> SEQUENCE: 426
ccauuguagc gaccacacaa uuccccaucg gacagcaug          39

<210> SEQ ID NO 427
<211> LENGTH: 40
<212> TYPE: RNA
<213> ORGANISM: Artificial Sequence
<220> FEATURE:
<223> OTHER INFORMATION: Synthetic

<400> SEQUENCE: 427
ccauuguagc gaccacacaa uuccccaucg gacagcgugg         40

<210> SEQ ID NO 428
<211> LENGTH: 40
<212> TYPE: RNA
<213> ORGANISM: Artificial Sequence
<220> FEATURE:
<223> OTHER INFORMATION: Synthetic

<400> SEQUENCE: 428
ccauuguagc gaccacacaa uuccccaucg gacagcacgg         40

<210> SEQ ID NO 429
<211> LENGTH: 40
<212> TYPE: RNA
<213> ORGANISM: Artificial Sequence
<220> FEATURE:
<223> OTHER INFORMATION: Synthetic

<400> SEQUENCE: 429
ccauuguagc gaccacacaa uuccccaucg gacagcaugc         40

<210> SEQ ID NO 430
<211> LENGTH: 40
<212> TYPE: RNA
<213> ORGANISM: Artificial Sequence
<220> FEATURE:
<223> OTHER INFORMATION: Synthetic

<400> SEQUENCE: 430
ccauuguagc gaccacacaa uuccccaucg gacagcaugg         40

<210> SEQ ID NO 431
<211> LENGTH: 40
<212> TYPE: RNA
<213> ORGANISM: Artificial Sequence
<220> FEATURE:
<223> OTHER INFORMATION: Synthetic

<400> SEQUENCE: 431
ccauuguagc gaccacacaa uuccccaucg gacagcaugu         40

<210> SEQ ID NO 432
<211> LENGTH: 40
<212> TYPE: RNA
<213> ORGANISM: Artificial Sequence

```
<220> FEATURE:
<223> OTHER INFORMATION: Synthetic

<400> SEQUENCE: 432
cucucgccgu ucccaggcac gacaaaauca acuucccgcu                              40

<210> SEQ ID NO 433
<211> LENGTH: 40
<212> TYPE: RNA
<213> ORGANISM: Artificial Sequence
<220> FEATURE:
<223> OTHER INFORMATION: Synthetic

<400> SEQUENCE: 433
cucucgccgu ucccaggcgc gacaaaauca acuucccgcu                              40

<210> SEQ ID NO 434
<211> LENGTH: 40
<212> TYPE: RNA
<213> ORGANISM: Artificial Sequence
<220> FEATURE:
<223> OTHER INFORMATION: Synthetic

<400> SEQUENCE: 434
cucucgccgu ucccgggcac gacaaaauca acuucccgcu                              40

<210> SEQ ID NO 435
<211> LENGTH: 40
<212> TYPE: RNA
<213> ORGANISM: Artificial Sequence
<220> FEATURE:
<223> OTHER INFORMATION: Synthetic

<400> SEQUENCE: 435
cucucgccgu ucccaggcac gacaaaauca acuucccgca                              40

<210> SEQ ID NO 436
<211> LENGTH: 40
<212> TYPE: RNA
<213> ORGANISM: Artificial Sequence
<220> FEATURE:
<223> OTHER INFORMATION: Synthetic

<400> SEQUENCE: 436
aagccaagcc gcggcccggc cuucccaugu gcuacuagag                              40

<210> SEQ ID NO 437
<211> LENGTH: 41
<212> TYPE: RNA
<213> ORGANISM: Artificial Sequence
<220> FEATURE:
<223> OTHER INFORMATION: Synthetic

<400> SEQUENCE: 437
aaagccaagc cgcggcccgg ccuucccaug ugcuacuaga g                            41

<210> SEQ ID NO 438
<211> LENGTH: 41
<212> TYPE: RNA
<213> ORGANISM: Artificial Sequence
<220> FEATURE:
<223> OTHER INFORMATION: Synthetic

<400> SEQUENCE: 438
aagccaaagc cgcggcccgg ccuucccaug ugcuacuaga g                            41
```

<210> SEQ ID NO 439
<211> LENGTH: 40
<212> TYPE: RNA
<213> ORGANISM: Artificial Sequence
<220> FEATURE:
<223> OTHER INFORMATION: Synthetic

<400> SEQUENCE: 439
gagccaagcc gcggcccggc cuucccaugu gcuacuagag        40

<210> SEQ ID NO 440
<211> LENGTH: 39
<212> TYPE: RNA
<213> ORGANISM: Artificial Sequence
<220> FEATURE:
<223> OTHER INFORMATION: Synthetic

<400> SEQUENCE: 440
agccaagccg cggcccggcc uucccaugug cuacuagag        39

<210> SEQ ID NO 441
<211> LENGTH: 40
<212> TYPE: RNA
<213> ORGANISM: Artificial Sequence
<220> FEATURE:
<223> OTHER INFORMATION: Synthetic

<400> SEQUENCE: 441
aagccaagcc guggcccggc cuucccaugu gcuacuagag        40

<210> SEQ ID NO 442
<211> LENGTH: 39
<212> TYPE: RNA
<213> ORGANISM: Artificial Sequence
<220> FEATURE:
<223> OTHER INFORMATION: Synthetic

<400> SEQUENCE: 442
ugccaagccg cggcccggcc uucccaugug cuacuagag        39

<210> SEQ ID NO 443
<211> LENGTH: 40
<212> TYPE: RNA
<213> ORGANISM: Artificial Sequence
<220> FEATURE:
<223> OTHER INFORMATION: Synthetic

<400> SEQUENCE: 443
aagccaagcc gaggcccggc cuucccaugu gcuacuagag        40

<210> SEQ ID NO 444
<211> LENGTH: 41
<212> TYPE: RNA
<213> ORGANISM: Artificial Sequence
<220> FEATURE:
<223> OTHER INFORMATION: Synthetic

<400> SEQUENCE: 444
ccaaaugcca aagccguagc ccggccagua gcccacacgu c        41

<210> SEQ ID NO 445
<211> LENGTH: 42
<212> TYPE: RNA
<213> ORGANISM: Artificial Sequence
<220> FEATURE:
<223> OTHER INFORMATION: Synthetic

<400> SEQUENCE: 445
ccaaaaugcc aaagccguag cccggccagu agcccacacg uc                42

<210> SEQ ID NO 446
<211> LENGTH: 41
<212> TYPE: RNA
<213> ORGANISM: Artificial Sequence
<220> FEATURE:
<223> OTHER INFORMATION: Synthetic

<400> SEQUENCE: 446
ccaaaugcca agcccguagc ccggccagua gcccacacgu c                 41

<210> SEQ ID NO 447
<211> LENGTH: 40
<212> TYPE: RNA
<213> ORGANISM: Artificial Sequence
<220> FEATURE:
<223> OTHER INFORMATION: Synthetic

<400> SEQUENCE: 447
ccauuacgcg acguaauucc cccaucguuu ccucguuaag                   40

<210> SEQ ID NO 448
<211> LENGTH: 40
<212> TYPE: RNA
<213> ORGANISM: Artificial Sequence
<220> FEATURE:
<223> OTHER INFORMATION: Synthetic

<400> SEQUENCE: 448
ccauuacgcg acguaauucc cccaucgucu ccucguuaag                   40

<210> SEQ ID NO 449
<211> LENGTH: 40
<212> TYPE: RNA
<213> ORGANISM: Artificial Sequence
<220> FEATURE:
<223> OTHER INFORMATION: Synthetic

<400> SEQUENCE: 449
ccauuacgcg acguaauucc cccaucgcuu ccucguuaag                   40

<210> SEQ ID NO 450
<211> LENGTH: 40
<212> TYPE: RNA
<213> ORGANISM: Artificial Sequence
<220> FEATURE:
<223> OTHER INFORMATION: Synthetic

<400> SEQUENCE: 450
ccauuacgcg gcguaauucc cccaucguuu ccucguuaag                   40

<210> SEQ ID NO 451
<211> LENGTH: 40
<212> TYPE: RNA
<213> ORGANISM: Artificial Sequence
<220> FEATURE:
<223> OTHER INFORMATION: Synthetic

<400> SEQUENCE: 451
ccauuacgcg acguaauucc cccaucguuu ccucguuagg                   40

<210> SEQ ID NO 452

```
<211> LENGTH: 40
<212> TYPE: RNA
<213> ORGANISM: Artificial Sequence
<220> FEATURE:
<223> OTHER INFORMATION: Synthetic

<400> SEQUENCE: 452
ccauuacgcg acguaauucc cccaucguuu ccucgcuaag                              40

<210> SEQ ID NO 453
<211> LENGTH: 40
<212> TYPE: RNA
<213> ORGANISM: Artificial Sequence
<220> FEATURE:
<223> OTHER INFORMATION: Synthetic

<400> SEQUENCE: 453
ccauuacgcg acguaauucc cccaucguuu ccucguuaug                              40

<210> SEQ ID NO 454
<211> LENGTH: 40
<212> TYPE: RNA
<213> ORGANISM: Artificial Sequence
<220> FEATURE:
<223> OTHER INFORMATION: Synthetic

<400> SEQUENCE: 454
ccauuacgcg acguaauucc cccaucguuu ccucguuaaa                              40

<210> SEQ ID NO 455
<211> LENGTH: 38
<212> TYPE: RNA
<213> ORGANISM: Artificial Sequence
<220> FEATURE:
<223> OTHER INFORMATION: Synthetic

<400> SEQUENCE: 455
ccaucuagau cuccguagau uccccggcuc uuucucgc                                38

<210> SEQ ID NO 456
<211> LENGTH: 38
<212> TYPE: RNA
<213> ORGANISM: Artificial Sequence
<220> FEATURE:
<223> OTHER INFORMATION: Synthetic

<400> SEQUENCE: 456
ccaucuagau cuccguagau uccccagcuc uuucucgc                                38

<210> SEQ ID NO 457
<211> LENGTH: 38
<212> TYPE: RNA
<213> ORGANISM: Artificial Sequence
<220> FEATURE:
<223> OTHER INFORMATION: Synthetic

<400> SEQUENCE: 457
ccaucuagau cuccguagau cccccggcuc uuucucgc                                38

<210> SEQ ID NO 458
<211> LENGTH: 38
<212> TYPE: RNA
<213> ORGANISM: Artificial Sequence
<220> FEATURE:
<223> OTHER INFORMATION: Synthetic

<400> SEQUENCE: 458
```
ccaucuagau cuccguagau uccccgcuc uuucucgc                                38

<210> SEQ ID NO 459
<211> LENGTH: 38
<212> TYPE: RNA
<213> ORGANISM: Artificial Sequence
<220> FEATURE:
<223> OTHER INFORMATION: Synthetic

<400> SEQUENCE: 459
ccaucuagau cuccguagau uccccggcuc uuccucgc                                38

<210> SEQ ID NO 460
<211> LENGTH: 38
<212> TYPE: RNA
<213> ORGANISM: Artificial Sequence
<220> FEATURE:
<223> OTHER INFORMATION: Synthetic

<400> SEQUENCE: 460
ccaucuagau cuccgugauu ccccggcuc uuucucgc                                 38

<210> SEQ ID NO 461
<211> LENGTH: 38
<212> TYPE: RNA
<213> ORGANISM: Artificial Sequence
<220> FEATURE:
<223> OTHER INFORMATION: Synthetic

<400> SEQUENCE: 461
ccaucuagau cuccguaguu ccccggcuc uuucucgc                                 38

<210> SEQ ID NO 462
<211> LENGTH: 38
<212> TYPE: RNA
<213> ORGANISM: Artificial Sequence
<220> FEATURE:
<223> OTHER INFORMATION: Synthetic

<400> SEQUENCE: 462
ccaucuagau ccccguagau uccccggcuc uuucucgc                                38

<210> SEQ ID NO 463
<211> LENGTH: 38
<212> TYPE: RNA
<213> ORGANISM: Artificial Sequence
<220> FEATURE:
<223> OTHER INFORMATION: Synthetic

<400> SEQUENCE: 463
ccaucuagau cuccguagau uccccggcuc cuucucgc                                38

<210> SEQ ID NO 464
<211> LENGTH: 38
<212> TYPE: RNA
<213> ORGANISM: Artificial Sequence
<220> FEATURE:
<223> OTHER INFORMATION: Synthetic

<400> SEQUENCE: 464
ccaucuauau cuccguagau uccccggcuc uuucucgc                                38

<210> SEQ ID NO 465
<211> LENGTH: 40
<212> TYPE: RNA

```
<213> ORGANISM: Artificial Sequence
<220> FEATURE:
<223> OTHER INFORMATION: Synthetic

<400> SEQUENCE: 465
acugucugca uacacgguau gcccaacgcc auccaaaccg                              40

<210> SEQ ID NO 466
<211> LENGTH: 41
<212> TYPE: RNA
<213> ORGANISM: Artificial Sequence
<220> FEATURE:
<223> OTHER INFORMATION: Synthetic

<400> SEQUENCE: 466
acugucugca uacacgguau gcccaacgcc auccaaaccg c                            41

<210> SEQ ID NO 467
<211> LENGTH: 40
<212> TYPE: RNA
<213> ORGANISM: Artificial Sequence
<220> FEATURE:
<223> OTHER INFORMATION: Synthetic

<400> SEQUENCE: 467
acugucugca uacaugguau gcccaacgcc auccaaaccg                              40

<210> SEQ ID NO 468
<211> LENGTH: 41
<212> TYPE: RNA
<213> ORGANISM: Artificial Sequence
<220> FEATURE:
<223> OTHER INFORMATION: Synthetic

<400> SEQUENCE: 468
acugucugca uacacgguau gcccaacgcc auccaaaacc g                            41

<210> SEQ ID NO 469
<211> LENGTH: 40
<212> TYPE: RNA
<213> ORGANISM: Artificial Sequence
<220> FEATURE:
<223> OTHER INFORMATION: Synthetic

<400> SEQUENCE: 469
accugcggcu auugccagcg ccauaagacc cuccacagua                              40

<210> SEQ ID NO 470
<211> LENGTH: 40
<212> TYPE: RNA
<213> ORGANISM: Artificial Sequence
<220> FEATURE:
<223> OTHER INFORMATION: Synthetic

<400> SEQUENCE: 470
accugcggcu auugccagcg ccauaagacc cuccacagca                              40

<210> SEQ ID NO 471
<211> LENGTH: 39
<212> TYPE: RNA
<213> ORGANISM: Artificial Sequence
<220> FEATURE:
<223> OTHER INFORMATION: Synthetic

<400> SEQUENCE: 471
ccugcggcua uugccagcgc cauaagaccc uccacagua                               39
```

<210> SEQ ID NO 472
<211> LENGTH: 40
<212> TYPE: RNA
<213> ORGANISM: Artificial Sequence
<220> FEATURE:
<223> OTHER INFORMATION: Synthetic

<400> SEQUENCE: 472
accugcggcu auugccagcg ccauaagacc uuccacagua                    40

<210> SEQ ID NO 473
<211> LENGTH: 40
<212> TYPE: RNA
<213> ORGANISM: Artificial Sequence
<220> FEATURE:
<223> OTHER INFORMATION: Synthetic

<400> SEQUENCE: 473
accugcggcu auugccagcg ccauaagacc cuccgcagua                    40

<210> SEQ ID NO 474
<211> LENGTH: 56
<212> TYPE: RNA
<213> ORGANISM: Artificial Sequence
<220> FEATURE:
<223> OTHER INFORMATION: Synthetic

<400> SEQUENCE: 474
ggaagaggga ugggugccag cuuugcauac cacgugcaau ucacuccacc cgucac    56

<210> SEQ ID NO 475
<211> LENGTH: 64
<212> TYPE: RNA
<213> ORGANISM: Artificial Sequence
<220> FEATURE:
<223> OTHER INFORMATION: Synthetic

<400> SEQUENCE: 475
gggagagagg aagagggaug ggagccagcu uugcauacca cgugcaauuc acuccacccg    60
ucac                                                               64

<210> SEQ ID NO 476
<211> LENGTH: 56
<212> TYPE: RNA
<213> ORGANISM: Artificial Sequence
<220> FEATURE:
<223> OTHER INFORMATION: Synthetic

<400> SEQUENCE: 476
gggaugggca caugguacgc ccaaagcgag gcccgcugcg uagugccaua acccag    56

<210> SEQ ID NO 477
<211> LENGTH: 61
<212> TYPE: RNA
<213> ORGANISM: Artificial Sequence
<220> FEATURE:
<223> OTHER INFORMATION: Synthetic

<400> SEQUENCE: 477
gggagagagg aagagggaug ggcacauggu acgcccaaag cgaggcccgc ugcguagugc    60
c                                                                   61

<210> SEQ ID NO 478

```
<211> LENGTH: 66
<212> TYPE: RNA
<213> ORGANISM: Artificial Sequence
<220> FEATURE:
<223> OTHER INFORMATION: Synthetic

<400> SEQUENCE: 478
gggaugggca cguccagcg cuaacuguac cugcugugcc acccaccgca uaacccagag    60
gucgau                                                              66

<210> SEQ ID NO 479
<211> LENGTH: 49
<212> TYPE: RNA
<213> ORGANISM: Artificial Sequence
<220> FEATURE:
<223> OTHER INFORMATION: Synthetic

<400> SEQUENCE: 479
gggaugggca cguccagcg cuaacuguac cugcugugcc acccaccgc                49

<210> SEQ ID NO 480
<211> LENGTH: 62
<212> TYPE: RNA
<213> ORGANISM: Artificial Sequence
<220> FEATURE:
<223> OTHER INFORMATION: Synthetic

<400> SEQUENCE: 480
gggagagagg aagagggaug ggcacggucc agcgcuaacu guaccugcug ugccacccac    60
cg                                                                  62

<210> SEQ ID NO 481
<211> LENGTH: 45
<212> TYPE: RNA
<213> ORGANISM: Artificial Sequence
<220> FEATURE:
<223> OTHER INFORMATION: Synthetic

<400> SEQUENCE: 481
gggagagagg aagagggaug ggcacggucc agcgcuaacu guacc                   45

<210> SEQ ID NO 482
<211> LENGTH: 53
<212> TYPE: RNA
<213> ORGANISM: Artificial Sequence
<220> FEATURE:
<223> OTHER INFORMATION: Synthetic

<400> SEQUENCE: 482
ggaagaggga ugggcacggu ccagcgcuaa cuguaccugc ugugccaccc acc          53

<210> SEQ ID NO 483
<211> LENGTH: 43
<212> TYPE: RNA
<213> ORGANISM: Artificial Sequence
<220> FEATURE:
<223> OTHER INFORMATION: Synthetic

<400> SEQUENCE: 483
gggaccacgc gccaacgugu cagcuacacg ccguguuccc cgg                    43

<210> SEQ ID NO 484
<211> LENGTH: 61
<212> TYPE: RNA
<213> ORGANISM: Artificial Sequence
```

<220> FEATURE:
<223> OTHER INFORMATION: Synthetic

<400> SEQUENCE: 484
gggaccacgc gccaacgugu cagcuacacg ccguguuccc cggcauaacc cagaggucga    60
u                                                                   61

<210> SEQ ID NO 485
<211> LENGTH: 62
<212> TYPE: RNA
<213> ORGANISM: Artificial Sequence
<220> FEATURE:
<223> OTHER INFORMATION: Synthetic

<400> SEQUENCE: 485
gggagagagg aagagggaug ggaccacgcg ccaacguguc agcuacacgc cguguucccc    60
gg                                                                  62

<210> SEQ ID NO 486
<211> LENGTH: 44
<212> TYPE: RNA
<213> ORGANISM: Artificial Sequence
<220> FEATURE:
<223> OTHER INFORMATION: Synthetic

<400> SEQUENCE: 486
gggaugggca cgguccagcg cuaacuguac cugcugugcc accc                    44

<210> SEQ ID NO 487
<211> LENGTH: 54
<212> TYPE: RNA
<213> ORGANISM: Artificial Sequence
<220> FEATURE:
<223> OTHER INFORMATION: Synthetic

<400> SEQUENCE: 487
gggaggaaga gggaugggca cgguccagcg cuaacuguac cugcugugcc accc          54

<210> SEQ ID NO 488
<211> LENGTH: 52
<212> TYPE: RNA
<213> ORGANISM: Artificial Sequence
<220> FEATURE:
<223> OTHER INFORMATION: Synthetic

<400> SEQUENCE: 488
gggaggaaga ggaugggcac gguccagcgc uaacuguacc ugcugugcca cc            52

<210> SEQ ID NO 489
<211> LENGTH: 52
<212> TYPE: RNA
<213> ORGANISM: Artificial Sequence
<220> FEATURE:
<223> OTHER INFORMATION: Synthetic

<400> SEQUENCE: 489
gggaggaaga gggaugggca cgguccagcg cacuguaccu gcugugccac cc            52

<210> SEQ ID NO 490
<211> LENGTH: 50
<212> TYPE: RNA
<213> ORGANISM: Artificial Sequence
<220> FEATURE:
<223> OTHER INFORMATION: Synthetic

```
<400> SEQUENCE: 490 ggggaggaaga ggaugggcac gguccagcgc acuguaccug cugugccacc          50

<210> SEQ ID NO 491
<211> LENGTH: 22
<212> TYPE: RNA
<213> ORGANISM: Artificial Sequence
<220> FEATURE:
<223> OTHER INFORMATION: Synthetic

<400> SEQUENCE: 491
gggagagagg aagagggaug gg                                          22

<210> SEQ ID NO 492
<211> LENGTH: 34
<212> TYPE: RNA
<213> ORGANISM: Artificial Sequence
<220> FEATURE:
<223> OTHER INFORMATION: Synthetic

<400> SEQUENCE: 492
cauaacccag aggucgauag uacuggaucc cccc                             34

<210> SEQ ID NO 493
<211> LENGTH: 710
<212> TYPE: PRT
<213> ORGANISM: Homo sapiens
<220> FEATURE:
<221> NAME/KEY: misc_feature
<223> OTHER INFORMATION: amino acid sequence for nucleolin

<400> SEQUENCE: 493
```

Met Val Lys Leu Ala Lys Ala Gly Lys Asn Gln Gly Asp Pro Lys Lys
1               5                   10                  15

Met Ala Pro Pro Pro Lys Glu Val Glu Glu Asp Ser Glu Asp Glu Glu
                20                  25                  30

Met Ser Glu Asp Glu Glu Asp Asp Ser Ser Gly Glu Glu Val Val Ile
            35                  40                  45

Pro Gln Lys Lys Gly Lys Lys Ala Ala Ala Thr Ser Ala Lys Lys Val
50                  55                  60

Val Val Ser Pro Thr Lys Lys Val Ala Val Ala Thr Pro Ala Lys Lys
65                  70                  75                  80

Ala Ala Val Thr Pro Gly Lys Lys Ala Ala Ala Thr Pro Ala Lys Lys
                85                  90                  95

Thr Val Thr Pro Ala Lys Ala Val Thr Thr Pro Gly Lys Lys Gly Ala
            100                 105                 110

Thr Pro Gly Lys Ala Leu Val Ala Thr Pro Gly Lys Lys Gly Ala Ala
        115                 120                 125

Ile Pro Ala Lys Gly Ala Lys Asn Gly Lys Asn Ala Lys Lys Glu Asp
130                 135                 140

Ser Asp Glu Glu Asp Asp Asp Ser Glu Glu Asp Glu Glu Asp Asp Asp
145                 150                 155                 160

Glu Asp Glu Asp Glu Asp Glu Asp Glu Ile Glu Pro Ala Ala Met Lys
                165                 170                 175

Ala Ala Ala Ala Ala Pro Ala Ser Glu Asp Glu Asp Asp Glu Asp Asp
            180                 185                 190

Glu Asp Asp Glu Asp Asp Asp Asp Glu Glu Asp Asp Ser Glu Glu
        195                 200                 205

Glu Ala Met Glu Thr Thr Pro Ala Lys Gly Lys Lys Ala Ala Lys Val

```
                    210                 215                 220
Val Pro Val Lys Ala Lys Asn Val Ala Glu Asp Glu Asp Glu Glu
225                 230                 235                 240

Asp Asp Glu Asp Glu Asp Asp Asp Glu Asp Asp Glu Asp Asp
                245                 250                 255

Asp Asp Glu Asp Asp Glu Glu Glu Glu Glu Glu Glu Glu Pro
                260                 265                 270

Val Lys Glu Ala Pro Gly Lys Arg Lys Glu Met Ala Lys Gln Lys
                275                 280                 285

Ala Ala Pro Glu Ala Lys Lys Gln Lys Val Glu Gly Thr Glu Pro Thr
290                 295                 300

Thr Ala Phe Asn Leu Phe Val Gly Asn Leu Asn Phe Asn Lys Ser Ala
305                 310                 315                 320

Pro Glu Leu Lys Thr Gly Ile Ser Asp Val Phe Ala Lys Asn Asp Leu
                325                 330                 335

Ala Val Val Asp Val Arg Ile Gly Met Thr Arg Lys Phe Gly Tyr Val
                340                 345                 350

Asp Phe Glu Ser Ala Glu Asp Leu Glu Lys Ala Leu Glu Leu Thr Gly
                355                 360                 365

Leu Lys Val Phe Gly Asn Glu Ile Lys Leu Glu Lys Pro Lys Gly Lys
                370                 375                 380

Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
                405                 410                 415

Ala Glu Ile Arg Leu Val Ser Lys Asp Gly Lys Ser Lys Gly Ile Ala
                420                 425                 430

Tyr Ile Glu Phe Lys Thr Glu Ala Asp Ala Glu Lys Thr Phe Glu Glu
                435                 440                 445

Lys Gln Gly Thr Glu Ile Asp Gly Arg Ser Ile Ser Leu Tyr Tyr Thr
                450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
                485                 490                 495

Ala Thr Glu Glu Thr Leu Gln Glu Val Phe Glu Lys Ala Thr Phe Ile
                500                 505                 510

Lys Val Pro Gln Asn Gln Asn Gly Lys Ser Lys Gly Tyr Ala Phe Ile
                515                 520                 525

Glu Phe Ala Ser Phe Glu Asp Ala Lys Glu Ala Leu Asn Ser Cys Asn
                530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
                565                 570                 575

Lys Gly Leu Ser Glu Asp Thr Thr Glu Glu Thr Leu Lys Glu Ser Phe
                580                 585                 590

Asp Gly Ser Val Arg Ala Arg Ile Val Thr Asp Arg Glu Thr Gly Ser
                595                 600                 605

Ser Lys Gly Phe Gly Phe Val Asp Phe Asn Ser Glu Glu Asp Ala Lys
                610                 615                 620

Ala Ala Lys Glu Ala Met Glu Asp Gly Glu Ile Asp Gly Asn Lys Val
625                 630                 635                 640
```

```
Thr Leu Asp Trp Ala Lys Pro Lys Gly Glu Gly Gly Phe Gly Gly Arg
                645                 650                 655
Gly Gly Gly Arg Gly Gly Phe Gly Gly Arg Gly Gly Arg Gly Gly
        660                 665                 670
Arg Gly Gly Phe Gly Gly Arg Gly Arg Gly Gly Phe Gly Gly Arg Gly
        675                 680                 685
Gly Phe Arg Gly Gly Arg Gly Gly Gly Gly Asp His Lys Pro Gln Gly
        690                 695                 700
Lys Lys Thr Lys Phe Glu
705                 710

<210> SEQ ID NO 494
<211> LENGTH: 49
<212> TYPE: RNA
<213> ORGANISM: Artificial Sequence
<220> FEATURE:
<223> OTHER INFORMATION: Synthetic

<400> SEQUENCE: 494
gggaugggaa gaucugcuaa gugcacgcac aaucaccauc gagcgucuc           49

<210> SEQ ID NO 495
<211> LENGTH: 63
<212> TYPE: RNA
<213> ORGANISM: Artificial Sequence
<220> FEATURE:
<223> OTHER INFORMATION: Synthetic

<400> SEQUENCE: 495
gggagagagg aagagggaug gaagaucug cuaagugcac gcacaaucac caucgagcgu   60
cuc                                                                63

<210> SEQ ID NO 496
<211> LENGTH: 54
<212> TYPE: RNA
<213> ORGANISM: Artificial Sequence
<220> FEATURE:
<223> OTHER INFORMATION: Synthetic

<400> SEQUENCE: 496
gggagagagg aagagggaug ggcacggucc agcgcuaacu guaccugcug ugcc        54

<210> SEQ ID NO 497
<211> LENGTH: 58
<212> TYPE: RNA
<213> ORGANISM: Artificial Sequence
<220> FEATURE:
<223> OTHER INFORMATION: Synthetic

<400> SEQUENCE: 497
gggagagaga gggaugggca cgguccagcg cuaacuguac cugcugugcc acccaccg    58

<210> SEQ ID NO 498
<211> LENGTH: 60
<212> TYPE: RNA
<213> ORGANISM: Artificial Sequence
<220> FEATURE:
<223> OTHER INFORMATION: Synthetic

<400> SEQUENCE: 498
gggagagagg aagaggaugg gcacggucca gcgcuaacug uaccugcugu gccaccaccg   60
```

```
<210> SEQ ID NO 499
<211> LENGTH: 60
<212> TYPE: RNA
<213> ORGANISM: Artificial Sequence
<220> FEATURE:
<223> OTHER INFORMATION: Synthetic

<400> SEQUENCE: 499
gggagagagg aagagggagg gcacggucca gcgcuaacug uaccugcugu gcccccaccg    60

<210> SEQ ID NO 500
<211> LENGTH: 52
<212> TYPE: RNA
<213> ORGANISM: Artificial Sequence
<220> FEATURE:
<223> OTHER INFORMATION: Synthetic

<400> SEQUENCE: 500
gggagagagg aagagggaug gguccagcgc uaacuguacc ugccacccac cg            52

<210> SEQ ID NO 501
<211> LENGTH: 58
<212> TYPE: RNA
<213> ORGANISM: Artificial Sequence
<220> FEATURE:
<223> OTHER INFORMATION: Synthetic

<400> SEQUENCE: 501
gggagagagg aagagggaug ggcgguccag cgcuaacugu accugcugcc acccaccg      58

<210> SEQ ID NO 502
<211> LENGTH: 58
<212> TYPE: RNA
<213> ORGANISM: Artificial Sequence
<220> FEATURE:
<223> OTHER INFORMATION: Synthetic

<400> SEQUENCE: 502
gggagagagg aagagggaug ggcacggucc agcgcuaugu cugcugugcc acccaccg      58

<210> SEQ ID NO 503
<211> LENGTH: 58
<212> TYPE: RNA
<213> ORGANISM: Artificial Sequence
<220> FEATURE:
<223> OTHER INFORMATION: Synthetic

<400> SEQUENCE: 503
gggagagagg aagagggaug ggcacggucc agcgcuaacu guaccugcug ugccaccc      58

<210> SEQ ID NO 504
<211> LENGTH: 58
<212> TYPE: RNA
<213> ORGANISM: Artificial Sequence
<220> FEATURE:
<223> OTHER INFORMATION: Synthetic

<400> SEQUENCE: 504
gggaggaaga gggaugggca cgguccagcg cuaacuguac cugcugugcc acccaccg      58

<210> SEQ ID NO 505
<211> LENGTH: 54
<212> TYPE: RNA
<213> ORGANISM: Artificial Sequence
<220> FEATURE:
<223> OTHER INFORMATION: Synthetic
```

<400> SEQUENCE: 505
ggaagaggga ugggcacggu ccagcgcuaa cuguaccugc ugugccaccc accg    54

<210> SEQ ID NO 506
<211> LENGTH: 58
<212> TYPE: RNA
<213> ORGANISM: Artificial Sequence
<220> FEATURE:
<223> OTHER INFORMATION: Synthetic

<400> SEQUENCE: 506
gagaggaaga gggaugggca cgguccagcg cuaacuguac cugcugugcc acccaccg    58

<210> SEQ ID NO 507
<211> LENGTH: 60
<212> TYPE: RNA
<213> ORGANISM: Artificial Sequence
<220> FEATURE:
<223> OTHER INFORMATION: Synthetic

<400> SEQUENCE: 507
gggagagagg aagagggaug ggcacggucc agcgcuaacu guaccugcug ugccacccac    60

<210> SEQ ID NO 508
<211> LENGTH: 60
<212> TYPE: RNA
<213> ORGANISM: Artificial Sequence
<220> FEATURE:
<223> OTHER INFORMATION: Synthetic

<400> SEQUENCE: 508
gggagagagg aagagggaug ggcacggucc agcgcuaacu guaccugcug ugccaccccg    60

<210> SEQ ID NO 509
<211> LENGTH: 60
<212> TYPE: RNA
<213> ORGANISM: Artificial Sequence
<220> FEATURE:
<223> OTHER INFORMATION: Synthetic

<400> SEQUENCE: 509
gggagagagg aagagggaug ggcacggucc gcgcuaacug uaccugcugg ccacccaccg    60

<210> SEQ ID NO 510
<211> LENGTH: 60
<212> TYPE: RNA
<213> ORGANISM: Artificial Sequence
<220> FEATURE:
<223> OTHER INFORMATION: Synthetic

<400> SEQUENCE: 510
gggagagagg aagagggaug ggcacggucc gcgcuaacug uaccgcugug ccacccaccg    60

<210> SEQ ID NO 511
<211> LENGTH: 60
<212> TYPE: RNA
<213> ORGANISM: Artificial Sequence
<220> FEATURE:
<223> OTHER INFORMATION: Synthetic

<400> SEQUENCE: 511
gggagagagg aagagggaug ggcacggucc agcgcacugu accgcugug ccacccaccg    60

<210> SEQ ID NO 512
<211> LENGTH: 62

```
<212> TYPE: RNA
<213> ORGANISM: Artificial Sequence
<220> FEATURE:
<223> OTHER INFORMATION: Synthetic

<400> SEQUENCE: 512
gggagagagg aagagggaug ggcacggucc agcgcuaacu guaccugcug ugccacccac    60
cg                                                                   62

<210> SEQ ID NO 513
<211> LENGTH: 60
<212> TYPE: RNA
<213> ORGANISM: Artificial Sequence
<220> FEATURE:
<223> OTHER INFORMATION: Synthetic

<400> SEQUENCE: 513
gggagaggaa gagggauggg cacguccag cgcuaacugu accugcugug ccacccaccg     60

<210> SEQ ID NO 514
<211> LENGTH: 60
<212> TYPE: RNA
<213> ORGANISM: Artificial Sequence
<220> FEATURE:
<223> OTHER INFORMATION: Synthetic

<400> SEQUENCE: 514
gggagaggaa gagggauggg cacguccag cgcuaacugu accugcugug ccacccaccg     60

<210> SEQ ID NO 515
<211> LENGTH: 56
<212> TYPE: RNA
<213> ORGANISM: Artificial Sequence
<220> FEATURE:
<223> OTHER INFORMATION: Synthetic

<400> SEQUENCE: 515
gaggaagagg gaugggcacg guccagcgcu aacuguaccu gcugugccac ccaccg        56
```

NUCLEOLIN-TARGETING APTAMERS AND METHODS OF USING THE SAME

CROSS-REFERENCE TO RELATED APPLICATIONS

This patent application is a national stage filing under 35 U.S.C. 371 of International Application No. PCT/US2018/050240, filed Sep. 10, 2018, which claims the benefit of priority of U.S. Provisional Patent Application No. 62/555,745, filed Sep. 8, 2017, both of which are incorporated herein by reference in their entirety.

STATEMENT REGARDING FEDERALLY SPONSORED RESEARCH

This invention was made with government support by the National Institutes of Health under Award Number CA159826. The government has certain rights in the invention.

SEQUENCE LISTING

This application is being filed electronically via EFS-Web and includes an electronically submitted Sequence Listing in .txt format. The .txt file contains a sequence listing entitled "2018-09-10_5667-00448_ST25.txt" created on Sep. 10, 2018 and is 101,860 bytes in size. The Sequence Listing contained in this .txt file is part of the specification and is hereby incorporated by reference herein in its entirety.

INTRODUCTION

The protein nucleolin plays a critical role in repair of DNA double-stranded breaks (DSB) (Goldstein et al, PNAS, 2013). Mechanistically, nucleolin functions as a histone chaperone at the DSB, escorting the histone proteins H2A and H2B away from the nucleosome at the DNA break. This nucleosome disruption is required for the recruitment of repair enzymes and the repair of the DNA breaks. Therefore, inhibition of nucleolin results in sensitization of cells to DNA damaging agents. Importantly, the majority of human tumors overexpress nucleolin on the cell surface relative to normal cells, thus making nucleolin a tumor-preferential target. A nucleolin inhibitor would have the unique ability to specifically sensitize only tumor cells to DNA damaging agents as it should only target and internalize into cancerous cells.

Aptamers, small artificial RNA or DNA oligonucleotide ligands, can be selected to inhibit protein function and are also emerging as important tumor-targeting molecules. Additionally, they have many advantages over traditional antibody targeting agents, including ease of synthesis and amenability to chemical modification (Keefe et al, Nat Rev Drug Discov, 2010). Moreover, they exhibit antibody-like target affinities and specificities at a fraction of the size, allowing more efficient tumor penetration while maintaining the ability to discriminate between proteins that differ by only a few amino acids (reviewed in Conrad et al, Methods Enzymol, 1996; Osborne et al, Chem Rev, 1997).

There is a need in the art for new aptamers that may bind to and/or inhibit the nucleolin protein. Such aptamers may be useful not only as new cancer treatments but also may facilitate the delivery of agents to the nucleus of a cell.

SUMMARY

In one aspect of the present invention, aptamers are provided. The aptamer may include a polynucleotide having at least 50%, 60%, 70%, 80%, 85%, 90%, 91%, 92%, 93%, 94%, 95%, 96%, 97%, 98%, 99%, or 100% sequence identity to any one of SEQ ID NOS: 1-490, 494-515, or any one of the sequences described in the Tables or Figures disclosed herein (for example, Tables 1-4, 6-8 or FIG. 11A-11B, 12A-12B, 13A-13C, 14A-14D, 15A-15B, 16, 17, 18, 19, 20, 21, 22, 23, 24, 25, 26, 27, 28A-28B, 29, 30, 31, 32, 33, 34, 35, 36 or 37A-37B). In another aspect, the present invention relates to dimers, trimers, and tetramers including any one of the aptamers described herein.

In a further aspect of the present invention, pharmaceutical compositions including any of the aptamers described herein are provided. The pharmaceutical compositions may include a pharmaceutical carrier, excipient, or diluent.

In a still further aspect, the present invention relates to methods for treating cancer in a subject. The methods may include administering to the subject a therapeutically effective amount of any one of the aptamers, dimers, trimers, tetramers, or pharmaceutical compositions described herein.

In a still further aspect, methods of labeling or inhibiting nucleolin are provided. The methods include contacting nucleolin with any one of the compositions described herein to allow binding and possibly inhibition of the activity of the nucleolin. This contacting can be in vitro by adding the nucleolin to cells or may be in vivo by administering the compositions described herein to a subject. The compositions and aptamers provided herein are capable of binding to and possibly inhibiting the function of nucleolin.

BRIEF DESCRIPTION OF THE DRAWINGS

FIGS. 2A-2D show binding of the SELEX and Cell-SELEX rounds to the nucleolin protein (NCL). RNA pools from SELEX rounds 3, 6, and 7 or from Cell-SELEX Rounds 7-8 MCF-7 or Rounds 7-8 Panc-1 were end-labeled with $^{32}$P. Nucleolin protein was serially diluted in 20 mM Hepes, 150 mM NaCl, 2 mM $CaCl_2$ and 0.01% bovine serum albumin and incubated with a trace amount of the $^{32}$P-labeled RNA pools. After incubation at 37° C., unbound RNA was captured on a nylon membrane and RNA-nucleolin complexes captured on a nitrocellulose membrane. The fraction of protein-bound RNA was determined via phosphorimaging of the nitrocellulose and nylon membranes.

(FIG. 3A) Map of truncated nucleolin mutants. From Chen et al. 2011, *JBC*. (FIG. 3B) Southwestern blot showing the binding of the initial RNA aptamer library (Sell) versus SELEX round 6 (R6 NCL) to truncated nucleolin mutants expressed in MCF7 cells.

FIGS. 5A-5F show binding of nucleolin aptamer truncates to the nucleolin protein. Aptamers were end-labeled with $^{32}$P. Nucleolin protein was serially diluted in 20 mM Hepes, 150 mM NaCl, 2 mM CaCl$_2$ and 0.01% bovine serum albumin and incubated with a trace amount of the $^{32}$P-labeled RNA pools. After incubation at 37° C., unbound RNA was captured on a nylon membrane and RNA-nucleolin complexes captured on a nitrocellulose membrane. The fraction of protein-bound RNA was determined via phosphorimaging of the nitrocellulose and nylon membranes.

FIG. 7 shows EV3 does not sensitize HFF (human foreskin fibroblasts), that do not express nucleolin on cell surface, to radiation. hTERT-immortalized HFF cells that do not express nucleolin on cell surface were treated with 5 µg of indicated aptamers and exposed to 2Gy IR 48 h later. Cells were cultivated for 10 d and survival was assessed by MTT assay.

FIGS. 11A-11B show predicted secondary structures for a representative Family B aptamer (SEQ ID NO: 8).

FIGS. 12A-12B show predicted secondary structures for a representative Family C aptamer (SEQ ID NO: 9).

FIGS. 13A-13C show predicted secondary structures for a representative Family D aptamer (SEQ ID NO: 10).

FIGS. 14A-14D show predicted secondary structures for a representative Family E aptamer (SEQ ID NO: 11).

FIGS. 15A-15B show predicted secondary structures for a representative Family F aptamer (SEQ ID NO: 12).

FIG. 25 shows predicted secondary structures for Ev3min11 truncate aptamer (SEQ ID NO: 506).

DETAILED DESCRIPTION

Figure 1:
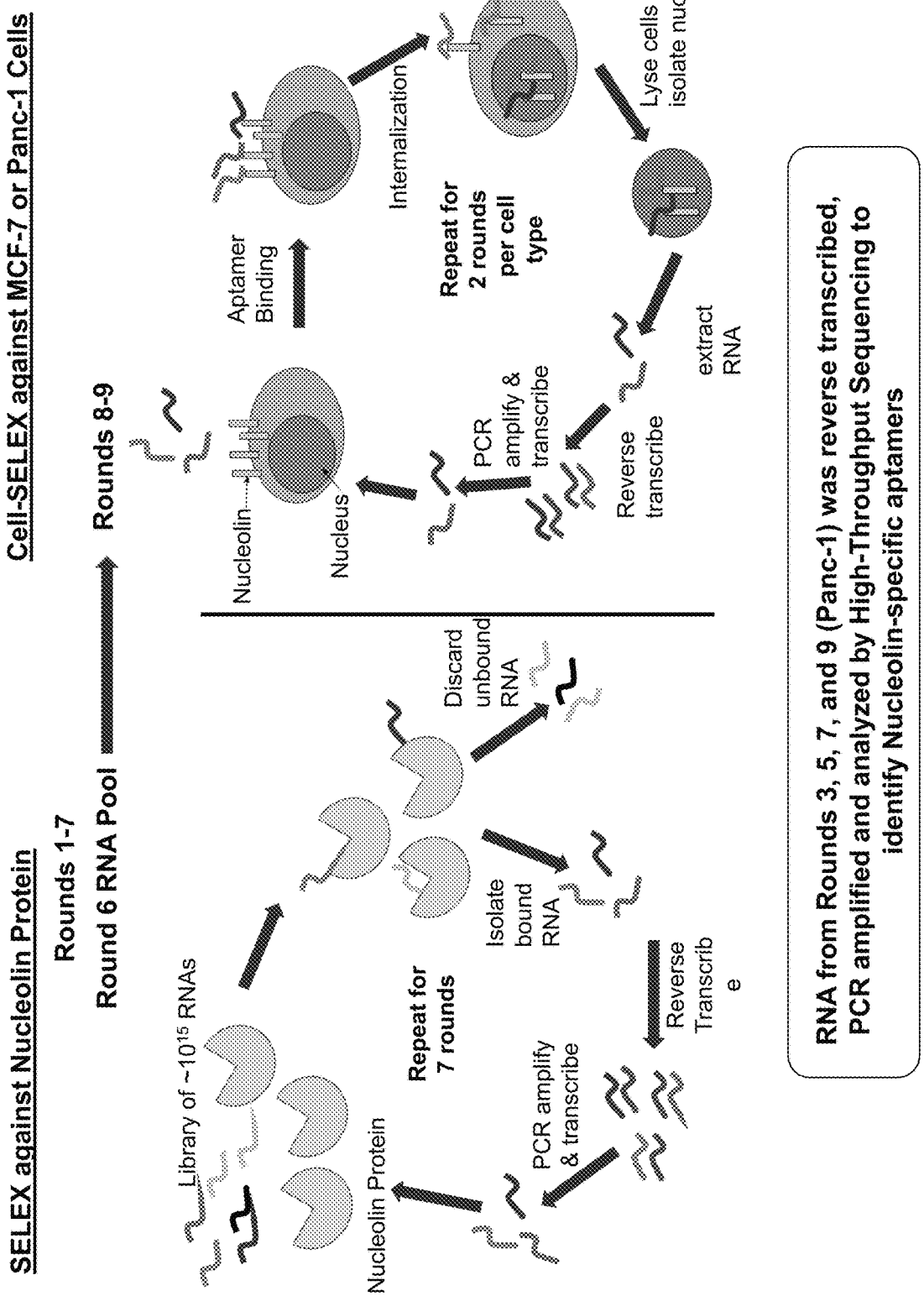
FIG. 1 shows the work flow demonstrating the selection of aptamer families capable of relocating into the nucleus after binding to nucleolin on cell surface. A random 2'Fluoro-pyrimidine RNA pool of sequences GGGAGAGAGGAAGAGGGAUGGG (SEQ ID NO: 491)-$N_{40}$-CAUAACCCAGAGGUCGAUAGUACUG-GAUCCCCCC (SEQ ID NO: 492) (where $N_{40}$ represents 40 random nucleotides) was incubated for 20 min at 37° C. with nucleolin protein (in 20 mM Hepes, 150 mM NaCl, 2 mM $CaCl_2$ and 0.01% bovine serum albumin) at ratios of RNA:protein varying from 187:1 to 133:1. RNA bound to protein was isolated by filtration through a 0.45 μm nitrocellulose membrane before RNA extraction, reverse transcription, PCR amplification and transcription to complete 1 round of selection. Each subsequent round of selection used the RNA pool transcribed from the previous round of selection, for a total of 7 rounds of SELEX against the nucleolin protein. The Round 6 RNA pool was also used to perform 2 Cell-SELEX rounds against both MCF-7 and Panc-1 cells. For the Cell-SELEX rounds, the Round 6 RNA pool was incubated with either MCF-7 or Panc-1 cells for 2 hrs at 37° C./5% $CO_2$ before using a high salt wash to remove non-internalized RNA. Cells were then tryspinized, washed again with high salt, and RNA extracted from the cell nuclei using the Invitrogen™ PARIS™ kit. RNA pools from Rounds 3, 5, 7 and 9 (Panc-1) were reverse transcribed, PCR amplified and analyzed by High-Throughput Sequencing.

Here, in the non-limiting Examples, the present inventors disclose new aptamers that may bind to and/or inhibit the nucleolin protein. The present inventors demonstrate that such aptamers may be useful not only to sensitize cancer cells to cancer treatments including, for example, ionizing radiation and chemotherapeutic agents, but also may facilitate the delivery of agents to the nucleus of a cell.

In one aspect of the present invention, aptamers are provided. As used herein, the term "aptamer" refers to single-stranded oligonucleotides that bind specifically to target molecules with high affinity. Aptamers can be generated against target molecules, such as nucleolin, by screening combinatorial oligonucleotide libraries for high affinity binding to the target (See, e.g., Ellington, Nature 1990; 346: 8 18-22 (1990), Tuerk, Science 249:505-1 0 (1990)). The aptamers disclosed herein may be synthesized using methods well-known in the art. For example, the disclosed aptamers may be synthesized using standard oligonucleotide synthesis technology employed by various commercial vendors including, without limitation, Integrated DNA Technologies, Inc. (IDT), Sigma-Aldrich, Life Technologies, or Bio-Synthesis, Inc.

The aptamer may include a polynucleotide having at least 50%, 60%, 70%, 80%, 85%, 90%, 91%, 92%, 93%, 94%, 95%, 96%, 97%, 98%, 99%, or 100% sequence identity to any one of SEQ ID NOS: 1-490, 494-515, or any one of the sequences described in the Tables or Figures disclosed herein (for example, Tables 1-4, 6-8 or FIG. 11A-11B, 12A-12B, 13A-13C, 14A-14D, 15A-15B, 16, 17, 18, 19, 20, 21, 22, 23, 24, 25, 26, 27, 28A-28B, 29, 30, 31, 32, 33, 34, 35, 36 or 37A-37B). The aptamers described herein (i.e., SEQ ID NOS: 1-490, 494-515) may or may not include a 5' constant region (GGGAGAGAGGAAGAGGGAUGGG (SEQ ID NO: 491)) that may be used, for example, to transcribe or purify the aptamers in vitro. The aptamers described herein (i.e., SEQ ID NOS: 1-490, 494-515) may or may not include a 3' constant region (CAUAACCCAGAG-GUCGAUAGUACUGGAUCCCCCC (SEQ ID NO: 492)) that may be used, for example, to transcribe or purify the aptamers in vitro. In some embodiments, the aptamer may include a polynucleotide having at least 50%, 60%, 70%, 80%, 85%, 90%, 91%, 92%, 93%, 94%, 95%, 96%, 97%, 98%, 99%, or 100% sequence identity to the polynucleotide sequence-5'-GGGAGAGAGGAAGAGGGAUGGG (SEQ ID NO: 491)-A Variable Region-CAUAACCCAGAGGU-CGAUAGUACUGGAUCCCCCC (SEQ ID NO: 492)-3', wherein the variable region may include any one of SEQ ID NOS: 13-473 or a portion thereof. The portion of the indicated aptamers should be capable of binding to nucleolin. In some embodiments, the aptamer may include a polynucleotide having at least 50%, 60%, 70%, 80%, 85%, 90%, 91%, 92%, 93%, 94%, 95%, 96%, 97%, 98%, 99%, or 100% sequence identity to SEQ ID NO: 480 (Ev3 Aptamer).

The terms "polynucleotide," "nucleotide sequence," "polynucleotide sequence," "nucleic acid" and "nucleic acid sequence" refer to a nucleotide, oligonucleotide, polynucleotide (which terms may be used interchangeably), or any fragment thereof. These phrases may refer to DNA or RNA of genomic, natural, or synthetic origin.

Regarding polynucleotide sequences, the terms "sequence identity," "percent identity," and "% identity" refer to the percentage of base matches between at least two nucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Sequence identity for a nucleotide sequence may be determined as understood in the art. (See, e.g., U.S. Pat. No. 7,396,664). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known nucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website.

Regarding polynucleotide sequences, sequence identity is measured over the length of an entire defined nucleotide sequence, for example, as defined by a particular sequence identified herein. Furthermore, sequence identity, as measured herein, is based on the identity of the nucleotide base in the nucleotide sequence, irrespective of any further modifications to the nucleotide sequence. For example, the polynucleotide nucleotide sequences described herein may include modifications to the nucleotide sequences such 2'flouro, 2'O-methyl, and inverted deoxythymidine (idT) modifications. These modifications are not considered in determining sequence identity. Thus if a base, for example, is a 2'fluoro adenine (or 2'O-methyl, etc.), it is understood to be an adenine for purposes of determining sequence identity with another sequence. Likewise, 3' idT modifications to the polynucleotide sequences described herein also should not be considered in determining sequence identity.

Based on the general aptamer structure presented, for example, in FIG. 11A-11B, 12A-12B, 13A-13C, 14A-14D, 15A-15B, 16, 17, 18, 19, 20, 21, 22, 23, 24, 25, 26, 27, 28A-28B, 29, 30, 31, 32, 33, 34, 35, 36 or 37A-37B, a person of ordinary skill in the art would readily recognize that several modifications could be made to the sequence while preserving the overall structure and presumably the function of the aptamer. For example, in FIG. 11A, a person of ordinary skill in the art could simply switch the first stem forming region GGGA and the tenth stem forming region UCCC to CCCU and AGGG, respectively, and still retain the stem structure of the aptamer. Additionally, modifications to the stem regions could be made that change the bases within the stem region but conserve the overall pyrimidine and purine base composition so that the stem region hybridizes at a similar melting temperature. A person of ordinary skill would also recognize that changes made to the aptamer that disturbed the general aptamer stem loop structure would likely result in an aptamer incapable of efficiently binding its target.

In some embodiments, the aptamer may have a dissociation constant ($K_D$) for the nucleolin protein that is less than 1000, 800, 600, 500, 450, 350, 250, 150, 125, 100, 90, 80, 70, 65, 60, 55, 50, 45, 40, 35, 30, 25, 20, 15, 10, 5, 2.5, 2, 1, 0.5, or 0.1 nanomolar (nM). The $K_D$ of an aptamer may be measured using the methodology used by the inventors in the Examples.

The aptamers may include a polynucleotide (RNA, DNA, or peptide nucleic acid (PNA)) that is in an unmodified form or may be in a modified form including at least one nucleotide base modification. Nucleotide base modifications of polynucleotides to, for example, protect the polynucleotide from nuclease degradation and/or increase the stability of the polynucleotide and are well-known in the art. Common nucleotide base modifications that may be used in accordance with the present invention include, without limitation, deoxyribonucleotides, 2'-O-Methyl bases, 2'-Fluoro bases, 2' Amino bases, inverted deoxythymidine bases, 5' modifications, and 3' modifications. In some embodiments, the aptamer may include a polynucleotide including a modified form including at least one nucleotide base modification selected from the group consisting of a 2'fluoro modification, a 2'O-methyl modification, a 5' modification, and a 3' modification.

Typical 5' modifications may include, without limitation, inverted deoxythymidine bases, addition of a linker sequence such as C6, addition of a cholesterol, addition of a reactive linker sequence which could be conjugated to another moiety such as a PEG. Typical 3' modifications may include, without limitation, inverted deoxythymidine bases, and inverted abasic residues.

As additional 5' and/or 3' modifications, the aptamer may include a polynucleotide including a 5' linker and/or a 3' linker. Common 5' and/or 3' linkers for polynucleotides are known in the art and may include peptides, amino acids, nucleic acids, as well as homofunctional linkers or heterofunctional linkers. Particularly useful conjugation reagents that can facilitate formation of a covalent bond with an aptamer may comprise an N-hydroxysuccinimide (NHS) ester and/or a maleimide or using click chemistry. Typical 5' and/or 3' linkers for polynucleotides may include without limitation, amino C3, C4, C5, C6, or C12-linkers.

The aptamer may further include an agent. Suitable agents may include, without limitation, stability agents, detectable agents such as reporter moieties, and/or therapeutic agents.

As used herein, a "stability agent" refers to any substance(s) that may increase the stability and/or increase the circulation time of a polynucleotide in vivo. Typical stability agents are known in the art and may include, without limitation, polyethylene glycol (PEG), cholesterol, albumin, or Elastin-like polypeptide.

As used herein, a "detectable agent" refers to any substance(s) that may be detected using appropriate equipment. Suitable detectable agents may be, without limitation, a fluorophore moiety, an enzyme moiety, an optical moiety, a magnetic moiety, a radiolabel moiety, an X-ray moiety, an ultrasound imaging moiety, a photoacoustic imaging moiety, a nanoparticle-based moiety, or a combination of two or more of the listed moieties.

A "fluorophore moiety" may include any molecule capable of generating a fluorescent signal. Various fluorophore moieties are well-known in the art and/or commercially available. Exemplary fluorophore moieties include, without limitation, fluorescein, FITC, Alexa Fluor 488, Alexa Fluor 660, Alexa Fluor 680, Alexa Fluor 750, and Alexa Fluor 790 (Life Technologies); Cy2, Cy3, Cy3.5, Cy5, Cy5.5 and Cy7 (GE Healthcare); DyLight 350, DyLight 488, DyLight 594, DyLight 650, DyLight 680, DyLight 755 (Life Technologies); IRDye 800CW, IRDye 800RS, and IRDye 700DX (Li-Cor); VivoTag680, VivoTag-S680, and VivoTag-S750 (PerkinElmer).

An "enzyme moiety" refers to polypeptides that catalyze the production of a detectable signal. Exemplary enzyme moieties may include, without limitation, horseradish peroxidase (HRP), alkaline phosphatase (AP), glucose oxidase, or β-galactosidase.

"Optical moieties" may include, for example, any agents that may be used to produce contrast or signal using optical imaging such as luminescence or acousto-optical moieties.

"Magnetic moieties" may include, for example, a chelating agent for magnetic resonance agents. Chelators for magnetic resonance agents can be selected to form stable complexes with paramagnetic metal ions, such as Gd(III), Dy(III), Fe(III), and Mn(II).

Other exemplary detectable agents may include radiolabel moieties. Exemplary radioactive labels may include, without limitation, $^{99}$Mo, $^{99m}$Tc, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I n, $^{X}$3N $^{15}$O, and $^{18}$F.

"X-ray moieties" may include, for example, any agents that may be used to produce contrast or signal using X-ray imaging such as iodinated organic molecules or chelates of heavy metal ions.

"Photoacoustic imaging moieties" may include photoacoustic imaging-compatible agents such as methylene blue, single-walled carbon nanotubes (SWNTs), and gold nanoparticles. Ultrasound imaging moieties may include, for example, any agents that may be used to produce contrast or signal using ultrasound imaging such as Levovist, Albunex, or Echovist.

A detectable agent may also be a nanoparticle-based moiety. A nanoparticle-based moiety is a nanoparticle that is capable of generating a signal. For example, silicon containing nanoparticles may be used to produce fluoresecence, luminescence, or another type of signal. Other exemplary nanoparticle-based moieties include, without limitation, nanospheres such as Kodak X-SIGHT 650, Kodak X-SIGHT 691, Kodak X-SIGHT 751 (Fisher Scientific); metal oxide nanoparticles; and quantum dots such as Evi-Tags (Evident Technologies) or Qdot probes (Life Technologies).

As used herein, a "therapeutic agent" may be any substance that provides a therapeutic functionality when conjugated to any one of the aptamers described herein. Suitable therapeutic agents may include, without limitation, cytotoxic compounds, and particularly those shown to be effective in other drug conjugates. As used herein, a "cytotoxic compound" refers to any substance that disrupts the functioning of cells and/or causes the death of cells. Various therapeutic cytotoxic compounds are known in the art and may include, without limitation, DNA damaging agents, anti-metabolites, natural products and their analogs. Exemplary classes of cytotoxic compounds include enzyme inhibitors such as dihydrofolate reductase inhibitors, and thymidylate synthase inhibitors, tubulin inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, auristatins, maytansinoids, differentiation inducers, and taxols. More specifically, suitable cytoxic compounds may include 5-fluorouracil, aclacinomycin, activated cytoxan, bisantrene, bleomycin, carmofur, CCNU, cis-platinum, daunorubicin, doxorubicin, DTIC, melphalan, methotrexate, mithromycin, mitomycin, mitomycin C, peplomycin pipobroman, plicamycin, procarbazine, retinoic acid, tamoxifen, taxol, tegafur, VP16, VM25, diphtheria toxin, botulinum toxin, geldanamycin, maytansinoids (including DM1), monomethylauristatin E (MMAE), monomethylauristatin F (MMAF), and maytansinoids (DM4) and their analogues. Exemplary cytotoxic compounds may also include therapeutic radiopharmaceuticals including, without limitation, $^{186}$Re, $^{188}$Re, $^{153}$Sm, $^{67}$Cu, $^{105}$Rh, $^{m}$Ag, and $^{192}$Ir.

The aptamer and agent may be "linked" either covalently or non-covalently. Additionally, the aptamer and agent may be linked using the 5' and/or 3' linkers described herein. The aptamer and agent may be linked at the 5' end and/or the 3' end of the aptamer. To link the aptamer and agent non-covalently, the aptamer and the agent may be linked by a tag system. A "tag system" may include any group of agents capable of binding one another with a high affinity. Several tag systems are well-known in the art and include, without limitation, biotin/avidin, biotin/streptavidin, biotin/NeutrAvidin, or digoxigenin (DIG) systems. In some embodiments, the tag system comprises biotin/avidin or biotin/streptavidin. In such embodiments, the aptamer may be modified at either the 5' or 3' end to include biotin while the agent may be modified to include streptavidin or avidin. Alternatively, the aptamer may be modified at either the 5' or 3' end to include streptavidin or avidin while the agent may be modified to include biotin.

In another aspect, the present invention relates to dimers, trimers, and tetramers including any one of the aptamers described herein. A "dimer" refers to the linking together of two aptamer molecules in order to, for example, to increase the stability and/or increase the circulation time of a polynucleotide in vivo. A "trimer" refers to the linking together of three aptamer molecules in order to, for example, to increase the stability and/or increase the circulation time of a polynucleotide in vivo. A "tetramer" refers to the linking together of four aptamer molecules in order to, for example, to increase the stability and/or increase the circulation time of a polynucleotide in vivo. The aptamer molecules may be linked together covalently, noncovalently, or a combination of both. The aptamer molecules may be linked at their 5' or 3' ends. To link the aptamers noncovalently, the aptamers may be linked by a tag system or through a scaffold system.

In a further aspect of the present invention, pharmaceutical compositions including any of the aptamers described herein are provided. The pharmaceutical compositions may include a pharmaceutical carrier, excipient, or diluent (i.e., agents), which are nontoxic to the cell or mammal being exposed thereto at the dosages and concentrations employed. Often a pharmaceutical composition may include an aqueous pH buffered solution. Examples of pharmaceutical carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant. In some embodiments, the pharmaceutical carrier may include a buffer including about 20 mM Hepes, pH 7.4; 150 mM NaCl; 1 mM $CaCl_2$; 1 mM $MgCl_2$; 5 mM KCl.

In a still further aspect, the present invention relates to methods for treating cancer in a subject. The methods may include administering to the subject a therapeutically effective amount of any one of the aptamers, dimers, trimers, tetramers, or pharmaceutical compositions described herein. The subject may be any mammal, suitably a human, domesticated animal such as a dog or cat, or a mouse or rat. Optionally, the present methods may further include administering a chemotherapeutic agent or radiation therapy to the subject.

Exemplary cancers in accordance with the present invention include, without limitation, colon, primary and metastatic breast, ovarian, liver, pancreatic, prostate, bladder, lung, osteosarcoma, pancreatic, gastric, esophageal, skin cancers (basal and squamous carcinoma; melanoma), testicular, colorectal, urothelial, renal cell, hepatocellular, leukemia, lymphoma, multiple myeloma, head and neck, and central nervous system cancers or pre-cancers.

Treating cancer includes, but is not limited to, reducing the number of cancer cells or the size of a tumor in the subject, reducing progression of a cancer to a more aggressive form, reducing proliferation of cancer cells or reducing the speed of tumor growth, killing cancer cells, reducing metastasis of cancer cells or reducing the likelihood of recurrence of a cancer in a subject. Treating a subject as used herein refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

Optionally, the present methods may further include administering a chemotherapeutic agent and/or radiation therapy to the subject. Without being limited by theory, the present inventors conjecture (and demonstrate in the Examples) that aptamers that block nucleolin function in cancer cells can sensitize cancer cells to DNA-damaging agents such as chemotherapeutic agents and radiation therapy. In some embodiments, the aptamer-containing composition described herein is administered prior to, simultaneously with, or after the chemotherapeutic agent and/or radiation therapy. In some embodiments, the aptamer-containing composition is administered prior to the administration of the optional chemotherapeutic agent and/or radiation therapy.

Chemotherapeutic agents are compounds that may be used to treat cancer. Suitable chemotherapy agents may include, without limitation, 5-fluorouracil, aclacinomycin, activated cytoxan, bisantrene, bleomycin, carmofur, CCNU, cis-platinum, daunorubicin, doxorubicin, DTIC, melphalan, methotrexate, mithromycin, mitomycin, mitomycin C, peplomycin pipobroman, plicamycin, procarbazine, retinoic acid, tamoxifen, taxol, tegafur, VP16, or VM25.

In some embodiments, the chemotherapeutic agent may be a DNA-damaging agent including, without limitation, cisplatin, carboplatin, picoplatin, oxaliplatin, methotrexate, doxorubicin, or daunorubicin, 5-fluorouracil, capecitabine, floxuridine, and gemcitabine, and the purine analogs 6-mercaptopurine, 8-azaguanine, fludarabine, and cladribine. The optional radiation therapy in the present methods may include one or more doses of between 1 Gy and 30 Gy. Suitably, the radiation therapy includes a single fraction dose of 12, 15, 18, 20, 21, 23, 25, or 28 Gy.

The chemotherapeutic agent and/or radiation therapy may be administered in any order in relation to the aptamer-containing compositions described herein, at the same time or as part of a unitary composition. The aptamer-containing composition and chemotherapeutic agent and/or radiation therapy may be administered such that one composition or therapy is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

An "effective amount" or a "therapeutically effective amount" as used herein means the amount of a composition that, when administered to a subject for treating a state, disorder or condition is sufficient to effect a treatment (as defined above). The therapeutically effective amount will vary depending on the composition, formulation or combination, the disease and its severity and the age, weight, physical condition and responsiveness of the subject to be treated.

The compositions (i.e., those including the aptamers described herein) described herein may be administered by any means known to those skilled in the art, including, but not limited to, intratumoral, oral, topical, intranasal, intraperitoneal, parenteral, intravenous, intramuscular, subcutaneous, intrathecal, transcutaneous, nasopharyngeal, or transmucosal absorption. Thus the compositions may be formulated as an ingestable, injectable, topical or suppository formulation. Within broad limits, administration of larger quantities of the aptamer-containing compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the aptamer-containing compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compound will reduce symptoms of the condition at least 10%, 20%, 30%, 40%, 50%, 60%, 70%, 80%, 90% or 100% compared to pre-treatment symptoms or symptoms is left untreated. It is specifically contemplated that pharmaceutical preparations and compositions may palliate or alleviate symptoms of the disease without providing a cure, or, in some embodiments, may be used to cure the disease or disorder.

The effectiveness of the aptamer-containing composition in treating the cancer or reducing the likelihood of resistance can be measured by tracking the growth of the tumor or the growth rate of the tumor or cancer cells. A decrease in tumor size or in the rate of tumor growth is indicative of treatment of the cancer.

The aptamers disclosed herein may also be used in methods of labeling or inhibiting nucleolin. As disclosed herein the aptamers provided bind to nucleolin and may be used to inhibit nucleolin. In some instances the aptamers are trafficked with the nucleolin to the nucleus of the cell when the aptamer is contacts the cell. The aptamers may be combined with an agent as described above and if the agent is a reporter moiety the agent may allow nucleolin to be labeled within the cell or to bring the agent in contact with nucleolin. Nucleolin may be contacted with the aptamer directly or indirectly in vivo, in vitro, or ex vivo. Contacting encompasses administration to a cell, a culture of cells, tissue, mammal, patient, or human expressing nucleolin. Further, contacting a cell includes adding an agent to a cell culture. Other suitable methods may include introducing or administering an agent to a cell, tissue, mammal, or patient using appropriate procedures and routes of administration as defined above.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Development of Nucleolin-Binding Aptamers

With the goal of developing an aptamer that binds and/or inhibits the nucleolin protein, we performed a dual protein and cell selection via systematic evolution of ligands by exponential enrichment (SELEX) using a modified RNA library (FIG. 1). First, SELEX was performed against a recombinant nucleolin protein (SEQ ID NO: 493) resulting in an RNA library enriched in clones specific for nucleolin after 6 rounds of selection (FIG. 2A). As a 7$^{th}$ round of SELEX did not improve the aptamer pool's affinity for the nucleolin protein (FIG. 2B), we moved forward with the pool of RNA from the 6$^{th}$ round of SELEX (R6 NCL). To identify nucleolin-specific RNAs capable of binding to nucleolin on cell surface and subsequently transporting to the nucleus, the R6 NCL RNA pool was incubated with either MCF-7 or Panc-1 cells (FIG. 1). The nuclei were then isolated and the aptamer pool that reached this compartment was amplified. After 2 rounds of cellular selection with either MCF-7 or Panc-1 cells, the RNA library was further enriched for aptamers capable of binding to the nucleolin protein (FIGS. 2C & 2D).

Figure 3A:
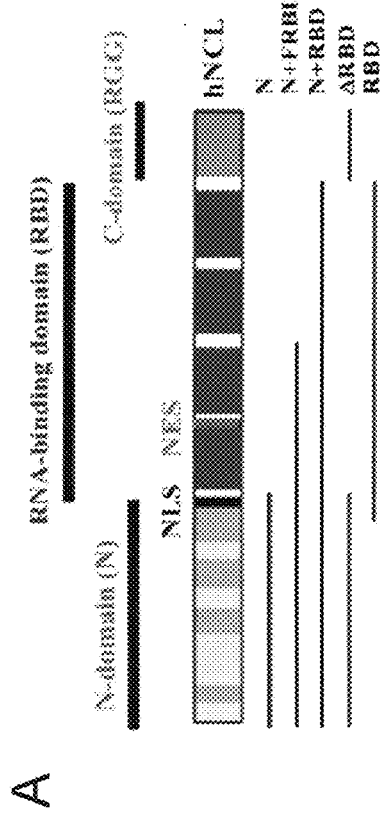
FIGS. 3A-3B show nucleolin-specific RNA aptamers bind to the RBD domain of nucleolin.
Figure 3B:
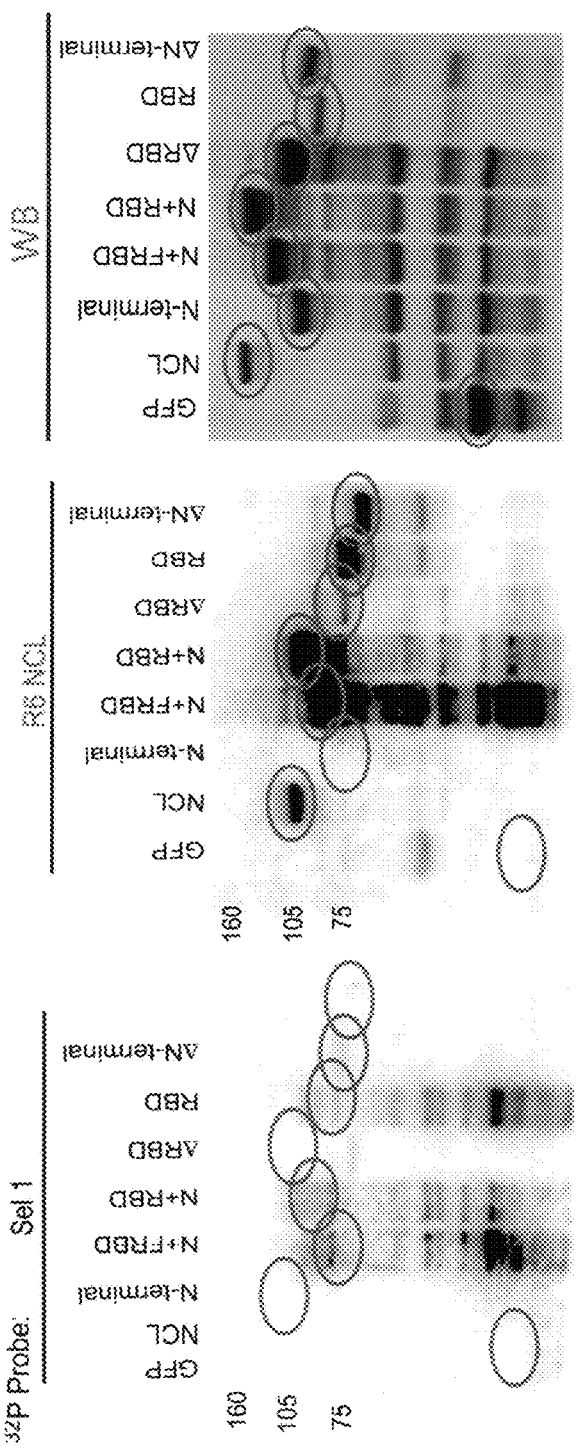

We previously demonstrated that nucleolin interacts with Rad50, a member of the MRN complex, through its C-terminal RGG domain and that this interaction is essential for recruitment of nucleolin to the DNA damage site and repair of the DSB (Goldstein et al. 2013, PNAS). Thus, we estimated that in order to achieve a disruption of the nucleolin-Rad50 interaction and the inhibition of DSB repair required for radiosensitization, our nucleolin aptamer would need to bind to either the RGG domain itself or to the RBD domain in the proximity of the C-terminus. In fact, we found that the R6 NCL RNA aptamer pool binds to the RBD domain (FIGS. 3A-3B), suggesting that these aptamers may be able to inhibit the nucleolin-Rad50 interaction that is crucial for DSB repair.

Figure 4:
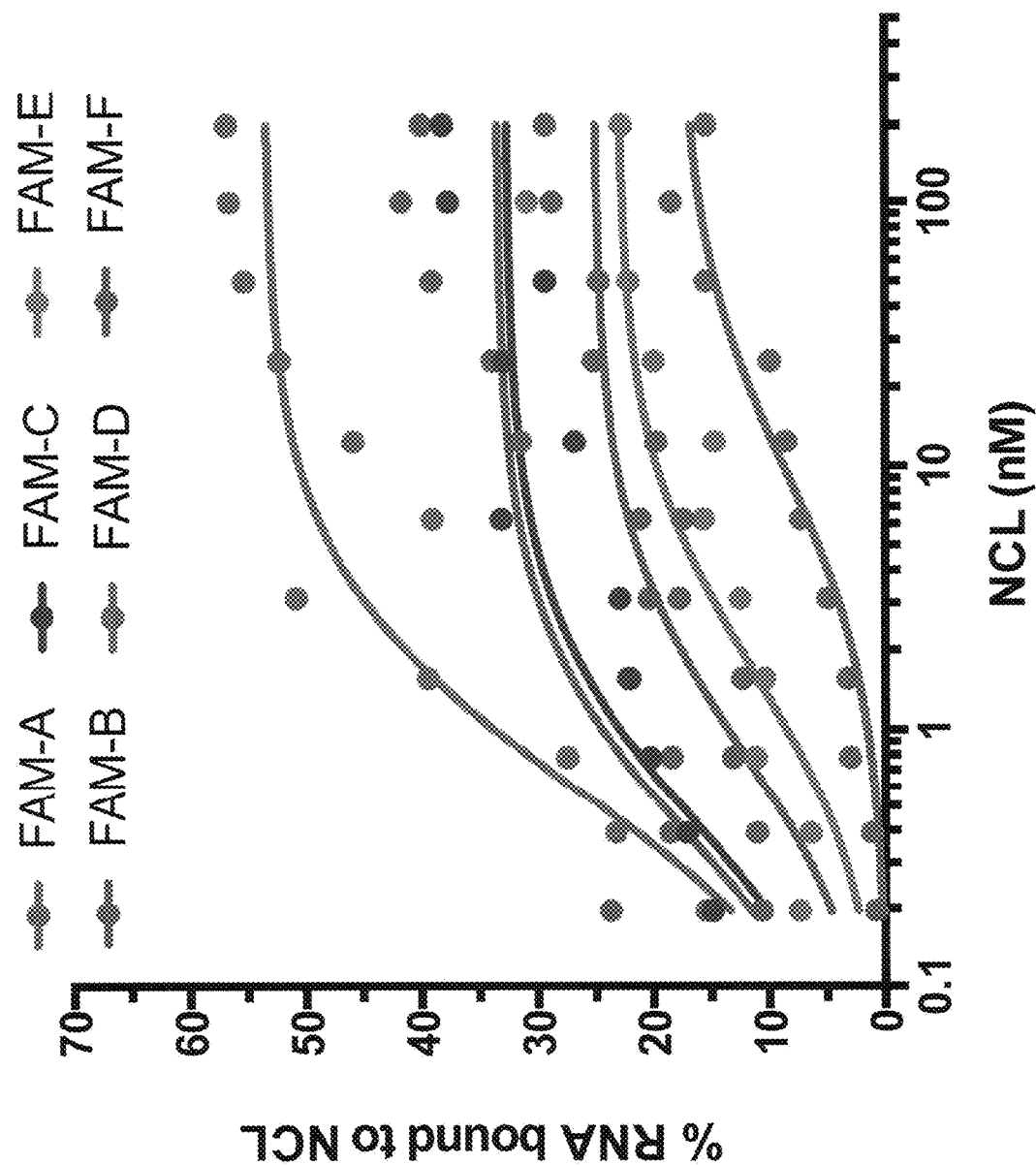
FIG. 4 shows binding analysis of the nucleolin (NCL) aptamers identified through high throughput sequencing. Aptamers were end-labeled with $^{32}$P. Nucleolin protein was serially diluted in 20 mM Hepes, 150 mM NaCl, 2 mM CaCl$_2$ and 0.01% bovine serum albumin and incubated with a trace amount of the $^{32}$P-labeled RNA pools. After incubation at 37° C., unbound RNA was captured on a nylon membrane and RNA-nucleolin complexes captured on a nitrocellulose membrane. The fraction of protein-bound RNA was determined via phosphorimaging of the nitrocellulose and nylon membranes.
Figure 5F:
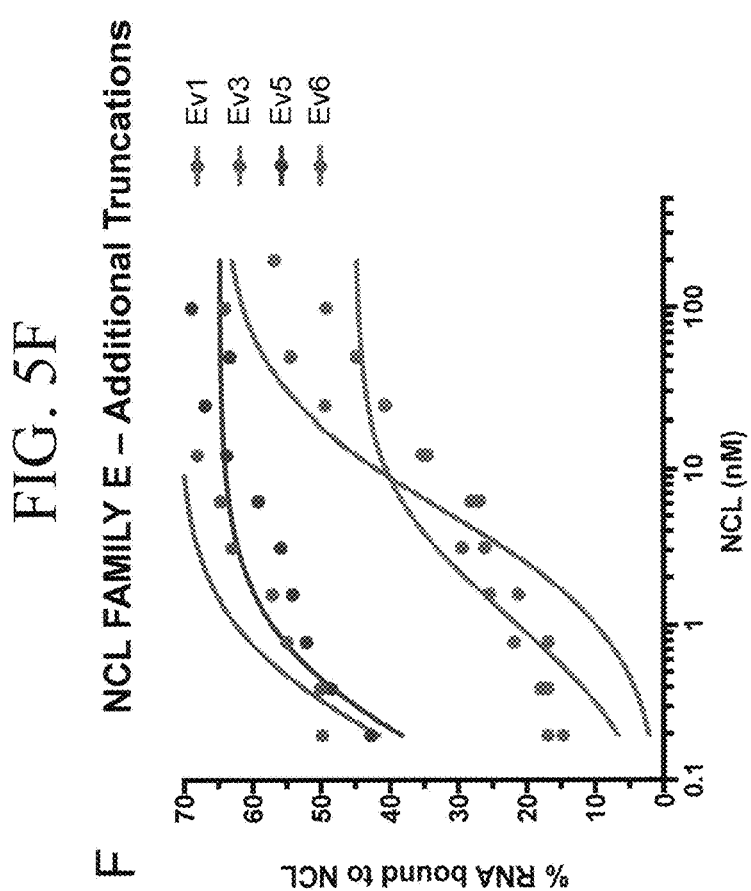
Figure 5E:
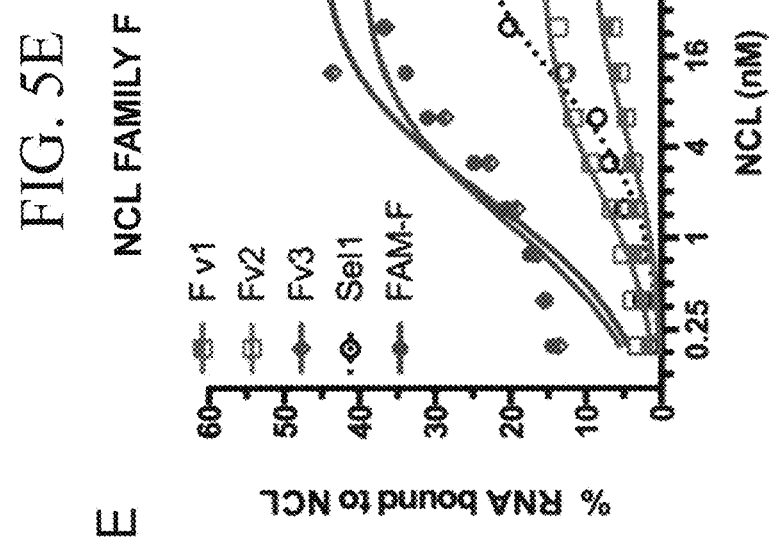

High throughput sequencing of the SELEX pools from various selection rounds (rounds 3, 5, 7, and 9—Panc-1 round 2), resulted in almost 8000 unique RNA families plus 78 ambiguous sequences, where RNA families are RNA sequences that differ by 4 nucleotides or less and ambiguous sequences are single RNA sequences that do not fit into a RNA family. The most representative sequence from each of the top 6 abundant families, designated Families A-F (FAM-A, etc., Tables 1-4), were transcribed to test their ability to bind to the nucleolin protein. Families B-F demonstrated specific binding to nucleolin while Family A did not appear to significantly bind the protein, suggesting that it may be an artifact resulting from PCR amplification (FIG. 4, Table 5). To make it easier to chemically synthesize the nucleolin aptamers, we sought to shorten their length. Thus, we designed truncates of the Families B-F aptamers (Tables 6-8). Several of these truncations resulted in improved affinity for nucleolin over the parent aptamers, with truncations Bvl, Dv2, Ev3, Ev5, and Fv3 demonstrating the best affinity (FIGS. 5A-5F). To further truncate the Ev3 aptamer, we designed 24 additional truncates of Ev3 (Tables 7 and 8). Several of these truncations, primarily Ev3.min21, Ev3.min22, and Ev3.min24 demonstrated a similar affinity for nucleolin compared to their parent Ev3 aptamer (FIGS. 9A-9D).

TABLE 1

Nucleolin Aptamer Sequences without 5' and 3' Constant Regions

| NCL Aptamer | Sequence |
|---|---|
| FAM-A | CCAUCUAGAUCUCCGUAGAUUCCCCCGGCUCUU UCUCGC (SEQ ID NO: 1) |
| FAM-B | AGCCAGCUUUGCAUACCACGUGCAAUUCACUCC ACCCGUCA (SEQ ID NO: 2) |
| FAM-C | AAGAUCUGCUAAGUGCACGCACAAUCACCAUCG AGCGUCU (SEQ ID NO: 3) |
| FAM-D | CACAUGGUACGCCCAAAGCGAGGCCCGCUGCGU AGUGC (SEQ ID NO: 4) |
| FAM-E | CACGGUCCAGCGCUAACUGUACCUGCUGUGCCA CCCACCG (SEQ ID NO: 5) |
| FAM-F | ACCACGCGCCAACGUGUCAGCUACACGCCGUGU UCCCCGG (SEQ ID NO: 6) |

TABLE 2

Nucleolin Aptamer Sequences with 5' and 3' Constant Regions

| NCL Aptamer | Sequence |
|---|---|
| FAM-A | GGGAGAGAGGAAGAGGGAUGGGCCAUCUAGAUCUC CGUAGAUUCCCCCGGCUCUUUCUCGCCAUAACCCA GAGGUCGAUAGUACUGGAUCCCCCC (SEQ ID NO: 7) |
| FAM-B | GGGAGAGAGGAAGAGGGAUGGGAGCCAGCUUUGCA UACCACGUGCAAUUCACUCCACCCGUCACAUAACC CAGAGGUCGAUAGUACUGGAUCCCCCC (SEQ ID NO: 8) |
| FAM-C | GGGAGAGAGGAAGAGGGAUGGGAAGAUCUGCUAAG UGCACGCACAAUCACCAUCGAGCGUCUCAUAACCC AGAGGUCGAUAGUACUGGAUCCCCCC (SEQ ID NO: 9) |
| FAM-D | GGGAGAGAGGAAGAGGGAUGGGCACAUGGUACGCC CAAAGCGAGGCCCGCUGCGUAGUGCCAUAACCCAG AGGUCGAUAGUACUGGAUCCCCCC (SEQ ID NO: 10) |
| FAM-E | GGGAGAGAGGAAGAGGGAUGGGCACGGUCCAGCGC UAACUGUACCUGCUGUGCCACCCACCGCAUAACCC AGAGGUCGAUAGUACUGGAUCCCCCC (SEQ ID NO: 11) |
| FAM-F | GGGAGAGAGGAAGAGGGAUGGGACCACGCGCCAAC GUGUCAGCUACACGCCGUGUUCCCCGGCAUAACCC AGAGGUCGAUAGUACUGGAUCCCCCC (SEQ ID NO: 12) |

TABLE 3

Representative Nucleolin Aptamer Sequences without 5' and 3' Constant Regions from All Families

| Family Name | Representative Sequence | SEQ ID NO: |
|---|---|---|
| A | CCAUCUAGAUCUCCGUAGAUUCCCC CGGCUCUUUCUCGC | 13 |

TABLE 3-continued

Representative Nucleolin Aptamer Sequences without 5' and 3' Constant Regions from All Families

| Family Name | Representative Sequence | SEQ ID NO: |
|---|---|---|
| B | AGCCAGCUUUGCAUACCACGUGCAAUUCACUCCACCCGUCA | 14 |
| C | AAGAUCUGCUAAGUGCACGCACAAUCACCAUCGAGCGUCU | 15 |
| D | CACAUGGUACGCCCAAAGCGAGGCCCGCUGCGUAGUGC | 16 |
| E | CACGGUCCAGCGCUAACUGUACCUGCUGUGCCACCCACCG | 17 |
| F | ACCACGCGCCAACGUGUCAGCUACACGCCGUGUUCCCCGG | 18 |
| G | AAGAUCCUCGCGCAUCUGCCGAGCAAUCACCAUCGGACG | 19 |
| H | CCAAAUGCCAAGCCGUAGCCCGGCCAGUAGCCCACACGUC | 20 |
| I | UGCCAAGCCGAGGCCCGGCCACCAUCCACUGAUAGUGGGC | 21 |
| J | AAGAUCCUGACGCGACACAGCAAUCACCAUCGAACCAGCU | 22 |
| K | AAGAUCUGCGGCAACGCACAAUCACCAUCGAUUCCGAAUU | 23 |
| L | GAGCUCUCGAUUUCCUCCGCGACACCCAUCCAAACCUCA | 24 |
| M | CUCUCCGGUCUACCAUCCGGACCGGCGACAAAGUCAACUU | 25 |
| N | AAGAUCUGCUAUGCACAAUCACCAUCGGGCGCUCCGGGAA | 26 |
| O | UUGACUCUGCUGCGUAGUUCGCACCAAGAUCAACCACUUC | 27 |
| P | UACCAAGUCGUGGCCCGACUACCCAGCACGAUGCGCAA | 28 |
| Q | CUAUUCGAGUUCCCACGAAUCCCCCCAUCGAGAACCUAC | 29 |
| R | UGCCAAGCCGAGGCCCGGCCACCGUCCCCGCGGCUGAUGA | 30 |
| S | AAUGAUCUCGCCAAUGGGCGACAAUCACCAUGUCUUCACA | 31 |
| T | UCAGUGCGCCAAGUGGAGGCCCCACCGCAGCCCAUCAA | 32 |
| U | UGUAUGCCAGCUUUGACGAUAACUGUCGCGCGUCAAUUCA | 33 |
| V | UACGCCAAAGUGGAGCCCACUCGUACCCCAUCAUGAGCUG | 34 |
| W | CCGCCAGCUUUGGGUACCCUGACCAAUUCACGGCCAUCCA | 35 |
| X | GUAAUUGUCUGAGACCACCGGACAAUCAACAAGAAAUCCU | 36 |
| Y | UCAGGCCAAAGUGUGAUAGCCACACCCGCACCCAUCAGGA | 37 |
| Z | CCGACCGCCGACCAGGGUGCCACUCGUACCCCUGUCCGCC | 38 |
| AA | UGCCAAGUCGAAGCCCGACCACGCCAUCCCUAACAGUGCC | 39 |
| AB | ACUUGUGCUGAGUCGCCAAAGUGAGGCCCACUCGCCAGCA | 40 |
| AC | CCGCCAGCUCCUCUGAGGCACAAGAGGUUCACGGUGAUCC | 41 |
| AD | CACCAGGUUCUGCUGUCCCCAAGCGCUGACCCAUCCUUCC | 42 |
| AE | AAGAUCCGGUAACUCCCCACCGCAAUCACCGUCGACUACU | 43 |
| AF | CCAUCUAGAUCUCCGUAGAUUCCCCCCGGCUCUUUCUCGC | 44 |
| AG | CCAUCUGAACCCACAGAUUCCCCCAUCAUCAGCCACAGUG | 45 |
| AH | CACUAAGUUGGUAGCCCCAACUGCCCCGACACGAGGAUGU | 46 |
| AI | UUGUGCUCCGUGGCUCCCCGGACAACCGCUUCCAGCAGU | 47 |
| AJ | CAAUCACGCGUAGUACGUCGCGGAAGAUCCCCAUGCCGA | 48 |
| AK | CACAUGGUACGCCCAAAGCGAGGCCCGCUGCGUAGUGC | 49 |
| AL | UGCCAUACGCGGUUCGAAGUCGAAGCCCGACAACCCGGCA | 50 |
| AM | GUUAUUCACAUGCCUCCCGUGAAUCAACAAGAAUUCCUUG | 51 |
| AN | AAAGAUCUAGACUGUAAGUCUCCAAUCGCCCAGUUAAUUC | 52 |
| AO | GCCCAAUCGCCAGUGGAACGCGCUGAAGGAUCUGCACCC | 53 |
| AP | UGCAACGUAAAAGAGAGUCAUCUCAGGCUAGUCGUCUACC | 54 |
| AQ | GUGUACGCCAAGUCGAGGCCCGACCGUACCCAUACGCGAC | 55 |
| AR | UUAGCUCUACUUUCCUCUUCAGUAAGACUAACCGCUUCUU | 56 |
| AS | UCCAAGCGGAGGCCCCGCACCCACCCUCCAACGGGCACGG | 57 |
| AT | UAUCGCUCCACAACGACUCCCGUGGACUACCCAAUUCCAA | 58 |
| AU | GUCGUGCCCAAGUGAAGGCCUCACGCACGCAUCCUAACCU | 59 |
| AV | AAGAUCUGCGCCAGCACAAUCACCAUCGUCCUGAGAAUGG | 60 |
| AW | AUGCCAAGCAGUGGCCCUGCCACCCACCUAUCACUGUCGA | 61 |

TABLE 3-continued

Representative Nucleolin Aptamer Sequences without 5' and 3' Constant Regions from All Families

| Family Name | Representative Sequence | SEQ ID NO: |
|---|---|---|
| AX | AACAGACCAAGCAGCGGCCCUGCUCUGCCAUCAUACGCCU | 62 |
| AY | GUCAUUCGCUGACGAAUCAACAUGAAUUCCUAACUGCUGA | 63 |
| AZ | ACACGCCAAGCUGGUAGCCCCAGCCGUGCCCAUUACGGCC | 64 |
| BA | UAGCCAAGCAGCAGCCCUGCCAACCCAUCCUACCCGGGCG | 65 |
| BB | GCCCAAGGCGAGGCCCGCCGCUCCAUCCAGACGCUGAGGG | 66 |
| BC | AAGAUCUCGUCAUGCUUUGACGUCAAUCACCAUUGUUCCC | 67 |
| BD | AUCCCCCAGGAUGAGCACGUUGCCAUGGACUGGCUAUCC | 68 |
| BE | CUGUUACAGUCUCGCGUAACCCCCCCAUCGAUGUCCUCGA | 69 |
| BF | AGCCAGCUUUCGGCAAACCGAAUUCACUCCACCCUGCUCA | 70 |
| BG | CACGGUAUAACCUCCUCAUAUACCUGCUGUGCCACCCGCG | 71 |
| BH | CCGGAAGAUCUGCUCGCACUAGCCGGAGCCCAAUCACGGC | 72 |
| BI | CCUGCCGAACGGCUAAGUCGCAGCCCGACCCGCGGCAGGG | 73 |
| BJ | CUCCGACCCGCGGACGAAGUCAACUUCCACAGUCCCACAC | 74 |
| BK | ACAUUAGGAUCUGCGUGAUGGGGAUCACCCGCUACAUGUC | 75 |
| BL | UCUAAGAUGGGGAAGAUCUCCGGAGCACCGGGCAAUCACC | 76 |
| BM | CUAUUCGAGUUCCCACGAAUCCCCCAUCGAGAACCUAC | 77 |
| BN | UGCCAAGCCGAGGCCCGGCCAGCAUCCCUCACGAGAGAGG | 78 |
| BO | GCCAAGCACGUAGCCCGUGCCCCCACCCGCCUGUGUGCUG | 79 |
| BP | UGCCAAGCACGAAGCCCGUGCCCCCAUCCAGAGUGUGAGA | 80 |
| BQ | AGCCAGCUUUUGCAUACCACGUGCAAUUCACUCCACCCGUCA | 81 |
| BR | CUUUGUAAACCCGGCAAACAAAAUCAACUUCCAUCAUCAA | 82 |
| BS | CCAUUGUAGCGACCACACAAUUCCCCAUCGGACAGCAUGG | 83 |
| BT | CUCUCGCCGUUCCCAGGCACGACAAAAUCAACUUCCCGCU | 84 |
| BU | AAGCCAAGCCGCGGCCCGGCCUUCCCAUGUGCUACUAGAG | 85 |

TABLE 3-continued

Representative Nucleolin Aptamer Sequences without 5' and 3' Constant Regions from All Families

| Family Name | Representative Sequence | SEQ ID NO: |
|---|---|---|
| BV | CCAAAUGCCAAAGCCGUAGCCCGGCCAGUAGCCCACACGUC | 86 |
| BW | CCAUUACGCGACGUAAUUCCCCAUCGUUUCCUCGUUAAG | 87 |
| BX | CCAUCUAGAUCUCCGUAGAUUCCCCGGCUCUUUCUCGC | 88 |
| BY | ACUGUCUGCAUACACGGUAUGCCCAACGCCAUCCAAACCG | 89 |
| BZ | ACCUGCGGCUAUUGCCAGCGCCAUAAGACCCUCCACAGUA | 90 |

TABLE 4

Variant Nucleolin Aptamer Sequences without 5' and 3' Constant Regions from All Families

| Family Name | All Family Sequences | SEQ ID NO: |
|---|---|---|
| A | CCAUCUAGAUCUCCGUAGAUUCCCCCGGCUCUUUCUCGC | 91 |
|   | CCAUCUAGAUCUCCGUAGAUUCCCCCGGCUCUUCCUCGC | 92 |
|   | CCAUCUAGAUCUCCGUAGAUUCCCCCAGCUCUUUCUCGC | 93 |
| B | AGCCAGCUUUGCAUACCACGUGCAAUUCACUCCACCCGUCA | 94 |
|   | AGCCAGCUUUGCAUACCACGUGCAAUUCACUCCACCCGUCG | 95 |
| C | AAGAUCUGCUAAGUGCACGCACAAUCACCAUCGAGCGUCU | 96 |
|   | AAGAUCUGCUAAGUGCACGCACAAUCACCAUCGAGCGUCC | 97 |
|   | AAGAUCUGCUAAGUGCACGCACAAUCACCAUCGAGCGCCU | 98 |
|   | AAGAUCUGCUAAGUGCACGCACAAUCACCAUCGAGCGUC | 99 |
|   | AAGAUCUGCUAAGUGCACGCACAAUCACCAUCGAGCGACU | 100 |
| D | CACAUGGUACGCCCAAAGCGAGGCCCGCUGCGUAGUGC | 101 |
|   | CACACGGUACGCCCAAAGCGAGGCCCGCUGCGUAGUGC | 102 |
| E | CACGGUCCAGCGCUAACUGUACCUGCUGUGCCACCCACCG | 103 |
|   | CACGGUCCAGCGCUAACUGUACCUGCUGUGCCACCCACCA | 104 |
|   | CACGGUCCAGCGCUAACUGUACCUGCUGUGCCACCCACUG | 105 |
|   | CACGGUCCAGCGCUAACUGUACCUGCUGUGCCACCCACCU | 106 |
|   | CACGGUCCAGCGCUAACUGUACCUGCUGUGCCACCCGCCG | 107 |
| F | ACCACGCGCCAACGUGUCAGCUACACGCCGUGUUCCCCGG | 108 |
|   | ACCACGCGCCAACGUGUCAGCUACACGCCGUGUUCCCCGA | 109 |
|   | ACCACGCGCCAACGUGUCAGCUACACGCCGUGUUCCCCG | 110 |

TABLE 4-continued

Variant Nucleolin Aptamer Sequences without
5' and 3' Constant Regions from All Families

| Family Name | All Family Sequences | SEQ ID NO: |
|---|---|---|
|  | CCACGCGCCAACGUGUCAGCUACAC GCCGUGUUCCCGG | 111 |
| G | AAGAUCCUCGCGCAUCUGCCGAGCA AUCACCAUCGGACG | 112 |
|  | AAGAUCCUCGCGCAUCUGCCGAGCA AUCACCAUCGGACC | 113 |
|  | AAGAUCCUCGCGCAUCUGCCGAGCA AUCACCAUCGGACA | 114 |
|  | AAGAUCCUCGCGCAUCUGCCGAGCA AUCACCAUCGGACU | 115 |
|  | AAAGAUCCUCGCGCAUCUGCCGAGC AAUCACCAUCGGACG | 116 |
|  | AAGAUCCUCGCGCACCUGCCGAGCA AUCACCAUCGGACG | 117 |
| H | CCAAAUGCCAAGCCGUAGCCCGGCC AGUAGCCCACACGUC | 118 |
|  | CCAAAAUGCCAAGCCGUAGCCCGGC CAGUAGCCCACACGUC | 119 |
|  | CCAAAUGCCAAGCCGUAGCCCGGCC AGUAGCCCACACGAC | 120 |
|  | CCAAAUGCCAAGCCGUAGCCCGGCC AGUAGCCCACACGUA | 121 |
| I | UGCCAAGCCGAGGCCCGGCCACCAU CCACUGAUAGUGGGC | 122 |
|  | UGCCAAGCCGAGGCCCGGCCACCAU CCACUGAUAGUGGGA | 123 |
|  | UGCCAAGCCGAGGCCCGGCCACCAU CCACUGAUAGUGGG | 124 |
|  | UGCCAAGCCGAGGCCCGGCCACCAU CCACUGAUAGUGGGU | 125 |
| J | AAGAUCCUGACGCGACACAGCAAUC ACCAUCGAACCAGCU | 126 |
|  | AAGAUCCUGACGCGACACAGCAAUC ACCAUCGAACCAGCC | 127 |
| K | AAGAUCUGCGGCAACGCACAAUCAC CAUCGAUUCCGAAUU | 128 |
|  | AAGAUCUGCGGCAACGCACAAUCAC CAUCGAUUCCGAAUG | 129 |
|  | AAGAUCUGCGGCAACGCACAAUCAC CAUCGAUUCCGAAUC | 130 |
|  | AAGAUCUGCGGCAACGCACAAUCAC CAUCGAUUCCGAACU | 131 |
|  | AAGAUCUGCGGCAACGUACAAUCAC CAUCGAUUCCGAAUU | 132 |
| L | GAGCUCUCGAUUUCCUCCGCGACAC CCAUCCAAACCUCA | 133 |
|  | AGCUCUCGAUUUCCUCCGCGACACC CAUCCAAACCUCA | 134 |
|  | GAGCUCUCGAUUUCCUCCGCGACAC CCAUCCAAACCUCG | 135 |
| M | CUCUCCGGUCUACCAUCCGGACCGG CGACAAAGUCAACUU | 136 |
|  | CUCUCCGGUCUACCACCCGGACCGG CGACAAAGUCAACUU | 137 |
| N | AAGAUCUGCUAUGCACAAUCACCAU CGGGCGCUCCGGGAA | 138 |
|  | AAGAUCUGCUAUGCACAAUCACCAU CGGGCGCUCCGGGAA | 139 |
|  | AAGAUCUGCUACGCACAAUCACCAU CGGGCGCUCCGGGAA | 140 |
| O | UUGACUCUGCUGCGUAGUUCGCACC AAGAUCAACCACUUC | 141 |
|  | UUGACUCUGCUGCGUAGUUCGCACC AAGAUCAACCACUUCC | 142 |
|  | UUGACUCUGCUGCGUAGCUCGCACC AAGAUCAACCACUUC | 143 |
|  | UUGACUCUGCUGCGCAGUUCGCACC AAGAUCAACCACUUC | 144 |
|  | UUGACUCUGCUGCGUAGUCCGCACC AAGAUCAACCACUUC | 145 |
| P | UACCAAGUCGUGGCCCGACUACCCA GCACGAUGCGCAA | 146 |
|  | UACCAAAGUCGUGGCCCGACUACCC AGCACGAUGCGCAA | 147 |
|  | UACCAAGUCGUGGCCCGACUACCCA GCACGGUGCGCAA | 148 |
|  | UACCAAGUCGUGGCCCGACUACCCA GCACGAUGCGCAG | 149 |
|  | UACCAAGUCGUGGCCCGACUACCCA GCACAAUGCGCAA | 150 |
|  | UACCAAGUCGCGGCCCGACUACCCA GCACGAUGCGCAA | 151 |
| Q | CUAUUCGAGUUCCCACGAAUCCCCC CAUCGAGAACCUAC | 152 |
|  | CUAUUCGAGUUCCCACGAAUCCCCC CAUCGAGAACCUA | 153 |
|  | CUAUUCGAGUUCCCACGAAUCCCCC CAUCGAGAACCUAU | 154 |
|  | CUAUUCGAGUUCCCACGAAUCCCCC CAUCGAGAACCUAA | 155 |
| R | UGCCAAGCCGAGGCCCGGCCACCGU CCCCGCGGCUGAUGA | 156 |
|  | UGCCAAAGCCGAGGCCCGGCCACCG UCCCCGCGGCUGAUGA | 157 |
|  | UGCCAAGCCGAGGCCCGGCCACCGU CCCCGCGGCUGAUCGA | 158 |
|  | UGCCAAGCCGAGGCCCGGCCACCGU CCCCGCGGCUGAUGG | 159 |
|  | UGCCAAGCCGAGGCCCGGCCACCGU CCCCGCGGCUGACGA | 160 |
| S | AAUGAUCUCGCCAAUGGGCGACAAU CACCAUGUCUUCACA | 161 |
|  | AACGAUCUCGCCAAUGGGCGACAAU CACCAUGUCUUCACA | 162 |
|  | AAUGAUCUCGCCAAUGGGCGACAAU CACCAUGUCUUCACG | 163 |
|  | AAUGAUCUCGCCAAUGUGCGACAAU CACCAUGUCUUCACA | 164 |
| T | UCAGUGCGCCAAGUGGAGGCCCCAC CGCAGCCCAUCAA | 165 |
|  | UCAGUGCGCCAAGUGGAGGCCCCAC CGCAGCCCAUCGA | 166 |
|  | UCAGUGCGCCAAGUGGAGGCCCCAC CGCAGCCCAUCAG | 167 |
| U | UGUAUGCCAGCUUUGACGAUAACUG UCGCGCGUCAAUUCA | 168 |
| V | UACGCCAAAGUGGAGCCCACUCGUA CCCCAUCAUGAGCUG | 169 |
|  | UACGCCAAAGUGGAGCCCACUCGUA CCCCAUCAUGAGCUG | 170 |
|  | UACGCCAAAGUGGAGCCCACUCGUA CCCCAUCAUGAGCUC | 171 |
|  | UACGCCAAAGUGGAGCCCACUCGUA CCCCAUCAUGGGCUG | 172 |
|  | UACGCCAAAGUGGAGCCCACUCGUA UCCCAUCAUGAGCUG | 173 |
|  | UACGCCAAAGUGGAGCCCACUCGUA CCCCAUCGUGAGCUG | 174 |
|  | UACGCCAAAGUGGAGCCCACUCGUA CUCCAUCAUGAGCUG | 175 |

TABLE 4-continued

Variant Nucleolin Aptamer Sequences without
5' and 3' Constant Regions from All Families

| Family Name | All Family Sequences | SEQ ID NO: |
|---|---|---|
| | CACGCCAAAGUGGAGCCCACUCGUACCCCAUCAUGAGCUG | 176 |
| | UACGCCAAAGUGGAGCCCACUCGCACCCCAUCAUGAGCUG | 177 |
| | UACGCCAAAGUGGAGCCCACUCGUACCCCAUCAUGAGCUA | 178 |
| W | CCGCCAGCUUUGGGUACCCUGACCAAUUCACGGCCAUCCA | 179 |
| | CCGCCAGCUUUGGGUACCCUGACCAAUUCACGGCCAUCCG | 180 |
| | CCGCCCAGCUUUGGGUACCCUGACCAAUUCACGGCCAUCCA | 181 |
| X | GUAAUUGUCUGAGACCACCGGACAAUCAACAAGAAAUCCU | 182 |
| | GUAAUUGUCUGAGACCACCGGACAAUCAACAAGAAAUCCU | 183 |
| | UAAUUGUCUGAGACCACCGGACAAUCAACAAGAAAUCCU | 184 |
| Y | UCAGGCCAAAGUGUGAUAGCCACACCCGCACCCAUCAGGA | 185 |
| | UCAGGCCAAAGUGUGAUAGCCACACCCGCACCCAUCAGA | 186 |
| | UCAGGCCAAAGUGUGAUAGCCACACCGCACCCAUCAGG | 187 |
| Z | CCGACCGCCGACCAGGGUGCCACUCGUACCCCUGUCCGCC | 188 |
| | CCGACCGCCGACCAGGGUGCCACUCGUACCCCUGUCCGCCC | 189 |
| | CCGACCGCCGACCAGGGUGCCACUCGUACCCCUGUCCCGCC | 190 |
| | CCGACCGCCGACCAGGGUGCCACUCGUACCCCUGUCCGC | 191 |
| AA | UGCCAAGUCGAAGCCCGACCACGCCAUCCCUAACAGUGCC | 192 |
| | UGCCAAAGUCGAAGCCCGACCACGCCAUCCCUAACAGUGCC | 193 |
| | UGCCAAGUCGAAGCCCGACCACGCCAUCCCUAACAGUGC | 194 |
| | UGCCAAGUCGAAGCCCGACCACGCCAUCCCUAACGGUGCC | 195 |
| | UGCCAAGUCGAAGCCCGACCACGCCAUCCCUAACAGUGCA | 196 |
| | UGCCAAGUCGAAGGCCCGACCACGCCAUCCCUAACAGUGCC | 197 |
| | UGCCAAGCCGAAGCCCGACCACGCCAUCCCUAACAGUGCC | 198 |
| AB | ACUUGUGCUGAGUCGCCAAAGUGAGGCCCACUCGCCAGCA | 199 |
| | GCUUGUGCUGAGUCGCCAAAGUGAGGCCCACUCGCCAGCA | 200 |
| | ACCUGUGCUGAGUCGCCAAAGUGAGGCCCACUCGCCAGCA | 201 |
| AC | CCGCCAGCUCCUCUGAGGCACAAGAGGUUCACGGUGAUCC | 202 |
| | CCGCCAGCUCCUCUGAGGCACAAGAGGUUCACGGUGAUCCC | 203 |
| AD | CACCAGGUUCUGCUGUCCCCAAGCGCUGACCCAUCCUUCC | 204 |
| | CACCAGGUUCUGCUAUCCCCAAGCGCUGACCCAUCCUUCC | 205 |
| | CACCAGGUUCUGCUGUCUCCAAGCGCUGACCCAUCCUUCC | 206 |
| | CACCAGGUUCUGCUGUUCCCAAGCGCUGACCCAUCCUUCC | 207 |
| | CACCAGGUCCUGCUGUCCCCAAGCGCUGACCCAUCCUUCC | 208 |
| | CACCAGGCUCUGCUGUCCCCAAGCGCUGACCCAUCCUUCC | 209 |
| | CACCAGGUUCUGCUGUCCUCAAGCGCUGACCCAUCCUUCC | 210 |
| AE | AAGAUCCGGUAACUCCCCACCGCAAUCACCGUCGACUACU | 211 |
| | AAGAUCCGGUGACUCCCCACCGCAAUCACCGUCGACUACU | 212 |
| | AAGAUCCGGUAACUCCCUACCGCAAUCACCGUCGACUACU | 213 |
| | AAAGAUCCGGUAACUCCCCACCGCAAUCACCGUCGACUACU | 214 |
| AF | CCAUCUAGAUCUCCGUAGAUUCCCCCGGGCUCUUUCUCGC | 215 |
| | CCAUCUAGAUCUCCGUAGAUUCCCCCGGGCUCUUUCUCGU | 216 |
| | CCAUCUAGAUCUCCGUAGAUUCCCCCGGGCUCUUUCUCGA | 217 |
| | CCAUCUAGAUCUCCGUAGAUUCCCCCGGGCUCUUUCUCG | 218 |
| | CCAUCUAGAUCUCCGUAGAUUCCCCCGGGCUCUUUCUCGC | 219 |
| | CCAUCUAGAUCUCCGUAGAUUCCCCCGGGCUCUUUCUCAC | 220 |
| | CCAUCUAGAUCUCCGUAGAUUCCCCCGGGCUCUUUCUCGC | 221 |
| | CCAUCUAGAUCUCCGUAGAUUCCCCCGGGCUCUUCCUCGC | 222 |
| | CCAUCUAGAUCUCCGUAGAUUCCCCCGGGCUCUCUCUCGC | 223 |
| | CCAUCUAGAUCUCCGUAGAUUCCCCCGGGCUCUUUCUUGC | 224 |
| | CCAUCUAGAUCUCCGUAGAUUCCCCCGGGCCCUUUCUCGC | 225 |
| | CCAUCUAGAUCUCCGUAGAUUCCCCCGGGCUCUUUCUCUC | 226 |
| | CCAUCUAGAUCUCCGUAGAUUCCCCCGGCCCUUUCUCGC | 227 |
| | CCAUCUAGAUCUCCGUAGAUUCCCCCGGGCUCUUUCUCCC | 228 |
| | CCAUCUAGAUCUCCGUAGAUUCCCCCGGGCUCUUUCUCGUC | 229 |
| AG | CCAUCUGAACCCACAGAUUCCCCCAUCAUCAGCCACAGUG | 230 |
| | CCAUCUGAACCCACAGAUUCCCCCAUCAUCAGCCACAGUA | 231 |
| | CCAUCUGAACCCACAGAUUCCCCCAUCAUCAGCCACAGCG | 232 |
| | CCAUCUGAACCCACAGAUUCCCCCAUCAUCAGCCACAGUC | 233 |
| | CCAUCUGAACCCACAGAUUCCCCCAUCAUCAGCCACGGUG | 234 |
| AH | CACUAAGUUGGUAGCCCCAACUGCCCCGACACGAGGAUGU | 235 |
| | CACUAAGUUGGUAGCCCCAACUGCCCCGACACGAGGAUGUC | 236 |
| | CACUAAGUUGGUAGCCCCAACUGCCCCGACACGAGGAUGC | 237 |
| AI | UUGUGCUCCGUGGCUCCCCGGACCAACCGCUUCCAGCAGU | 238 |
| | UUGUGUUCCGUGGCUCCCCGGACCAACCGCUUCCAGCAGU | 239 |
| | UUGUGCUCCGUGGCUCCCCGGACCAACCGCUUCCAGCAGC | 240 |
| | UUGCGCUCCGUGGCUCCCCGGACCAACCGCUUCCAGCAGU | 241 |

TABLE 4-continued

Variant Nucleolin Aptamer Sequences without 5' and 3' Constant Regions from All Families

| Family Name | All Family Sequences | SEQ ID NO: |
|---|---|---|
| AJ | CAAUCACGCGUAGUACGUCGCGGAAGAUCCCCAUGCCGA | 242 |
| | CAAUCACGCGUAGUACGUCGCGGAAGAUCCCCAUGCCGG | 243 |
| | CAAUCACGCGUAGUACGUCGCGGAAGAUCCCCAUGCCAA | 244 |
| | CAAUCACGCGUAGUACGUCGCGGAAGAUCCCCAUGCCGU | 245 |
| | CAAUCACGCUAGUACGUCGCGGAAGAUCCCCAUGCCGA | 246 |
| | CAAUCACGCGUAGUACGUCGCGGAGGAUCCCCAUGCCGA | 247 |
| AK | CACAUGGUACGCCCAAAAGCGAGGCCCGCUGCGUAGUGC | 248 |
| | CACAUGGUACGCCCAAAAGCGAGGCCCGCUGCGUAGUGC | 249 |
| | CACAUGGUACGCCCAAAAGCCGAGGCCCGCUGCGUAGUGC | 250 |
| | CACAUGGUACGCCCAAAAGCGAGGCCCGCUGCGUAGUG | 251 |
| AL | UGCCAUACGCGGUUCGAAGUCGAAGCCCGACAACCCGGCA | 252 |
| | UGCCAUACGCGGUUCGAAGUCGAAGCCCGACAACCCGGCA | 253 |
| | UGCCAUACGCGGUUCGAAGUCGAGGCCCGACAACCCGGCA | 254 |
| AM | GUUAUUCACAUGCCUCCCGUGAAUCAACAAGAAUUCCUUG | 255 |
| | UUAUUCACAUGCCUCCCGUGAAUCAACAAGAAUUCCUUG | 256 |
| | GUUAUUCACAUGCCUCCCGUGAAUCAACAAGAAUUCCUCG | 257 |
| | GUUAUUCACAUGCCUCUCGUGAAUCAACAAGAAUUCCUUG | 258 |
| | | 259 |
| AN | AAAGAUCUAGACUGUAAGUCUCCAAUCGCCCAGUUAAUUC | 260 |
| | AAAAGAUCUAGACUGUAAGUCUCCAAUCGCCCAGUUAAUUC | 261 |
| | AAAGAUCUAGACUGUAAGUCUCCAAUCGCCCAGUAAUUC | 262 |
| AO | GCCCAAUCGCCAGUGGAACGCGCUGAAGGAUCUGCACCC | 263 |
| | GCCCAAUCGCCAGUGGAACGCGCUGAAGGAUCUGCACC | 264 |
| | GCCCAAUCGCCAGUGGAACGCACUGAAGGAUCUGCACCC | 265 |
| | GCCCAAUCGCCAGUGGAACGCGCUGAAGGAUCUGCACCCC | 266 |
| | CCCAAUCGCCAGUGGAACGCGCUGAAGGAUCUGCACCC | 267 |
| | GCCCAAUCGCCAGCGGAACGCGCUGAAGGAUCUGCACCC | 268 |
| AP | UGCAACGUAAAAGAGAGUCAUCUCAGGCUAGUCGUCUACC | 269 |
| | UGCAACGUAAAAGAGAGUCAUCUCAGGCUAGUCGUCUAC | 270 |
| AQ | GUGUACGCCAAGUCGAGGCCCGACCGUACCCAUACGCGAC | 271 |
| | UGUACGCCAAGUCGAGGCCCGACCGUACCCAUACGCGAC | 272 |
| | GUGUACGCCAAGUCGAGGCCCGACCGUACCCAUACGCGGC | 273 |
| | GUGUACGCCAAGUCGAGGCCCGACCGUACCCAUACGCGAU | 274 |
| AR | UUAGCUCUACUUUCCUCUUCAGUAAGACUAACCGCUUCUU | 275 |
| | UUAGCUCUACUUUCCUCUUCAGUAAGACUAACCGCUUCCU | 276 |
| | UUAGCUCUACUUUCCUCUUCAGUAAGACUAACCGCUUCUC | 277 |
| | UUAGCUCUACUUUCCUCUUCAGUAAGACUAACCGCUCCUU | 278 |
| AS | UCCAAGCGGAGGCCCCGCACCCACCCUCCAACGGGCACGG | 279 |
| | UCCAAGCGGAGGCCCCGCACCCACCCUCCAACGGGCACGG | 280 |
| | UCCAAGCGGAGGCCCCGUACCCACCCUCCAACGGGCACGG | 281 |
| | UCCAAGCGGAGGCCCCGCACCCACCCCCCAACGGGCACGG | 282 |
| | UCCAAGCGGAGGCCCCGCACCCACCCUCCAACGGGCACGA | 283 |
| | UCCAAAGCGGAGGCCCCGCACCCACCCUCCAACGGGCACGG | 284 |
| | UCCAAGCGGAGGCCCCGCACCCACCCUCCAACGGGCACAG | 285 |
| AT | UAUCGCUCCACAACGACUCCCGUGGACUACCCAAUUCCAA | 286 |
| | UAUCGCUCCACAACGACUCCCGUGGACUACCCAAUUCCAG | 287 |
| | UAUCGCUCCACAACGACUCCCGUGGACUACCCAAUUCCAAA | 288 |
| | UAUCGCUCCACAACGACUCCCGUGGACUACCCAAUUCCAU | 289 |
| AU | GUCGUGCCCAAGUGAAGGCCUCACGCACGCAUCCUAACCU | 290 |
| | UCGUGCCCAAGUGAAGGCUCACGCACGCAUCCUAACCU | 291 |
| | GUCGUGCCCAAGUGAAGGCCUCACGCACGCAUCCUAACCC | 292 |
| AV | AAGAUCUGCGCCAGCACAAUCACCAUCGUCCUGAGAAUGG | 293 |
| | AAGAUCUGCGCCAGCACAAUCACCAUCGUCCUGAGAAUGC | 294 |
| | AAGAUCUGCGCCAGCACAAUCACCAUCGUCCUGAGAAUGA | 295 |
| | AAGAUCUGCGCCAGCACAAUCACCAUCGUCCUGAGAGUGG | 296 |
| | AAGAUCUGCGCCAGCACAAUCACCAUCGUCCUGGGAAUGG | 297 |
| AW | AUGCCAAGCAGUGGCCCUGCCACCCACCUAUCACUGUCGA | 298 |
| | AUGCCAAGCAGUCGGCCUGCCACCCACCUAUCACUGUCGA | 299 |
| | AUGCCAAGCAGUGGCCCUGCCACCCACCUAUCACUAUCGA | 300 |
| | AUGCCAAGCAGUGGCCCUGCCACCCACCUACCACUGUCGA | 301 |
| | AUGCCAAGCAGCGGCCCUGCCACCCACCUAUCACUGUCGA | 302 |
| AX | AACAGACCAAGCAGCGGCCCUGCUCUGCCAUCAUACGCCU | 303 |
| | GACAGACCAAGCAGCGGCCCUGCUCUGCCAUCAUACGCCU | 304 |
| | AACAGACCAAGCAGUGGCCCUGCUCUGCCAUCAUACGCCU | 305 |
| | AACAGACCAAGCAGCGGCCCUGCUCUGCCAUCAUACGCCC | 306 |
| | AACAGACCAAGCAGCGGCCCUGCUCUGCCAUCAUACACCU | 307 |

TABLE 4-continued

Variant Nucleolin Aptamer Sequences without 5' and 3' Constant Regions from All Families

| Family Name | All Family Sequences | SEQ ID NO: |
|---|---|---|
|  | ACAGACCAAGCAGCGGCCCUGCUCUGCCAUCAUACGCCU | 308 |
|  | AACAGACCAAGCAGCGGCCCUGCUCUGCCAUCAUACGCCCU | 309 |
| AY | GUCAUUCGCUGACGAAUCAACAUGAAUUCCUAACUGCUGA | 310 |
|  | UCAUUCGCUGACGAAUCAACAUGAAUUCCUAACUGCUGA | 311 |
|  | GUCAUUCGCUGACGAAUCAACAUGAAUUCCUAACUGCCGA | 312 |
|  | GUCAUUCGCUGACGAAUCAACAUGAAUUCCUAACUGCUGG | 313 |
| AZ | ACACGCCAAGCUGGUAGCCCCAGCCGUGCCCAUUACGGCC | 314 |
|  | ACACGCCAAGCUGGUAGCCCCAGCCGUGCCCAUUACGGC | 315 |
|  | ACACGCCAAGCUGGUAGCCCCAGCCGUGCCCAUUACGGUC | 316 |
|  | ACACGCCAAGCUGGUAGCCCCAGCCGUACCCAUUACGGCC | 317 |
| BA | UAGCCAAGCAGCAGCCCUGCCAACCCAUCCUACCCGGGCG | 318 |
|  | UAGCCAAGCAGCAGCCCUGCCAACCCAUCCUACCCGGCG | 319 |
|  | UAGCCAAGCAGCAGCCCUGCCAACCCAUCCUACCCGGGCA | 320 |
|  | UAGCCAAGCAGCAGCCCUGCCAACCCAUCCUACCCGGGUG | 321 |
|  | UAGCCAAGCAGCGGCCCUGCCAACCCAUCCUACCCGGGCG | 322 |
| BB | GCCCAAGGCGAGGCCCGCCGCUCCAUCCAGACGCUGAGGG | 323 |
|  | GCCCAAGGCGAGGCCCGCCGCUCCAUCCAGACGCUGAGG | 324 |
|  | CCCAAGGCGAGGCCCGCCGCUCCAUCCAGACGCUGAGGG | 325 |
|  | CCCAAGGCGAGGCCCGCCGCUCCAUCCAGACGCUGAGG | 326 |
|  | GCCCAAGGCGAGGCCCGCCGCUCCAUCCAGACGCUGAGGC | 327 |
|  | GCCCAAAGGCGAGGCCCGCCGCUCCAUCCAGACGCUGAGGG | 328 |
|  | GCCCAAGGCGAGGCCCGCCGCUCCAUCCAGACGCUGAGGA | 329 |
|  | GCCCCAAGGCGAGGCCCGCCGCUCCAUCCAGACGCUGAGGG | 330 |
| BC | AAGAUCUCGUCAUGCUUUGACGUCAAUCACCAUUGUUCCC | 331 |
|  | AAGAUCUCGUCAUGCUUUGACGUCAAUCACCAUUGUUCC | 332 |
|  | AAGAUCUCGUCAUGCUUUGACGUCCAAUCACCAUUGUUCCC | 333 |
|  | AAGAUCUCGUCAUGCUUUGACGUCAAUCACCAUUGUUCCA | 334 |
|  | AAGAUCUCGUCAUGCUUUGACGUCAAUCACCAUUGUUCCU | 335 |
|  | AAGAUCUCGUCAUGCUUUGACGUCAAUCACCAUUGUUCCCC | 336 |
|  | AAAGAUCUCGUCAUGCUUUGACGUCAAUCACCAUUGUUCCC | 337 |
|  | AAGAUCUCGUCAUGCCUUGACGUCAAUCACCAUUGUUCCC | 338 |
| BD | AUCCCCCAGGAUGAGCACGUUGCCAUGGACUGGCUAUCC | 339 |
|  | AUCCCCCAGGAUGAGCACGUUGCCAUGGACUGGCUAUCC | 340 |
| BE | CUGUUACAGUCUCGCGUAACCCCCCCAUCGAUGUCCUCGA | 341 |
|  | CUGUUACAGUCUCGCGUAACCCCCCCAUCGAUGUCCUCGG | 342 |
|  | CUGUUACAGUCUCGAGUAACCCCCCCAUCGAUGUCCUCGA | 343 |
|  | CUGUUACAGUCUCGCGUAACCCCCUCCAUCGAUGUCCUCGA | 344 |
|  | CUGUUACAGCCUCGCGUAACCCCCCCAUCGAUGUCCUCGA | 345 |
|  | CUGUUACAGUCUCCCGUAACCCCCCCAUCGAUGUCCUCGA | 346 |
| BF | AGCCAGCUUUCGGCAAACCGAAUUCACUCCACCCUGCUCA | 347 |
|  | AGCCAGCUUUCGGCAAACCGAAUUCACUCCACCCUCCUCA | 348 |
|  | AGCCAGCUUUCGGCAAACCGAAUUCACUCCGCCCUGCUCA | 349 |
|  | AGCCAGCUUUCGGCAAACCGAAUUCACUCCACCCUGCU | 350 |
|  | AGCCAGCUUUCGGCGAACCGAAUUCACUCCACCCUGCUCA | 351 |
|  | AGCCAGCUUUCGGCAAACCGAAUUCACUCCACCCUGCUCG | 352 |
|  | AGCCAGCUUUCGGCAAACCGAAUUCACUCCACCCUGCUC | 353 |
|  | AGCCAGCUUUCGGCAAACCGAAUUCACUCCACCCUGCACA | 354 |
| BG | CACGGUAUAACCUCCUCAUAUACCUGCUGUGCCACCCGCG | 355 |
|  | CACGGUAUAACCUCCUCAUAUACCUGCUGUGCCACCCGCA | 356 |
|  | CACGGUAUAACCUCCUCAUAUACCUGCUGUGCCACCCACCG | 357 |
|  | CACGGUAUAACCUCCUCAUAUACCUGCUGUGCCACCCGCU | 358 |
|  | CACGGUAUAACCUCCUCAUAUACCUGCUGUGCCACCCACG | 359 |
|  | CACGGUAUAACCUCCUCAUAUACCUGCUGUGCCACCCGUG | 360 |
|  | CACGGUAUAACCUCCUCAUAUACCUGCUGUGCCGCCCGCG | 361 |
| BH | CCGGAAGAUCUGCUCGCACUAGCCGGAGCCCAAUCACGGC | 362 |
|  | CCGGAAGAUCUGCUCGCACUAGUCGGAGCCCAAUCACGGC | 363 |
|  | CCGGAGGAUCUGCUCGCACUAGCCGGAGCCCAAUCACGGC | 364 |
|  | CCGGAAGAUCUGCUCGCAUUAGCCGGAGCCCAAUCACGGC | 365 |
| BI | CCUGCCGAACGGCUAAGUCGCAGCCCGACCCGCGGCAGGG | 366 |
|  | CCUGCCGAACGGCUAAGUCGCAGCCCGACCCGCGGCAGG | 367 |
|  | CCUGCCGAACGGCUAAGUCGCAGCCCGACCCGCGGCAGGA | 368 |
|  | CCUGCCGAACGGCAAGUCGCAGCCCGACCCGCGGCAGGG | 369 |
|  | CCUGCCGAACGGCUAAGUCGCGGCCCGACCCGCGGCAGGG | 370 |
| BJ | CUCCGACCCGCGGACGAAGUCAACUUCCACAGUCCCACAC | 371 |
|  | CUCCGACCCGCGGACGAAGUCAACUUCCACAGUCCCACAA | 372 |
|  | CUCCGACCCGCGGACGAAGUCAACUUCCACAGUCCCACACAC | 373 |
|  | CUCCGACCCGCGGACGAAGUCAACUUCCACAGUCUCACAC | 374 |

TABLE 4-continued

Variant Nucleolin Aptamer Sequences without 5' and 3' Constant Regions from All Families

| Family Name | All Family Sequences | SEQ ID NO: |
|---|---|---|
| | CUCCGACCCGCGGACGAAGUCAACUUCCACAGUCCCACAU | 375 |
| | CUCCGACCCGCGGACGAAGUCAACUUCCACAGUCCCGCAC | 376 |
| | CUCCGACCCGCGGACGAAGUCAACUUCCACGGUCCCACAC | 377 |
| | CUCCGACCCGCGGACGAAGUCAACUUCCACAGUCCCAUAC | 378 |
| BK | ACAUUAGGAUCUGCGUGAUGGGGAUCACCCGCUACAUGUC | 379 |
| | ACAUUUAGGAUCUGCGUGAUGGGGAUCACCCGCUACAUGUC | 380 |
| | GCAUUAGGAUCUGCGUGAUGGGGAUCACCCGCUACAUGUC | 381 |
| | ACAUUAGGAUCUGCGCGAUGGGGAUCACCCGCUACAUGUC | 382 |
| BL | UCUAAGAUGGGGAAGAUCUCCGGAGCACCGGGCAAUCACC | 383 |
| | UCUAAGAUGGGGAAGAUCUCCGGAGCACCGGGCAAUCACCC | 384 |
| | CCUAAGAUGGGGAAGAUCUCCGGAGCACCGGGCAAUCACC | 385 |
| | UCUAAGGUGGGGAAGAUCUCCGGAGCACCGGGCAAUCACC | 386 |
| | UCUAAGAUGGGGAAGAUCUCCGGAGCGCCGGGCAAUCACC | 387 |
| BM | CUAUUCGAGUUCCCACGAAUCCCCCAUCGAGAACCUAC | 388 |
| | CUAUUCGAGUUCCCACGAAUCCCCCCAUCAGAACCUAC | 389 |
| | CUACUCGAGUUCCCACGAAUCCCCCAUCGAGAACCUAC | 390 |
| | CUAUUCGAGUUCCCACGAAUCCCCCAUCAAGAACCUAC | 391 |
| BN | UGCCAAGCCGAGGCCCGGCCAGCAUCCCUCACGAGAGAGG | 392 |
| | UGCCAAAGCCGAGGCCCGGCCAGCAUCCCUCACGAGAGAGG | 393 |
| | UGCCAAGCCGAGGCCCGGCCAGCAUCCCUCACGAGAGAGC | 394 |
| | UGCCAAGCCGAGGCCCGGCCAGCAUCCCUCACGAGAGAG | 395 |
| | UGCCAAGCCGAGGCCCGGCCAGCAUCCCCCACGAGAGAGG | 396 |
| | UGCCAAGCCGAGGCCCGGCCAGCAUCCCUCACGAGAGA | 397 |
| | UGCCAAGCCGGGGCCCGGCCAGCAUCCCUCACGAGAGAGG | 398 |
| | UGCCAAGCCGAGGCCCGGCCAGCAUCCCUCACGAGAGGG | 399 |
| BO | GCCAAGCACGUAGCCCGUGCCCCCACCCGCCUGUGUGCUG | 400 |
| | CCAAGCACGUAGCCCGUGCCCCACCCGCCUGUGUGCUG | 401 |
| | GCCAAGCACGUAGCCCGUGCCCCACCCGCCUGUGUGCGG | 402 |
| | GCCAAGCACGUAGCCCGUGCCCCACCCACCUGUGUGCUG | 403 |
| | GCCAAGCACGUAGCCCGUGCCCCACCCGCCUGUGUGCUC | 404 |
| | GCCAAGCACGUAGCCCGUGCCCCACCCGCCUGUGUGCCG | 405 |
| | GCCAAAGCACGUAGCCCGUGCCCCACCCGCCUGUGUGCUG | 406 |
| | GCCAAGCACGUAGCCCGUGCCCCACCCGCCUGUGUGCUA | 407 |
| BP | UGCCAAGCACGAAGCCCGUGCCCCCAUCCAGAGUGUGAGA | 408 |
| | UGCCAAAGCACGAAGCCCGUGCCCCCAUCCAGAGUGUGAGA | 409 |
| | UGCCAAGCACGAAGCCCGUGCCCCCAUCCAGAGUGUGGGA | 410 |
| | UGCCAAGCACGAGGCCCGUGCCCCCAUCCAGAGUGUGAGA | 411 |
| | UGCCAAGCACGAAGCCCGUGCCCCCAUUCAGAGUGUGAGA | 412 |
| | UGCCAAGCACGAAGCCCGUGCCCCCAUCCAGAGUGCGAGA | 413 |
| | UGCCAAGCACGAAGCCCGUGCCCCCAUCCAGAGCGUGAGA | 414 |
| | UGCCAAGCACGAAGCCCGUGCCCCCAUCCAGAGUGUGAGG | 415 |
| | UGCCAAGCACGAAGCCCGUGCCCCCAUCCAGGGUGUGAGA | 416 |
| BQ | AGCCAGCUUUUGCAUACCACGUGCAAUUCACUCCACCCGUCA | 417 |
| | AGCCAGCUUUGCCAUACCACGUGCAAUUCACUCCACCCGUCA | 418 |
| | AGCCAGCCUUUGCAUACCACGUGCAAUUCACUCCACCCGUCA | 419 |
| | AGCCAGCUUUUGCAUACCACGUGCAAUUCACUCCACCCGUCG | 420 |
| | AGCCAGCUUUUGCACACCACGUGCAAUUCACUCCACCCGUCA | 421 |
| | AGCCAAGCUUUUGCAUACCACGUGCAAUUCACUCCACCCGUCA | 422 |
| BR | CUUUGUAAACCCGGCAAACAAAAUCAACUUCCAUCAUCA | 423 |
| | CUUUGUAAACCCGGCAAACAAAAUCAACUUCCAUCACCAA | 424 |
| BS | CCAUUGUAGCGACCACACAAUUCCCCAUCGGACAGCAUGG | 425 |
| | CCAUUGUAGCGACCACACAAUUCCCCAUCGGACAGCAUG | 426 |
| | CCAUUGUAGCGACCACACAAUUCCCCAUCGGACAGCGUGG | 427 |
| | CCAUUGUAGCGACCACACAAUUCCCCAUCGGACAGCACGG | 428 |
| | CCAUUGUAGCGACCACACAAUUCCCCAUCGGACAGCAUGC | 429 |
| | CCAUUGUAGCGACCACACAAUCCCCCAUCGGACAGCAUGG | 430 |
| | CCAUUGUAGCGACCACACAAUUCCCCAUCGGACAGCAUGU | 431 |
| BT | CUCUCGCCGUUCCCAGGCACGACAAAAUCAACUUCCCGCU | 432 |
| | CUCUCGCCGUUCCCAGGCGCGACAAAAUCAACUUCCCGCU | 433 |
| | CUCUCGCCGUUCCCGGGCACGACAAAAUCAACUUCCCGCU | 434 |
| | CUCUCGCCGUUCCCAGGCACGACAAAAUCAACUUCCCGCA | 435 |
| BU | AAGCCAAGCCGCGGCCCGGCCUUCCCAUGUGCUACUAGAG | 436 |
| | AAAGCCAAGCCGCGGCCCGGCCUUCCAUGUGCUACUAGAG | 437 |
| | AAGCCAAAGCCGCGGCCCGGCCUUCCAUGUGCUACUAGAG | 438 |
| | GAGCCAAGCCGCGGCCCGGCCUUCCCAUGUGCUACUAGAG | 439 |
| | AGCCAAGCCGCGGCCCGGCCUUCCCAUGUGCUACUAGAG | 440 |

TABLE 4-continued

Variant Nucleolin Aptamer Sequences without 5' and 3' Constant Regions from All Families

| Family Name | All Family Sequences | SEQ ID NO: |
|---|---|---|
| | AAGCCAAGCCGUGGCCCGGCCUUCCCAUGUGCUACUAGAG | 441 |
| | UGCCAAGCCGCGGCCCGGCCUUCCCAUGUGCUACUAGAG | 442 |
| | AAGCCAAGCCGAGGCCCGGCCUUCCCAUGUGCUACUAGAG | 443 |
| BV | CCAAAUGCCAAAGCCGUAGCCCGGCCAGUAGCCCACACGUC | 444 |
| | CCAAAAUGCCAAAGCCGUAGCCCGGCCAGUAGCCCACACGUC | 445 |
| | CCAAAUGCCAAGCCCGUAGCCCGGCCAGUAGCCCACACGUC | 446 |
| BW | CCAUUACGCGACGUAAUUCCCCCAUCGUUUCCUCGUUAAG | 447 |
| | CCAUUACGCGACGUAAUUCCCCAUCGUCUCCUCGUUAAG | 448 |
| | CCAUUACGCGACGUAAUUCCCCCAUCGCUUCCUCGUUAAG | 449 |
| | CCAUUACGCGGCGUAAUUCCCCCAUCGUUUCCUCGUUAAG | 450 |
| | CCAUUACGCGACGUAAUUCCCCCAUCGUUUCCUCGUUAGG | 451 |
| | CCAUUACGCGACGUAAUUCCCCCAUCGUUUCCUCGUAAG | 452 |
| | CCAUUACGCGACGUAAUUCCCCCAUCGUUUCCUCGUUAUG | 453 |
| | CCAUUACGCGACGUAAUUCCCCCAUCGUUUCCUCGUUAAA | 454 |
| BX | CCAUCUAGAUCUCCGUAGAUUCCCCGGCUCUUUCUCGC | 455 |
| | CCAUCUAGAUCUCCGUAGAUUCCCCAGCUCUUUCUCGC | 456 |
| | CCAUCUAGAUCUCCGUAGAUCCCCCGGCUCUUUCUCGC | 457 |
| | CCAUCUAGAUCUCCGUAGAUUCCCCCGCUCUUUCUCGC | 458 |
| | CCAUCUAGAUCUCCGUAGAUUCCCCGGCUCUUCCUCGC | 459 |
| | CCAUCUAGAUCUCCGUGAUUCCCCGGCUCUUUCUCGC | 460 |
| | CCAUCUAGAUCUCCGUAGUUCCCCGGCUCUUUCUCGC | 461 |
| | CCAUCUAGAUCCCCGUAGAUUCCCCGGCUCUUUCUCGC | 462 |
| | CCAUCUAGAUCUCCGUAGAUUCCCCGGCUCCUUCUCGC | 463 |
| | CCAUCUAUAUCUCCGUAGAUUCCCCGGCUCUUUCUCGC | 464 |
| BY | ACUGUCUGCAUACACGGUAUGCCCAACGCCAUCCAAACCG | 465 |
| | ACUGUCUGCAUACACGGUAUGCCCAACGCCAUCCAAACCGC | 466 |
| | ACUGUCUGCAUACAUGGUAUGCCCAACGCCAUCCAAACCG | 467 |
| | ACUGUCUGCAUACACGGUAUGCCCAACGCCAUCCAAAACCG | 468 |
| BZ | ACCUGCGGCUAUUGCCAGCGCCAUAAGACCCUCCACAGUA | 469 |
| | ACCUGCGGCUAUUGCCAGCGCCAUAAGACCCUCCACAGCA | 470 |
| | CCUGCGGCUAUUGCCAGCGCCAUAAGACCCUCCACAGUA | 471 |
| | ACCUGCGGCUAUUGCCAGCGCCAUAAGACCUUCCACAGUA | 472 |
| | ACCUGCGGCUAUUGCCAGCGCCAUAAGACCCUCCGCAGUA | 473 |

TABLE 5

Nucleolin Binding of Aptamer Families A-F

| Clone | Kd (nM) | Bmax (%) | $R^2$ |
|---|---|---|---|
| FAM-A | 10.07 | 17.66 | 0.9499 |
| FAM-B | 0.8508 | 25.2 | 0.8335 |
| FAM-C | 0.4285 | 32.76 | 0.869 |
| FAM-D | 0.586 | 53.6 | 0.9447 |
| FAM-E | 1.69 | 23.08 | 0.7941 |
| FAM-F | 0.37 | 33.6 | 0.6520 |

TABLE 6

Nucleolin Aptamer Truncates

| NCL Aptamer | Sequence |
|---|---|
| Bv1 | GGAAGAGGGAUGGGUGCCAGCUUUGCAUACCACGUGCAAUUCACUCCACCCGUCAC (SEQ ID NO: 474) |
| Bv2 | GGGAGAGAGGAAGAGGGAUGGGAGCCAGCUUUGCAUACCACGUGCAAUUCACUCCACCCGUCAC (SEQ ID NO: 475) |
| Dv1 | GGGAUGGGCACAUGGUACGCCCAAAGCGAGGCCCGCUGCGUAGUGCCAUAACCCAG (SEQ ID NO: 476) |
| Dv2 | GGGAGAGAGGAAGAGGGAUGGGCACAUGGUACGCCCAAAGCGAGGCCCGCUGCGUAGUGCC (SEQ ID NO: 477) |
| Ev1 | GGGAUGGGCACGGUCCAGCGCUAACUGUACCUGCUGUGCCACCCACCGCAUAACCCAGAGGUCGAU (SEQ ID NO: 478) |
| Ev2 | GGGAUGGGCACGGUCCAGCGCUAACUGUACCUGCUGUGCCACCCACCGC (SEQ ID NO: 479) |
| Ev3 | GGGAGAGAGGAAGAGGGAUGGGCACGGUCCAGCGCUAACUGUACCUGCUGUGCCACCCACCG (SEQ ID NO: 480) |
| Ev4 | GGGAGAGAGGAAGAGGGAUGGGCACGGUCCAGCGCUAACUGUACC (SEQ ID NO: 481) |
| Ev5 | GGAAGAGGGAUGGGCACGGUCCAGCGCUAACUGUACCUGCUGUGCCACCCACC (SEQ ID NO: 482) |
| Fv1 | GGGACCACGCGCCAACGUGUCAGCUACACGCCGUGUUCCCCGG (SEQ ID NO: 483) |
| Fv2 | GGGACCACGCGCCAACGUGUCAGCUACACGCCGUGUUCCCCGGCAUAACCCAGAGGUCGAU (SEQ ID NO: 484) |
| Fv3 | GGGAGAGAGGAAGAGGGAUGGGACCACGCGCCAACGUGUCAGCUACACGCCGUGUUCCCCGG (SEQ ID NO: 485) |

TABLE 7

Ev3 Truncates

| NCL Aptamer | Sequence |
|---|---|
| Ev3.min21 | GGGAUGGGCACGGUCCAGCGCUAACUGUACCUGCUGUGCCACCC (SEQ ID NO: 486) |
| Ev3.min22 | GGGAGGAAGAGGGAUGGGCACGGUCCAGCGCUAACUGUACCUGCUGUGCCACCC (SEQ ID NO: 487) |

TABLE 7-continued

Ev3 Truncates

| NCL Aptamer | Sequence |
|---|---|
| Ev3.min23 | GGGAGGAAGAGGGAUGGGCACGGUCCAGCGCUAACU GUACCUGCUGUGCCACC (SEQ ID NO: 488) |
| Ev3.min24 | GGGAGGAAGAGGGAUGGGCACGGUCCAGCGCACUG UACCUGCUGUGCCACCC (SEQ ID NO: 489) |
| Ev3.min25 | GGGAGGAAGAGGAUGGGCACGGUCCAGCGCACUGU ACCUGCUGUGCCACC (SEQ ID NO: 490) |

TABLE 8

Additional Nucleolin Aptamers

| NCL Aptamer | Sequence |
|---|---|
| Cv1 | GGGAUGGGAAGAUCUGCUAAGUGCACGCACAAU CACCAUCGAGCGUCUC (SEQ ID NO: 494) |
| Cv2 | GGGAGAGAGGAAGAGGGAUGGGAAGAUCUGCUA AGUGCACGCACAAUCACCAUCGAGCGUCUC (SEQ ID NO: 495) |
| Ev6 | GGGAGAGAGGAAGAGGGAUGGGCACGGUCCAGC GCUAACUGUACCUGCUGUGCC (SEQ ID NO: 496) |
| Ev3min2 | GGGAGAGAGAGGGAUGGGCACGGUCCAGCGCUA ACUGUACCUGCUGUGCCACCCACCG (SEQ ID NO: 497) |
| Ev3min3 | GGGAGAGAGGAAGAGGGAUGGGCACGGUCCAGCG CUAACUGUACCUGCUGUGCCACCACCG (SEQ ID NO: 498) |
| Ev3min4 | GGGAGAGAGGAAGAGGGAGGGCACGGUCCAGCG CUAACUGUACCUGCUGUGCCCCACCG (SEQ ID NO: 499) |
| Ev3min5 | GGGAGAGAGGAAGAGGGAUGGGUCCAGCGCUAA CUGUACCUGCCACCCACCG (SEQ ID NO: 500) |
| Ev3min6 | GGGAGAGAGGAAGAGGGAUGGGCGGUCCAGCGC UAACUGUACCUGCUGCCACCCACCG (SEQ ID NO: 501) |
| Ev3min7 | GGGAGAGAGGAAGAGGGAUGGGCACGGUCCAGC GCUAUGUCUGCUGUGCCACCCACCG (SEQ ID NO: 502) |
| Ev3min8 | GGGAGAGAGGAAGAGGGAUGGGCACGGUCCAGC GCUAACUGUACCUGCUGUGCCACCC (SEQ ID NO: 503) |
| Ev3min9 | GGGAGGAAGAGGGAUGGGCACGGUCCAGCGCUA ACUGUACCUGCUGUGCCACCCACCG (SEQ ID NO: 504) |
| Ev3min10 | GGAAGAGGGAUGGGCACGGUCCAGCGCUAACUG UACCUGCUGUGCCACCCACCG (SEQ ID NO: 505) |
| Ev3min11 | GAGAGGAAGAGGGAUGGGCACGGUCCAGCGCUA ACUGUACCUGCUGUGCCACCCACCG (SEQ ID NO: 506) |
| Ev3min12 | GGGAGAGAGGAAGAGGGAUGGGCACGGUCCAGC GCUAACUGUACCUGCUGUGCCACCCAC (SEQ ID NO: 507) |
| Ev3min13 | GGGAGAGAGGAAGAGGGAUGGGCACGGUCCAGC GCUAACUGUACCUGCUGUGCCACCCCG (SEQ ID NO: 508) |
| Ev3min14 | GGGAGAGAGGAAGAGGGAUGGGCACGGUCCGCG CUAACUGUACCUGCUGGCCACCCACCG (SEQ ID NO: 509) |
| Ev3min15 | GGGAGAGAGGAAGAGGGAUGGGCACGGUCCGCG CUAACUGUACCGCUGUGCCACCCACCG (SEQ ID NO: 510) |
| Ev3min16 | GGGAGAGAGGAAGAGGGAUGGGCACGGUCCAGC GCACUGUACCUGCUGUGCCACCCACCG (SEQ ID NO: 511) |
| Ev3min17 | GGGAGAGAGGAAGAGGGAUGGGCACGGUCCAGC GCUAACUGUACCUGCUGUGCCACCCACCG (SEQ ID NO: 512) |
| Ev3min18 | GGGAGAGGAAGAGGGAUGGGCACGGUCCAGCGC UAACUGUACCUGCUGUGCCACCCACCG (SEQ ID NO: 513) |
| Ev3min19 | GGGAGAGGAAGAGGGAUGGGCACGGUCCAGCGC UAACUGUACCUGCUGUGCCACCCACCG (SEQ ID NO: 514) |
| Ev3min20 | GAGGAAGAGGGAUGGGCACGGUCCAGCGCUAAC UGUACCUGCUGUGCCACCCACCG (SEQ ID NO: 515) |

Example 2—Sensitizing Cancer Cells with Nucleolin Aptamers

Figure 6B:
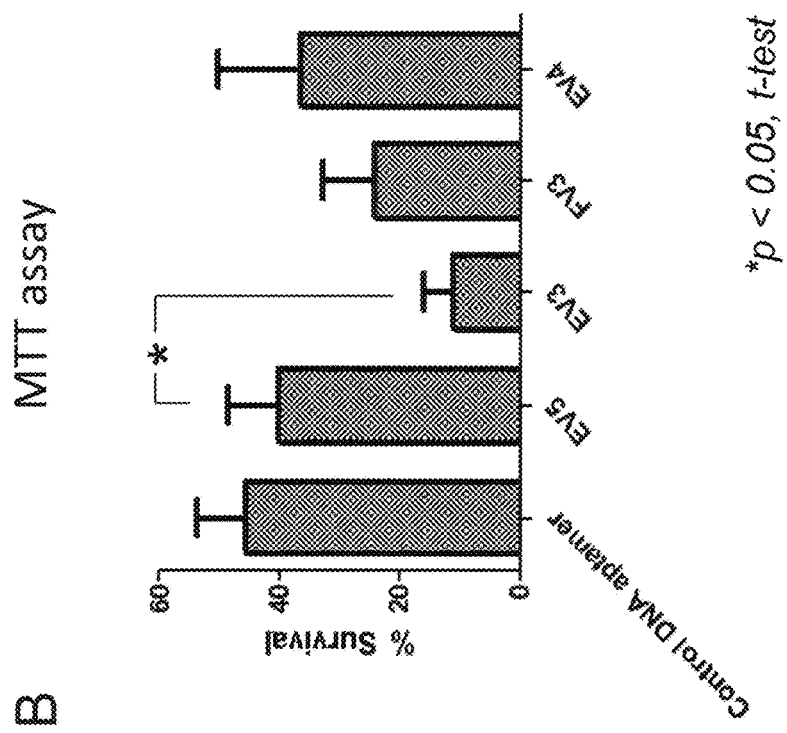
FIGS. 6A-6B show nucleolin specific RNA aptamer EV3 sensitizes colon cancer cells to ionizing radiation. HCT 116 p53 -/- colon cancer cells were treated with 5 µg of indicated aptamers and exposed to 2Gy IR 48 h later. Cells were cultivated for 10 d and survival was assessed by MTT assay.
Figure 6A:
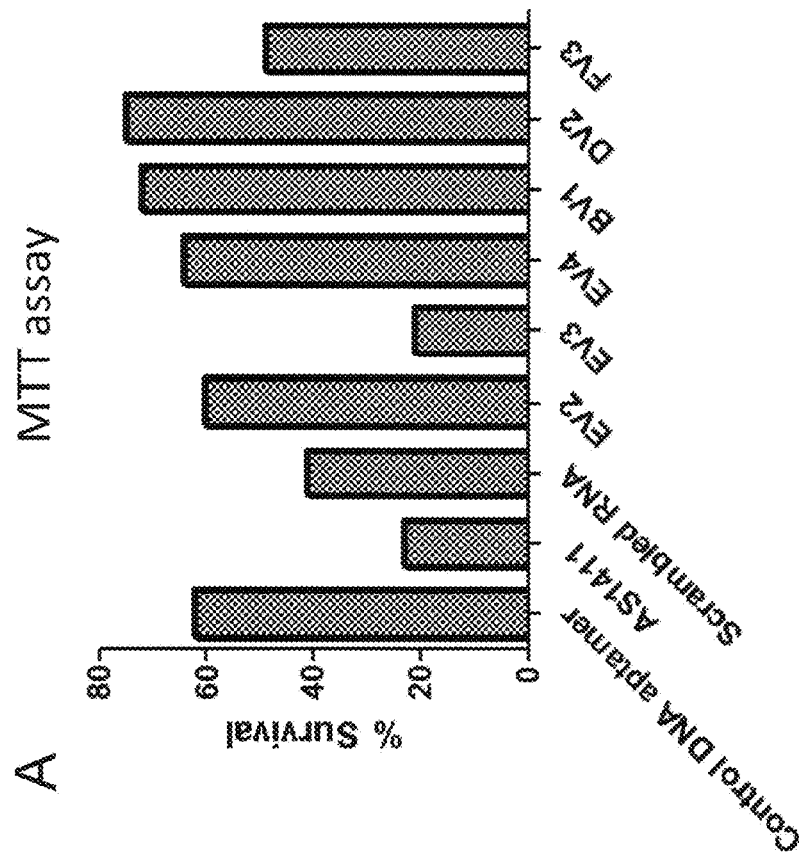

We next tested the ability of the nucleolin aptamer truncates Bvl, Ev3, Ev4, Dv2, and Fv3 to sensitize cancer cells that overexpress nucleolin on the cell surface to ionizing radiation (IR). We also included the Ev2 aptamer as a non-binding aptamer control. As shown in FIG. 6A, Ev3 appears to be a potent radiosensitizer, significantly decreasing post-IR survival in HCT116 p53-null cells. Further radiation sensitization studies showed that Ev3 decreased post-IR survival by approximately 5-fold in HCT116 p53-null cells compared to the aptamer control Ev5, which was used as a control due to its ability to bind nucleolin protein yet lack of radiosensitizing properties (FIG. 6B). Given that a large number of tumors lack functional p53, which is associated with resistance to therapy, it is encouraging that the specific nucleolin aptamer Ev3 can efficiently sensitize p53-null cells to IR.

To determine whether the Ev3 aptamer's ability to sensitize cancer cells to ionizing radiation was specific to the nucleolin protein, we tested the aptamer on hTERT-immortalized HFF cells (FIG. 7). hTERT-immortalized HFF cells that do not express nucleolin on cell surface were treated with 5 ug of indicated aptamers and exposed to 2Gy IR 48 h later. Cells were cultivated for 10 d and survival was assessed by MTT assay. As seen in FIG. 7, Ev3 does not sensitize HFF (human foreskin fibroblasts) that do not express nucleolin on cell surface to radiation.

Figure 8:
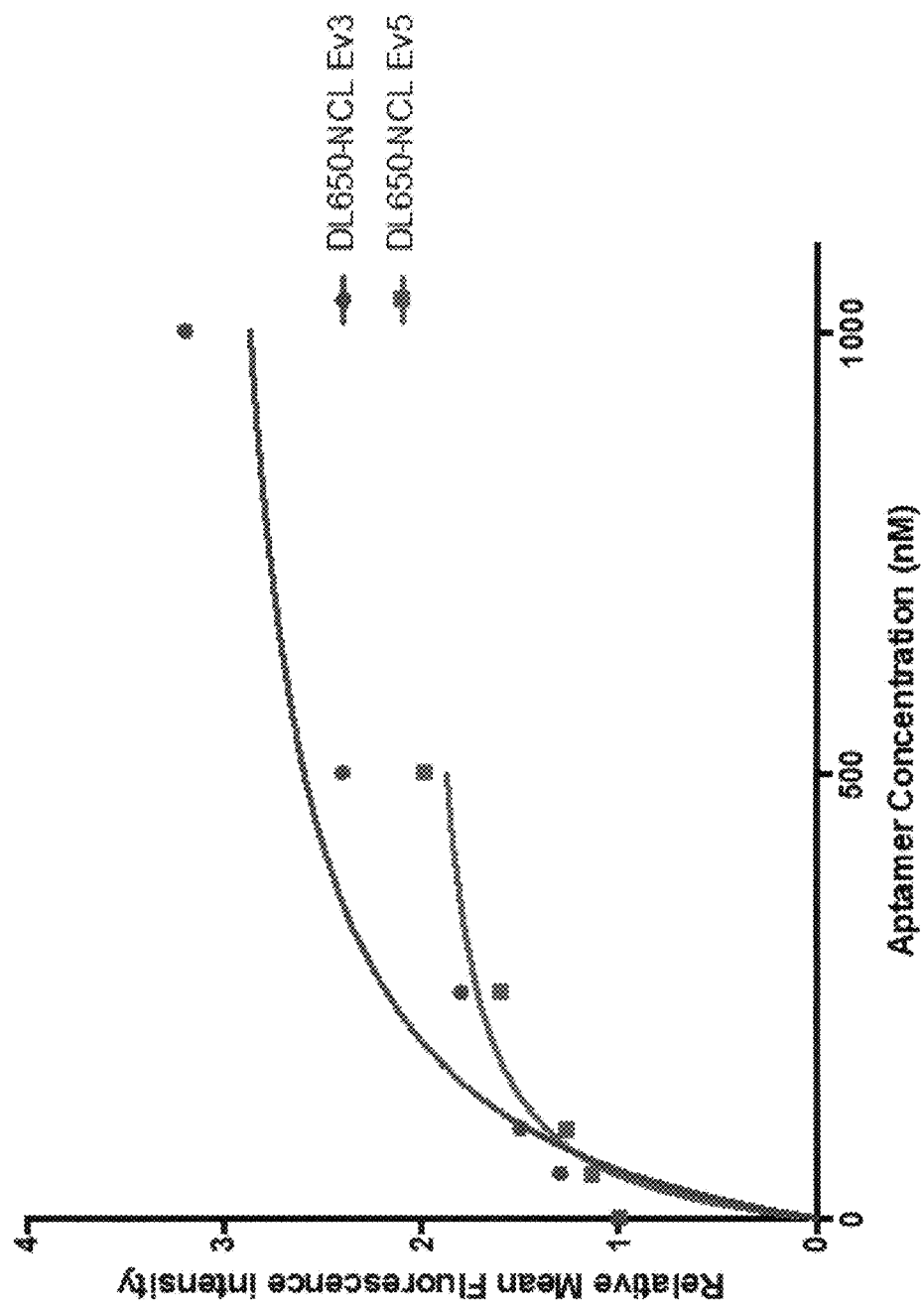
FIG. 8 shows EV3 and EV5 bind to nucleolin expressed on the cell surface in a concentration dependent manner. Flow cytometry analysis of MFI (mean fluorescence intensity) of DL650-labeled EV3 and EV5 after incubation of HCT116 p53-/- cells with the indicated aptamer concentrations.
Figure 9A:
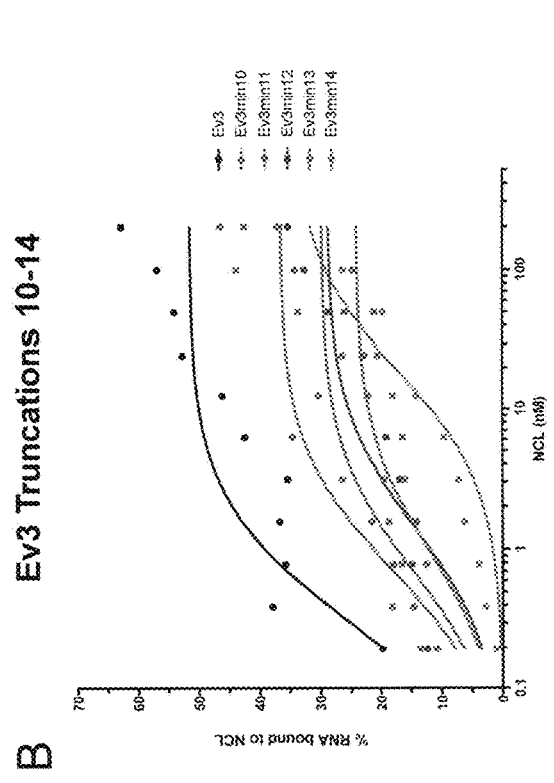
FIGS. 9A-9D show binding of Ev3 aptamer truncates to the nucleolin protein. Aptamers were end-labeled with $^{32}$P. Nucleolin protein was serially diluted in 20 mM Hepes, 150 mM NaCl, 2 mM CaCl$_2$ and 0.01% bovine serum albumin and incubated with a trace amount of the $^{32}$P-labeled RNA pools. After incubation at 37° C., unbound RNA was captured on a nylon membrane and RNA-nucleolin complexes captured on a nitrocellulose membrane. The fraction of protein-bound RNA was determined via phosphorimaging of the nitrocellulose and nylon membranes.
Figure 9B:
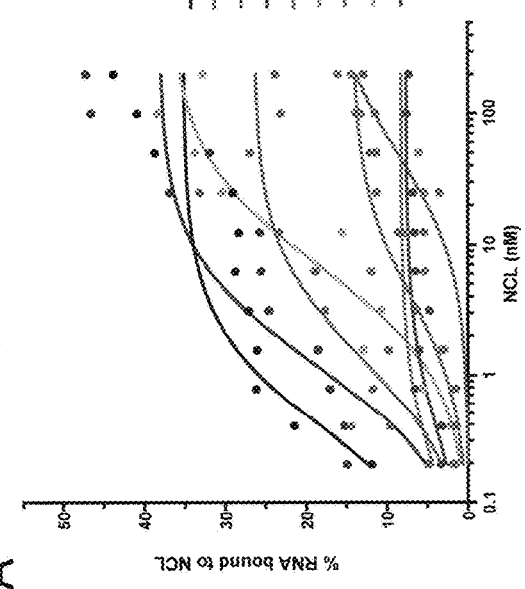
Figure 9C:
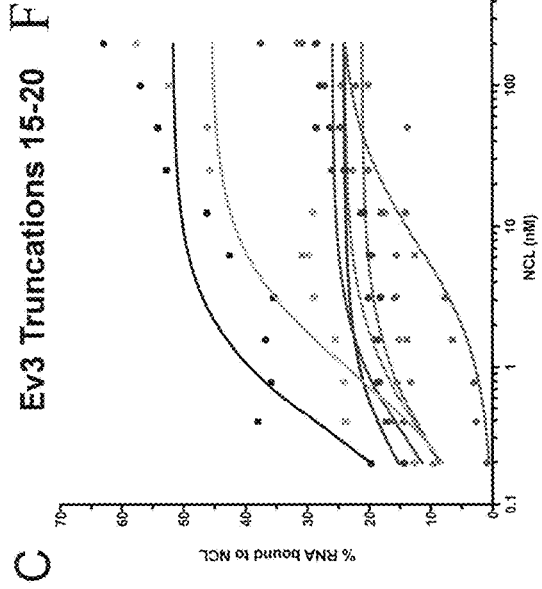
Figure 9D:
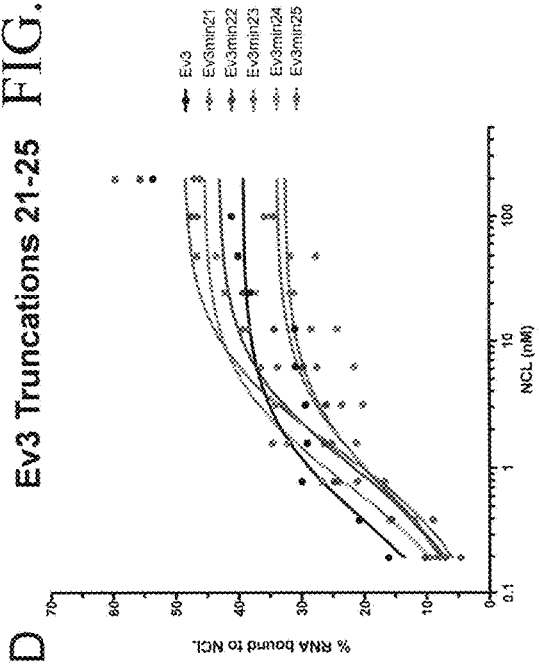

To determine the Ev3 and Ev5 aptamers could bind nucleolin expressed on a cell surface in a concentration-dependent manner, we performed a flow cytometry analysis with HCT116 p53-/- cells. Flow cytometry analysis of MFI (mean fluorescence intensity) of DL650-labeled Ev3 and Ev5 after incubation of HCT116 p53-/- cells with indicated aptamer concentrations. As shown in FIG. 8 and Table 9, Ev3 and Ev5 bind to nucleolin expressed on the cell surface in a concentration dependent manner.

TABLE 9

Ev3 and Ev5 Binding Data

| Best-fit values | One site binding (hyperbola) | |
| --- | --- | --- |
| | DL650-NCL Ev3 | DL650-NCL Ev5 |
| Bmax | 3.214 | 2.064 |
| Kd | 119.2 | 50.7 |

Figure 10:
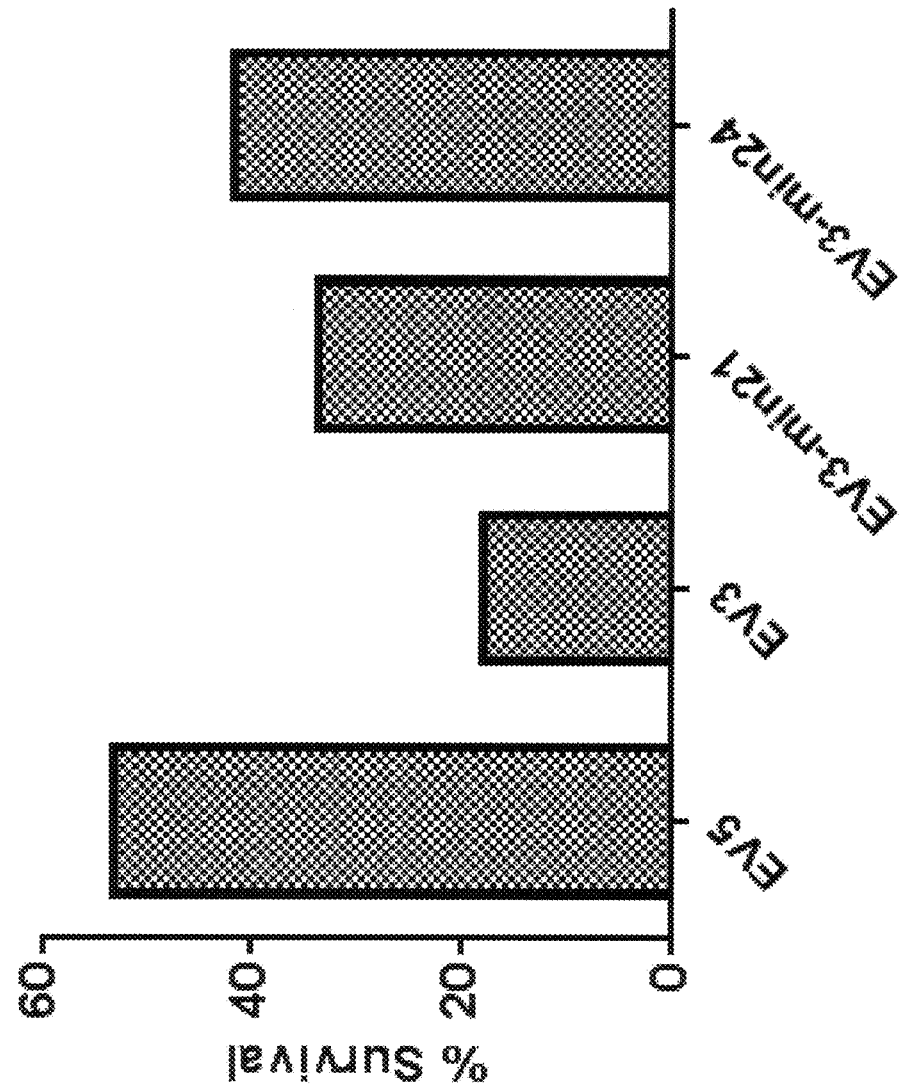
FIG. 10 shows truncation of EV3 resulted in reduced activity as radiosensitizer. HCT 116 p53 -/- colon cancer cells were treated with 5 µg of indicated full-length aptamers or EV3 truncates and exposed to 2Gy IR 48 h later. Cells were cultivated for 10 d and survival was assessed by MTT assay.
Figure 11B:
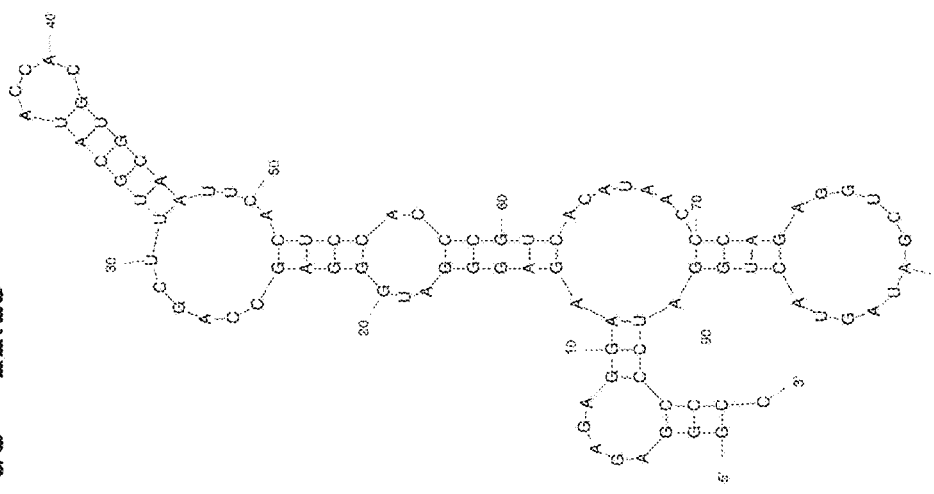
Figure 12B:
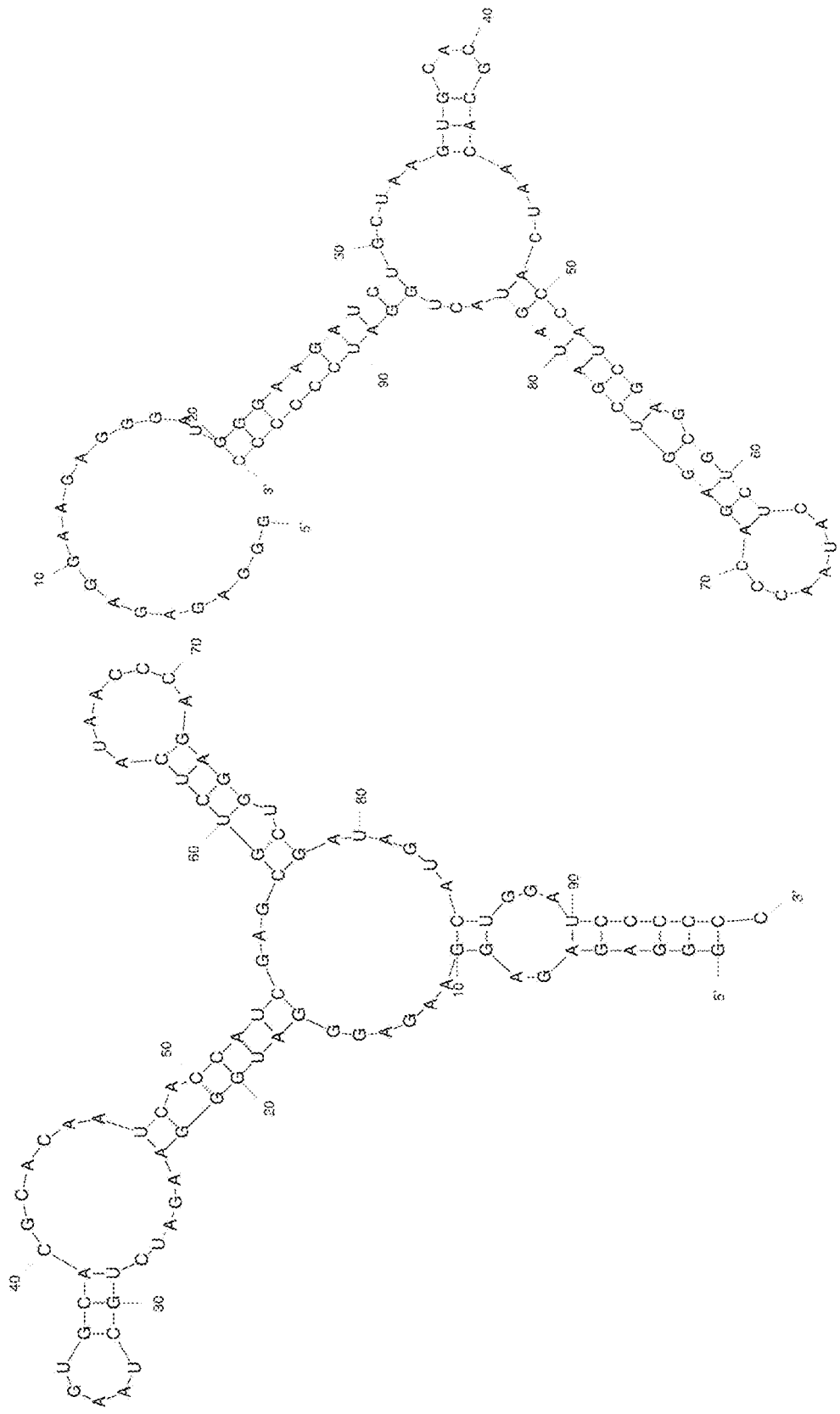
Figure 13B:
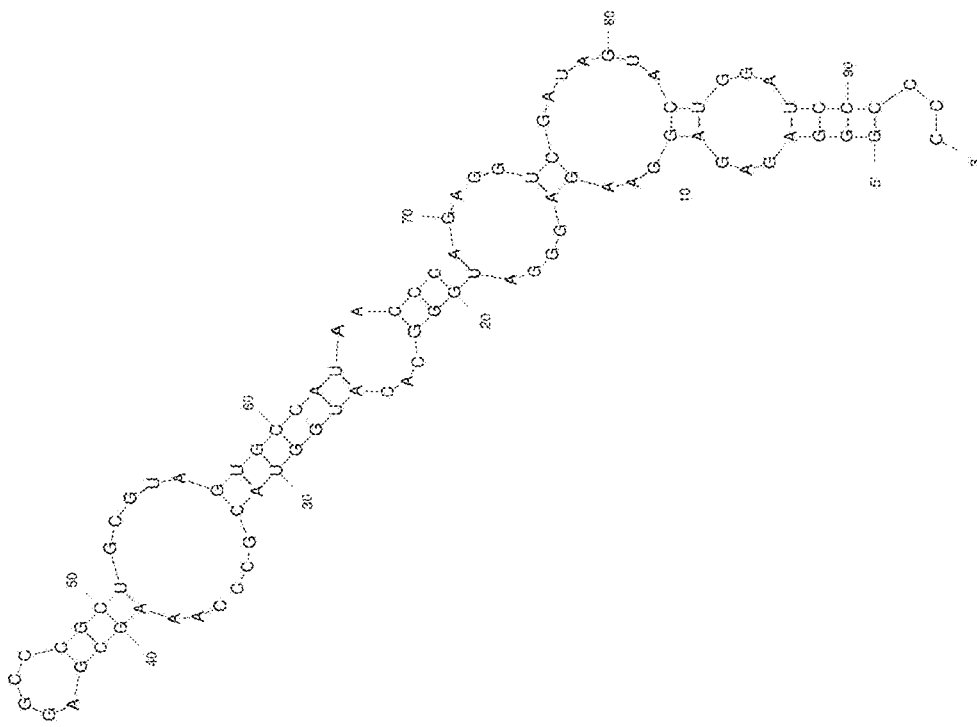
Figure 13C:
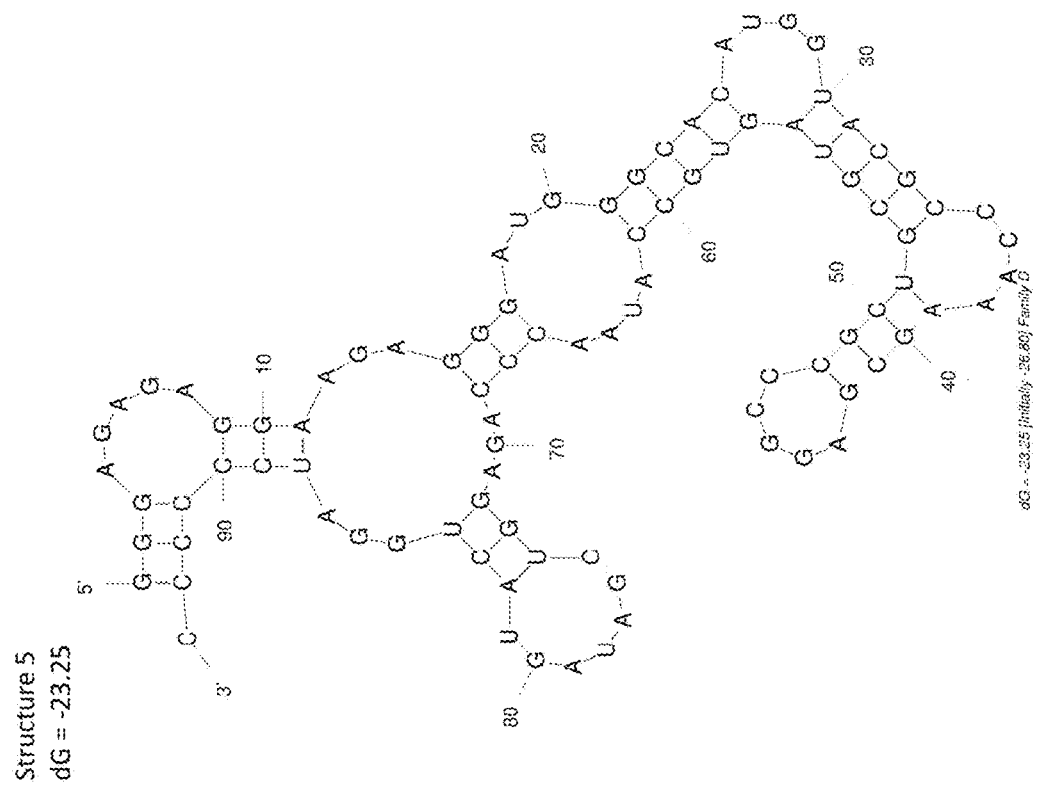
Figure 14D:
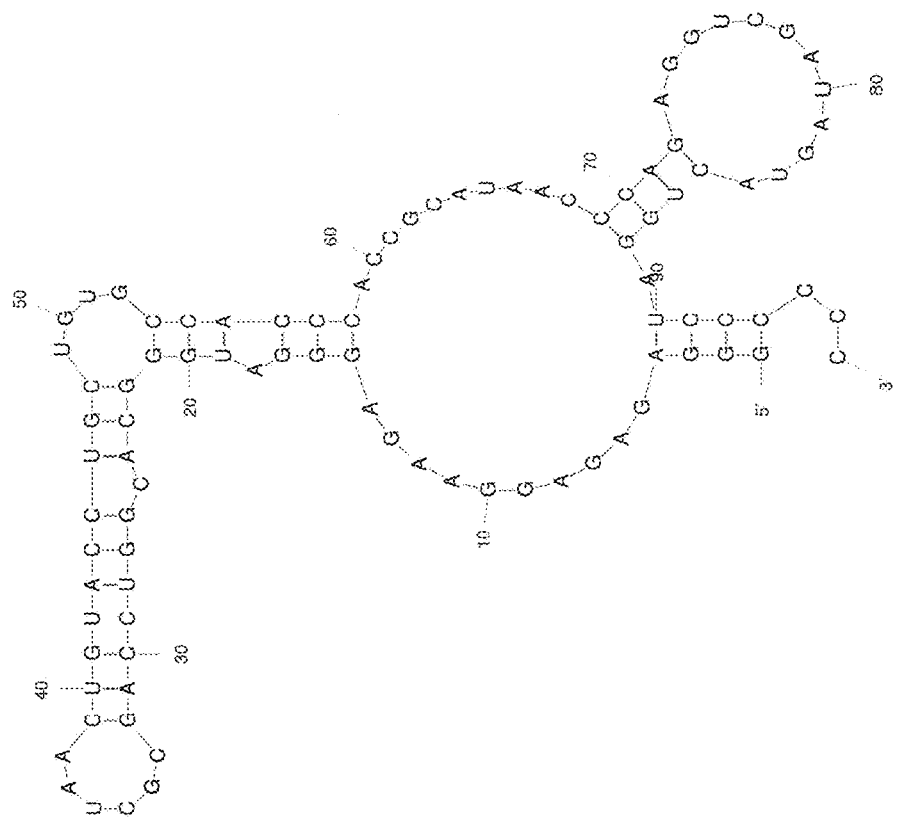
Figure 15B:
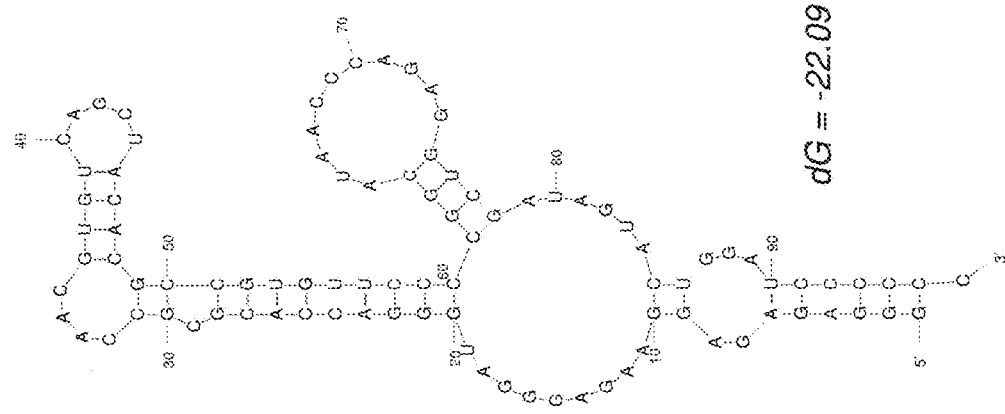
Figure 16:
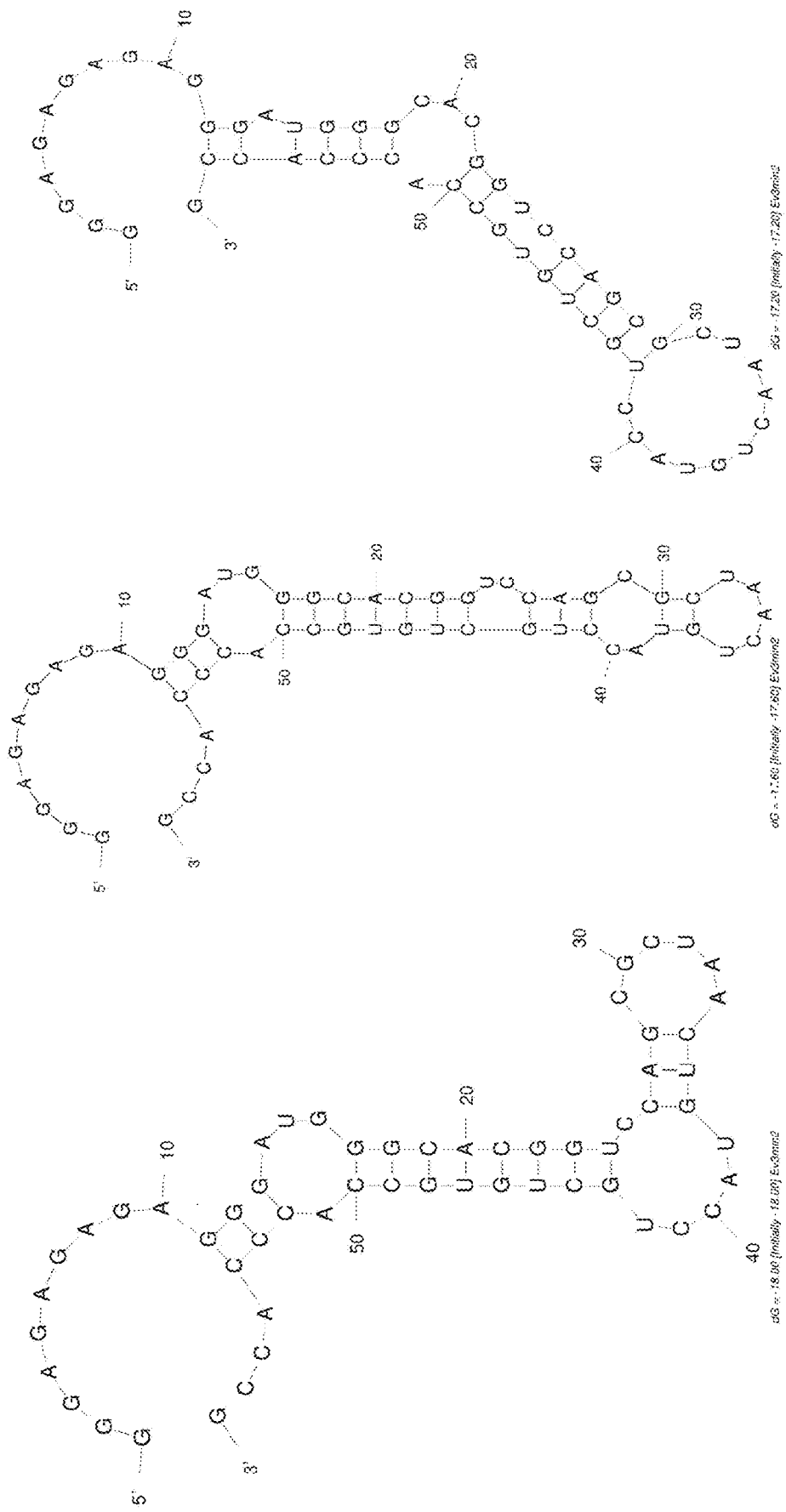
FIG. 16 shows predicted secondary structures for Ev3min2 truncate aptamer (SEQ ID NO: 497).
Figure 17:
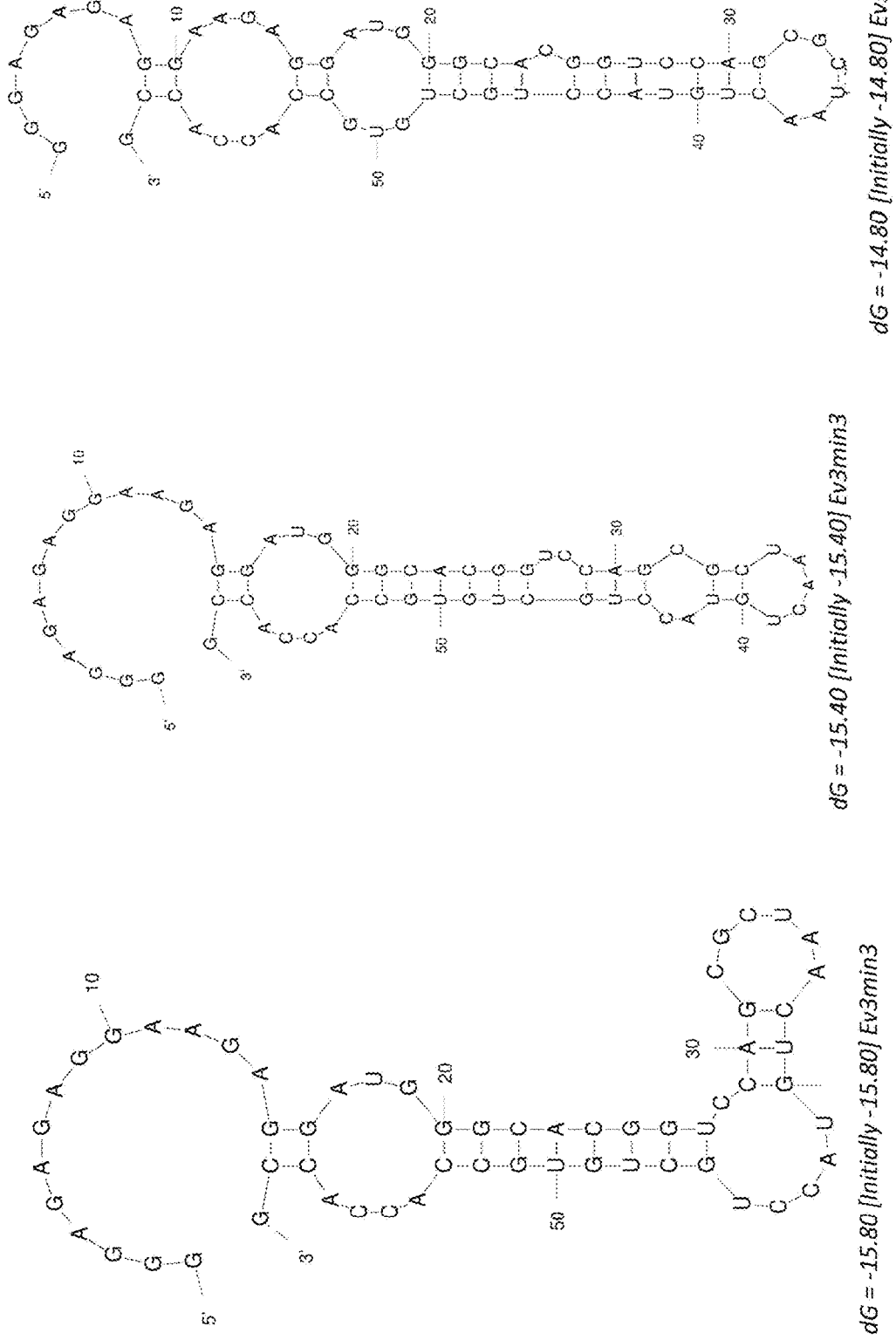
FIG. 17 shows predicted secondary structures for Ev3min3 truncate aptamer (SEQ ID NO: 498).
Figure 18:
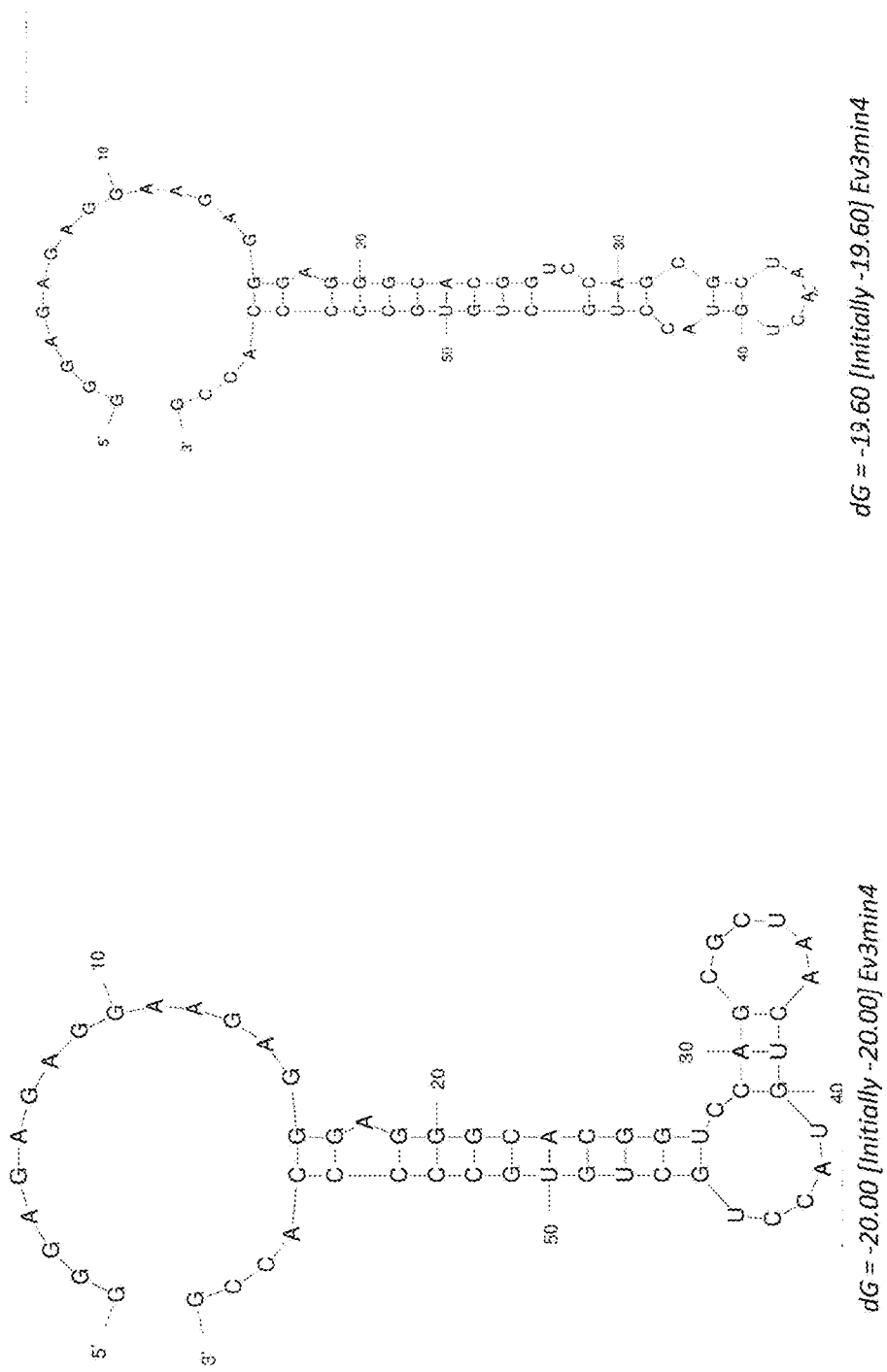
FIG. 18 shows predicted secondary structures for Ev3min4 truncate aptamer (SEQ ID NO: 499).
Figure 19:
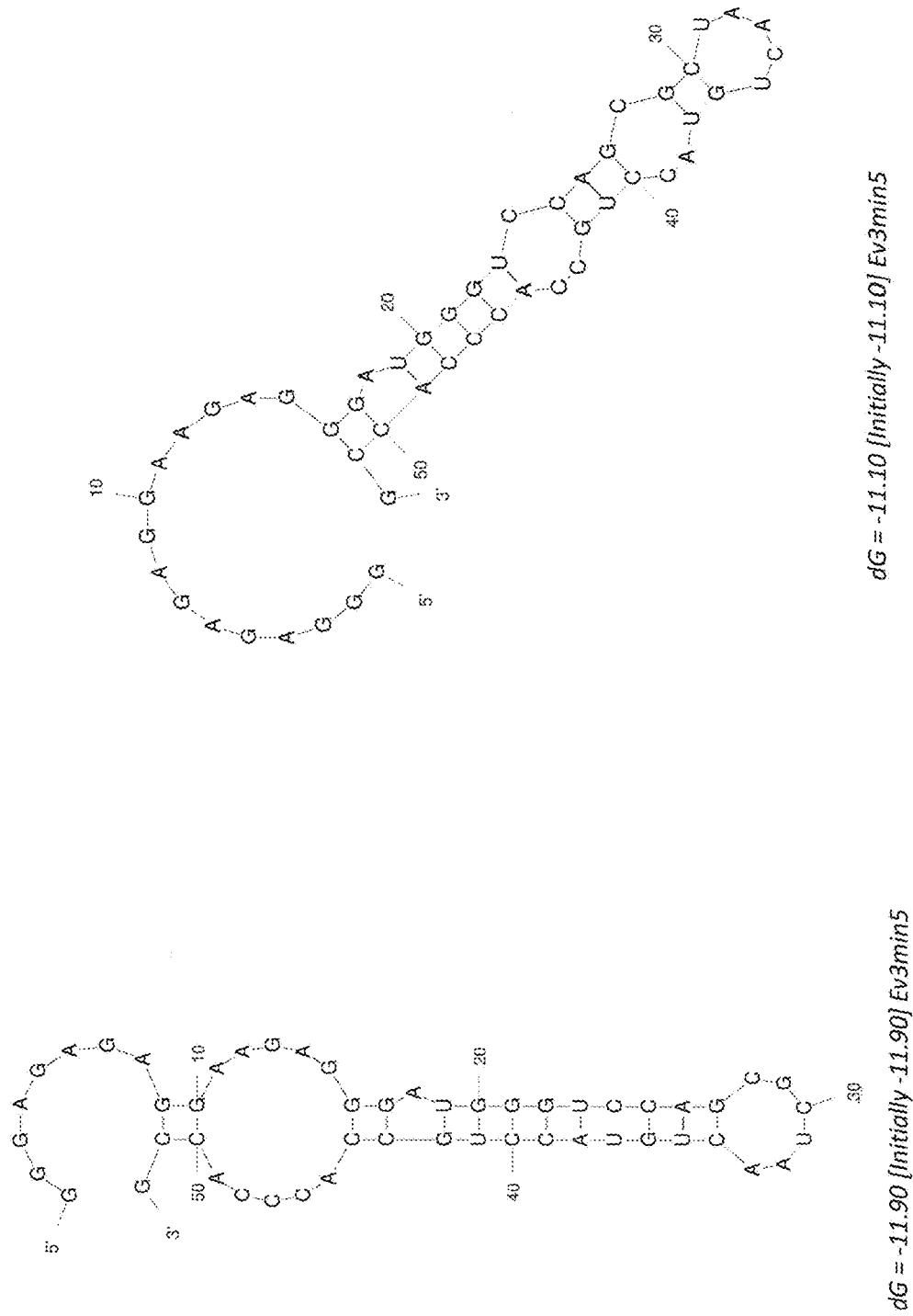
FIG. 19 shows predicted secondary structures for Ev3min5 truncate aptamer (SEQ ID NO: 500).
Figure 20:
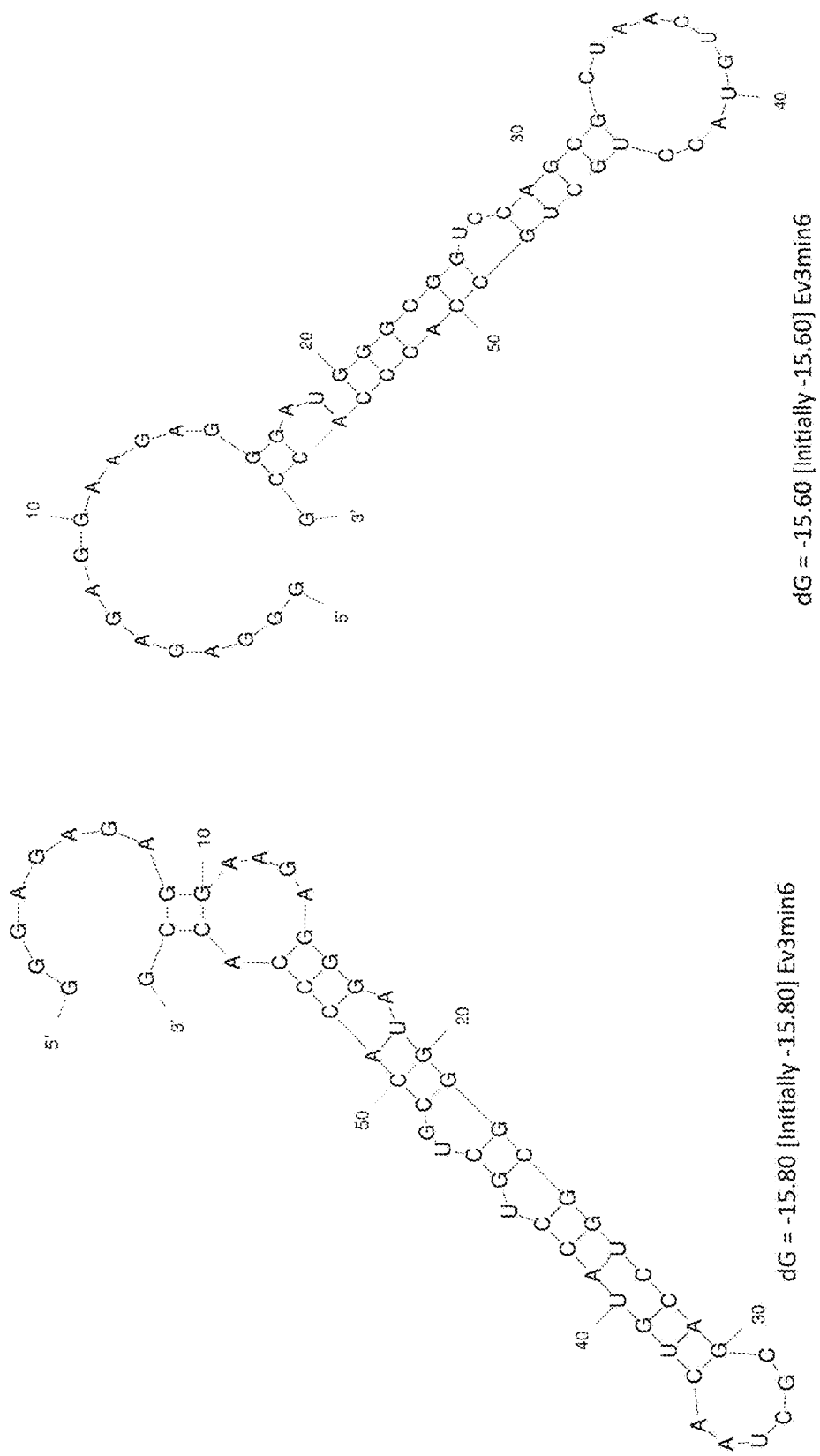
FIG. 20 shows predicted secondary structures for Ev3min6 truncate aptamer (SEQ ID NO: 501).
Figure 21:
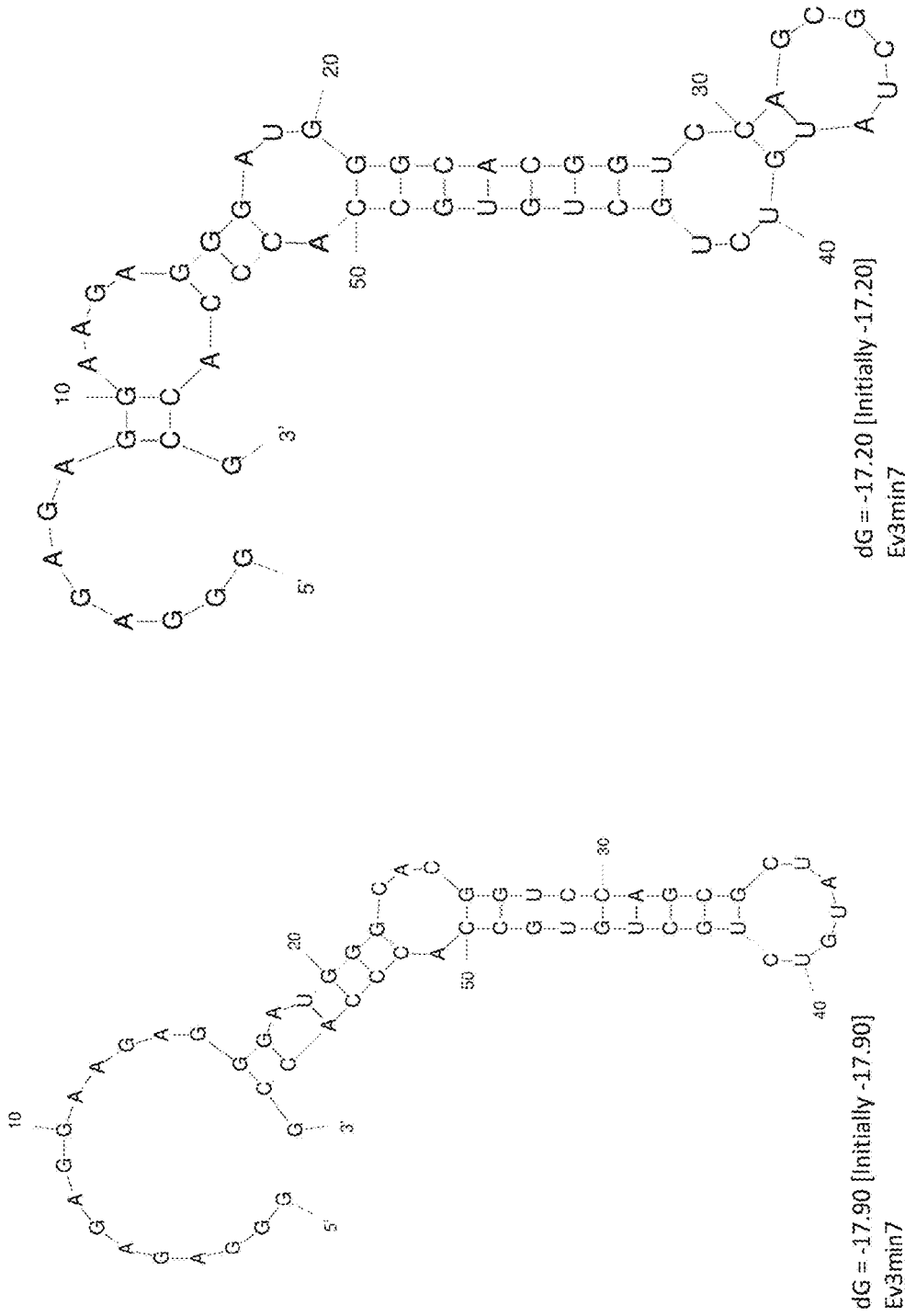
FIG. 21 shows predicted secondary structures for Ev3min7 truncate aptamer (SEQ ID NO: 502).
Figure 22:
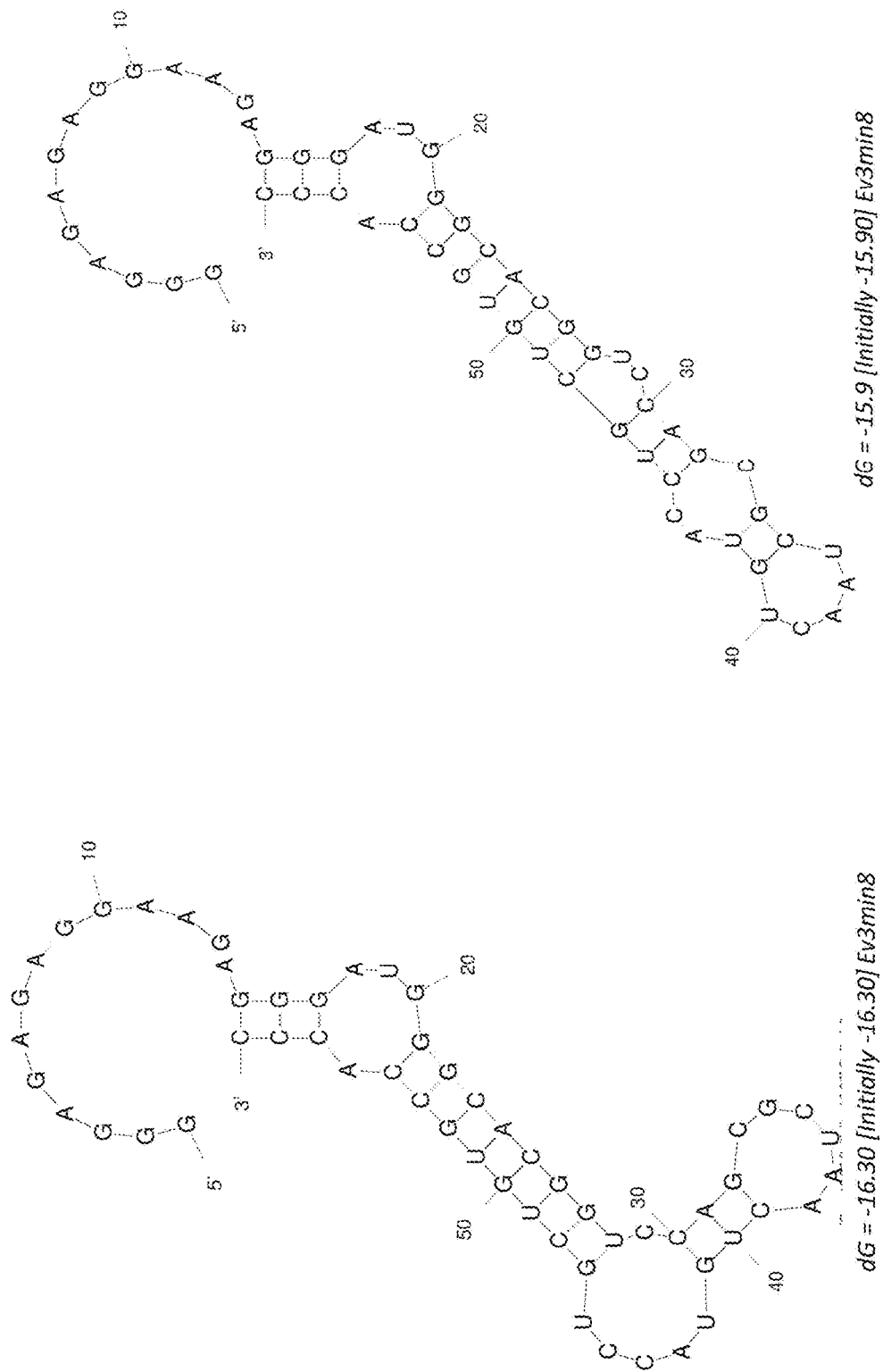
FIG. 22 shows predicted secondary structures for Ev3min8 truncate aptamer (SEQ ID NO: 503).
Figure 23:
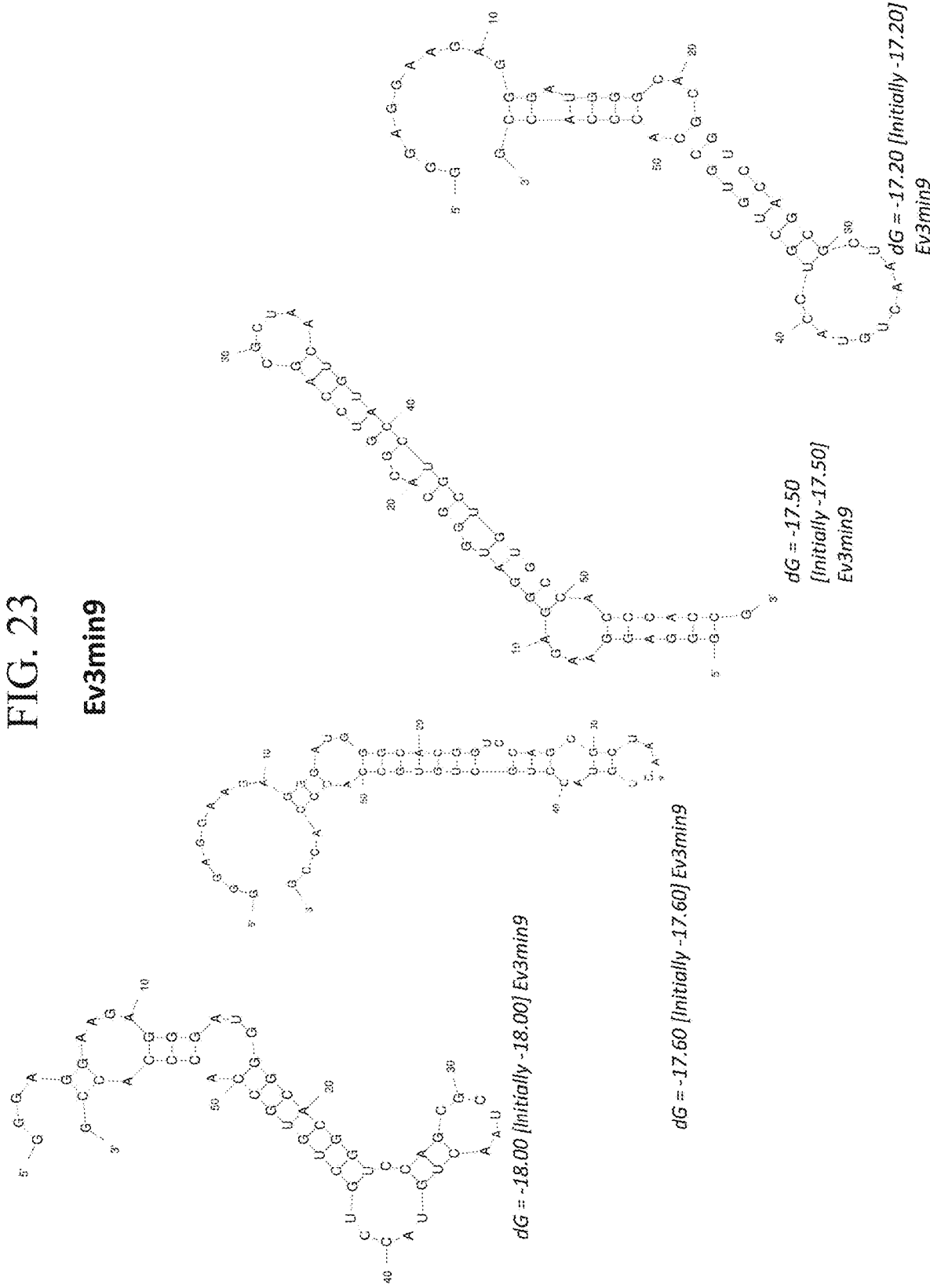
FIG. 23 shows predicted secondary structures for Ev3min9 truncate aptamer (SEQ ID NO: 504).
Figure 24:
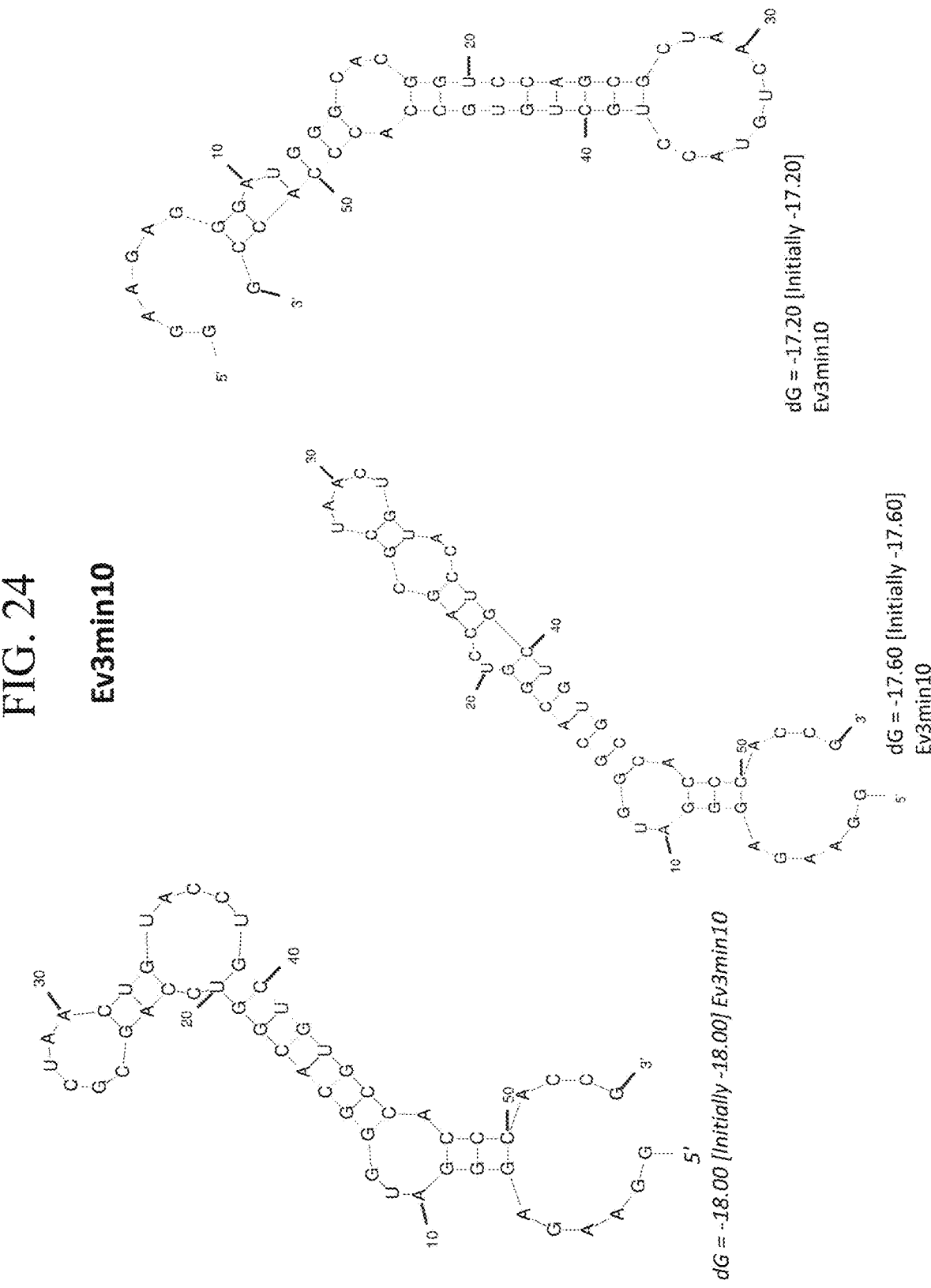
FIG. 24 shows predicted secondary structures for Ev3min10 truncate aptamer (SEQ ID NO: 505).
Figure 26:
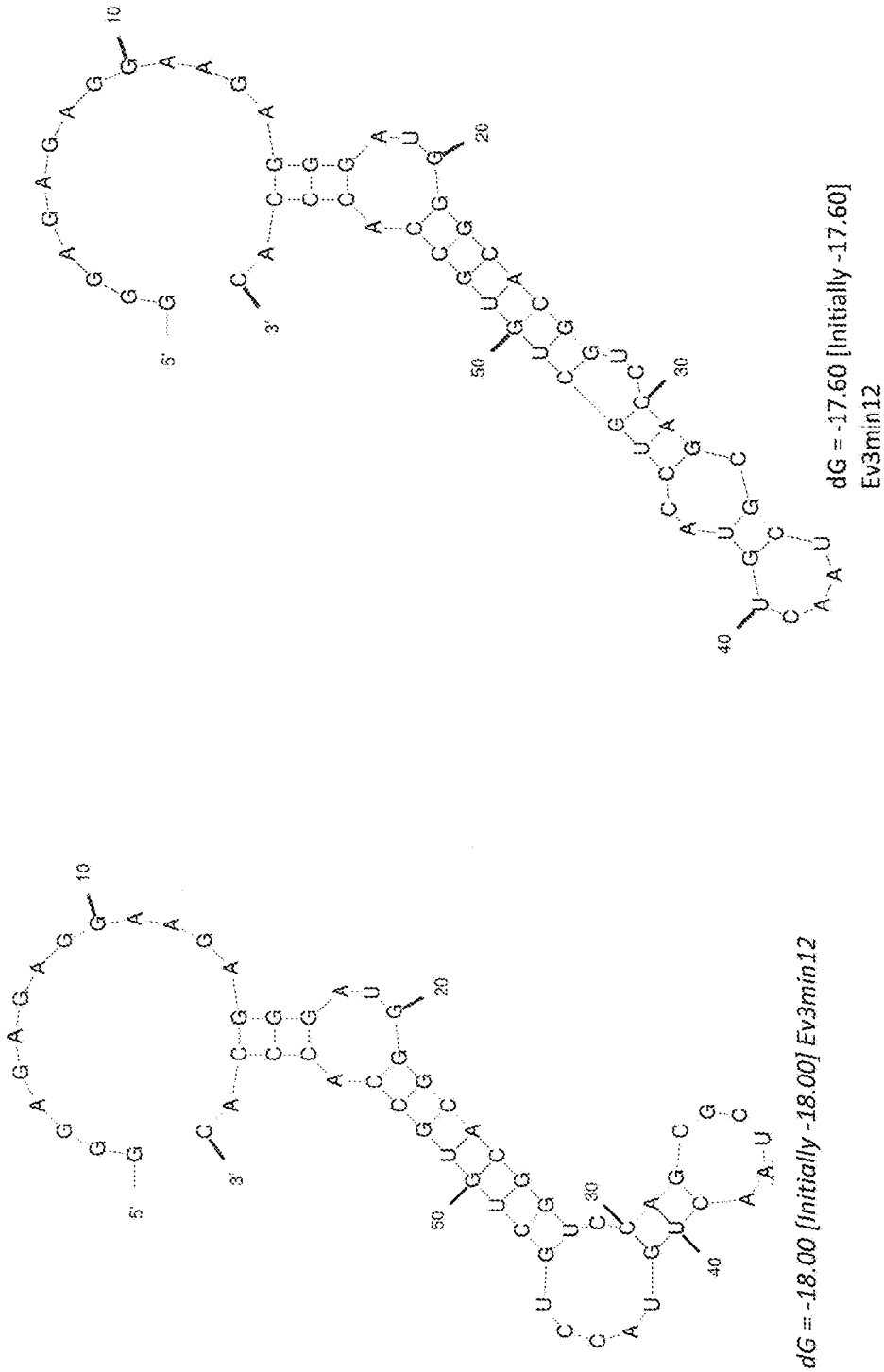
FIG. 26 shows predicted secondary structures for Ev3min12 truncate aptamer (SEQ ID NO: 507).
Figure 27:
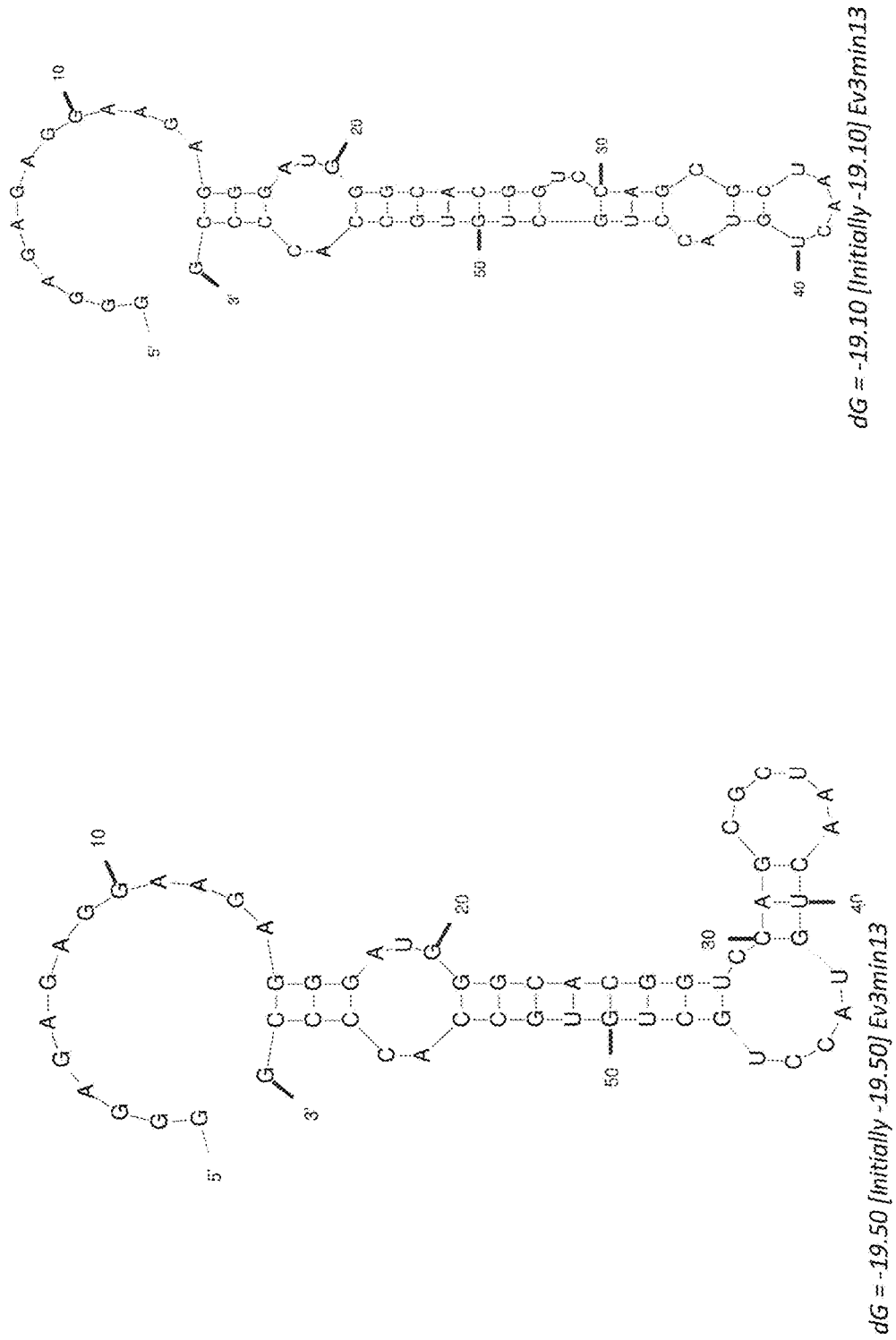
FIG. 27 shows predicted secondary structures for Ev3min13 truncate aptamer (SEQ ID NO: 508).
Figure 28A:
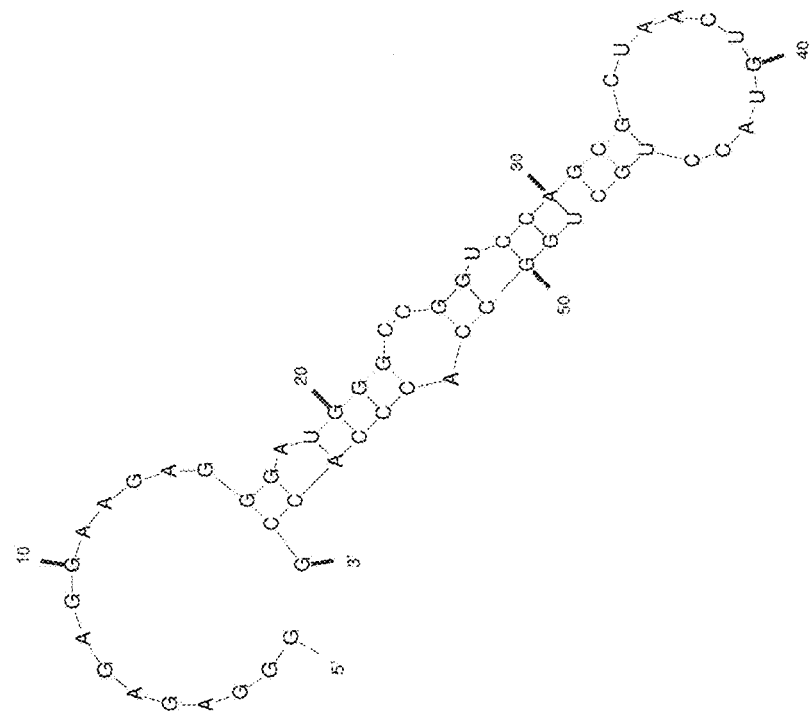
FIGS. 28A-28B show predicted secondary structures for Ev3min14 truncate aptamer (SEQ ID NO: 509) and Ev3min15 truncate aptamer (SEQ ID NO: 510).
Figure 28B:
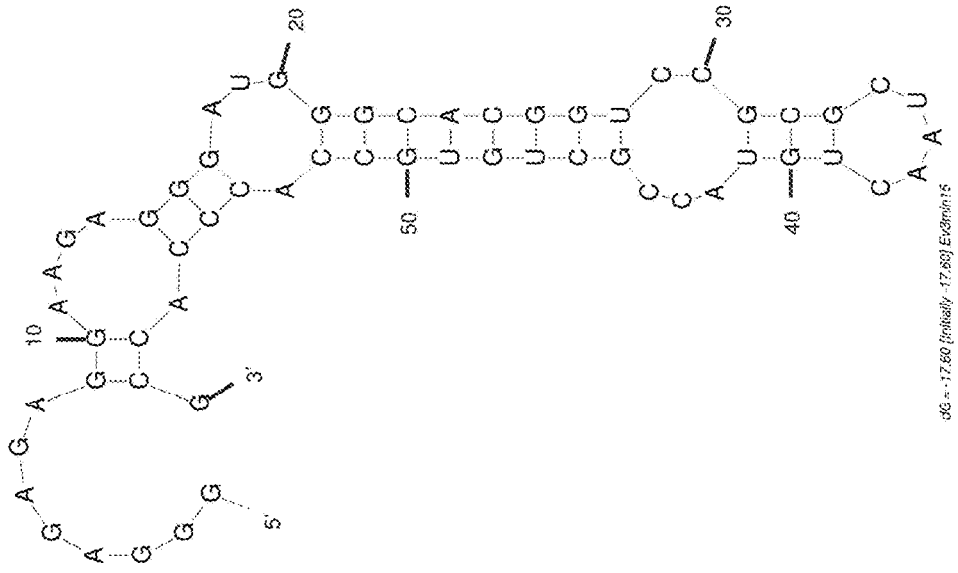
Figure 29:
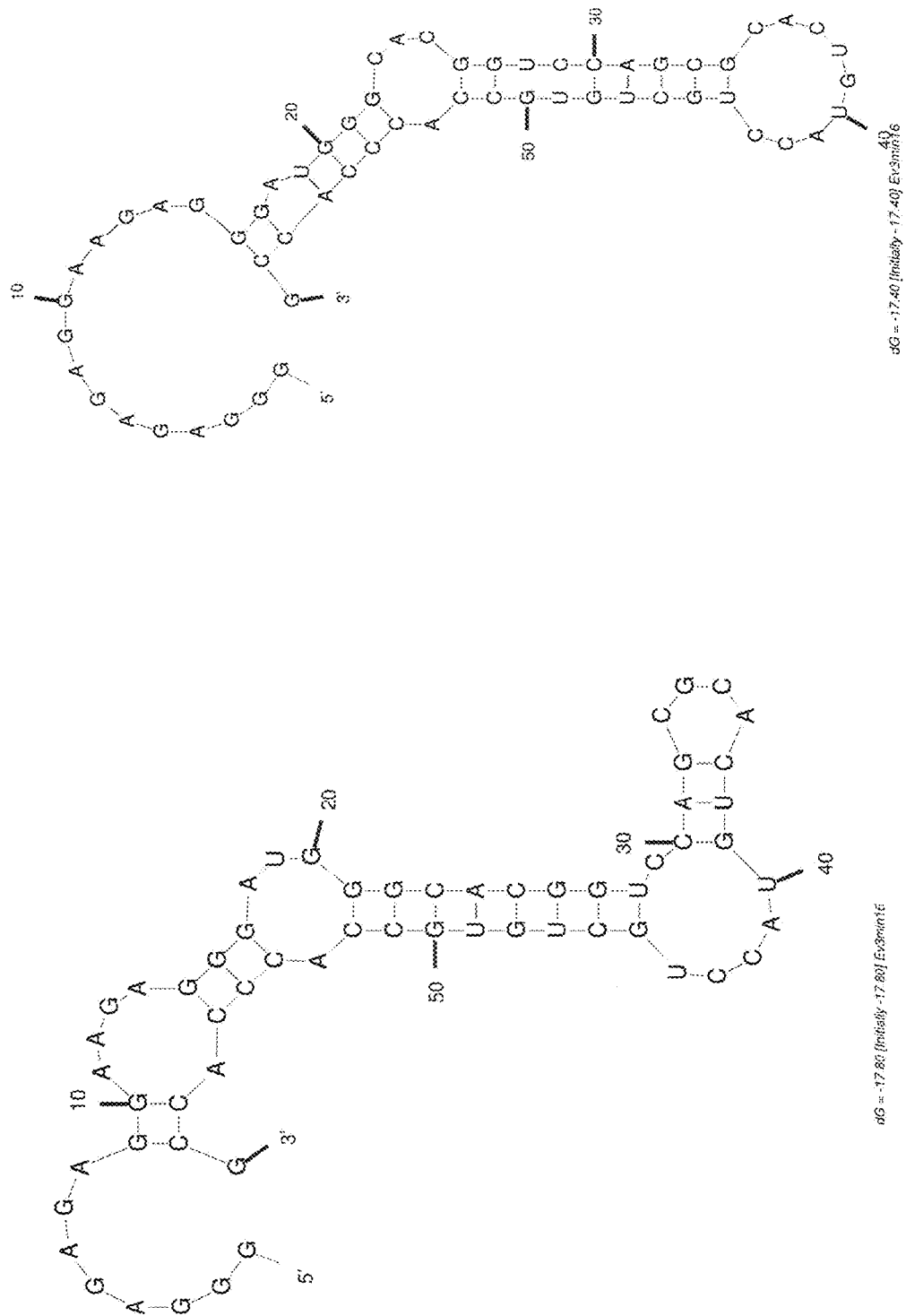
FIG. 29 shows predicted secondary structures for Ev3min16 truncate aptamer (SEQ ID NO: 511).
Figure 30:
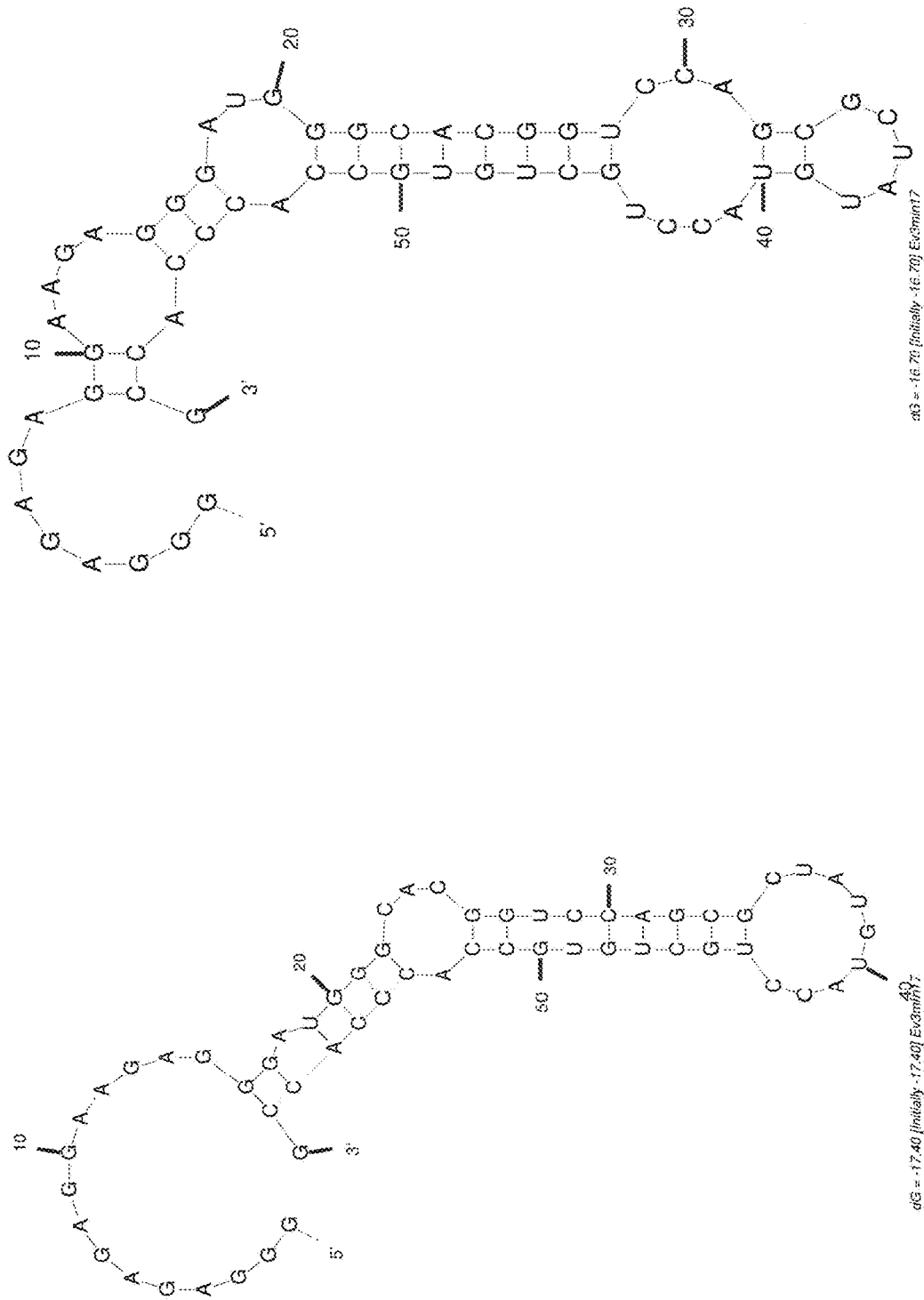
FIG. 30 shows predicted secondary structures for Ev3min17 truncate aptamer (SEQ ID NO: 512).
Figure 31:
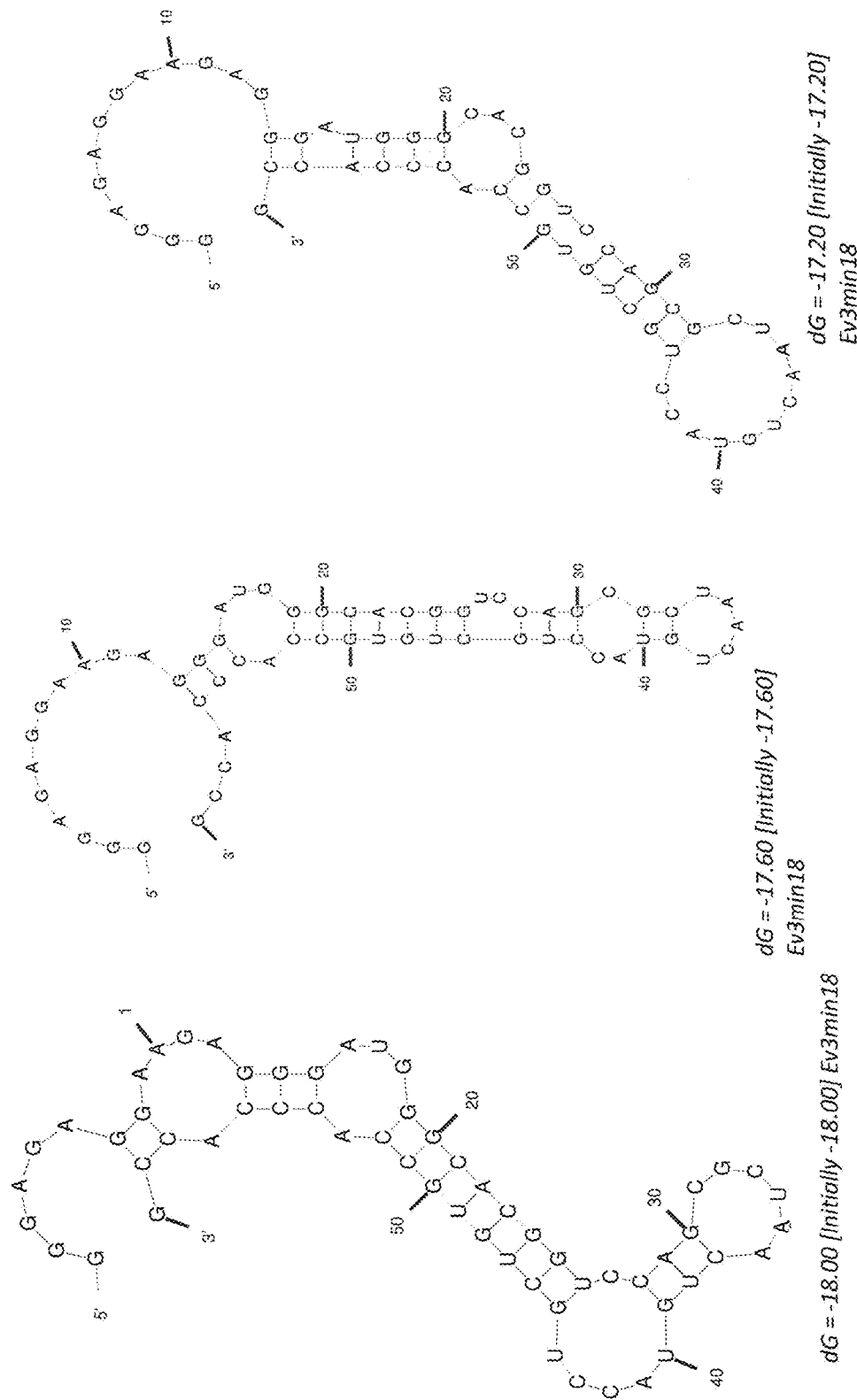
FIG. 31 shows predicted secondary structures for Ev3min18 truncate aptamer (SEQ ID NO: 513).
Figure 32:
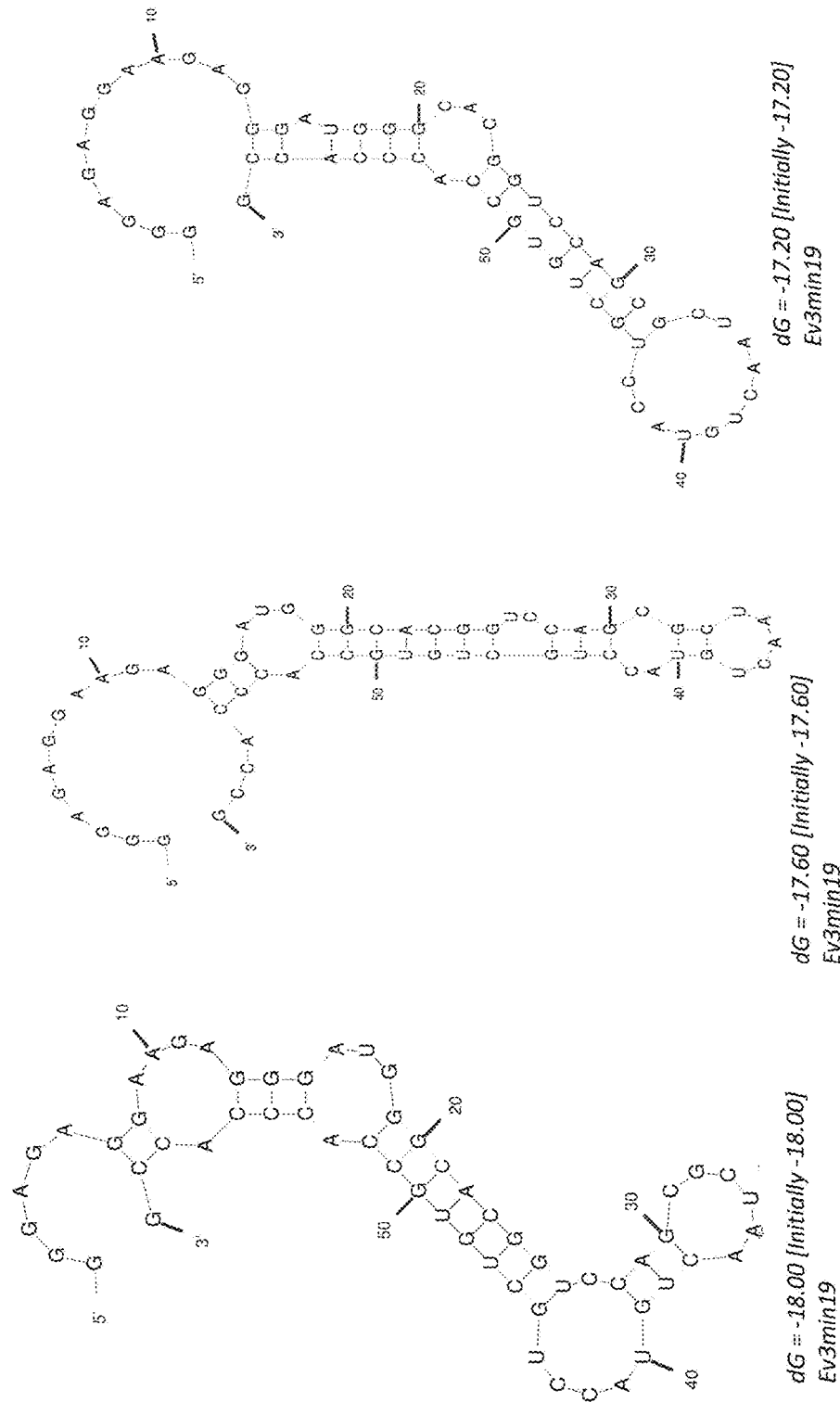
FIG. 32 shows predicted secondary structures for Ev3min19 truncate aptamer (SEQ ID NO: 514).
Figure 33:
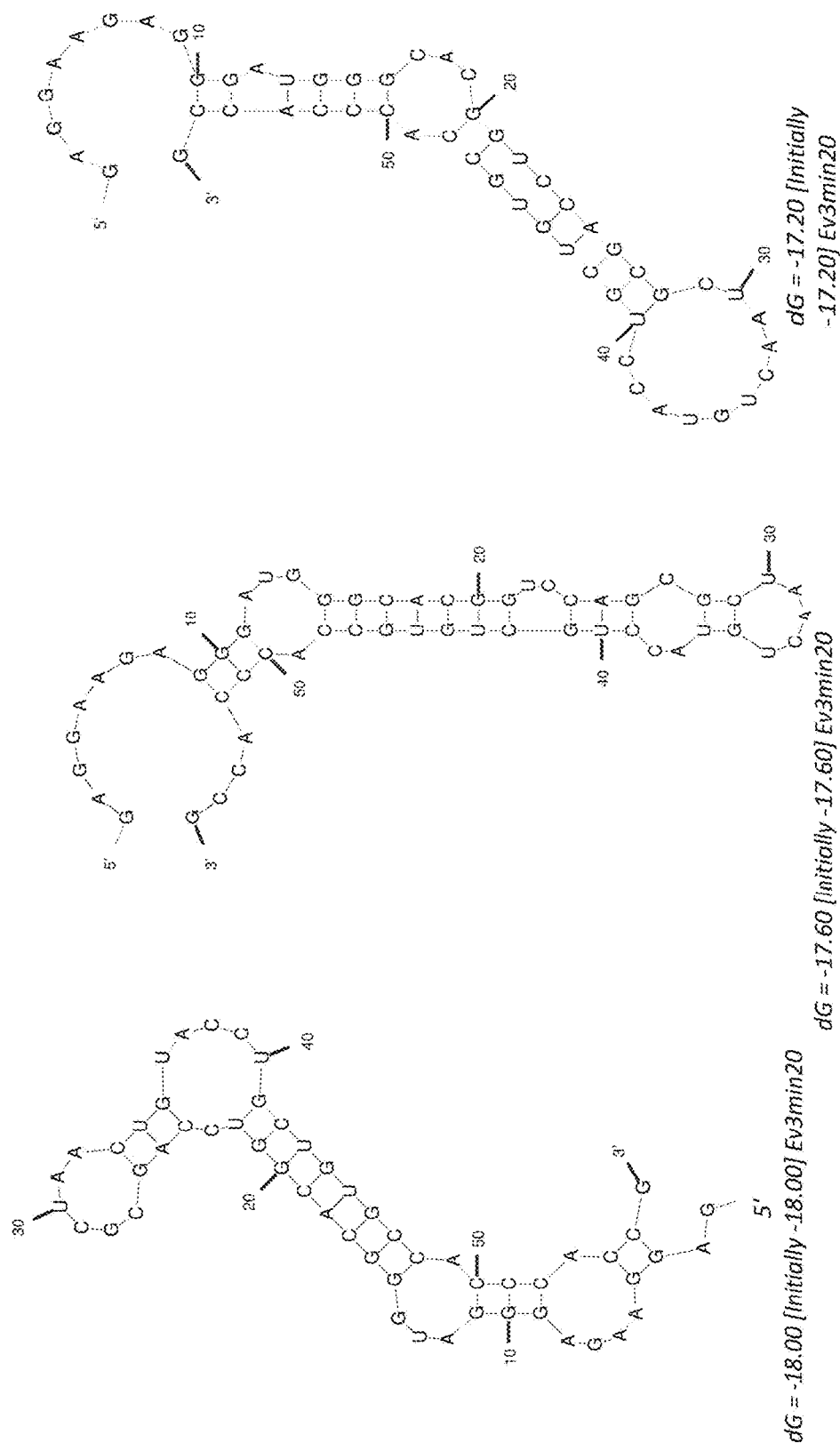
FIG. 33 shows predicted secondary structures for Ev3min20 truncate aptamer (SEQ ID NO: 515).
Figure 34:
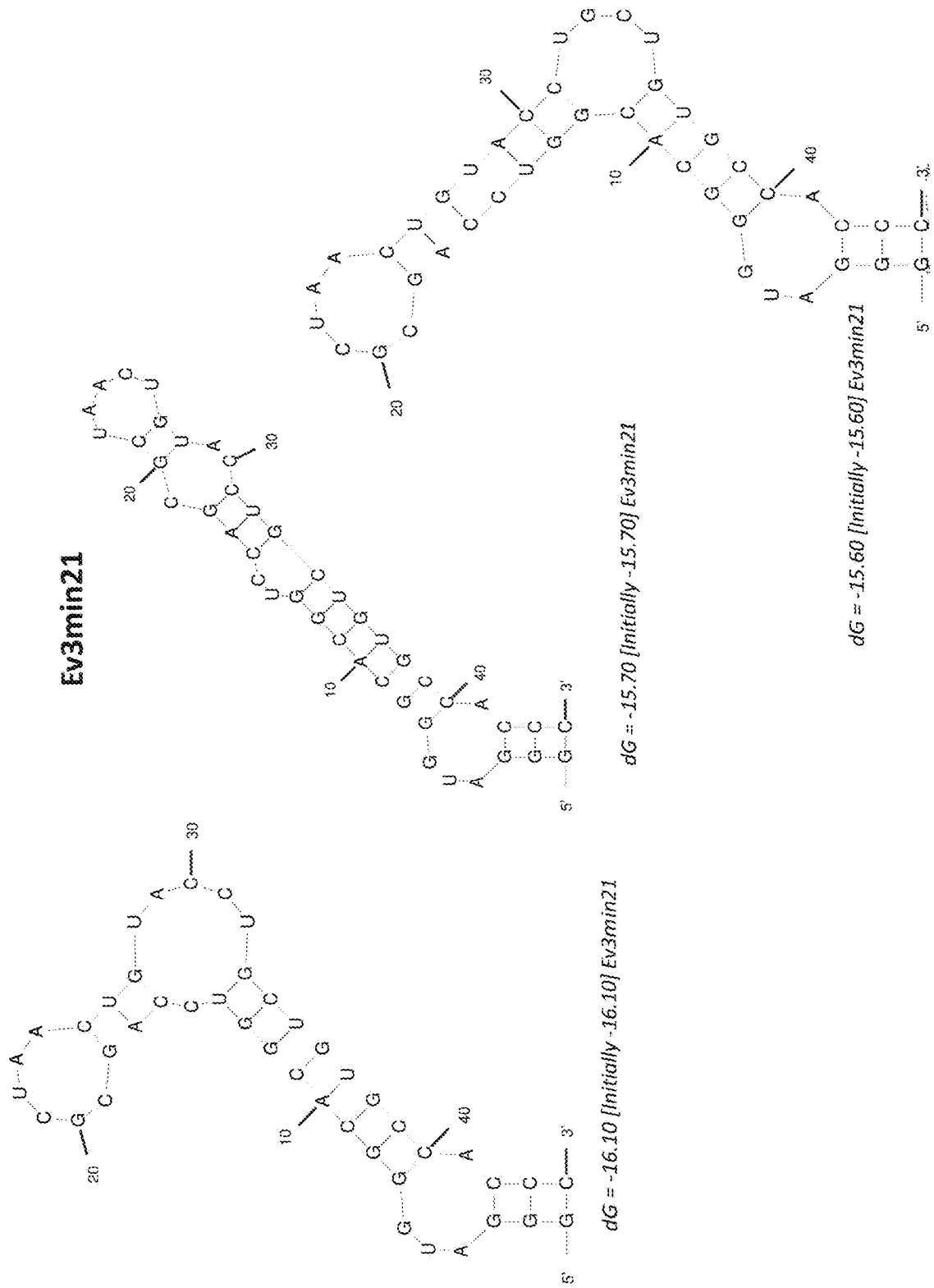
FIG. 34 shows predicted secondary structures for Ev3min21 truncate aptamer (SEQ ID NO: 486).
Figure 35:
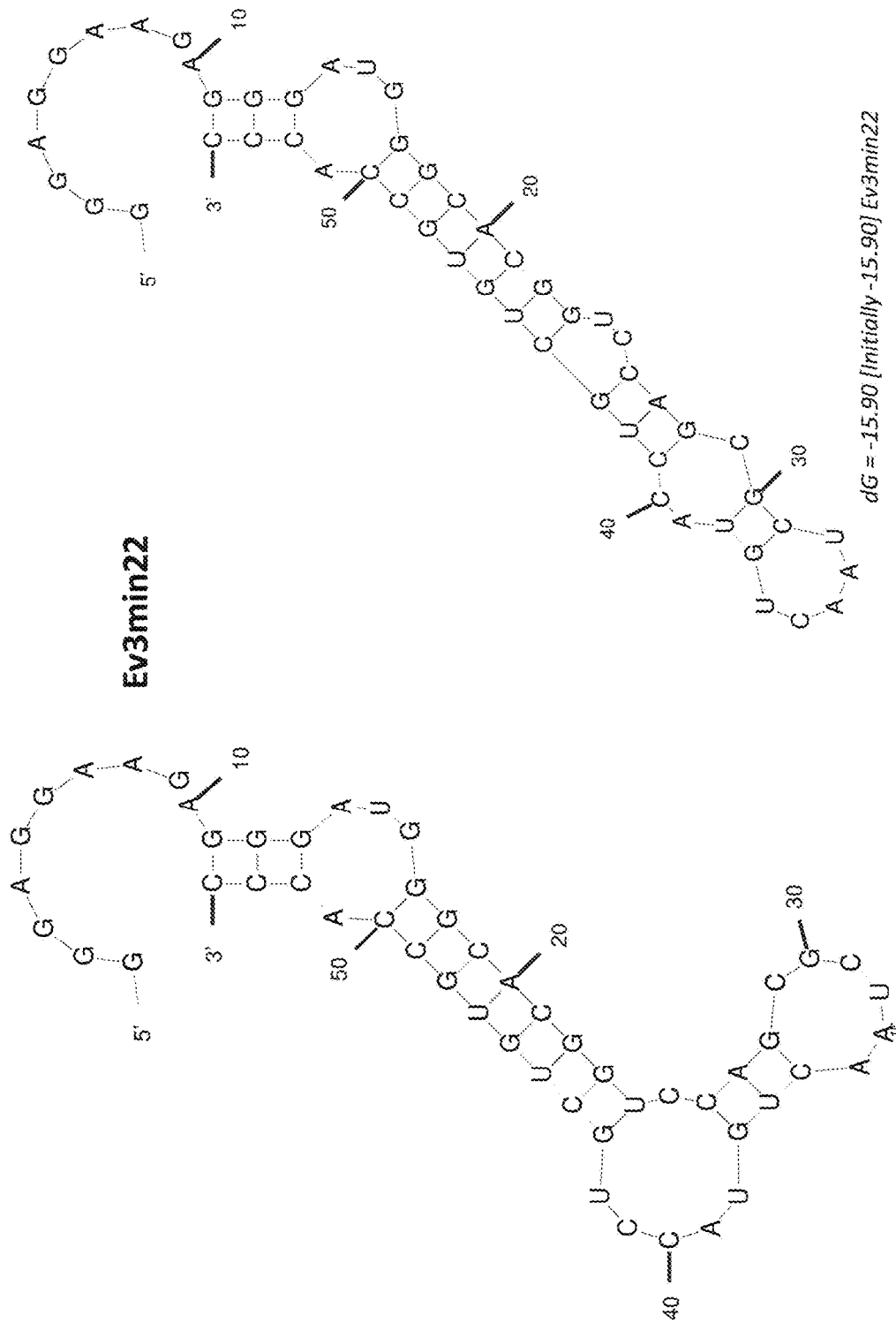
FIG. 35 shows predicted secondary structures for Ev3min22 truncate aptamer (SEQ ID NO: 487).
Figure 36:
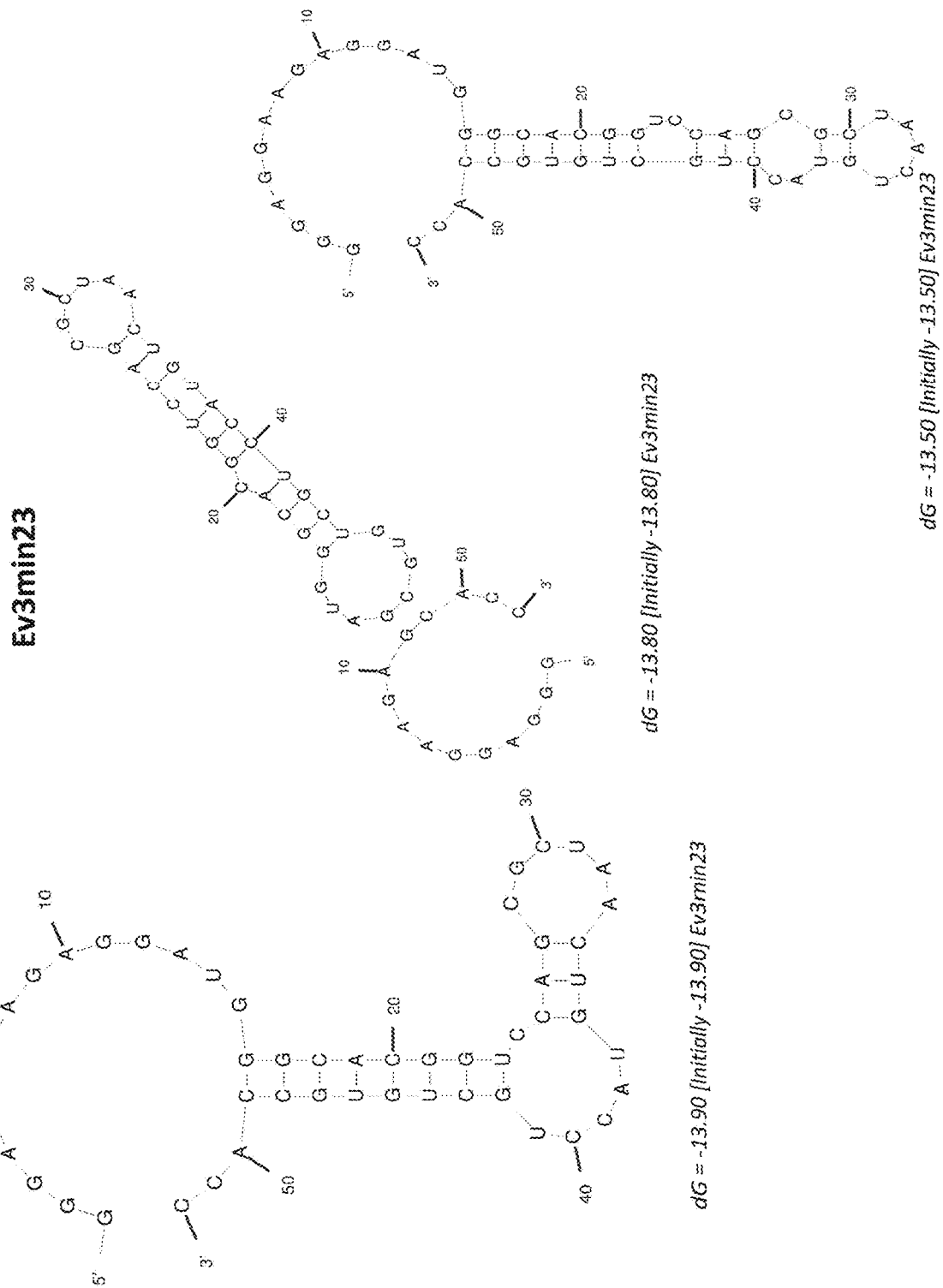
FIG. 36 shows predicted secondary structures for Ev3min23 truncate aptamer (SEQ ID NO: 488).
Figure 37B:
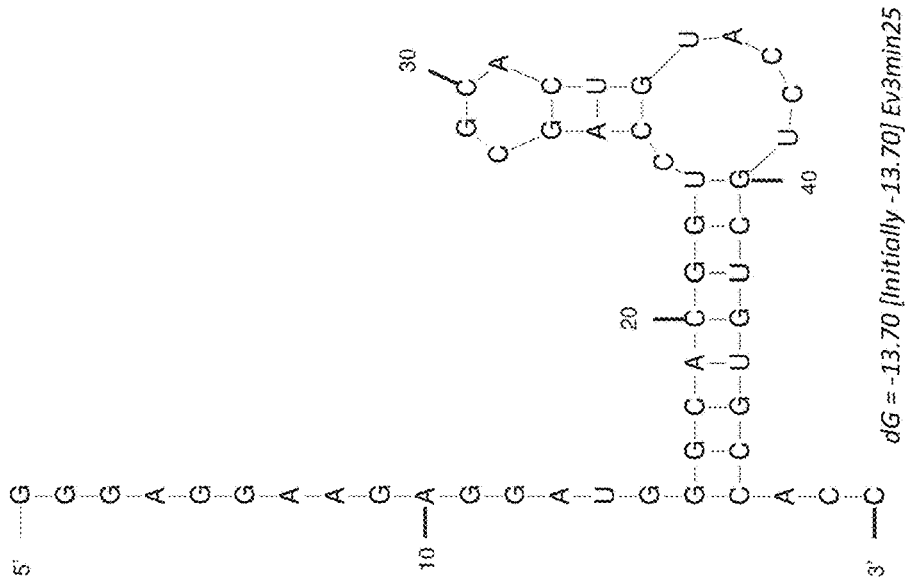
FIGS. 37A-37B show predicted secondary structures for Ev3min24 truncate aptamer (SEQ ID NO: 489) and Ev3min25 truncate aptamer (SEQ ID NO: 490).
Figure 37A:
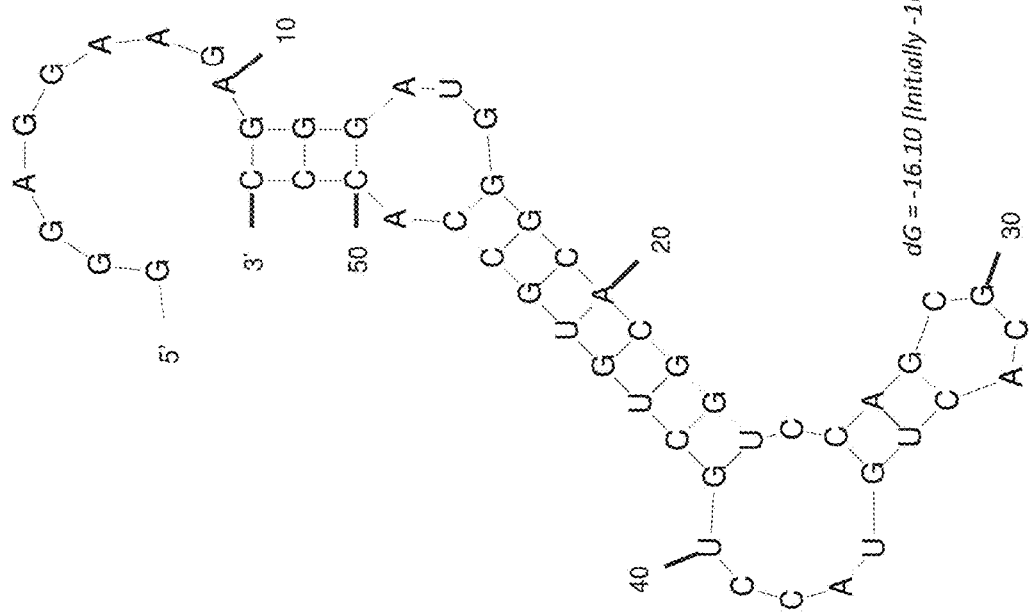

To determine whether the EV3 aptamer could be truncated without affecting its radiosensitization function, we tested some Ev3 aptamer truncates (FIG. 10). HCT 116 p53 -/- colon cancer cells were treated with 5 ug of indicated full-length aptamers or Ev3 truncates and exposed to 2Gy IR 48 h later. Cells were cultivated for 10 d and survival was assessed by MTT assay. FIG. 10 shows truncation of Ev3 resulted in reduced activity as radiosensitizer.

The Ev3 nucleolin aptamer has the potential for clinical application as a cancer-specific radio- and chemosensitizer and could improve the current regimens of cancer therapy. Further, the aptamer can be radiolabeled for use as a DNA damaging agent that will preferentially target tumors and simultaneously blunt the ability of the tumor cell to repair the radiation damage, thus enhancing the sensitivity of the tumor to the radioisotope.

Example 3—Predicted Secondary Structures for Nucleolin Aptamers

Predicted secondary structures for nucleolin aptamers were generated using the mfold Web Server RNA Folding Form. Predicted structures for representative aptamers from families B, C, D, E, and F are shown in FIGS. 11A-11B, 12A-12B, 13A-13C, 14A-14D, and 15A-15B. Predicted structures for Ev3 truncates (Ev3.min2-25) are shown in FIGS. 16-37.

We claim:

1. An aptamer comprising
a polynucleotide having at least 80% sequence identity to any one of SEQ ID NOS: 480, 13-21, 485, 474, 482, 511, 487, 489, 503 or 488,
wherein the polynucleotide consists of an unmodified form or a modified form comprising at least one nucleotide base modification.

2. The aptamer of claim 1, wherein the aptamer comprises a polynucleotide having at least 90% sequence identity to 5'-GGGAGAGAGGAAGAGGGAUGGG (SEQ ID NO: 491)-A Variable Region-CAUAACCCAGAGGUCGAU-AGUACUGGAUCCCCC (SEQ ID NO: 492)-3', wherein the variable region comprises any one of SEQ ID NOS: 13-21 or a portion thereof.

3. The aptamer of claim 1, wherein the aptamer comprises a polynucleotide having at least 90% sequence identity to SEQ ID NO: 480 (Ev3 Aptamer).

4. The aptamer of claim 1, wherein the dissociation constant ($K_D$) of the aptamer for a nucleolin protein is less than 100 nanomolar (nM).

5. The aptamer of claim 1, wherein the polynucleotide comprises an RNA polynucleotide.

6. The aptamer of claim 1, wherein the polynucleotide comprises a modified form comprising at least one nucleotide base modification selected from the group consisting of a 2'fluoro modification, a 2'O-methyl modification, a 5' modification, and a 3'modification.

7. The aptamer of claim 1, wherein the polynucleotide comprises a 5' linker and/or a 3' linker.

8. The aptamer of claim 1, wherein the polynucleotide further comprises an agent.

9. The aptamer of claim 8, wherein the agent is a stability agent selected from the group consisting of polyethylene glycol (PEG), cholesterol, albumin, and Elastin-like polypeptide or a reporter moiety.

10. The aptamer of claim 9, wherein said reporter moiety is selected from the group consisting of a fluorophore moiety, an optical moiety, a magnetic moiety, a radiolabel moiety, an X-ray moiety, an ultrasound imaging moiety, a photoacoustic imaging moiety, a nanoparticle-based moiety, and a. combination of two or more of the reporter moieties.

11. The aptamer of claim 8, wherein the polynucleotide and the agent are linked by a covalent bond or a tag system.

12. A dimer, trimer, or tetramer comprising the aptamer of claim 1.

13. A method for treating cancer in a subject comprising administering to the subject a therapeutically effective amount of the aptamer of claim 1.

14. The method of claim 13, further comprising administering a chemotherapeutic agent or radiation therapy to the subject.

15. The method of claim 14, wherein the aptamer is administered prior to the administration of the chemotherapeutic agent or the radiation therapy.

16. The method of claim 13, wherein the cancer is colon cancer.

17. The method of claim 13, wherein the subject is a mammal.

18. A method of labeling or inhibiting nucleolin comprising contacting nucleolin with the aptamer of claim 1.

19. The method of claim 18, wherein the nucleolin is contacted by adding the aptamer to cells comprising nucleolin in vitro.

20. The method of claim 18, wherein the nucleolin is contacted by administering the aptamer to a subject.

* * * * *